United States Patent
Rottiers et al.

(10) Patent No.: US 12,246,046 B2
(45) Date of Patent: *Mar. 11, 2025

(54) COMPOSITIONS AND METHODS FOR THE TREATMENT OF TYPE 1 DIABETES

(71) Applicant: INTREXON ACTOBIOTICS N.V., Zwijnaarde (BE)

(72) Inventors: Pieter Rottiers, De Pinte (BE); Lothar Steidler, Lokeren (BE)

(73) Assignee: INTREXON ACTOBIOTICS N.V., Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/463,461

(22) Filed: Sep. 8, 2023

(65) Prior Publication Data

US 2024/0082323 A1 Mar. 14, 2024

Related U.S. Application Data

(60) Continuation of application No. 17/150,352, filed on Jan. 15, 2021, now Pat. No. 11,786,567, which is a division of application No. 16/069,947, filed as application No. PCT/IB2017/050204 on Jan. 13, 2017, now Pat. No. 10,905,727.

(60) Provisional application No. 62/278,493, filed on Jan. 14, 2016, provisional application No. 62/350,472, filed on Jun. 15, 2016.

(51) Int. Cl.
*A61K 35/747* (2015.01)
*A61K 35/744* (2015.01)
*A61K 35/745* (2015.01)
*A61K 39/00* (2006.01)
*A61K 39/395* (2006.01)

(52) U.S. Cl.
CPC .......... *A61K 35/747* (2013.01); *A61K 35/744* (2013.01); *A61K 35/745* (2013.01); *A61K 39/3955* (2013.01); *A61K 2039/523* (2013.01)

(58) Field of Classification Search
None
See application file for complete search history.

(56) References Cited

U.S. PATENT DOCUMENTS

| | | | |
|---|---|---|---|
| 4,518,584 A | 5/1985 | Mark et al. | |
| 4,564,593 A | 1/1986 | Tsukamoto et al. | |
| 4,752,585 A | 6/1988 | Koths et al. | |
| 4,919,918 A | 4/1990 | Cole et al. | |
| 5,223,285 A | 6/1993 | DeMichele et al. | |
| 5,229,109 A | 7/1993 | Grimm et al. | |
| 5,470,561 A | 11/1995 | Klugkist et al. | |
| 5,559,007 A | 9/1996 | Suri et al. | |
| 5,695,746 A | 12/1997 | Garlick, Jr. et al. | |
| 5,700,782 A | 12/1997 | Cope et al. | |
| 5,869,118 A | 2/1999 | Morris et al. | |
| 5,972,685 A | 10/1999 | Beitz et al. | |
| 5,993,785 A | 11/1999 | Johansen et al. | |
| 6,117,417 A | 9/2000 | Wicks et al. | |
| 6,165,494 A | 12/2000 | Picciano | |
| 6,171,611 B1 | 1/2001 | Picciano | |
| 6,348,187 B1 | 2/2002 | Pan et al. | |
| 6,387,352 B1 | 5/2002 | Johansen et al. | |
| 6,790,444 B2 | 9/2004 | Le et al. | |
| 7,029,842 B2 | 4/2006 | Duffner et al. | |
| 7,569,215 B2 | 8/2009 | Wittrup et al. | |
| 8,759,088 B2 | 6/2014 | Steidler et al. | |
| 10,905,727 B2* | 2/2021 | Rottiers | A61K 35/747 |
| 11,786,567 B2* | 10/2023 | Rottiers | A61K 38/28 424/93.45 |
| 2002/0044910 A1 | 4/2002 | Johansen et al. | |
| 2003/0152530 A1 | 8/2003 | Johansen et al. | |
| 2004/0076590 A1 | 4/2004 | Wilkins, Jr. | |
| 2006/0269515 A1 | 11/2006 | Denis-Mize et al. | |
| 2007/0243303 A1 | 10/2007 | Dan Hengst et al. | |
| 2010/0080774 A1 | 4/2010 | Steidler et al. | |
| 2012/0039853 A1 | 2/2012 | Corveleyn et al. | |

(Continued)

FOREIGN PATENT DOCUMENTS

| | | |
|---|---|---|
| CN | 101378783 A | 3/2009 |
| CN | 104413334 A | 3/2015 |

(Continued)

OTHER PUBLICATIONS

Robert et al. Diabetes 63: 2876-2887, 2014.*
Mallone et al. Diabetes 63: 2603-2605, 2014.*
Antonioli, L., et al., Trends Mol. Med. 2013, 19(6): 355-367.
Arden, S. D., T. Zahn, S. Steegers, S. Webb, B. Bergman, R. M. O'Brien, J. C. Hutton. 1999. Molecular cloning of a pancreatic islet-specific glucose-6-phosphatase catalytic subunit-related protein. Diabetes 48: 531-542.
Argos in EMBO J., 8:779-785 (1989).
Batchelor et al. Int. J. Pharm., 238: 123-32, 2002.

(Continued)

*Primary Examiner* — S. Devi
(74) *Attorney, Agent, or Firm* — BANNER & WITCOFF, LTD.

(57) ABSTRACT

Provided herein are compositions and methods for the treatment of type 1 diabetes (T1D) in mammalian subjects. The compositions include lactic acid fermenting bacteria (LAB) expressing an IL-2 gene and a T1D-specific self-antigen (e.g., proinsulin (PINS)) gene. Exemplary methods include: orally administering to a mammalian subject, a therapeutically effective amount of the composition. The composition can be administered to the subject mucosally, resulting in delivery of the LAB into the gastrointestinal tract, where the LAB is released. Bioactive polypeptides expressed by the LAB are thus administered via mucosal delivery. The LAB may be selected to deliver a low-dose of IL-2 to the subject. The methods may not require concomitant systemic anti-CD3 antibody treatment. The methods may be suited for subjects possessing residual beta-cell function, e.g., those with recent-onset T1D.

13 Claims, 22 Drawing Sheets

Specification includes a Sequence Listing.

(56) References Cited

U.S. PATENT DOCUMENTS

| | | |
|---|---|---|
| 2012/0244112 A1 | 9/2012 | Ast et al. |
| 2014/0004080 A1 | 1/2014 | Klatzmann et al. |
| 2014/0105863 A1 | 4/2014 | Vanden-Broucke et al. |
| 2015/0218260 A1 | 8/2015 | Klein et al. |

FOREIGN PATENT DOCUMENTS

| | | | |
|---|---|---|---|
| CN | 105980410 A | | 9/2016 |
| EP | 88195 A2 | | 9/1983 |
| EP | 91539 A1 | | 10/1983 |
| EP | 0569604 A1 | | 11/1993 |
| EP | 1730184 A2 | | 12/2006 |
| EP | 1748296 A1 | | 1/2007 |
| GB | 227835 A | | 4/1925 |
| JP | 2012-504116 A | | 2/2012 |
| JP | 2013-530187 A | | 7/2013 |
| JP | 2014-527826 A | | 10/2014 |
| JP | 2023-166421 A | * | 11/2023 |
| WO | WO-92/14837 A1 | | 9/1992 |
| WO | WO-93/17117 A1 | | 9/1993 |
| WO | WO-96/32487 A1 | | 10/1996 |
| WO | WO-97/14806 A2 | | 4/1997 |
| WO | WO-97/38712 A1 | | 10/1997 |
| WO | WO-00/23471 A2 | | 4/2000 |
| WO | WO-2000/018377 | | 4/2000 |
| WO | WO-2000/22909 A2 | | 4/2000 |
| WO | WO-01/02570 A1 | | 1/2001 |
| WO | WO-2001/02576 A1 | | 1/2001 |
| WO | WO-2001/62944 A2 | | 8/2001 |
| WO | WO-01/94585 A1 | | 12/2001 |
| WO | WO-02/090551 A2 | | 11/2002 |
| WO | WO-2004/046346 A2 | | 6/2004 |
| WO | WO-2004/069177 A2 | | 8/2004 |
| WO | WO-2005/071088 A2 | | 8/2005 |
| WO | WO-2005/086751 A2 | | 9/2005 |
| WO | WO-2005/086798 A2 | | 9/2005 |
| WO | WO-2008/084115 A2 | | 7/2008 |
| WO | WO-2010-034844 A1 | | 4/2010 |
| WO | WO-2011-160062 A2 | | 12/2011 |
| WO | WO-2013/036914 A1 | | 3/2013 |
| WO | WO-2013/041673 A1 | | 3/2013 |

OTHER PUBLICATIONS

Bruschi, M. L., & de Freitas, O. (2005). Oral bioadhesive drug delivery systems. Drug Development and Industrial Pharmacy, 31(3), 293-310.
Gazzaniga, A., Iamartino, P., Maffione, G., and Sangalli, M. E. Oral delayed-release system for colonic specific delivery. Int. J. Pharm. 1994, 108(1): 77-83).
Demeester et al., Diabetes Care 2015, 38(4): 644-651.
Devos et al., Nucleic Acids Res. 1983, 11(13): 4307-23.
Suarez-Pinzon, WL et al., Diabetes 2008; 57:3281-8.
Dogra et al., Diabetologia 2006; 49(5):953-7.
Drouault S, et al., Appl. Environ. Microbiol. 1999; 65(11): 4881-6.
Gagliani, N et al., Nat. Med. 2013, 19(6): 739-746.
Gasson MJ, J. Bacteriol. 1983, 154(1):1-9.
Glenting et al. Appl. Environ. Microbiol. (2002) 68:5051-5056.
Grinberg-Bleyer Y. et al., J. Exp. Med. 2010; 207(9):1871-1878.
Hartemann A. et al., Lancet Diabetes Endocrinol. 2013; 1:295-305.
Jones A.G. and Hattersley A.T., Diabetic Medicine 2013, 30: 803-817.
Law J., et al., J. Bacteriol. 1995; 177(24):7011-7018.
Little RR et al., Clin. Chem. 2008, 54: 1023-1026.
Martin et al., J. Biol. Chem. 2001; 276(27):25197-207.
Mayer, L. and Shao, L., Therapeutic potential of oral tolerance. Nat Rev Immunol 2004. 4: 407-419.
Pp. 341-344 of Harwood and Cutting, "Molecular Biological Methods for Bacillus," John Wiley & Co. 1990.
Rapoport: "Gene Expression Using Bacillus", Current Opinion in Biotechnology, vol. 1, 1990, pp. 21-27.
Robert et al. (2015) Trimming of two major type 1 diabetes driving antigens, GAD65 and IA-2, allows for successful expression in Lactococcus lactis. Benef Microbes 6(4):591-601.
Robert S. and Steidler L., Microb. Cell Fact. 2014, 13 Suppl. 1: S11.
Robert, S. et al., Diabetes 2014, 63: 2876-2887.
Rosenzwajg M. et al., J Autoimmun. 2015; 58:48-58.
Sanders et al., J. Bacteriol. 1995, 177(18):5254-5260.
Schotte, et al. (2000) Enzyme Microb. Technol. 27(10):761-765.
Sorensen et al. (2000) Appl. Environ. Microbiol. 66: 1253-1258.
Steidler et al., Nat. Biotechnol. 2003; 21(7):785-789.
Steidler et al., Science 2000; 289(5483): 1352-1355.
Strobel et al., Immunology 1983, 49:451-456.
Takiishi, T. et al., J. Clin. Inv. 2012, 122(5): 1717-1725.
Tang Q, Bluestone JA. Nat. Immunol. 2008; 9(3): 239-244.
Taniguchi et al., Nature 1983, 302(5906):305-10.
Van Asseldonk et al. Functional analysis of the Lactococcus lactis usp45 secretion signal in the secretion of a homologous proteinase and a heterologous alpha-amylase.(1993) Mol. Gen. Genet. 240:428-434.
Van Belle, T.L. et al., Physiol. Rev. 2011, 91(1): 79-118.
Waterfield, N. R., R. W. Le Page, P. W. Wilson, and J. M. Wells. 1995. The isolation of lactococcal promoters and their use in investigating bacterial luciferase synthesis in Lactococcus lactis. Gene 165:9-15.
Wiedmeyer et al., Clin. Chem. 2007, 53: 784-787.
Yu, A., et al., Diabetes 2015, 64: 2172-2183.
Zheng Y, Rudensky AY. Nat. Immunol. 2007; 8(5): 457-462.
Mallone R. et al., Diabetes, 2014, 63 (8): 2603-2605.
International Search Report mailed Mar. 13, 2017 for PCT/IB2017/050204.
Written Opinion mailed Mar. 13, 2017 for PCT/IB2017/050204.
Steidler et al., "Mucosal Delivery of Murine Interleukin-2 (IL-2) and IL-6 by Recombinant Strains of Lactococcus lactis Coexpressing Antigen and Cytokine," Infection and Immunity, 1998, vol. 66, No. 7, pp. 3183-3180.
Mosmann, et al., "Species-Specificity of T cell stimulating activities of IL 2 and BSF-1 (IL 4): comparison of normal and recombinant, mouse and human IL 2 and BSF-1 (IL 4)," Journal of Immunology, 1987, vol. 138, No. 6, pp. 1813-1816.
Kok et al., "Construction of Plasmid Cloning Vectors for Lactic Streptococci Which Also Replicate in Bacillus subtilis and Escherichia coli," Applied and Environmental Microbiology, vol. 48, No. 4, pp. 726-731, Oct. 1984.
Goulding et al., "Distinctive Profiles of Infection and Pathology in Hamsters Infected with Clostridium difficile Strains 630 and B1," Infection and Immunity, vol. 77, No. 12, pp. 5478-5485, Dec. 2009.
Selleck et al., "Recombinant protein complex expression in E. coli," NIH Public Access, Current Protocol in Protein Science, Chapter: Unit 5.21, May 2008.
Madison et al., "cis Elements of the Villin Gene Control Expression in Restricted Domains of the Vertical (Crypt) and Horizontal (Duodenum, Cecum) Axes of the Intestine," The Journal of Biological Chemistry, vol. 277, No. 36, pp. 33275-33283, Sep. 6, 2002.
Keffer et al., "Transgenic mice expressing human tumour necrosis factor: a predictive genetic model of arthritis," The EMBO Journal, vol. 10, No. 13, pp. 4025-4031, 1991.
Stemmer et al., "Single-step assembly of a gene and entire plasmid from large numbers of oligodeoxyribonucleotides," Gene, vol. 164, pp. 49-53, 1995.
Tan et al., "The pST44 polycistronic expression system for producing protein complexes in Escherichia coli," Protein Expression and Purification, vol. 40, pp. 385-395, 2005.
O'Kane et al., Integrable a-Amylase Plasmid for Generating Random Transcriptional Fusions in Bacillus subtilis. Journal of Bacteriology, Nov. 1986, p. 973-981.
Dunn et al., A vector for promoter trapping in Bacillus cereus vector for promoter trapping in Bacillus cereus. Gene 226 (1999) 297-305.
Mota et al., Control of the Arabinose Regulon in Bacillus subtilis by AraR In Vivo: Crucial Roles of Operators, Cooperativity, and DNA Looping. J Bacterial. Jul. 2001; 183(14): 4190-4201.
Zuber et al., Use of a lacZ Fusion to Study the Role of the spoO Genes of Bacillus subtilisin Developmental Regulation. Cell. 35:275-283. Nov. 1983.
Schirrmann et al., Production systems for recombinant antibodies. Frontiers in Bioscience, vol. 13, 4576-4594, May 1, 2008.

(56) References Cited

OTHER PUBLICATIONS

Rosey et al., "Nucleotide and Deduced Amino Acid Sequences of the lacR, lacABCD, and lacFE Genes Encoding the Repressor, Tagatose 6-Phosphate Gene Cluster, and Sugar-Specific Phosphotransferase System Components of the Lactose Operon of *Streptococcus mutans*", Journal of Bacteriology, Oct. 1992, p. 6159-6170, vol. 174, No. 19, American Society for Microbiology, USA.

Peschel, et al., "Inactivation of the dit Operon in *Staphylococcus aureus* Confers Sensitivity to Defensins, Protegrins, and Other Antimicrobial Peptides", J. Biol. Chem., Mar. 1999, p. 8405-8410, vol. 274, No. 13, Germany.

Bruckner, Reinhold, "Gene replacement in *Staphylococcus carnosus* and *Staphylococcus xylosus*," Federation of European Microbiological Societies, Jun. 1997, vol. 151, No. 1, p. 1-8, Elsevier Science B.V., Germany.

Dobinsky, et al., "Influence of Tn917 Insertion on Transcription of the icaADBC Operon in Six Biofilm-Negative Transposon Mutants of *Staphylococcus epidermidis*", Academic Press, Jan. 2002, vol. 47, No. 1, p. 10-17, Elsevier Science B.V., Germany.

Qiao, et al., "Regulation of the nisin operons in Lactococcus lactis N8", Journal of Applied Bacteriology, Dec. 1995, vol. 80, p. 626-634, The Society for Applied Bacteriology, Finland.

Luesink, et al., "Molecular Characterization of the Lactococcus lactis ptsHI Operon and Analysis of the Regulatory Role of HPr", Journal of Bacteriology, Feb. 1999, vol. 181, No. 3, p. 764-771, American Society for Microbiology, USA.

International Search Report dated Aug. 27, 2012 for PCT/EP2012/060431.

International Preliminary Report on Patentability dated Dec. 12, 2013 for PCT/EP2012/060431.

Dominguez et al., "Non-conventional yeasts as hosts for heterologous protein production", Int. Microbial., 1998, val. 1(2), 131-142.

Ishiai et al., "Purification, gene cloning, and reconstitution of the heterotrimeric single-stranded DNA-binding protein from Schizosaccharomyces pombe", J. Bioi. Chem., 1996, val. 271(34), 20868-20878.

Li et al., "Coexpression of nuclear receptor partners increases their solubility and biological activities", Proc. Natl. Acad. Sci. USA, 1997, val. 94(6), 2278-2283.

Smolke et al., "Coordinated, Differential Expression of Two Genes through Directed mRNA Cleavage and Stabilization by Secondary Structures", Appl. Environ. Microbial., 2000, vol. 66(12), 5399-5405.

Tirode et al., "Reconstitution of the transcription factor TFIIH: assignment of functions for the three enzymatic subunits, XPB, XPD, and cdk7", Mol. Cell, 1999, vol. 3(1), 87-95.

Hultberg et al., "Lactobacilli expressing llama VHH fragments neutralise Lactococcus phages", BMC Biotechnol., 2007, vol. 7, 58.

Kyne et al., "Asymptomatic Carriage of Clostridium difficile and Serum Levels of IgG Antibody against Toxin A", N Engl J Med, 2000;342(6):390-397.

Lowy et al., "Treatment with Monoclonal Antibodies against Clostridium difficile Toxins", N Engl J Med, 2010, 362(3):197-205.

Mazor et al., "Isolation of engineered, full-length antibodies from libraries expressed in *Escherichia coli*", Nat. Biotechnol., 2007, vol. 25(5), 563-565.

Perez-Martinez et al., "Protein export elements from Lactococcus lactis", Mol. Gen. Genet., 1992, vol. 234, 401-11.

Sibakov et al., "Secretion of TEM ?-lactamase with signal sequences isolated from the chromosome of *Lactococcus lactis* subsp. *lactis*", Appl. Environ. Microbial., 1991, vol. 57(2), 341-348.

Steidler et al., "Secretion of biologically active murine interleukin-2 by *Lactococcus lactis* subsp. *lactis*", Appl. Environ. Microbial., 1995, vol. 61(4), 1627-1629.

Sougioultzis et al., "Clostridium difficile Toxoid Vaccine in Recurrent C. difficile-Associated Diarrhea", Gastroenterology, 2005;128(3):764-770.

Wilcox, "Descriptive study of intravenous immunoglobulin for the treatment of recurrent Clostridium difficile diarrhoea", J Antimicrob Chemother, 2004;53(5):882-884.

Jana, S. et al., "Strategies for efficient production of heterologous proteins in *Escherichia coli*", Appl. Microbial. Biotechnol., 2005, vol. 67(3), 289-298.

Beninati et al., "Therapy of mucosal candidiasis by expression of an anti-idiotype in human commensal bacteria", Nature Biotechnology, 2000, vol. 18(10), 1060-1064.

Johnston et al., "Coexpression of proteins in bacteria using T7-based expression plasmids: expression of heteromeric cell-cycle and transcriptional regulatory complexes", Protein Expr. Purif., 2000, vol. 20(3), 435-443.

Leenhouts et al., "A lactococcal pWV01-based integration toolbox for bacteria", Methods in Cell Science, 1998; 20:35-50.

Leung et al., "Treatment with intravenously administered gamma globulin of chronic relapsing colitis induced by Clostridium difficile toxin", J Pediatr, 1991 ; 18(4 Pt 1):633-637.

Simmons et al., "Expression of full-length immunoglobulins in *Escherichia coli*: rapid and efficient production of aglycosylated antibodies", J. Immunol. Methods., 2002. val. 263(1-2), 133-147.

Smolke & Keasling, "Effect of Gene Location, mRNA Secondary Structures, and RNase Sites on Expression of Two Genes in an Engineered Operon", Biotechnol. Bioeng., 2002, val. 80(7), 762-776.

Tan, "A modular polycistronic expression system for overexpressing protein complexes in *Escherichia coli*," Protein. Expr. Purif., 2001, vol. 21 (1), 224-234.

Yuvaraj et al., "Human scFv SlgA expressed on Lactococcus lactis as a vector for the treatment of mucosal disease", Mol. Nutr. Food. Res., 2008, val. 52(8), 913-920.

Hooks et al., "Muromonab CD-3: a review of its pharmacology, pharmacokinetics, and clinical use in transplantation," Pharmacotherapy, 1991, val. 11 (1), 26-37.

Written Opinion of the International Searching Authority for PCT/EP2012/060431 dated Dec. 2, 2013.

International Search Report for PCT/EP2012/060431 dated Dec. 6, 2012.

Gross et al., "The Functional and Regulatory Roles of Sigma Factors in Transcription," Cold Spring Harbor Symposia on Quantitative Biology, vol. LXIII., pp. 141-155, 1998, downloaded from symposium.cshlp.org on Aug. 30, 2017.

Haugen et al., "Advances in bacterial promoter recognition and its control by factors that do not bind DNA," Nat Rev Microbiol., vol. 6, No. 7, 2008.

Office Action issued Jul. 24, 2017 is Russian Patent Application No. 2013157300 (4 pages) with an English translation (2 pages).

Lewis et al., Compartmentalization of transcription and translation in Bacillus subtilis. the EMBO Journal vol. 19 No. 4 pp. 710-718, 2000 (Year: 2000).

Delisa et al., Folding quality control in the export of proteins by the bacterial twin-arginine translocation pathway. PNAS, 2003, 100:6115-6120.

Wu et al., Enhanced Secretory Production of a Single-Chain Antibody Fragment from Bacillus subtilis by Coproduction of Molecular Chaperones. J Bacteriology, 1998, 180:2830-2835 (Year: 1998).

Gil et al., Determination of the Core of a Minimal Bacterial Gene Set (Micro Mol Bio Rev, 2004, 68:518-537) (Year: 2004).

Campbell et al. Developing the next generation of monoclonal antibodies for the treatment of rheumatoid arthritis (BJP, 2011, 162: 1470-1484) (Year: 2011).

Steidler, Lothar, and Klaas Vandenbroucke. "Genetically Modified Lactococcus Lactis: Novel Tools for Drug Delivery." International Journal of Dairy Technology 59.2 (2006): 140-146.

Q. Tang, J. Y. Adams, C. Penaranda et al., "Central role of defective interleukin-2 production in the triggering of islet autoimmune destruction," Immunity, vol. 28, No. 5, pp. 687-697, 2008.

NCBI, GenBank accession No. of AF210773. *Streptococcus gordonii* lac operon, partial sequence, first deposited by Boken et al. 1999, p. 1-4 (Year: 1999).

NCBI, GenBank accession No. of M28357. Lactococcus lactis phospho-beta-galactosidase (lacG) gene, complete cds, first deposited by De Vos et al. 1989, p. 1-3 (Year: 1989).

(56) References Cited

OTHER PUBLICATIONS

Payne et al., Exploitation of chromosomally integrated lactose operon for controlled gene expression in Lactococcus lactis. FEMS Microbiology Letters 136 (1996) 19-24 (Year: 1996).

Drouault et al., The Peptidyl-Prolyl Isomerase Motif Is Lacking in PmPA, the PrsA-Like Protein Involved in the Secretion Machinery of Lactococcus lactis. Applied and Environmental Microbiology, Aug. 2002, p. 3932-3942 (Year: 2002).

Russian Office Action mailed Jun. 9, 2020 in Russian patent application No. 2018126399.

Kravchenko P.N., et al., "The System of Regulatory T Cells and Autoimmunity," Transactions of Karelian Research Centre of Russian Academy of Science, No. 3, Experimental biology, 2013, pp. 18-30.

Nair, "A simple practice guide for dose conversion between animals and human," 2016 Journal of Basic and Clinical Pharmacy, vol. 7, No. 2, pp. 27-31.

McNally et al., "Coexpression and assembly of myosin heavy chain and myosin light chain in *Escherichia coli*", Proc. Natl. Acad. Sci. USA, 1988, vol. 85(19), 7270-7273.

Henricksen et al., "Recombinant Replication Protein A: Expression, Complex Formation, and Functional Characterization", J. Biol. Chem., 1994, vol. 269(15), 11121-11132.

Chancey et al., "Lactobacilli-expressed single-chain variable fragment (scFv) specific for intercellular adhesion molecule 1 (ICAM-1) blocks cell-associated HIV-1 transmission across a cervical epithelial monolayer", J. Immunol., 2006, vol. 176(9), 5627-5636.

Kruger et al., "In situ delivery of passive immunity by lactobacilli producing single-chain antibodies", Nature Biotechnology, 2002, vol. 20(7), 702-706.

Japanese Office Action issued in Japanese patent application No. 2018-536741, dated Jul. 13, 2021.

Chinese Office Action issued in Chinese patent application No. 201780011344.4, dated Apr. 23, 2021.

Office Action issued Apr. 27, 2021 in Russian patent application No. 2018126399 (7 pages) with English translation (7 pages).

Krishnamurthy B. et al. Responses against islet antigens in NOD mice are prevented by tolerance to proinsulin but not IGRP. J Clin Invest. 2006; 116 (12): 3258-3265.

Notice of Refusal issued Sep. 3, 2024 in Japanese Patent Application No. 2023-133189 (4 pages) with a machine English translation (4 pages).

* cited by examiner

```
  1 aactgaagat tcaacaatct cagacatcgc tgttgcaact aacgctggtc aaatcaaaac tggttcactt tcacgtacag accgtatggc taaatacaac
    >>.............................................................................................../enoA..>

101 caattgcttc gtattgaaga ccaattggct gaagttgctc aatacaaagg tcttaaagca tcttacaacc ttaaaaaata ttctacaacc ttaaaaaata aggaggaaaa aatgaaaaaa
    >.............................................................................................../enoA.........>>.IRrpmD.>>

201 aagattatct cagctatttt aatgtctaca gtgatactt ctgctgcagc ccgtttgtca ggtgtttacg ccgtccaac ttcatcatca
    >.............................................................SSusp45.........>>.................hil-2.........

301 ctcaattgca acttgaacac ttgcttttgg atctttcaaat gatcttgaac ggtatcaaca cccaaaaactt actcgtatgt tgactttta
    >.............................................................................................hil-2........>

401 attttacatg ccaaaaaaag ctactgaact taaacacttg caatgtcttg aagaagaatt gaaaccactt gaagaagttt tgaaccttgc tcaatcaaaa
    >.............................................................................................hil-2........>

501 aacttcact tgcgtccacg tgatctttatc tcaaacatca acgttatcgt tttggaactt aaaggttcag aaactacttt tatgtgtgaa tacgctgatg
    >.............................................................................................hil-2........>

601 aaactgctac tatcgttgaa ttttgaacc gttggatcac tttttgtcaa tcaatcatct caactttgac ttaaggttta gatgtttta attagcaata
    >.............................................................................................hil-2........>>
```

FIG. 1

```
  1 tcagctaacg gagctcaact tgttaaaact gtatcttggt acgataacga aatgtcatac acttcaaacc ttgttcgtac acttgcatac ttcgctaaaa
    >..................................................................................../gapB..........>

101 tcgctaaata aggaggaaaa aatgaagaag aaaatcatta gtgccatctt aatgtctaca gtgattcttt cagctgcagc tcctttatca ggcgtttatg
    >../gapB..>>   >>.IRFpmD.>>                                                                            >
                                                                                               >>.SSusp45............

201 catttgtgaa ccaacacctg tgcggctcac acctggtgga agctctctac ctagtgtgcg gggaacgagg cttcttctac acacccaaga cccgccggga
    >> SSusp45................                                                                                      >
                                    >.....................................pins................................

301 ggcagaggac ctgcaggtgg ggcaggtgga gctgggcggg ggccctggtg caggcagcct gcagcccttg gccctggagg ggtccctgca gaagcgtggc
    >...........................................pins............................................................ >

401 attgtggaac aatgctgtac cagcatctgc tccctctacc agctggagaa ctactgcaac taattttccg attttaacgg tataaaaacc agtcttcggg
    >.............................pins................>>
```

COMPOSITIONS AND METHODS FOR THE TREATMENT OF TYPE 1 DIABETES

CROSS REFERENCE TO RELATED APPLICATIONS

This application is a continuation of U.S. patent application Ser. No. 17/150,352, filed Jan. 15, 2021, now U.S. Pat. No. 11,786,567, which is a divisional application of U.S. patent application Ser. No. 16/069,947, filed Jul. 13, 2018, now U.S. Pat. No. 10,905,727, which is the National Stage Entry of PCT/IB2017/050204, filed Jan. 13, 2017, which claims benefit to U.S. Provisional Application No. 62,278,493, filed Jan. 14, 2016, and U.S. Provisional Application No. 62,350,472, filed Jun. 15, 2016, the contents of each of which are incorporated herein in their entirety.

REFERENCE TO SEQUENCE LISTING

The instant application contains a Sequence Listing XML which has been submitted electronically and is hereby incorporated by reference in its entirety. Said Sequence Listing XML copy, created on Aug. 12, 2023, is named INX00325US-C1.xml and is 151,060 bytes in size.

BACKGROUND

Approximately 10-15 million people suffer from type 1 diabetes mellitus (T1D), the most common metabolic disorder in infancy and adolescence, affecting 112,000 children younger than 16 years of age in Europe alone. T1D results from a progressive immune-mediated destruction of the pancreatic insulin-producing islet beta-cells ("beta-cells") in genetically-susceptible individuals, leading to chronic hyperglycemia which instigates micro- and macrovascular complications. See, e.g., van Belle, T. L. et al., *Physiol. Rev.* 2011, 91(1): 79-118. While therapeutic options are available for some autoimmune diseases, no therapies are currently approved far T1D. Patients with T1D require lifelong treatment with insulin. Moreover, long-term management requires a multidisciplinary approach that includes physicians, nurses, dieticians, and other specialists.

Blocking autoreactive effector T cells using generalized immunosuppression, either in the context of short-term therapy or chronic regimens, has been the sole therapeutic strategy in autoimmune diseases. It is believed that activating or expanding regulatory T (Treg) cells can restore a balance between effector T cells and Treg cells, and may achieve the same objective without the toxicity associated with immunosuppression.

Interleukin-2 ("IL-2") has key functions of the immune system, primarily via its direct effects on T cells. In the thymus, where T cells mature, it prevents autoimmune diseases by promoting the differentiation of certain immature T cells into regulatory T cells, which suppress other T cells that are otherwise primed to attack healthy cells in the body. At higher concentrations, IL-2 also promotes the differentiation of T cells into effector T cells and into memory T cells when the initial T cell is also stimulated by an antigen, thus helping the body fight off infections.

Native IL-2 was initially identified as a lymphocyte growth factor, and thought to primarily promote effector T cell responses in vivo, and recombinant IL-2 was developed for the treatment of conditions calling for the boosting of effecter T cells, i.e. cancer and infectious diseases. However, it was shown that IL-2 is dispensable for the differentiation, survival and function of effector T cells, as IL-2 knockout mice develop T-cell-mediated autoimmune disease. IL-2 is now known to be a cytokine critical for Treg cell development, expansion, survival and peripheral activity. A deficiency in IL-2 production or lack of IL-2 responsiveness leads to a loss of Treg cell function and an increase in autoimmunity. Treg cells constitutively express the trimeric high affinity receptor for IL-2 (IL-2Rαβγ) at higher levels than $CD4^+$ and $CD8^+$ effector T cells, NK cells, and eosinophils. Induction of STAT5a signaling occurs at lower doses of IL-2 in Treg cells than in effector T cells. Hence, low dose IL-2 appears to stimulate preferential activation and promote the survival of Treg cells in vivo. See, e.g., Yu, A., et al., *Diabetes* 2015, 64: 2172-2183.

In clinical studies, administration of IL-2 induced immunological changes, but did not change variables of glucose metabolism. See, e.g., Hartemann A. et al., *Lancet Diabetes Endocrinol.* 2013; 1:295-305; and Rosenzwajg M. et al., *J Autoimmun.* 2015; 58:48-58.

Pharmaceutical IL-2 preparations are administered by injection. Although oral delivery is attractive, e.g., as a result of the ease of administration, gastrointestinal degradation and low levels of absorption generally render this route ineffective for the delivery of polypeptides. Alternative routes such as nasal, rectal, pulmonary, and ocular routes are being investigated for polypeptide-based therapeutics.

Genetically modified bacteria have been used to deliver therapeutic molecules to the mucosal tissues. See, e.g., Steidler, L., et al., *Nat. Biotechnol.* 2003, 21(7): 785-789; and Robert S. and Steidler L., *Microb. Cell Fact.* 2014, 13 Suppi. 1: S11.

Intestinal introduction of antigens implicated in beta-cell autoimmunity via genetically-altered *Lactococcus lactis*, has been shown to arrest T1D in NOD mice via induction of Foxp3+ Treg cells. Oral administration of genetically-altered *Lactococcus lactis* targets human pro-insulin (PINS) along with human IL-10 to the gastrointestinal (GI) mucosa, and in combination with systemic low-dose anti-CD3 antibody, resets the immune system towards long-term tolerance in nearly 60% of new-onset diabetic NOD mice. See, e.g., Robert, S. et al., *Diabetes* 2014, 63: 2876-2887; and Takiishi, T. et al., *J. Clin. Inv.* 2012, 122(5): 1717-1725. However, clinical translation of such antigen-specific combination therapy involving additional immuno-modulators, such as anti-CD3 antibodies, is being hampered, e.g., because Fc-modified anti-human CD3 antibodies have not been approved by regulatory agencies for the treatment of T1D.

There is a need in the art for efficacious, targeted, and controlled methods for the treatment of T1D, without off-target activities and systemic toxicities. Such strategies should facilitate administration, increase safety, and ideally, improve efficacy and reduce therapeutically effective doses. The present disclosure addresses these needs.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

BRIEF SUMMARY

Accordingly, provided are compositions and methods involving live lactic acid fermenting bacteria (LAB), e.g., genetically modified *Lactococcus lactis* (LL) strains, as delivery vehicles for the mucosal delivery of low-dose IL-2, e.g., in combination with T1D-specific self-antigens, such as proinsulin (PINS). The LAB are genetically modified to express the bioactive polypeptides, which induce biological responses, which in turn, block further autoimmune destruction of pancreatic beta-cells. Such strategy can reverse established T1D, e.g., in subjects with sufficient residual beta-cell function, and thus represent a "true" treatment for auto-immune diabetes. The compositions may be administered orally, e.g., in the form of an enterically coated pharmaceutical formulation which transports the bacteria to the gastrointestinal tract, e.g., to the lower part of the gastrointestinal tract (e.g., distal parts of the colon), where they will secrete a suitable low-dose of IL-2, optionally in combination with a T1D-specific antigen (e.g., PINS).

The provided composition comprises a lactic acid fermenting bacterium (LAB) comprising an exogenous nucleic acid encoding an interleukin-2 (IL-2) polypeptide and an exogenous nucleic acid encoding a type-1 diabetes mellitus (T1D)-specific antigen potypeptide. Alternatively, the provided composition comprises a first LAB comprising an exogenous nucleic acid encoding an interleukin-2 (IL-2) polypeptide, and a second LAB comprising an exogenous nucleic acid encoding a type-1 diabetes mellitus (T1D)-specific antigen polypeptide. The composition may further comprise a pharmaceutically acceptable carrier. Said LAB may be adapted for mucosal delivery of low-dose IL-2 when administered to a mammalian subject.

In one aspect, said LAB may be selected from the group consisting of: a *Lactococcus* species, a *Lactobacillus* species, a *Bifidobacterium* species, a *Streptococcus* species, and an *Enterococcus* species. Said LAB may be a *Lactococcus* species. For example, said LAB may be *Lactococcus lactis*. Alternatively, said LAB may be selected from the group consisting of: *Lactocaccus garvieae, Lactococcus lactis, Lactococcus lactis* subsp. *cremoris, Lactococcus lactis* subsp. *hordniae, Lactococcus lactis* subsp. *Lactis, Lactococcus piscium, Lactococcus plantarum, Lactococcus raffinolactis, Lactobacillus acetotolerans, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarius, Lactobacillus aviarius* subsp. *araffinosus, Lactobacillus aviarius* subsp. *aviarius, Lactobacillus bavaricus, Lactobacillus bifermentans, Lactobacillus brevis, Lactobacillus buchneri, Lactobacillus bulgaricus, Lactobacillus carnis, Lactobacillus casei, Lactobacillus casei* subsp. *alactosus, Lactobacillus casei* subsp. *casei, Lactobacillus casei* subsp. *pseudoplantarum, Lactobacillus casei* subsp. *rhamnosus, Lactobacillus casei* subsp. *tolerans, Lactobacillus catenaformis, Lactobacillus cellobiosus, Lactobacillus collinoides, Lactobacillus confusus, Lactobacillus coryniformis, Lactobacillus coryniformis* subsp. *coryniformis, Lactobacillus coryniformis* subsp. *torquens, Lactobacillus crispatus, Lactobacillus curvatus, Lactobacillus curvatus* subsp. *curvatus, Lactobacillus curvatus* subsp. *melibiosus, Lactobacillus delbrueckii, Lactobacillus delbrueckii* subsp. *bulgaricus, Lactobacillus delbrueckii* subsp. *delbrueckii, Lactobacillus delbrueckii* subsp. *lactis, Lactobacillus divergens, Lactobacillus farciminis, Lactobacillus fermentum, Lactobacillus fornicalis, Lactobacillus fructivorans, Lactobacillus fructosus, Lactobacillus gallinarum, Lactobacillus gasseri, Lactobacillus graminis, Lactobacillus halotolerans, Lactobacillus hamsteri, Lactobacillus helveticus, Lactobacillus heteriochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefiranofaciens, Lactobacillus kefirgranum, Lactobacillus kunkeei, Lactobacillus lactis, Lactobacillus leichmannii, Lactobacillus lindneri, Lactobacillus malefermentans, Lactobacillus mali, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus paracasei* subsp. *paracasei, Lactobacillus paracasei* subsp. *tolerans, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus reuteri, Lactobacillus rhamnosus, Lactobacillus rimae, Lactobacillus rogosae, Lactobacillus ruminis, Lactobacillus sakei, Lactobacillus sakei* subsp. *camosus, Lactobacillus sakei* subsp. *sakei, Lactobacillus salivarius, Lactobacillus salivarius* subsp, *salicinius, Lactobacillus salivarius* subsp. *salivarius, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis, Lactobacillus yamanashiensis* subsp, *mali, Lactobacillus yamanashiensis* subsp. *Yamanashiensis, Lactobacillus zeae, Bifidobacterium adolescentis, Bifidobacterium angulatum, Bifidobacterium bifidum, Bifidobacterium breve, Bifidobacterium catenulatum, Bifidobacterium longum, Bifidobacterium infantis, Enterococcus alcedinis, Enterococcus aquimarinus, Enterococcus asini, Enterococcus avium, Enterococcus caccae, Enterococcus camelliae, Enterococcus canintestini, Enterococcus canis, Enterococcus casseliflavus, Enterococcus cecorum, Enterococcus columbae, Enterococcus devriesei, Enterococcus diestrammenae, Enterococcus dispar, Enterococcus durans, Enterococcus curekensis, Enterococcus faecalis, Enterococcus faecium, Enterococcus gallinarum, Enterococcus gilvus, Enterococcus haemoperoxidus, Enterococcus hermanniensis, Enterococcus hirae, Enterococcus italicus, Emerococcus lactis, Enterococcus lemanii, Enterococcus malodoratus, Enterococcus moraviensis, Enterococcus mundtii, Enterococcus olivae, Enterococcus pallens, Enterococcus phoeniculicola, Enterococcus plantarum, Enterococcus pseudoavium, Enterococcus quebecensis, Enterococcus raffinosus, Entcrococcus ratti, Enterococcus rivorum, Enterococcus rotai, Enterococcus saccharolyticus, Enterococcus silesiacus, Enterococcus solitarius, Enterococcus sulfureus, Enterococcus termitis, Enterococcus thailandicus, Enterococcus ureasiticus, Enterococcus ureilyticus, Enterococcus viikkiensis, Enterococcus villorum, Enterococcus xiangfangensis, Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus milleri, Streptococcus mitis, Streptococcus mutans, Streptococcus oralis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus viridans,* and *Streptococcus zooepidemicus.*

In another aspect, said T1D-specific antigen may be selected from the group consisting of: proinsulin (PINS), glutamic acid decarboxylase (GAD65), insulinoma-associated protein 2 (IA-2), islet-specific glucose-6-phosphatase catalytic subunit-related protein (IGRP), zinc transporter 8 (ZnT8), chromogranin A, (prepro) islet amyhold polypeptide (ppIAPP), peripherin, and citrullinated glucose-regulated protein (GRP). For example, said T1D-specific antigen may be PINS.

in another aspect, a LAB may comprise said exogenous nucleic acid encoding an IL-2 polypeptide and said exogenous nucleic acid encoding a T1D-specific antigen polypeptide. Alternatively, a first LAB may comprise said exogenous nucleic acid encoding an IL-2 polypeptide, and a second LAB may comprise said exogenous nucleic acid encoding a T1D-specific antigen polypeptide. Said exogenous nucleic acid encoding an IL-2 polypeptide may be integrated into the chromosome of said LAB. Said exogenous nucleic acid encoding a T1D-specific antigen polypeptide may be integrated into the chromosome of said LAB, or may be present on a plasmid contained in said LAB. Said exogenous nucleic acid encoding an IL-2 polypeptide and said exogenous nucleic acid encoding a T1D-specific antigen polypeptide may be both integrated into the chromosome of said LAB. Said exogenous nucleic acid encoding an IL-2 polypeptide and said exogenous nucleic acid encoding a T1D-specific antigen polypeptide may be part of a polycistronic expression unit, driven by the same promoter.

In yet another aspect, said IL-2 may be a membrane bound form of IL-2 or a soluble form of IL-2. Said exogenous nucleic acid encoding an IL-2 polypeptide may encode an IL-2 variant polypeptide. Said IL-2 variant polypeptide may have a diminished IL-2 activity or an enhanced IL-2 activity, when compared to a corresponding wild-type IL-2 polypeptide. Said IL-2 variant polypeptide may be selected from the group consisting of: aldesleukin, teceleukin, and bioleukin. For example, said IL-2 variant polypeptide comprises (a) a first amino acid substitution relative to mature, wild-type IL-2, selected from the group consisting of L72G, L72A, L72S, L72T, L72Q, L72E, L72N, L72D, L72R, and L72K; or (b) a second amino acid substitution relative to mature, wild-type IL-2, selected from the group consisting of F42A, F42G, F42S, F42T, F42Q, F42E, F42N, F42D, F42R, and F42K; or (c) a third amino acid substitution relative to mature, wild-type IL-2, selected from the group consisting of Y45A, Y45G, Y45S, Y45T, Y45Q, Y45E, Y45N, Y45D, Y45R, and Y45K; cr (d) a combination thereof.

The provided composition may comprise a *Lactococcus lactis*, wherein said *Lactococcus lactis* comprises an exogenous nucleic acid encoding an IL-2 polypeptide and an exogenous nucleic acid encoding PINS, and wherein said *Lactococcus lactis* is adapted for mucosal delivery of low-dose IL-2 when administered to a mammalian subject. Said low-dose IL-2 delivery may be the range of from about 0.01 M IU/day/subject to about 5.4 M IU/day/subject; from about 0.02 M IU/day/subject to about 3.0 M IU/day/subject; from about 0.1 M IU/day/subject to about 3.0 M IU/day/subject; or from about 0.2 M IU/day/subject to 2.0 M IU/day/subject.

Also provided is the use of the composition for the treatment of T1D in a mammalian subject in need thereof. The provided method of treating type 1 diabetes mellitus (T1D) comprising administering to a mammalian subject in need thereof a therapeutically effective amount of the composition.

In one aspect, no anti-CD3 antibody is administered to said subject in the method of treating T1D. Alternatively, the method of treating T1D further con orrises administering an anti-CD3 antibody to said subject. Said anti-CD3 antibody may be administered in a low-dose simultaneously with said composition to said subject. Said anti-CD3 antibody may be administered intravenously to said subject.

In another aspect, said subject may have residual beta-cell function. Said subject may have recent-onset T1D. Said subject may have a blood or urine C-peptide concentration indicative of residual beta-cell function. Said subject may be a human patient having a fasting blood C-peptide concentration of less than about 1 nmol/L, but at least about 0.2 nmol/L; or has a stimulated blood C-peptide concentration of less than about 4 nmol/L, but at least about 0.5 nmol/L. Said subject may have been diagnosed with T1D within the previous 12 months prior to administering said composition.

In a further aspect, said composition may be mucosally administered to said subject. Said composition may be administered to said subject in a liquid form. Said composition may be administered to said subject in the form of a food product, a dietary supplement, or a suppository product. Said composition may be administered in a unit dosage form comprising from about $1 \times 10^4$ to about $1 \times 10^{12}$; about $1 \times 10^6$ to about $1 \times 10^{12}$; or about $1 \times 10^9$ to about $1 \times 10^{12}$ colony-forming units (cfu). Said unit dosage form may be selected from the group consisting of: a capsule, a tablet, a granule, a suppository, and a metered aerosol dose. Said composition may be in a dry-powder form or a compressed version thereof.

Further provided is a genetically modified microorganism comprising an exogenous nucleic acid encoding an IL-2 polypeptide; and an exogenous nucleic acid encoding a T1D-specific antigen polypeptide. For example, said microorganism may be a LAB. Said exogenous nucleic acid encoding an interleukin-2 and/or T1D-specific antigen polypeptide may be stably integrated into the chromosome of the microorganism.

BRIEF DESCRIPTION OF THE DRAWINGS

FIG. 1 depicts a nucleotide sequence (SEQ ID NO: 46) encoding a fusion of usp45 secretion leader (SSusp45) and the hIL-2 gene, encoding human interlettkin-2 (hIL-2; UniProt: P60568, aa 21-153), downstream of the highly expressed phosphopyruvate hydratase gene (eno; Gene ID: 4797432; location: NC_009004.1 (606184 . . . 607485)) comprising an intergenic region preceding the highly expressed *L. lactis* MG1363 50S ribosomal protein L30 gene (rpmD; Gene ID: 4797873; location: NC_009004.1 (2316732 . . . 2316911, complement)) between eno and SSusp45.

FIG. 6 depicts a nucleotide sequence (SEQ ID NO: 57) encoding a fusion of usp45 secretion leader (SSusp45) with the pins gene, encoding human proinsulin (PINS; UniProt: P01308, aa 25-110), downstream of the highly expressed glyceraldehyde 3-phosphate dehydrogenase gene (gapB; Gene ID: 4797877; location: NC_009001.1 (2492509 . . . 2493519, complement)) comprising an intergenic region preceding the highly expressed *L. lactis* MG1363 50S ribosomal protein L30 gene (rpmD; Gene ID: 4797873; location: NC_009004.1 (2316732 . . . 2316911, complement), see, e.g., Steidler et al., *Nat. Biotechnol.* 2003; 21(7):785-789) between gapB and pins.

FIG. 14B: CFU/g, respectively) in different tissues of the GI tract at different timepoints after administration of a single dose ($10^{10}$ CFU) of LL-IL-2 to non-obese diabetic mice. All bars represent an average of 3 mice (n=3). SIP=proximal small intestine; SID=distal small intestine; CAE=caecum; COP=proximal colon; COD=distal colon.

FIG. 16 depicts a western blot showing the presence of full-length, plasmid derived PINS in LL-PINS culture supernatants.

DETAILED DESCRIPTION

Figure 2:
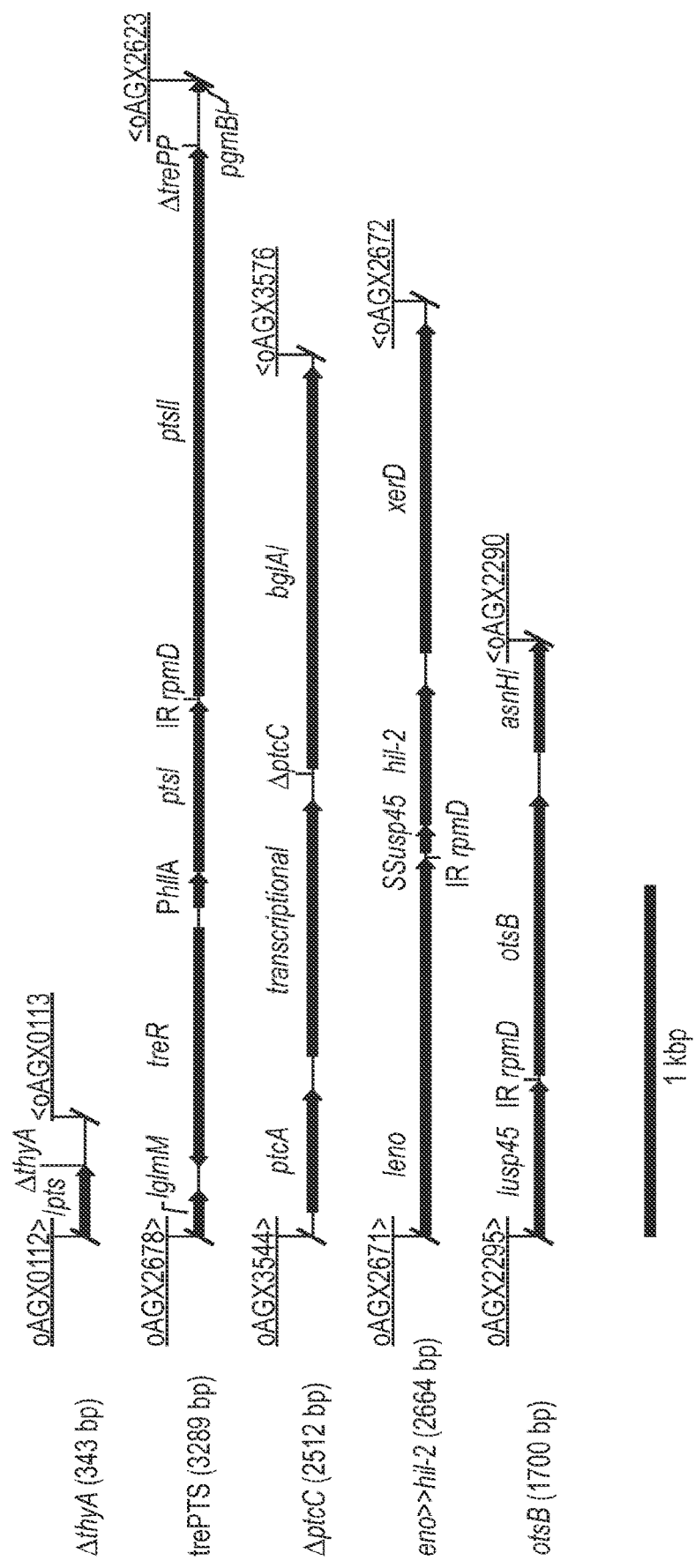
FIG. 2 depicts a schematic overview of genetic loci of LL-IL-2 (ΔthyA, trePTS (ΔtrePP), otsB, ΔptcC, and eno>>hIL-2) with intergenic regions, and PCR amplification product sizes (bp).
Figure 3:
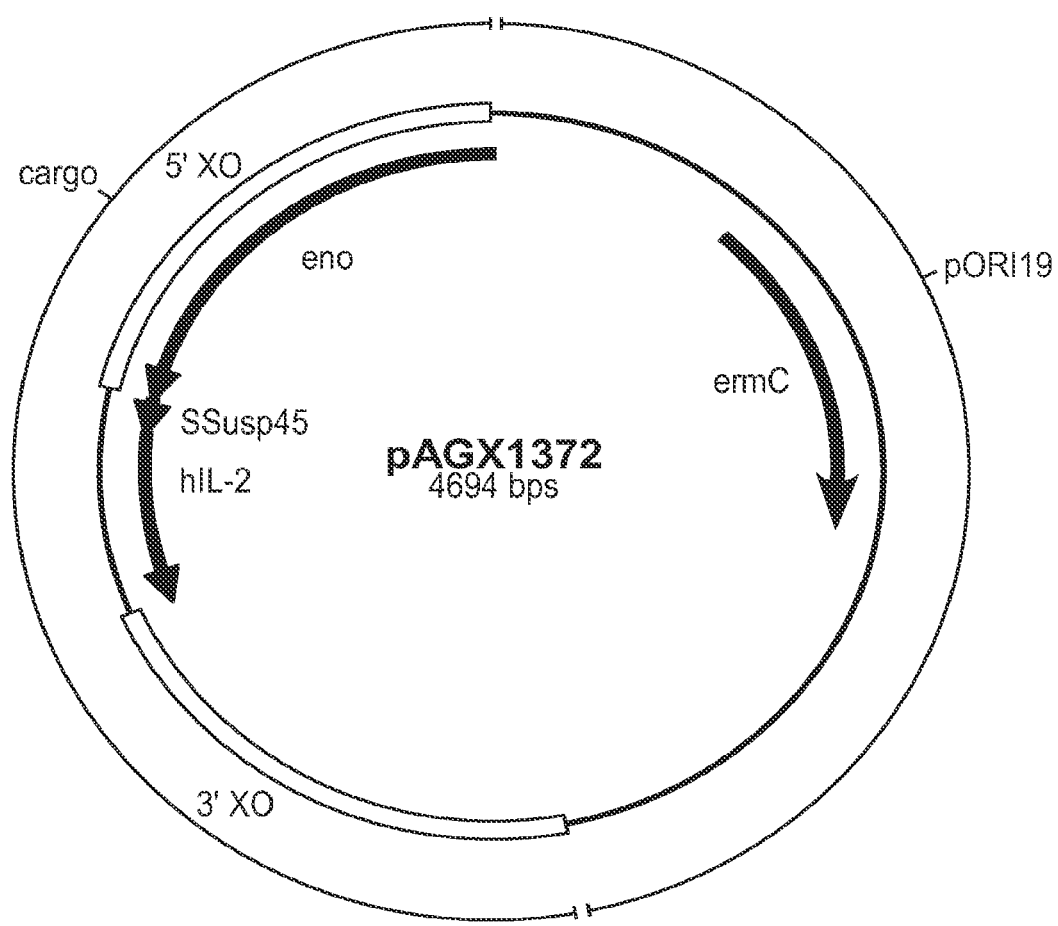
FIG. 3 depicts an exemplary carrier plasmid with a backbone that exists of a pORI19 fragment to which a PhllA>>β-glueurotidase (uidA: Gene ID: 946149) expression module was added; a cargo region comprising pins downstream of gapB coupled by the rpmD intergenic region, flanked by cross over (XO) areas, positioned 5' and 3' of eno>>hIl-2; as well as an erythromycin selection marker: erythromycin resistant 23S RNA methylase gene (ermC).

Abbreviations and Acronyms used in herein may include:
BD Becton Dickinson
BSA bovine serum albumin
CAE caecum
CDS coding sequence
CFU colony forming units
COD or DCO distal colon
COP or PCO proximal colon
DCO distal colon
EDTA ethylenediaminetetraacedic acid
ELISA enzyme-linked immunosorbent assay
FACS fluorescence-activated cell sorting
FCS fetal calf serum
FOS fructo-oligosaccharides
GAD65 glutamic acid decarboxylase
GRP citrullinated glucose-regulated protein
GUS glucuronidase
HRP horseradish peroxidase
IA-2 insulinoma-associated protein 2
IAA insulin auto-antibodies
IC insulin content determination
IGRP islet-specific glucose-6-phosphatase catalytic subunit-related protein
IL-2 interieukin-2
INS insulin
IU international unit
LAB lactic acid fermenting bacterium/bacteria
LL *Lactococcus lactis*
LLOQ limit of quantification
MCT oil medium chain triglycerides
MLN mesenteric lymph nodes
MMTT mixed meal tolerance test
MTT 3-(4,5-Dimethyltinazol-2-yl)-2,5-Diphenyltetrazolium Bromide
MWM molecular weight marker
NCBI National Center for Biotechnology Information
NIBSC National Institute for Biological Standards and Control
NK cells natural killer cells
NOD mice non-obese diabetic mice
PBS phosphate-buffered saline
PCR polymerase chain reaction
PFA paraformaldehyde
PINS proinsulin
PLN pancreatic draining lymph nodes
ppIAPP (prepro) islet amyloid polypeptide
PTPRN protein tyrosine phosphatase, receptor type N
PTS phosphotransferase system
RIA Radioimmunoassay (RIA)
SID/DSI distal small intestine
SIP/PSI proximal small intestine
SPL spleen
T1D type-1 diabetes mellitus
TSLP Thymic stromal lymphopoietin (TSLP)
WHO World Health Organization
XO cross over
ZnT8 zinc transporter 8

Currently provided are compositions and methods for the treatment of T1D, for the induction of Tregs and/or for restoring tolerance to T1D-specific antigens (i.e., self-antigens) in a subject.

Provided herein are compositions comprising (1) a LAB comprising an interleukin-2 (IL-2) gene and a T1D-specific antigen gene, or (2) a first LAB comprising an interleukin-2 (IL-2) gene, and a second LAB comprising a T1D-specific antigen. In some examples, the LAB expresses the IL-2 gene and/or the T1D-specific antigen gene to produce IL-2 and T1D-specific antigen (e.g., PINS). In some embodiments, the compositions are pharmaceutical compositions comprising the LAB and a pharmaceutically acceptable carrier. Exemplary carriers are described herein, in some examples, the pharmaceutical composition is adapted for mucosal delivery of the composition to the subject.

Methods are provided for the treatment of T1D in a mammalian subject in need thereof. The methods include administering (e.g., via a mucosal route) to the subject a composition according to the present disclosure. Exemplary methods include: administering to the subject a therapeutically effective amount of the LAB capable of expressing IL-2 and a T1D-specific antigen (e.g., PINS).

Unexpectedly, it is discovered that subjects with significant residual beta-cell function respond particularly well to the therapeutic methods described herein. Thus, in some embodiments, the mammalian subject in the herein described methods, has recently been diagnosed with T1D andlor has recent-onset T1D. In some examples, the subject may have been diagnosed with T1D within the previous 12 months, the previous 24 months, or the previous 36 months prior to administering the composition comprising the LAB described herein.

In some examples in the herein described methods, the IL-2 and antigen polypeptides are delivered to the mucosa. This approach may result in delivering low-dose IL-2 concentrations that are even lower than those required for low-dose systemic administration. Off-target toxicities associated with systemic delivery of IL-2 may thus be avoided.

Definitions

As used herein, the singular forms and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds for such treatment or preparation unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding any other component in more than trace elements of other ingredients and substantial method steps for administering the compositions described herein. Embodiments defined by each of these transition terms are within the scope of present disclosure.

As used herein, the term "expressing" a gene or polypeptide or "producing" a polypeptide (e.g., an IL-2 polypeptide or T1D-specific antigen polypeptide) is meant to include "capable of expressing" and "capable of producing," respectively. For example, a microorganism, which contains an exogenous nucleic acid can under sufficient conditions (e.g., sufficient hydration and/or in the presence of nutrients) produce a polypeptide encoded by the exogenous nucleic acid). However, the microorganism may not always actively produce the encoded polypeptide. The LAB (e.g., *Lactococcus lactis*) may be dried (e.g., freeze-dried), and in that state can be considered dormant (i.e., is not actively producing polypeptide). However, once the LAB is subjected to sufficient conditions, e.g., is administered to a subject and is released (e.g., into the gastro-intestinal tract of a subject) it may begin producing polypeptide. Thus, a LAB "expressing" a gene or polypeptide or "producing" a polypeptide of the current disclosure includes the LAB in its "dormant" state.

The term "about" in relation to a reference numerical value, and its grammatical equivalents as used herein, can include the reference numerical value itself and a range of values plus or minus 10% from that reference numerical value. For example, the term "about 10" includes 10 and any amounts from and including 9 to 11. In some cases, the term "about" in relation to a reference numerical value can also include a range of values plus or minus 10%, 9%, 8%, 7%, 6%, 5%, 4%, 3%, 2%, or 1% from that reference numerical value.

An "IL-2 gene" refers to an interleukin 2 gene encoding an "IL-2 polypeptide." The term "IL-2 gene" includes "IL-2 variant genes" encoding "IL-2 variant polypeptides."

The term "IL-2" or "IL-2 polypeptide" refers to a functional, e.g., full-length, interleukin 2 polypeptide (e.g., human IL-2 polypeptide), including membrane-bound forms and soluble forms, as well as "IL-2 variant polypeptides."

An "IL-2 variant" or "IL-2 variant polypeptide" refers to a modified (e.g., truncated or mutated), but functional IL-2 polypeptide, e.g., a truncated or mutated version of human IL-2. The term "IL-2 variant polypeptide" includes IL-2 polypeptides with enhanced activity or diminished activity when compared to a corresponding wild-type IL-2 polypeptide. An "IL-2 variant polypeptide" retains at least some IL-2 activity.

T1D-Specific Antigen

The terms "T1D-specific self-antigen," "T1D-specific antigen," "disease-specific antigen," "self-antigen," "auto-antigen," or "antigen" are used interchangeably herein. The terms are used herein in accordance with the art recognized meaning of self-antigen or auto-antigen, and generally refer to a polypeptide/protein originating from within a subjects own body (produced by the subject's own body), wherein the antigen is recognized by the subject's own immune system, and typically produces antibodies against such antigen. Autoimmune diseases are generally associated with certain disease-specific self-antigens. In T1D a subject's immune system may produce antibodies against at least one antigen associated with the beta-cell destruction process. Such self-antigens include proinsulin (PINS), glutamic acid decarboxylase (GAD65), insulinoma-associated protein 2 (IA-2), islet-specific glucose-6-phosphatase catalytic subunit-related protein (IGRP) and zinc transporter (ZnT) 8. Clinical T1D may further be associated with additional candidate target molecules expressed by beta-cells such as chromogranin A, (prepro) islet amyloid polypeptide (ppI-APP), peripherin and citruilinated glucose-regulated protein (GRP).

The term "T1D-specific antigen gene" refers to a gene encoding the above "T1D-specific antigen." The term "T1D-specific antigen gene" includes "T1D-specific antigen variant genes" encoding "T1D-specific antigen variant polypeptides."

The term "T1D-specific antigen polypeptide" refers to a functional, e.g., full-length, polypeptide, as well as "T1D-specific antigen variant polypeptides," which may have enhanced activity or diminished activity when compared to a corresponding wild-type polypeptide.

The term "T1D-specifie antigen variant" or "T1D-specific antigen variant polypeptide" refers to a modified (e.g., truncated or mutated), but functional polypeptide, e.g., a truncated or mutated version of human PINS. The term "variant polypeptide" includes polypeptides with enhanced activity or diminished activity when compared to a corresponding wild-type polypeptide. A "variant polypeptide" retains at least some biological activity (functional polypeptide). Exemplary variants of GAD65 and IA-2 include trimmed versions thereof (e.g., $GAD65_{370-575}$, and $IA-2_{635-979}$, respectively; relative to NCBI accession numbers NP_000809.1 (SEQ ID NO: 7) and NP_002837.1 (SEQ ID NO: 9, respectively) retaining antigenic properties, and are thus useful in the compositions and methods of the current disclosure, e.g., in stimulating Tregs and inducing tolerance in a subject. Generally, trimmed or truncated versions of a T1D-specific antigen are efficiently expressed and secreted by the LAB (e.g., *Lactococcus lactis*).

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Subject

A "subject" is an organism, which may benefit from being administered a composition of the present disclosure, e.g., according to methods of the present disclosure. The subject may be a mammal ("mammalian subject"). Exemplary mammalian subjects include humans, farm animals (such as cows, pigs, horses, sheep, goats), pets (such as a dogs, cats, and rabbits), and other animals, such as mice, rats, and primates. In some examples, the mammalian subject is a human patient.

Low-Dose IL-2

The term "low-dose IL-2" refers to a dose or a concentration of IL-2 polypeptide which can promote competence and stability of regulatory T (Treg) cell populations and/or promotes the development of naïve CD4+ T cells into Treg cells in the respective subject, but is below a threshold dose/concentration, which stimulates the differentiation of naïve T cells into effector T cells and/or memory T cells in a subject. It has been shown that Treg cells have a 10-20 fold lower activation threshold for IL-2 than effector T cells, e.g., when measured in terms of STAT5 (pSTAT5). Downstream of pSTAT5, the activation of numerous genes important for cell function require IL-2 doses that are 100-times lower for Treg cells than for effector T-cells (see, e.g., Yu, et al., *Diabetes* 2015, 64: 2172-2183). However, in connection with known treatment regimens in humans, a minimum dose of IL-2 necessary to stimulate Treg cells has not been established.

In some embodiments, in the context of human treatment, low-dose IL-2 typically refers to a dose of IL-2 polypeptide or IL-2 variant polypeptide that can be in the range of from about 0.01 M IU/day/subject to about 5.4 M IU/day/subject. The low dose can be in the range of from about 0.01 M IU/day/subject to about 3.0 M IU/day/subject. The low dose can be in the range of from about 0.02 M IU/day/subject to about 3 M IU/day/subject, from about 0.03 M IU/day/subject to about 3 M IU/day/subject, from about 0.04 M IU/day/subject to about 3 M IU/day/subject, from about 0.05 M IU/day/subject to about 3 M IU/day/subject, from about 0.06 M IU/day/subject to about 3 M IU/day/subject, from about 0.07 M IU/day/subject to about 3 M IU/day/subject, from about 0.08 M IU/day/subject to about 3 M IU/day/subject, from about 0.09 M IU/day/subject to about 3 M IU/day/subject, from about 0.1 M IU/day/subject to about 3 M IU/day/subject, from about 0.2 M IU/day/subject to about 3 M IU/day/subject, from about 0.3 M IU/day/subject to about 3 M IU/day/subject, from about 0.4 M IU/day/subject to about 3 M IU/day/subject, from about 0.5 M IU/day/subject to about 3 M IU/day/subject, from about 0.6 M IU/day/subject to about 3 M IU/day/subject, from about 0.7 M IU/day/subject to about 3 M IU/day/subject, from about 0.8 M IU/day/subject to about 3 M IU/day/subject, from about 0.9 M IU/day/subject to about 3 M IU/day/subject, or from about 1.0 M IU/day/subject to about 3 M IU/day/subject. The low dose can be in the range of from about 0.02 M IU/day/subject to about 2.5 M IU/day/subject. The low dose also can be in the range of from about 0.05 M IU/day/subject to about 2.0 M IU/day/subject. The low dose can be in the range of from about 0.1 M IU/day/subject to about 1.5 M IU/day/subject. In still other embodiments, the low dose can be in the range of from about 0.3 M IU/day/subject to about 1.0 M IU/day/subject. The low dose can be in the range of from 0.5 M IU/day/subject to about 1.0 M IU/day/subject.

The term "international unit" (IU) is used herein in accordance with its art-recognized meaning and represents an amount of a substance (e.g., polypeptide). The mass or volume that constitutes one international unit varies based on which substance is being measured. The World Health Organization (WHO) provides unit characterizations for bioactive polypeptides. For example, 1 IU of human IL-2 is equivalent to about 73 pg of bioactive polypeptide (WHO International Standard; NIBSC 86/500), Low-Dose Anti-CD3

The term "low-dose anti-CD3" refers to a cumulative dose or a concentration of anti-CD3 antibody which is below a standard dose of anti-CD3 antibody, or a regulatory approved dose of anti-CD3 antibody in humans to treat disease such as T1D or cancer. For example, in humans, a low-dose anti-CD3 treatment can comprise a dose of less than 50 mg (cumulative) of anti-CD3 antibody in a human. For example, a low-dose anti-CD3 can comprise about 1 mg to about 50 mg; about 5 mg to about 40 mg; about 10 mg to about 30 mg; about 15 mg to about 25 mg; about 20 mg to about 30 mg; about 15 mg to about 20 mg; or about 30 mg to about 35 mg of cumulative anti-CD antibody treatment. A lose-dose anti-CD3 can comprise less than about 50 mg; about 45 mg; about 40 mg; about 35 mg; about 30 mg; about 25 mg; about 20 mg; about 15 mg; about 10 mg; or about 5 mg of cumulative anti-CD antibody treatment.

For example, in some cases, the cumulative dosage of anti-CD3 antibody dosed in in humans can be about 34 mg or about 17 mg, given over a specific time periods, e.g., in a 14 day period. This means that about 2.43 mg or 1.21 mg of anti-CD3 antibody is given over the course of the 14 day period.

A low-dose anti-CD3 treatment can also comprise a dose of about 80%; about 70%; about 60%; about 50%; about 40%; about 30%; about 20%; about 10%; about 5%; about 2%; about 1%; from about 80% to about 70%; from about 70% to 60%; from about 60% to 50%; from about 50% to 25%; from about 40% to 15%; or from about 30% to 5% of a regulatory approved dose of anti-CD3 antibody to treat T1D or cancer.

In other mammals such as mice, the low-dose anti-CD3 can refer to a dosage less than about 5 µg; 2.5 µg; or 1 µg. For example, about 5 µg can be used for the treatment in a mouse. In some instances, about 2.5 µg can be used for the treatment in a mouse. In other cases, 1 µg can be used for the treatment in a mouse. Total dosage for mice can be 12.5 µg or 6 µg of anti-CD3.

Anti-CD3 can be given at least once a day to up to 5 times a day. For example, once a day, 2 times a day, or 3 times a day, as long as the long as the cumulative dosage is met. For example, if the dose to be given is 2.43 mg/day, and dosing occurs twice a day, then 1.215 mg per dose can be given.

To achieve a low dose anti-CD3 regime, dosages can be given at least once a day continuously for at least 3 days; 4 days; 5 days; 6 days; 7 days; 8 days; 9 days; 10 days; 11 days; 12 days; 13 days; 14 days; 15 days; 16 days; 17 days; 18 days; 19 days; 20 days; 30 days; or 40 days as long as the long as the cumulative dosage is met. For example, if a 34 mg anti-CD3 dosage regime is given (a low-dose anti-CD3) for 14 days, approximately 2.43 mg/day can be given to the subject. In some cases, the low-dose anti-CD can be given at least once a day continuously for at least 1 month, 2 months, 3 months, 6 months, 1 year, or more.

Low-dose anti-CD3 can be given intravenously simultaneously with the administration of the composition described herein. Optionally, low-dose anti-CD3 can be given 1 day; 2 days; 3 days; 4 days; 5 days; 6 days; 7 days; 2 weeks; 3 weeks; or 1 month after the first administration of the composition described herein. Additionally, in some instances, low-dose anti-CD3 can be given 1 day; 2 days; 3 days; 4 days; 5 days; 6 days; 7 days; 2 weeks; 3 weeks; or 1 month before the first administration of the composition described herein.

In some cases, the standard dose of anti-CD3 antibody, or a regulatory approved dose of anti-CD3 antibody in humans to treat disease such as T1D and cancer, can be given to the patients before or after the administration of the compositions described herein.

In certain embodiments, anti-CD3 antibody can be teplizumab.

Patient Sub-Populations

The subject being treated using the methods described herein can have significant (e.g., measurable) residual beta-cell function. Under such circumstances, the subject may maintain disease remission, even after treatment is interrupted or stopped altogether. Newly diagnosed patients often have a certain minimal number of pancreatic islet beta-cells (beta-cells) remaining at the time of diagnosis, so that such patients are able to produce a certain minimal amount of endogenous insulin. Such patient population can benefit particularly well when treated with the compositions and methods of the current disclosure (e.g., low-dose IL-2 and PINS therapy). The treatments described herein can prevent further destruction of beta-cells and may thus induce disease remission. It was found that initial beta-cell mass may affect the efficacy of treatment. For example, in 57% of recent-onset NOD mice treated with the compositions of the current disclosure, and having a blood glucose concentration of about 350 mg/dL or less at treatment initiation, diabetes could be reversed. Reversal of disease was accomplished in only 22% of mice having an initial glucose concentration of more than 350 mg/dL. Further, in recent-onset mice, reversal of disease remained stable after treatment was stopped, indicating that the methods of the current disclosure (involving mucosal delivery of the bioactive polypeptides) can effectively correct hyperglycemia and restore long-term tolerance to beta-cells. However, once a subject's beta-cells are destroyed, such subject may no longer benefit from the described treatment in the same manner.

Treating

The terms "treatment", "treating", and the like, as used herein means ameliorating or alleviating characteristic symptoms or manifestations of a disease or condition, e.g., T1D. For example, treatment of T1D can result in the restoration or induction of antigen-specific immune tolerance in the subject. In other examples, treatment means arresting auto-immune diabetes, or reversing autoimmune diabetes. For example, treatment may result in the maintenance of remaining beta-cell mass. In other examples, treatment of T1D involves increasing the frequency or activation of Treg cells. In other examples, treatment may expand antigen-specific Treg cells (e.g., in the thymus), and/or induces migration of Treg cells into peripheral blood. In yet other examples, treatment involves improving at least one of a subject's (a human patients) clinical marker. For example, treatment may raise blood and/or urine C-peptide levels. In other examples, treatment may lower the subject's (e.g., a human patient's) blood glucose levels (e.g., in response to food ingestion or fasting glucose levels); reduce the amount of injected insulin required to maintain appropriate blood glucose levels in the subject, reduce diabetes-related auto-antibody levels in a subject, and/or increase/preserve C-peptide levels (e.g., following an oral glucose tolerance test). Treatment can mean continuous/chronic treatment, or treatment, in which the subject is free of clinical symptoms of the disease or condition for a significant amount of time (e.g., at least 6 months, at least 1 year, at least 2 years, at least 3 years, at least 4 years, or at least 5 years), after the treatment is stopped.

As used herein, these terms also encompass, preventing or delaying the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition described herein to a patient that is not at the time of administration afflicted with the disease or condition. "Preventing" also encompasses preventing the recurrence or relapse-prevention of a disease or condition or of symptoms associated therewith, for instance after a period of improvement.

Therapeutically Effective Amount

As used herein, the term "therapeutically effective amount" refers to an amount of a non-pathogenic microorganism or a composition of the present disclosure that will elicit a desired therapeutic effect or response when administered according to the desired treatment regimen. The compounds or compositions are typically provided in a unit dosage form, for example a tablet or capsule, which contains an amount of the active component equivalent with the therapeutically effective amount when administered once, or multiple times per day.

A person of ordinary skill in the art will appreciate that a therapeutically effective amount of a recombinant microorganism, which is required to achieve a desired therapeutic effect (e.g., for the effective treatment of T1D), will vary, e.g., depending on the nature of the IL-2 polypeptide expressed by the microorganism, the nature of the antigen polypeptide expressed by the LAB, the route of administration, and the age, weight, and other characteristics of the recipient.

Recent-Onset T1D

In some embodiments, the subject has recent-onset T1D. The term "recent-onset T1D," new-onset T1D," or "recent-onset disease" refers to a subject's (e.g., a human patient's) condition, which has recently been diagnosed with T1D (e.g., within about 3 months, within about six months, within about 9 months, within about 12 months, within about 15 months, within about 18 months, within about 24 months, within about 30 months, within about 36 months, within about 42 months, within about 48 months, within about 54 months, or within about 60 months).

In humans, the decline of beta-cell function, which occurs prior to and after the diagnosis of T1D, can be measured using diagnostic marker compounds. For example, C-peptide is produced in equal amounts to insulin (during enzymatic cleavage of pro-insulin) and can therefore be used as a measure of endogenous insulin secretion (including in patients being treated with insulin). C-peptide has been used in the clinical management of patients with diabetes, and assay systems for measuring C-peptide are known to those of skill in the art. See, e.g., Jones A. G. and Hattersley A. T., *Diabetic Medicine* 2013, 30: 803-817; Little R R et al., *Clin. Chem.* 2008, 54: 1023-1026; Wiedmeyer et al., *Clin. Chem.* 2007, 53: 784-787.

C-peptide values can be measured in nmol/L (wherein 1 nmol/L is 1000 pmol/L, and is equivalent to about 3 ng/mL). C-peptide can be measured in the blood or the urine of a subject. Blood C-peptide levels can be determined in non-fasting subjects (random C-peptide), in fasting subjects (fasting C-peptide), or in subjects stimulated with a dietary stimulator, such as a mixed liquid meal, or glucagon (stimulated C-peptide). C-peptide in the urine can be measured as the total amount of C-peptide secreted by the subject over a period of 24 hours. Often, C-peptide contained in the urine is measured as a ratio between C-peptide and creatinine.

In some embodiments, a subject (e.g., human) prior to administering the composition of the present disclosure (e.g., a subject with recent-onset T1D) has a fasting blood C-peptide concentration of less than about 1 nmol/L, but at least about 0.5 nmol/L, at least about 0.4 nmol/L, at least about 0.3 nmol/L, or at least about 0.2 nmol/L. In other embodiments, a subject (e.g., human) has a stimulated blood C-peptide concentration of less than about 4 nmol/L, but at least about 1 nmol/L, at least about 0.9 nmol/L, at least about 0.8 nmol/L, at least about 0.7 nmol/L, at least about 0.6 nmol/L, or at least about 0.5 nmol/L. In yet other embodiments, a subject (e.g., human) with recent-onset T1D has a post-meal urine C-peptide:creatinine ratio (nmol/mmol) of less than about 4, but at least about 1, at least about 0.9, at least about 0.8, at least about 0.7, at least about 0.6, at least about 0.5, at least about 0.4, or at least about 0.3.

In other embodiments, a recent onset T1D subject (e.g., human patient) can be identified by measuring insulin auto-antibodies (IAA) in the serum or blood of the subject. In some examples, the subjects tests positive for IAA. Serum IAA concentration may also be used to measure disease progression or treatment progress. Methods for measuring insulin auto-antibodies have been described. See, e.g., Demeester et al., *Diabetes Care* 2015, 38(4): 644-651.

Mucosa

The term "mucosa" or "mucous membrane" is used herein in accordance with its art recognized meaning. The "mucosa" can be any mucosa found in the body, such as oral mucosa, rectal mucosa, gastric mucosa, intestinal mucosa, urethral mucosa, vaginal mucosa, ocular mucosa, buccal mucosa, bronchial or pulmonary mucosa, and nasal or olfactory mucosa.

The term "mucosal delivery" as used herein is used in accordance with its art recognized meaning, i.e., delivery to the mucosa, e.g., via contacting a composition of the present disclosure with a mucosa. Oral mucosal delivery includes buccal, sublingual and gingival routes of delivery. Accordingly, in some embodiments, "mucosal delivery" includes gastric delivery, intestinal delivery, rectal delivery, buccal delivery, pulmonary delivery, ocular delivery, nasal delivery, vaginal delivery and oral delivery.

The term "mucosal tolerance" refers to the inhibition of specific immune responsiveness to an antigen in a mammalian subject (e.g., a human patient), after the subject has been exposed to the antigen via the mucosal route. Typically, said mucosal tolerance is systemic tolerance. Low dose oral tolerance is oral tolerance induced by low doses of antigens, and is characterized by active immune suppression, mediated by cyclophosphamide sensitive regulatory T-cells that can transfer tolerance to naïve hosts. High dose oral tolerance is oral tolerance induced by high doses of antigens, is insensitive to cyclophosphamide treatment, and proceeds to induction of T cell hyporesponsiveness via anergy and/or deletion of antigen specific T-cells. The difference in sensitivity to cyclophosphamide can be used to make a distinction between low dose and high dose tolerance. Strobel et al., *Immunology* 1983, 49:451-456. An exemplary oral tolerance is low dose oral tolerance as described in Mayer and Shao, *Nature Rev. Immunol.* 2004, 4:407-419.

Immune-Modulating Compound

In some embodiments, the present disclosure provides methods for the treatment of T1D, in which the subject is not concomitantly treated with an additional immune-modulating compound (i.e., in addition to IL-2). Thus the subject is treated with the T1D-specific antigen and the IL-2 alone.

In some embodiments, the present disclosure provides methods for the treatment of T1D, in which the subject is concomitantly treated with an additional immune-modulating compound. Thus the subject is treated with the T1D-specific antigen, the IL-2, and the additional immune-modulating compound.

The terms "immuno-modulating compound" or immuno-modulator" are used herein in accordance with their art-recognized meaning. The immuno-modulating compound can be any immune-modulating compound known to a person skilled in the art. A skilled person in the art may opt to include or not include an immune-modulating compound in the treatment described herein. The decision to include an immune-modulating compound in a treatment regimen can be determined by the performance of the treatment described herein, a subject's genetic traits, and/or physiological conditions, among other factors.

In some embodiments, the inirmino-modulating compound is a tolerance inducing compound. Tolerance induction can be obtained, e.g., by inducing regulatory T-cells, or in an indirect way, e.g., by activation of immature dendritic cells to make tolerant dendritic cells and/or inhibiting Th2 immune response inducing expression of "co-stimulation" factors on mature dendritic cells. Immune-modulating and immuno-suppressing compounds are known to the person skilled in the art and include, but are not limited to, bacterial metabolites such as spergualin, fungal and streptomycal metabolites such as tacrolimus or cyclosporin, immuno-suppressing cytokines such as IL-4, IL-10, IFNα, TGFβ (as selective adjuvant for regulatory T-cells) Flt3L, TSLP and Rank-L (as selective tolerogenic DC inducers), antibodies and/or antagonist such as anti-CD40L, anti-CD25, anti-CD20, anti-IgE, anti-CD3, and proteins, peptides or fusion proteins such as the CTL-41 g or CTLA-4 agonist fusion protein. In some embodiments, the immune-modulating compound is an immuno-suppressing compound. The immune-suppressing compound can be an immuno-suppressing cytokine or antibody. In other embodiments, the immune-suppressing cytokine is a tolerance-enhancing cytokine or antibody. It will be appreciated by the person skilled in the art that the term "immuno-modulating compound" also includes functional homologues thereof. A functional homologue is a molecule having essentially the same or similar function for the intended purposes, but can differ structurally. In some examples, the immuno-modulating compound is anti-CD3, or a functional homologue thereof.

LAB

The present disclosure relates to the use of genetically modified lactic acid fermenting bacteria (LAB). The LAB strain can be a *Lactococcus* species, a *Lactobacillus* species, a *Bifidobacterium* species, a *Streptococcus* species, or an *Enterococcus* species.

As used herein, *Lactococcus* or *Lactobacillus* is not limited to a particular species or subspecies, but meant to include any of the *Lactococcus* or *Lactobacillus* species or subspecies. Exemplary *Lactococcus* species include *Lactococcus garvieae*, *Lactococcus lactis*, *Lactococcus piscium*, *Lactococcus plantarum*, and *Lactococcus raffinolactis*. In some examples, the *Lactococcus lactis* is *Lactococcus lactis* subsp. *cremoris*, *Lactococcus lactis* subsp. *hordniae*, or *Lactococcus lactis* subsp. *lactis*.

Exemplary *Lactobacillus* species include *Lactobacillus acetotolerans*, *Lactobacillus acidophilus*, *Lactobacillus agilis*, *Lactobacillus algidus*, *Lactobacillus alimentarius*, *Lactobacillus amylolyticus*, *Lactobacillus amylophilus*, *Lactobacillus amylovorus*, *Lactobacillus animalis*, *Lactobacillus aviarius*, *Lactobacillus aviarius* subsp. *araffinosus*, *Lactobacillus aviarius* subsp. *aviarius*, *Lactobacillus bavaricus*, *Lactobacillus bifermentans*, *Lactobacillus brevis*, *Lactobacillus buchneri*, *Lactobacillus bulgaricus*, *Lactobacillus carnis*, *Lactobacillus casei*, *Lactobacillus casei* subsp. *alactosus*, *Lactobacillus casei* subsp. *casei*, *Lactobacillus casei* subsp. *pseudoplantarum*, *Lactobacillus casei* subsp. *rhamnosus*, *Lactobacillus casei* subsp. *tolerans*, *Lactobacillus catenaformis*, *Lactobacillus cellobiosus*, *Lactobacillus collinoides*, *Lactobacillus confusus*, *Lactobacillus coryniformis*, *Lactobacillus coryniformis* subsp. *coryniformis*, *Lactobacillus coryniformis* subsp. *torquens*, *Lactobacillus crispatus*, *Lactobacillus curvatus*, *Lactobacillus curvatus* subsp. *curvatus*, *Lactobacillus curvatus* subsp. *melibiosus*, *Lactobacillus delbrueckii*, *Lactobacillus delbrucckii* subsp. *bulgaricus*, *Lactobacillus delbrueckii* subsp. *delbrueckii*, *Lactobacillus delbrueckii* subsp. *lactis*, *Lactobacillus divergens*, *Lactobacillus farciminis*, *Lactobacillus fermentum*, *Lactobacillus fornicalis*, *Lactobacillus fructivorans*, *Lactobacillus fructosus*, *Lactobacillus gallinarum*, *Lactobacillus gasseri*, *Lactobacillus graminis*, *Lactobacillus halotolerans*, *Lactobacillus hamsteri*, *Lactobacillus helveticus*, *Lactobacillus heterohiochii*, *Lactobacillus hilgardii*, *Lactobacillus homohiochii*, *Lactobacillus iners*, *Lactobacillus intestinalis*, *Lactobacillus jensenii*, *Lactobacillus johnsonii*, *Lactobacillus kandleri*, *Lactobacillus kefiri*, *Lactobacillus kefiranofaciens*, *Lactobacillus kefirgranum*, *Lactobacillus kunkeei*, *Lactobacillus lactis*, *Lactobacillus leichmannii*, *Lactobacillus lindneri*, *Lactobacillus malefermentans*, *Lactobacillus mali*, *Lactobacillus maltaromicus*, *Lactobacillus manihotivorans*, *Lactobacillus minor*, *Lactobacillus minutus*, *Lactobacillus mucosae*, *Lactobacillus murinus*, *Lactobacillus nagelii*, *Lactobacillus oris*, *Lactobacillus panis*, *Lactobacillus parabuchneri*, *Lactobacillus paracasei*, *Lactobacillus paracasei* subsp. *paracasei*, *Lactobacillus paracasei* subsp. *tolerans*, *Lactobacillus parakefiri*, *Lactobacillus paralimentarius*, *Lactobacillus paraplantarum*, *Lactobacillus pentosus*, *Lactobacillus perolens*, *Lactobacillus piscicola*, *Lactobacillus plantarum*, *Lactobacillus pontis*, *Lactobacillus reuteri*, *Lactobacillus rhamnosus*, *Lactobacillus rimae*, *Lactobacillus rogosae*, *Lactobacillus ruminis*, *Lactobacillus sakei*, *Lactobacillus sakei* subsp. *camosus*, *Lactobacillus sakei* subsp. *sakei*, *Lactobacillus salivarius*, *Lactobacillus salivarius* subsp. *salicinius*, *Lactobacillus salivarius* subsp. *salivarius*, *Lactobacillus sanfranciscensis*, *Lactobacillus sharpeae*, *Lactobacillus suebicus*, *Lactobacillus trichodes*, *Lactobacillus uli*, *Lactobacillus vaccinostercus*, *Lactobacillus vaginalis*, *Lactobacillus viridescens*, *Lactobacillus vitulinus*, *Lactobacillus xylosus*, *Lactobacillus yamanashiensis*, *Lactobacillus yamanasiensis* subsp. *mali*, *Lactobacillus yamanashiensis* subsp. *Yamanashiensis*, *Lactobacillus zeae*, *Bifidobacterium adolescentis*, *Bifidobacterium angulatum*, *Bifidobacterium bifidum*, *Bifidobacterium breve*, *Bifidobacterium catenulatum*, *Bifidobacterium longum*, and *Bifidobacterium infantis*. In some examples, the LAB is *Lactococcus lactis* (LL).

In further examples, the bacterium is selected from the group consisting of *Enterococcus alcedinis*, *Enterococcus aquimarinus*, *Enterococcus asini*, *Enterococcus avium*, *Enterococcus caccae*, *Enterococcus camelliae*, *Enterococcus canintestini*, *Enterococcus canis*, *Enterococcus casseliflavus*, *Enterococcus cecorum*, *Enterococcus columbae*, *Enterococcus devriesei*, *Enterococcus diestrammenae*, *Enterococcus dispar*, *Enterococcus durans*, *Enterococcus eurekensis*, *Enterococcus faecalis*, *Enterococcus faecium*, *Enterococcus gallinarum*, *Enterococcus gilvus*, *Enterococcus haemoperoxidus*, *Enterococcus hermanniensis*, *Enterococcus hirae*, *Enterococcus italicus*, *Enterococcus lactis*, *Enterococcus lemanii*, *Enterococcus malodoratus*, *Enterococcus moraviensis*, *Enterococcus mundtii*, *Enterococcus olivae*, *Enterococcus pallens*, *Enterococcus phoeniculicola*, *Enterococcus plantarum*, *Enterococcus pseudoavium*, *Enterococcus quebecensis*, *Enterococcus raffinosus*, *Enierococcus ratti*, *Enterococcus rivorum*, *Enterococcus rotai*, *Enterococcus saccharolyticus*, *Enterococcus silesiacus*, *Enterococcus solitarius*, *Enterococcus sulfureus*, *Enterococcus termitis*, *Enterococcus thailandicus*, *Enterococcus ureasiticus*, *Enterococcus ureilyticus*, *Enterococcus viikkiensis*, *Enterococcus villorum*, and *Enterococcus xiangfangensis*, In further examples, the bacterium is selected from the group consisting of *Streptococcus agalactiae*, *Streptococcus anginosus*, *Streptococcus bovis*, *Streptococcus canis*, *Streptococcus constellatus*, *Streptococcus dysgalactiae*, *Streptococcus equinus*, *Streptococcus iniae*, *Streptococcus intermedius*, *Streptococcus milleri*, *Streptococcus mitis*, *Streptococcus mutans*, *Streptococcus oralis*, *Streptococcus parasanguinis*, *Streptococcus peroris*, *Streptococcus pneumoniae*, *Streptococcus pseudopneumoniae*, *Streptococcus pyogenes*, *Streptococcus ratti*, *Streptococcus salivarius*, *Streptococcus tigurinus*, *Streptococcus thermophilus*, *Streptococcus sanguinis*, *Streptococcus sobrinus*, *Streptococcus suis*, *Streptococcus uberis*, *Streptococcus vestibularis*, *Streptococcus viridans*, and *Streptococcus zooepidemicus*.

The exemplary LAB strain may be *Lactococcus lactis* or any of its subspecies, including *Lactococcus lactis* subsp. *cremoris*, *Lactococcus lactis* subsp. *hordniae*, *Lactococcus lactis* and *Lactococcus lactis* subsp. *lactis*. In another aspect, the LAB strain may be a biologically contained system, such as the plasmid free *Lactocaccus lactis* strain MG1363, that lost the ability of normal growth and acid production in milk as described in Gasson, M. J. (1983) *J. Bacterid.* 154:1-9; or the threonine- and pyrimidine-auxotroph derivative *L. lactis* strains as described in Sorensen et al. (2000) *Appl. Environ. Mierobiol.* 66:1253-1258; and Glenting et al. (2002) 68:5051-5056.

The recombinant bacterial host-vector system can be a biologically contained system. Biological containment is known to the person skilled in the art and can be realized by the introduction of an auxotrophic mutation, for example, a suicidal auxotrophic mutation such as the ThyA mutation, or its equivalents. Alternatively, the biological containment can be realized at the level of the plasmid carrying the gene encoding the IL-2 polypeptide or IL-2 variant, such as, for example, by using an unstable episomal construct, which is lost after a few generations. Several levels of containment, such as plasmid instability and auxotrophy, can be combined to ensure a high level of containment, if desired.

Constructs

As described herein, the LAB delivers the IL-2 polypeptide and the T1D-specific antigen at the intended site, i.e., the mucosa. For example, the LAB expresses the IL-2 polypeptide, after which the IL-2 polypeptide is exposed on the cell surface (if a membrane-bound form of IL-2 is used) or secreted (if a secreted form of IL-2 is used). Hence, in a particular embodiment the LAB, such as *L. lactis*, comprises an expression vector capable of expressing the IL-2 polypeptide and the T1D-specific antigen, intracellularly. For example, the polypeptides is exposed on the cell surface under conditions present at the intended mucosa, e.g., in the gastrointestinal tract. The LAB can comprise expression vectors capable of expressing the IL-2 polypeptide intracellularly, such that the IL-2 polypeptide is exposed on the cell surface to a degree sufficient to provide a low-dose of IL-2 that is effective in treating T1D in the recipient. When using LAB strains expressing higher amounts of IL-2 polypeptide and T1D-specific antigen, less frequent and lower LAB doses may be required for the treatment of T1D. Thus, one of skill in the art may adjust the amount of LAB strains provided to deliver the desired amount of IL-2 polypeptide and T1D-specific antigen.

Usually, the expression system will comprise a genetic construct comprising at least one nucleotide sequence encoding arm IL-2 polypeptide and/or a TD1-specific antigen polypeptide, typically operably linked to a promoter capable of directing expression of the sequence(s) in the hosting microorganism. Suitably the IL-2 polypeptide and the T1D-specific antigen to be expressed can be encoded by a nucleic acid sequence that is adapted to the preferred codon usage of the host. The construct may further contain (all) other suitable element(s), including enhancers, transcription initiation sequences, signal sequences, reporter genes, transcription termination sequences, etc., operable in the selected host, as is known to the person skilled in the art.

The construct is typically in a form suitable for transformation of the host and/or in a form that can be stably maintained in the host, such as a vector, plasmid or minichromosome. Suitable vectors comprising nucleic acid for introduction into LAB strains, e.g., *L. lactis*, can be chosen or constructed, containing appropriate regulatory sequences, including promoter sequences, terminator fragments, enhancer sequences, marker genes and other sequences as appropriate. Vectors may be plasmids, viral e.g., phage, or phagemid, as appropriate. Further details can be found in, for example, *Molecular Cloning; a Laboratory Manual* 2nd edition, Sambrook et al., 1989, Cold Spring Harbor Laboratory Press.

Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al., eds., John Wiley & Sons, 1992. In one embodiment, the coding sequence for the IL-2 polypeptide can be contained in an operon, i.e., a nucleic acid construct for multi-cistronic expression. In an operon, transcription from the promoter results in a mRNA which comprises more than one coding sequence, each with its own suitably positioned ribosome binding site upstream. Thus, more than one polypeptide can be translated from a single mRNA. Use of an operon enables expression of the IL-2 polypeptide and T1D-specific antigen polypeptide to be coordinated. Polycistronic expression systems in bacterial host cells are described, e.g., in U.S. Patent Application No. 2014/0105863.

To obtain stably transfected LAB strains, i.e., the gene coding for the IL-2 polypeptide and/or the T1D-specific antigen gene can be integrated into the host LAB's genome. Techniques for establishing stably transfected LAB strains are known in the art. For instance, the IL-2 polypeptide and/or the T1D-specific antigen gene may be cloned into the host's genome via homologous recombination. Typically, an essential gene of the host is disrupted by the homologous recombination event, such as deletion of the gene, one or more amino acid substitutions leading to an inactive form of the protein encoded by the essential gene, or to a frameshift mutation resulting in a truncated form of the protein encoded by the essential gene. In an embodiment, the essential gene is the thyA gene. An exemplary technique is described in WO 02/090551. The transforming plasmid is not particularly limited, as long as it cannot complement the disrupted essential gene, e.g., thyA gene. The plasmid may be a self-replicating, typically carrying one or more genes of interest and one or more resistance markers, or the plasmid is an integrative plasmid. In the latter case, the integrative plasmid itself may be used to disrupt the essential gene, by causing integration at the locus of the essential gene, e.g., thyA site, because of which the function of the essential gene, e.g., the thyA gene, is disrupted. Typically, the essential gene, such as the thyA gene, is replaced by double homologous recombination by a cassette comprising the gene or genes of interest, flanked by targeting sequences that target the insertion to the essential gene, such as the thyA target site. It will be appreciated that that these targeting sequences are sufficiently long and sufficiently homologous to enable integration of the gene of interest into the target site.

The genetic construct encoding the IL-2 polypeptide and/or the T1D-specific antigen may thus be present in the host cell extra-chromosomally, typically autonomously replicating using an own origin of replication, or may be integrated into the LAB genomic DNA, e.g., *Lactococcus* chromosome. In the latter case, a single or multiple copies of the nucleic acid may be integrated; the integration may occur at a random site of the chromosome or, as described above, at a predetermined site thereof, for example, in the thyA locus of *Lactococcus*, e.g., *Lactococcus lactis*.

Hence, the genetic construct encoding the IL-2 polypeptide and/or the T1D-specific antigen may further comprise sequences configured to effect insertion of the genetic construct into the genome, a chromosome, of a host LAB cell.

In an example, insertion of the genetic construct into particular sites within a genome, e.g., chromosome, of a host LAB cell may be facilitated by homologous recombination. For instance, the genetic constructs described herein may comprise one or more regions of homology to the said site of integration within the genome e.g., a chromosome, of the host LAB cell. The sequence at the said genome, e.g., chromosome, site may be natural, i.e., as occurring in nature, or may be an exogenous sequence introduced by previous genetic engineering.

For instance, the region(s) of homology may be at least 50 bp, 100 bp, 200 bp, 300 bp, 400 bp, 500 bp, 600 bp 700 bp, 800 bp, 900 bp, 1000 bp, or more.

In one example, two regions of homology may be included, one flanking each side of the relevant expression units present in the genetic constructs described herein. Such configuration may advantageously insert the relevant sequences, i.e., at least the ones encoding and effecting the expression of the antigen of interest, in host cells. Ways of performing homologous recombination, especially in bacterial hosts, and selecting for recombinants, are generally known in the art.

Transformation methods of LAB strains are known to the person skilled in the art, for example, protoplast transformation and electroporation.

A high degree of expression can be achieved by using homologous expression and/or secretion signals on the expression vectors present in the LAB, e.g., *L. lactis*. Expression signals will be apparent to the person skilled in the art. The expression vector can be optimized for expression depending on the LAB, e.g, *L. lactis*, it is incorporated in. For instance, specific expression vectors that gave sufficient levels of expression in *Lactococcus*, *Lactobacillus lactis, casei* and *plantarum* are known. Moreover, systems are known which have been developed for the expression of heterologous antigens in the non-pathogenic, non-colonizing, non-invasive food-grade bacterium *Lactococcus lactis* (e.g., UK patent GB2278358B). An exemplary construct comprises the multi-copy expression vector described in PCT/NL95/00135 (WO 96/32487), in which the nucleotide sequence encoding the IL-2 polypeptide T1D-specific antigen has been described. Such a construct may be suitable for expression of a desired antigen in a lactic acid bacterium, in particular in a *Lactobacillus*, at a high level of expression, and also can be used advantageously to direct the expressed product to the surface of the bacterial cell. The constructs (e.g., of PCT/NL95/0015) may be characterized in that the nucleic acid sequence encoding the IL-2 polypeptide and/or T1D-specific antigen is preceded by a 5' non-translated nucleic acid sequence comprising at least the minimal sequence required for ribosome recognition and RNA stabilization. This can be followed by a translation initiation codon which may be (immediately) followed by a fragment of at least 5 codons of the 5' terminal part of the translated nucleic acid sequence of a gene of a lactic acid bacterium or a structural or functional equivalent of the fragment. The fragment may also be controlled by the promoter. One aspect of the present disclosure provides a method which permits the high level regulated expression of heterologous genes in the host and the coupling of expression to secretion. In another embodiment, the T7 bacteriophage RNA polymerase and its cognate promoter are used to develop a powerful expression system according to WO 93/17117. In one embodiment, the expression plasmid may be derived from pT1 NX.

A promoter employed herein is typically expressed constitutively in the bacterium. The use of a constitutive promoter avoids the need to supply an inducer or other regulatory signal for expression to take place. Typically, the promoter directs expression at a level at which the bacterial host cell remains viable, i.e., retains some metabolic activity, even if growth is not maintained. Advantageously then, such expression may be at a low level. For example, where the expression product accumulates intracellularly, the level of expression may lead to accumulation of the expression product at less than about 10% of cellular protein, optionally about or less than about 5%, for example about 1-3%. The promoter may be homologous to the bacterium employed, one found in that bacterium in nature. For example, a Lactococcal promoter may be used in a *Lactococcus*. An exemplary promoter for use in *Lactococcus lactis* (or other *Lactococci*) is "P1" derived from the chromosome of *Lactococcus lactis* (Waterfield N R et al., *Gene* 1995, 165(1): 9-15). Another example of a promoter is the usp45 promoter.

Other useful promoters are described in U.S. Pat. No. 8,759,088 and U.S. Patent Application No. 2014/0105863.

The nucleic acid construct or constructs may comprise a secretory signal sequence. Thus, in some embodiments the nucleic acid encoding IL-2 and/or the T1D-specific antigen may provide for secretion of the polypeptides, by appropriately coupling a nucleic acid sequence encoding a signal sequence to the nucleic acid sequence encoding the polypeptide). Ability of a bacterium harboring the nucleic acid to secrete the antigen may be tested in vitro in culture conditions which maintain viability of the organism. Exemplary secretory signal sequences include those with activity in LAB strains. Such sequences may include the α-amylase secretion leader of *Bacillus amyloliquetaciens* or the secretion leader of the *Staphylokinase* enzyme secreted by some strains of *Staphylococcus*, which is known to function in both Gram-positive and Gram-negative hosts (Rapoport, *Current Opinion in Biotechnology* 1990, 1: 21-27), or leader sequences from numerous other *Bacillus* enzymes or S-layer proteins (see pp 341-344 of Harwood and Cutting, "Molecular Biological Methods for *Bacillus*," John Wiley & Co. 1990). In one embodiment, said secretion signal is derived from usp45 (Van Asseldonk et al. (1993) *Mol. Gen. Genet.* 240:428-434). In some embodiments, the IL-2 polypeptide or IL-2 variant may be constitutively secreted.

IL-2 Polypeptides

Examples of IL-2 polypeptides include wild-type human IL-2 in either membrane bound or secreted forms, and any IL-2 variant polypeptide, e.g., polypeptides having at least about 60%, at least about 70%, at least about 80%, at least about 90%, at least about 95%, or at least about 98% sequence identity with wild-type IL-2, or the corresponding mature IL-2 polypeptide. An exemplary amino acid sequence of wild-type human IL-2 is represented by SEQ ID NO: 1, while an exemplary IL-2 encoding nucleic acid sequence is represented by SEQ ID NO: 2. Mature wild-type human IL-2 is represented by SEQ NO: 3.

The signal peptide for IL-2 (SEQ ID NO: 4) is underlined and represents amino acids 1-20 of SEQ ID NO: 1. The signal peptide of IL-2 may be substituted with a bacterial secretory signal sequence (e.g., SSusp45) as described herein. An exemplary nucleotide sequence according to this embodiment is represented by SEQ ID NO: 5.

The term "IL-2 variant" includes IL-2 polypeptides characterized by amino acid insertions, deletions, substitutions, and/or modifications at one or more sites of the native IL-2 polypeptide chain. In accordance with this disclosure any such insertions, deletions, substitutions, and modifications result in an IL-2 variant polypeptide that retains at least some IL-2RP binding activity. Exemplary variants include polypeptides with substitutions of 1, 2, 3, 4, 5, 6, 7, 8, 9, 10 or more amino acids, IL-2 variants can have conservative modifications and substitutions at other positions of IL-2 (i.e., those that have a minimal effect on the secondary or tertiary structure of the variant polypeptide). Such conservative substitutions include those described by Dayhoff in 'The Atlas of Protein Sequence and Structure 5' (1978), and by Argos in *EMBO J.,* 8:779-785 (1989). For example, amino acids belonging to one of the following groups represent conservative changes: Group I: ala, pro, gly, gln, asn, ser, thr; Group II: cys, ser, tyr, thr; Group II: val, ile, leu, met, ala, phe; Group IV: lys, arg, his; Group V: phe, tyr, trp, his; and Group VI: asp, glu.

In some examples, the IL-2 is a variant as described in U.S. Pat. No. 4,518,584, in which the cysteine normally occurring at position 125 of the wild-type or native molecular has been replaced by a neutral amino acid such as serine or alanine. Alternatively or conjunctively, the IL-2 variant may be one as described in U.S. application Ser. No. 06/810,656 filed Dec, 17, 1985, in which the methionine normally occurring at position 104 of the wild-type or native molecule has been replaced by a neutral amino acid such as alanine. In some examples, the IL-2 variant may have one or more of the first five N-terminal amino acids of the native IL 2 deleted. IL-2 muteins were also generated with decreased binding affinity to CD122 (to achieve lower IL-2 toxicity), such as BAY 50-4798 (containing an N88R mutation of IL 2).

Other forms of IL-2 that may be used include IL-2 variant sequences such as those found in aldesleukin, or proleukin (Prometheus Laboratories), teceleukin (Roche), bioleukin (Glaxo), as well as variants as described in Taniguchi. et al., *Nature* 1983, 302(5906):305-10 and Devos et al., *Nucleic Acids Res.* 1983, 11(13): 4307-23; European Patent Application Nos. 91,539 and 88,195; U.S. Pat. No. 4,518,584. U.S. Patent Publication No. 2012/0244112; U.S. Pat. Nos. 7,569,215; 5,229,109; U.S. Patent Publication No. 2006/0269515; EP Patent Publication No. EP 1730184A2; and PCT Publication WO 2005/086751.

In some embodiments, the IL-2 variant has diminished capacity to bind to the high-affinity IL-2 receptor, hut preserves affinity of the variant IL-2 to bind intermediate-affinity IL-2 receptor compared to wild-type IL-2 polypeptide. In some embodiments, the mature IL-2 polypeptide is characterized by one, two, or three amino acid substitutions, e.g., wherein the substituted amino acid residues are selected from L72, F42, and Y45. In some embodiments, the IL-2 variant is characterized by a substitution of L72, e.g., comprises a first amino acid substitution selected from the group consisting of L72G, L72A, L72S, L72T, L72Q, L72E, L72N, L72D, L72R, and L72K. The IL-2 variant can be characterized by a substitution of F42, e.g., comprises a second amino acid substitution selected from the group consisting of F42A, F42G, F42S, F42T, F42Q, F42E, F42N, F42D, F42R, and F42K. In further embodiments, the IL-2 variant is characterized by a substitution of Y45, e.g., comprises a third amino acid substitution selected from the group consisting of Y45A, Y45G, Y45S, Y45T, Y45Q, Y45E, Y45N, Y45D, Y45R, and Y45K. The IL-2 variant of the present disclosure may contain any combination of the above recited first, second, and third amino acid substitutions.

The IL-2 variants as described herein may be about 75%, about 80%, about 85%, about 90%, about 95%, about 96%, about 97%, about 98%, or about 99% identical to a corresponding wild type IL-2, provided that the IL-2 variant polypeptide retains some IL-2 activity (functional polypeptide).

The percentage identity of polypeptide sequences can be calculated using commercially available algorithms which compare a reference sequence (e.g., SEQ ID NO: 1 of the present disclosure) with a query sequence.

A person of ordinary skill in the art will appreciate that the optimal amount of IL-2 to be delivered to the subject using the methods of the present disclosure varies, e.g., with the LAB expressing the IL-2 polypeptide, and the genetic construct, e.g., the strength of the promoter used in the genetic construct. Typically, the LAB may be administered in an amount equivalent to a particular amount of expressed IL-2 polypeptide, or in an amount, which generates a desired PK profile for the respective IL-2 polypeptide in the respective subject. Exemplary daily IL-2 polypeptide doses are from about 10 fg to about 100 µg of active polypeptide per day. Other exemplary dose ranges are from about 1 pg to about 100 µg per day; or from about 1 ng to about 100 µg per day.

The above doses may be realized by administering to the subject effective amounts of the microorganism per day, wherein the microorganism is adapted to express a sufficient amount of IL-2 to realize the desired dose, such as those above. The LAB secreting the IL-2 polypeptide may be delivered in a dose of from about $10^4$ colony forming units (cfu) to about $10^{12}$ cfu per day, in particular from about $10^6$ cfu to about $10^{12}$ cfu per day, more in particular from about $10^9$ cfu to about $10^{12}$ cfu per day. The amount of secreted IL-2 polypeptide can be determined based on cfu, for example in accordance with the methods described in Steidler et al., *Science* 2000; 289(5483): 1352-1355, or by using ELISA. For example, a LAB may secrete at least about 1 ng to about 1 µg of active polypeptide per $10^9$ cfu. Based thereon, the skilled person can calculate the range of IL-2 polypeptide secreted at other cfu doses.

Each of the above doses/dose ranges may be administered in connection with any dosing regimen as described herein. The daily dose may be administered in 1, 2, 3, 4, 5, or 6 portions throughout the day. Further the daily closes may be administered for any number of days, with any number of rest periods between administration periods. For example, the subject may be administered microorganism at a dose equivalent to about 0.1 to about 3 MIU/day or every other day, for a period of at least about 1 week, at least about 2 weeks, at least about 3 weeks, at least about 4 weeks, at least about S weeks, or at least about 6 weeks. In some examples, the subject is administered the LAB at a dose equivalent to about 0.1 to about 5 MIU/day, or about 0.3 to about 3 MIU, e.g., for about 5 days, about 7 days, or about 14 days. Exemplary doses are described, e.g., in Hartemann et al., *Lancet Diabetes Endocrinol.* 2013, 1(4): 295-305.

T1D-Specific Antigen Polypeptides

The LAB of the present disclosure contains at least one disease-specific (i.e., T1D-specific) self-antigen gene, and can express such gene under conditions sufficient for expression. Exemplary T1D-specific self-antigens include islet antigens associated with the beta-cell destruction process. Examples include but are not limited to: proinsulin (PINS), glutamic acid decarboxylase (GAD65), insulinoma-associated protein 2 (IA-2), islet-specific glucose-6-phosphatase catalytic subunit-related protein (IGRP) and zinc transporter 8 (ZnT8) 8. Other examples include molecules expressed by beta beta-cells, such as chromogranin A, (prepro) islet amyloid polypeptide (ppIAPP), peripherin and citrullinated glucose-regulated protein (GRP).

Examples of PINS polypeptides include wild-type human PINS and polypeptides having at least about 60%, at least about 70%, at least about 80%, at least about 90%, at least about 95%, at least about 96%, at least about 97%, at least about 98%, or at least about 99% sequence identity with such wild-type human PINS. An exemplary amino acid sequence of wild-type human PINS is represented by SEQ ID NO: 6, while an exemplary PINS encoding nucleic acid sequence is represented by SEQ ID NO: 7 (see CDS contained in accession number NM_000207.2).

Additional exemplary PINS nucleotide sequences are represented by the coding sequences of NCBI accession numbers AY899304 (complete CDS, alternatively spliced; SEQ ID NO: 8); NM_000207 (transcript variant 1; SEQ ID NO: 9); NM_001185097 (transcript variant 2; SEQ ID NO: 10); NM_001185098 (transcript variant 3; SEQ ID NO: 11);

NM_001291897 (transcript variant 4; SEQ ID NO: 12), and partial functional sequences thereof. Exemplary PINS amino acid sequences include those encoded by any one of the above PINS nucleic acid sequences.

Any nucleotide sequence encoding the amino acid sequence of SEQ ID NO: 6, or any nucleotide sequence encoding at least about 20, at least about 30, at least about 40, at least about 50, at least about 60, at least about 70, at least about 80, at least about 90, or at least about 100 consecutive amino acids thereof, or any nucleotide sequence encoding a polypeptide having at least about 60%, at least about 70%, at least about 80%, at least about 90%, at least about 95%, at least about 96%, at least about 97%, at least about 98%, or at least about 99% sequence identity with SEQ ID NO: 6 may be used.

Additional PINS polypeptides are described, e.g., in UniProtKB—P01308 and links therein. In some examples, the PINS polypeptide is represented by amino acid residues 25-110 (numbering according to SEQ ID NO: 6).

Exemplary GAD (e.g., GAD65) polypeptides include wild-type human GAD65, and potypeptides having at least about 60%, at least about 70%, at least about 80%, at least about 90%, at least about 95%, at least about 96%, at least about 97%, at least about 98%, or at least about 99% sequence identity with such wild-type GAD65. An exemplary amino acid sequence of wild-type human GAD65 is represented by SEQ ID NO: 13, while an exemplary GAD65 encoding nucleic acid sequence is represented by SEQ ID NO: 14 (see, e.g., CDS contained in accession number M81882.1).

Any nucleotide sequence encoding the above amino acid sequence represented by SEQ ID NO: 13, or any nucleotide sequence encoding at least about 100, at least about 200, at least about 300, at least about 400, or at least about 500 consecutive amino acids thereof, or any nucleotide sequence encoding a polypeptide having at least about 60%, at least about 70%, at least about 80%, at least about 90%, at least about 95%, at least about 96%, at least about 97%, at least about 98%, or at least about 99% sequence identity with SEQ ID NO: 13 may be used.

Other exemplary glutamate decarboxylase (e.g., GAD65) sequences are described, e.g., in UniProtKB—Q05329 and links therein. In some example, the GAD polypeptide is a trimmed variant containing less than about 500, less than about 400, or less than about 300 of the wild-type amino acids. Exemplary polypeptide fragments (trimmed GAD65 variants) are described, e.g., in Robert et al., *Benef. Microbes* 2015, 6(4): 591-601. In some examples, the trimmed GAD variants are efficiently expressed and secreted by a LAB (i.e., *Lactococcus lactis*). An exemplary trimmed GAD variant is $GAD65_{370-575}$ (amino acid numbering relative to NCBI accession number NP_000809.1, i.e., SEQ ID NO: 13).

Other exemplary GAD nucleotide sequences are represented by NCBI accession numbers M81882 (GAD65; SEQ ID NO: 15); M81883 (GAD67; SEQ ID NO: 16); NM_000818 (GAD2 variant 1; SEQ ID NO: 17); and NM_001134366 (GAD2 variant 2; SEQ ID NO: 18); and open reading frames (CDS) contained therein. Exemplary amino acid sequences include sequences encoded by the above nucleotide sequences of accession numbers M81882, M81883, NM_001134366, and NM_000818.

Examples of IA-2 polypeptides include wild-type human IA-2 and polypeptides having at least about 60%, at least about 70%, at least about 80%, at least about 90%, at least about 95%, at least about 96%, at least about 97%, at least about 98%, or at least about 99% sequence identity with such wild-type IA-2. An exemplary amino acid sequence of wild-type human IA-2 is represented by SEQ ID NO: 19, while an exemplary IA-2 encoding nucleic acid sequence is represented by SEQ ID NO: 20 (see, e.g., open reading frame of accession number NM_002846.3).

Any nucleotide sequence encoding the above amino acid sequence represented by SEQ ID NO: 19, or any nucleotide sequence encoding at least about 100, at least about 200, at least about 300, at least about 400, at least about 500, at least about 600, or at least about 800 consecutive amino acids thereof, or any nucleotide sequence encoding a polypeptide having at least about 60%, at least about 70%, at least about 80%, at least about 90%, at least about 95%, at least about 96%, at least about 97%, at least about 98%, or at least about 99% sequence identity with SEQ ID NO: 19 may be used.

Exemplary IA-2 nucleotide sequences are represented by NCBI accession numbers NM_002846 (human IA-2 or protein tyrosine phosphatase, receptor type N (PTPRN), transcript variant 1; SEQ ID NO: 21); NM_001199763 (Human IA-2 or protein tyrosine phosphatase, receptor type, N (PTPRN), transcript variant 2; SEQ ID NO: 22); NM_901199764 (Human IA-2 or protein tyrosine phosphatase, receptor type, N (PTPRN), transcript variant 3; SEQ ID NO: 23). Exemplary IA-2 amino acid sequences include those encoded by the above nucleotide sequences.

Other exemplary IA-2 sequences are described, e.g., UniProtKB—Q16849 and links therein. In some example, the IA-2 polypeptide can be a trimmed variant containing less than about 700, less than about 600, less than about 500, or less than about 400 of the wild-type amino acids. Exemplary polypeptide fragments (trimmed IA-2 variants) are described, e.g., in Robert el al., *Benef. Microbes* 2015, 6(4): 591-601. In some examples, the trimmed IA-2 variants can be efficiently expressed and secreted by a LAB (i.e., *Lactococcus lactis*). In one example, the trimmed IA-2 variant is $IA-2_{635-979}$ (amino acid numbering relative to NCBI accession number NP_002837.1; i.e., SEQ ID NO: 19).

Examples of IGRP polypeptides include wild-type human IGRP, and polypeptides having at least about 60%, at least about 70%, at least about 80%, at least about 90%, at least about 95%, at least about 96%, at least about 97%, at least about 98%, or at least about 99% sequence identity with such wild-type IGRP. An exemplary amino acid sequence of wild-type human IGRP is represented by SEQ ID NO: 24, while an exemplary IGRP encoding nucleic acid sequence is represented by SEQ ID NO: 25 (see open reading frame of NCBI accession number BC113376.1).

Any nucleotide sequence encoding the above amino acid sequence represented by SEQ ID NO: 24, or any nucleotide sequence encoding at least 50, at least 100, at least 200, or at least 300 amino acids thereof, or any nucleotide sequence encoding a polypeptide having at least about 60%, at least about 70%, at least about 80%, at least about 90%, at least about 95%, at least about 96%, at least about 97%, at least about 98%, or at least about 99% sequence identity with SEQ ID NO: 24 may be used.

Further exemplary nucleotide sequences are represented by NCBI accession numbers NM_021176 (G6PC2 transcript variant 1; SEQ ID NO: 26); NM_001081686 (human glucose-6-phosphatase, catalytic, 2 (G6PC2) transcript variant 2; SEQ ID NO: 27); and NM_001270397 (G6PC, transcript variant 2; SEQ ID NO: 28). Exemplary IGRP amino acid sequences include those encoded by the above nucleotide sequences.

Other exemplary sequences are described, e.g., in UniProtKB—Q9NQR9 and links therein, as well as in Arden et al., *Diabetes* 1999; 48(3):531-542; Martin et al., *J. Biol.*

*Chem.* 2001; 276(27):25197-207; and Dogra et al., *Diabetologia* 2006; 49(5):953-7. In some examples, the IGRP polypeptide is a trimmed variant containing less than about 300, less than about 200, less than about 100, or less than about 50 of the wild-type amino acids. In some examples, the trimmed IGRP variants are selected to be efficiently expressed and secreted by a LAB (i.e., *Lactococcus lactis*).

Examples of ZnT8 polypeptides include wild-type human ZnT8, and polypeptides having at least about 60%, at least about 70%, at least about 80%, at least about 90%, at least about 95%, at least about 96%, at least about 97%, at least about 98%, or at least about 99% sequence identity with such wild-type ZnT8. An exemplary amino acid sequence of wild-type human ZnT8 is represented by SEQ ID NO: 29, while an exemplary ZnT8 encoding nucleic acid sequence is represented by SEQ ID NO: 30 (see, e.g., open reading frame contained in NCBI accession NM_173851.2).

Any nucleotide sequence encoding the above amino acid sequence represented by SEQ ID NO: 29, or any nucleotide sequence encoding at least 50, at least 100, at least 200, at least 250, or at least 300 amino acids thereof, or any nucleotide sequence encoding a polypeptide having at least about 60%, at least about 70%, at least about 80%, at least about 90%, at least about 95%, at least about 96%, at least about 97%, at least about 98%, or at least about 99% sequence identity with SEQ ID NO: 29 may be used.

Further exemplary ZnT8 nucleotide sequences are represented by NCBI accession numbers AY212919.1 (human sine transporter 8, complete cds; SEQ ID NO: 31); NM_173851.2 (human zinc transporter 8, transcript variant 1; SEQ ID NO: 32); NM_001172814.1 (human zinc transporter 8, transcript variant 2; SEQ ID NO: 33); NM_001172811.1 (human zinc transporter 8, transcript variant 3; SEQ ID NO: 34); NM_001172813.1 (human zinc transporter 8, transcript variant 4; SEQ ID NO: 35); NM_001172815.2 (human zinc transporter 8, transcript variant 5; SEQ ID NO: 36), and partial sequences thereof. Exemplary ZnT8 amino acid sequences include those encoded by the above nucleotide sequences.

Other exemplary sequences are described, e.g., in UniProtKB—Q8IWU4 and links therein. In some examples, the ZnT8 polypeptide is a trimmed variant containing less than about 300, less than about 200, or less than about 100 of the wild-type amino acids. In some examples, the trimmed ZnT8 variants are selected to be efficiently expressed and secreted by a LAB (i.e., *Lactococcus lactis*).

Examples of ppIAPP polypeptides include wild-type human ppIAPP, and polypeptides having at least about 60%, at least about 70%, at least about 80%, at least about 90%, at least about 95%, at least about 96%, at least about 97%, at least about 98%, or at least about 99% sequence identity with such wild-type ppIAPP. An exemplary amino acid sequence of wild-type human ppIAPP is represented by SEQ ID NO: 37, while an exemplary ppIAPP encoding nucleic acid sequence is represented by SEQ ID NO: 38 (see, e.g., open reading frame of NCBI accession number NM_000415.2).

Any nucleotide sequence encoding the above amino acid sequence represented by SEQ ID NO: 37, or any nucleotide sequence encoding at least 50, at least 100, at least 200, at least 250, or at least 300 amino acids thereof, or any nucleotide sequence encoding a polypeptide having at least about 60%, at least about 70%, at least about 80%, at least about 90%, at least about 95%, at least about 96%, at least about 97%, at least about 98%, or at least about 99% sequence identity with SEQ ID NO: 37 may be used.

Other exemplary ppIAPP polypeptide sequences are disclosed, e.g., in UniProtKB—P10997 and links therein. In some examples, the ppIAPP polypeptide can be a trimmed variant containing less than about 80, less than about 60, less than about 40, or less than about 20 of the wild-type amino acids. In some examples, the trimmed ppIAPP variants are selected to be efficiently expressed and secreted by a LAB strain (i.e., *Lactococcus lactis*).

Examples of peripherin polypeptides include wild-type human peripherin, and polypeptides having at least about 60%, at least about 70%, at least about 80%, at least about 90%, at least about 95%, at least about 96%, at least about 97%, at least about 98%, or at least about 99% sequence identity with such wild-type. An exemplary amino acid sequence of wild-type human peripherin is represented by SEQ ID NO: 39, while an exemplary peripherin encoding nucleic acid sequence is represented by SEQ ID NO: 40 (see, e.g., open reading frame of NCBI accession number NM_906262.3).

Any nucleotide sequence encoding the above amino acid sequence represented by SEQ ID NO: 39, or any nucleotide sequence encoding at least about 100, at least about 200, at least about 300, or at least about 400 consecutive amino acids thereof, or any nucleotide sequence encoding a polypeptide having at least about 60%, at least about 70%, at least about 80%, at least about 90%, at least about 95%, at least about 96%, at least about 97%, at least about 98%, or at least about 99% sequence identity with SEQ ID NO: 39 may be used.

Other exemplary peripherin sequences are disclosed, e.g., in UniProtKB—P41219 and links therein. In some examples, the peripherin polypeptide is a trimmed variant containing less than about 400, less than about 300, less than about 200, or less than about 100 of the wild-type amino acids. In some examples, the trimmed peripherin variants are selected to be efficiently expressed and secreted by a LAB (i.e., *Lactococcus lactis*).

Further exemplary nucleotide sequences are represented by NCBI accession numbers NM_006262.3 (human peripherin; PRPH; SEQ ID NO: 41); XM_005269025.1 (predicted human peripherin, transcript variant X1; SEQ ID NO: 42); XR_944623.1 (predicted human peripherin, transcript variant X2; SEQ ID NO: 43), and partial sequences thereof. Exemplary peripherin amino acid sequences include those encoded by the above nucleotide sequences.

Examples of GRP polypeptides include wild-type human GRP78/BiP, and polypeptides having at least about 60%, at least about 70%, at least about 80%, at least about 90%, at least about 95%, at least about 96%, at least about 97%, at least about 98%, or at least about 99% sequence identity with such wild-type GRP. An exemplary amino acid sequence of wild-type human GRP is represented by SEQ ID NO: 44, while an exemplary GRP encoding nucleic acid sequence is represented by SEQ ID NO: 45 (see, e.g., open reading frame in NCBI accession number X87949.1).

Any nucleotide sequence encoding the above amino acid sequence represented by SEQ ID NO: 44, or any nucleotide sequence encoding at least about 100, at least about 200, at least about 300, at least about 400, or at least about 500 consecutive amino acids thereof, or any nucleotide sequence encoding a polypeptide having at least about 60%, at least about 70%, at least about 80%, at least about 90%, at least about 95%, at least about 96%, at least about 97%, at least about 98%, or at least about 99% sequence identity with SEQ ID NO: 44 may be used.

Other exemplary GRP sequences are disclosed, e.g., in UniProtKB—P11021 and links therein. In some examples, the GRP polypeptide is a trimmed variant containing less than about 500, less than about 400, less than about 300, or less than about 200 of the wild-type amino acids. In some examples, the trimmed GRP variants are selected to be efficiently expressed and secreted by a LAB strain (i.e., *Lactococcus lactis*).

A person of ordinary skill in the art will appreciate that the optimal amount of self-antigen to be delivered to the subject using the methods of the present disclosure varies, e.g., with the type of antigen, the microorganism expressing the antigen, and the genetic construct, e.g., the strength of the promoter used in the genetic construct. Typically, the microorganism will be administered in an amount equivalent to a particular amount of expressed antigen, or in an amount, which generates a desired PK profile for the respective antigen polypeptide in the respective subject. Exemplary daily antigen doses can be from about 10 fg to about 100 µg of active polypeptide per day. Other exemplary dose ranges can be from about 1 pg to about 100 µg per day; or from about 1 ng to about 100 µg per day.

The above antigen doses may be realized by administering to the subject effective amounts of the LAB per day, wherein the LAB is adapted to express a sufficient amount of bioactive polypeptide to realize the desired dose, such as those above. The LAB secreting the antigen polypeptide may be delivered in a dose of from about $10^4$ colony forming units (cfu) to about $10^{12}$ cfu per day, e.g., from about $10^6$ cfu to about $10^{12}$ cfu per day, or from about $10^9$ cfu to about $10^{12}$ cfu per day.

The amount of secreted antigen polypeptide can be determined based on cfu, for example in accordance with the methods described in Steidler et al., *Science* 2000; 289 (5483): 1352-1355, or by using ELISA. For example, a LAB may secrete at least about 1 ng to about 1 µg of active polypeptide per $10^9$ cfu. Based thereon, the skilled person can calculate the range of antigen polypeptide secreted at other cfu doses.

Each of the above doses/dose ranges may be administered in connection with any dosing regimen as described herein. The daily dose of active polypeptide may be administered in 1, 2, 3, 4, 5, or 6 portions throughout the day. Further the daily doses may be administered for any number of days, with any number of rest periods between administration periods. For example, a dose of from about 0.1 to about 3.0 M IU/day/subject may be administered every other day for a total of 6 weeks.

Formulations and Regimens

In the methods described herein, the IL-2 and the T1D may be expressed by the same or different LAB. When the two polypeptides are expressed by different microorganisms, those may be administered to the subject in the same (e.g., combined) formulation or may be administered in separate (e.g., different) formulations. Separate formulations may be administered at the same time or at different time points. For example, the of IL-2 and T1D-specific antigen producing microorganisms in their respective formulations can be administered to the subject simultaneously or may be administered sequentially, e.g., with a rest period between administrations.

The IL-2 and T1D-specific antigen producing LAB strains can be administered simultaneously. In some examples, the IL-2-producing microorganism, and the T1D-specific antigen-producing microorganism can be comprised in the same pharmaceutical formulation, or in more than one pharmaceutical formulation taken at the same time. In exemplary embodiments, the two bioactive polypeptides are delivered to the subject using a single LAB strain producing both the IL-2 and the T1D-specific antigen.

In some embodiments, the composition described herein will be administered, once, twice, three, four, five, or six times daily, e.g., using an oral formulation. In some embodiments, the LAB strains are administered every day, every other day, once per week, twice per week, three times per week, or four times per week. In other embodiments, treatment occurs once every two weeks. In other embodiments, treatment occurs once every three weeks. In other embodiments, treatment occurs once per month.

The duration of a treatment cycle for the method may be, for example, 7 days to the subject's lifetime, as needed to treat or reverse T1D, or prevent relapse. A treatment cycle can last for about 30 days to about 2 years. In other embodiments, the subject can have a treatment cycle that lasts from 30 days to 1.5 years. In other embodiments, the subject can have a treatment cycle that lasts from 30 days to 1 year. In other embodiments, the subject can have a treatment cycle that lasts from 30 days to 11 months. In other embodiments, the subject can have a treatment cycle that lasts from 30 days to 10 months. In other embodiments, the subject can have a treatment cycle that lasts from 30 days to 9 months. The subject can have a treatment cycle that lasts from 30 days to 8 months. The subject can have a treatment cycle that lasts from 30 days to 7 months. The subject can have a treatment cycle that lasts from 30 days to 6 months. The subject can have a treatment cycle that lasts from 30 days to 5 months. The subject can have a treatment cycle that lasts from 30 days to 4 months. The subject can have a treatment cycle that lasts from 30 days to 3 months. The subject can have a treatment cycle that lasts from 30 days to 2 months.

Daily maintenance doses can be given for a period clinically desirable in the subject, for example from 1 day up to several years (e.g. for the subject's entire remaining life); for example from about (2, 3 or 5 days, 1 or 2 weeks, or 1 month) upwards and/or for example up to about (5 years, 1 year, 6 months, 1 month, 1 week, or 3 or 5 days). Administration of the daily maintenance dose for about 3 to about 5 days or for about 1 week to about 1 year is typical. Nevertheless, unit doses optionally may be administered from twice daily to once every two weeks until a therapeutic effect is observed.

The LAB strains producing the IL-2 polypeptide and the antigen polypeptide may be delivered in mono- or combination therapy for the treatment of T1D. In some embodiments, the compositions of the present disclosure include additional therapeutically active agents. In some embodiments, the treatment of the subject does not involve other active components, e.g., does not involve additional immune-modulating substances, such as antibodies (e.g., anti-CD3). Thus, in some examples, the pharmaceutical compositions of the present disclosure consist essentially of the LAB as described herein (expressing the therapeutic IL-2 and antigen polypeptides), and a pharmaceutically acceptable carrier.

Pharmaceutical Compositions and Carriers

The LAB strains described herein (e.g., *L. lactis*) may be administered in pure form, combined with other active ingredients, and/or combined with pharmaceutically acceptable (i.e., nontoxic) excipients or carriers. The term "pharmaceutically acceptable" is used herein in accordance with its art-recognized meaning and refers to carriers that are compatible with the other ingredients of a pharmaceutical composition, and are not deleterious to the recipient thereof.

The compositions described herein can be prepared in any known or otherwise effective dosage or product form suitable for use in providing systemic delivery of the LAB strains (e.g., *L. lactis*) to the mucosa, which would include pharmaceutical compositions and dosage forms as well as nutritional product forms.

In some embodiments, the formulation is an oral formulation or pharmaceutical composition. In some examples according to this embodiment, the formulation or pharmaceutical composition comprises the LAB strains in a dry-powder form (e.g., freeze-dried form) or in compacted form thereof, optionally in combination with other dry carriers. Oral formulations will generally include an inert diluent carrier or an edible carrier.

In some examples, the oral formulation comprises a coating or utilizes an encapsulation strategy, which facilitates the delivery of the formulation into the intestinal tract, and/or allows the microorganism be released and hydrated in the intestinal tract (e.g., the ileum, small intestine, or the colon). Once the LAB is released from the formulation and sufficiently hydrated, it begins expressing the bioactive polypeptide, which is subsequently released into the surroundings, or expressed on the surface of the microorganism. Such coating and encapsulation strategies (i.e., delayed-release strategies) are known to those of skill in the art. See, U.S. Pat. No. 5,972,685; WO 2000/18377; and WO 2000/22909.

A pharmaceutical composition is provided that can comprise the LAB stains in a lyophilized or freeze dried form, optionally in conjunction with other components, such as dextrans, sodium glutamate, and polyols. Exemplary freeze dried compositions are described, e.g., in U.S. Pub. No. 2012/0039853. Exemplary formulations comprise freeze-dried bacteria (e.g., a therapeutically effective amount of the bacteria) and a pharmaceutically acceptable carrier. Freeze-dried bacteria may be prepared in the form of capsules, tablets, granulates and powders, each of which may be administered orally. Alternatively, freeze-dried bacteria may be prepared as aqueous suspensions in suitable media, or lyophilized bacteria may be suspended in a suitable medium, such as a drink, just prior to use.

For oral administration, the formulation may be a gastro-resistant oral dosage form. For example, the oral dosage form (e.g., capsules, tablets, pellets, micro-pellets, granulates, and the like) may be coated with a thin layer of excipient (usually polymers, cellulosic derivatives and/or lipophilic materials) that resists dissolution or disruption in the stomach, but not in the intestine, thereby allowing transit through the stomach in favor of disintegration, dissolution and absorption in the intestine (e.g., the small intestine, or the colon).

In some examples, oral formulations may include compounds providing controlled release, sustained release, or prolonged release of the microorganism, and thereby provide controlled release of the desired protein encoded therein. These dosage forms (e.g., tablets or capsules) typically contain conventional and well known excipients, such as lipophilic, polymeric, cellulosic, insoluble, and swellable excipients. Controlled release formulations may also be used for any other delivery sites including intestinal, colon, bioadhesion or sublingual delivery (i.e., dental mucosal delivery), and bronchial delivery. When the compositions described herein are to be administered rectally or vaginally, pharmaceutical formulations may include suppositories and creams. In this instance, the host cells are suspended in a mixture of common excipients also including lipids. Each of the aforementioned formulations are well known in the art and are described, for example, in the following references: Hansel et al. (1990, PHARMACEUTICAL DOSAGE FORMS AND DRUG DELIVERY SYSTEMS, 5th edition, William and Wilkins); Chien 1992, NOVEL DRUG DELIVERY SYSTEM, 2nd edition, M. Dekker); Prescott el al. (1989, NOVEL DRUG DELIVERY, J. Wiley & Sons); Cazzaniga el al., (1994, *Int. J. Pharm.* 108(1): 77-83).

The oral formulations and compositions described herein can further include compounds that can enhance mucosal delivery and/or mucosal uptake of the bioactive polypeptides expressed by the LAB. The formulations/compositions described herein can also include compounds, which enhance the viability of the microorganism within the formulation, and/or once released.

The LAB as described herein can be suspended in a pharmaceutical formulation for administration to the human or animal having the disease to be treated. Such pharmaceutical formulations include but are not limited to live LAB and a medium suitable for administration. The LAB may be lyophilized in the presence of common excipients such as lactose, other sugars, alkaline and/or alkali earth stearate, carbonate and/or sulphate (e.g., magnesium stearate, sodium carbonate and sodium sulphate), kaolin, silica, flavorants and aromas. Bacteria so-lyophilized may be prepared in the form of capsules, tablets, granulates and powders (e.g., a mouth rinse powder), each of which may be administered by the oral route. Alternatively, the LAB strains may be prepared as aqueous suspensions in suitable media, or lyophilized bacteria may be suspended in a suitable medium just prior to use, such medium including the excipients referred to herein and other excipients such as glucose, glycine, and sodium saccharinate.

In some examples, the LAB is locally delivered to the gastrointestinal tract of the subject using any suitable method. For example, microsphere delivery systems could be employed to enhance delivery to the gut. Microsphere delivery systems include microparticles having a coating that provides localized release into the gastrointestinal tract of the subject (e.g., controlled release formulations such as enteric-coated formulations and colonic formulations).

For oral administration, gastroresistant oral dosage forms may be formulated, which dosage forms may also include compounds providing controlled release of the LAB strains and thereby provide controlled release of the desired protein encoded therein at different points in digestion (e.g., IL-2). For example, the oral dosage form (including capsules, tablets, pellets, granulates, powders) may be coated with a thin layer of excipient (e.g., polymers, cellulosic derivatives and/or lipophilic materials) that resists dissolution or disruption in the stomach, but not in the intestine, thereby allowing transit through the stomach in favor of disintegration, dissolution and absorption in the intestine.

The oral dosage form may be designed to allow slow release of the LAB strains and of the produced exogenous proteins, for instance as controlled release, sustained release, prolonged release, sustained action tablets or capsules. These dosage forms usually contain conventional and well-known excipients, such as lipophilic, polymeric, cellulosic, insoluble, and swellable excipients. Such formulations are described, for example, in the following references: Hansel et al., PHARMACEUTICAL DOSAGE FORMS AND DRUG DELIVERY SYSTEMS, 5th edition, William and Wilkins, 1990; Chien 1992, NOVEL DRUG DELIVERY SYSTEM, 2nd edition, M. Dekker; Prescott et al., NOVEL DRUG DELIVERY, J. Wiley & Sons, 1989; and Cazzaniga el al., *Int. J. Pharm.* 108(1):77-83 (1994).

The pharmaceutical dosage form (e.g. capsule) is typically coated with pH-dependent Eudragit® polymers to obtain gastric juice resistance and for the intended delivery at the terminal ileum and colon, where the polymers dissolve at pH 6.5. By using other Eudragit® polymers or a different ratio between the polymers, the delayed release profile could be adjusted, to release the bacteria for example in the duodenum or jejunum.

Pharmaceutical compositions commonly contain at least one pharmaceutically acceptable carrier. Non-limiting examples of suitable excipients, diluents, and carriers include preservatives, inorganic salts, acids, bases, buffers, nutrients, vitamins, fillers and extenders such as starch, sugars, mannitol, and silicic derivatives; binding agents such as carboxymethyl cellulose and other cellulose derivatives, alginates, gelatin, and polyvinyl pyrolidone; moisturizing agents such as glycerol/disintegrating agents such as calcium carbonate and sodium bicarbonate; agents for retarding dissolution such as paraffin; resorption accelerators such as quaternary ammonium compounds; surface active agents such as acetyl alcohol, glycerol monostearate; adsorptive carriers such as kaolin and bentonite; carriers such as propylene glycol and ethyl alcohol, and lubricants such as talc, calcium and magnesium stearate, and solid polyethyl glycols.

Pharmaceutically compatible binding agents, and/or adjuvant materials can be included as part of the composition. Tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or enteric agents. Further, a syrup may contain, in addition to the active compounds, sucrose as a sweetening agent and certain preservatives, dyes, colorings, and flavorings. It will be appreciated that the form and character of the pharmaceutically acceptable carrier is dictated by the amount of active ingredient with which it is to be combined, the route of administration and other well-known variables. The carrier(s) must be "acceptable" in the sense of being compatible with the other ingredients of the formulation and not deleterious to the recipient thereof.

Alternative preparations for administration include sterile aqueous or nonaqueous solutions, suspensions, and emulsions. Examples of non-aqueous solvents are dimethylsulfoxide, alcohols, propylene glycol, polyethylene glycol, vegetable oils such as olive oil and injectable organic esters such as ethyl oleate. Aqueous carriers include mixtures of alcohols and water, buffered media, and saline. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like. Various liquid formulations are possible for these delivery methods, including saline, alcohol, DMSO, and water based solutions.

Oral aqueous formulations include excipients, such as pharmaceutical grades of mannitol, lactose, starch, magnesium stearate, sodium saccharine, cellulose, magnesium carbonate and/or the like. These compositions take the form of solutions such as mouthwashes and mouth rinses, further comprising an aqueous carrier such as for example water, alcoholic/aqueous solutions, saline solutions, parenteral vehicles such as sodium chloride, Ringer's dextrose, and the like.

Aqueous mouthwash formulations are well-known to those skilled in the art. Formulations pertaining to mouthwashes and oral rinses are discussed in detail, for example, in U.S. Pat. Nos. 6,387,352, 6,348,187, 6,171,611, 6,165,494, 6,117,417, 5,993,785, 5,695,746, 5,470,561, 4,919,918, U.S. Patent Appl. No. 2004/0076590, U,S. Patent Appl. No. 2003/0152530, and U.S. Patent Appl. No. 2002/0044910.

Other additives may be present in the formulations of the present disclosure, such as flavoring, sweetening or coloring agents, or preservatives. Mint, such as from peppermint or spearmint, cinnamon, eucalyptus, citrus, cassia, anise and menthol are examples of suitable flavoring agents. Flavoring agents are optionally present in the oral compositions in an amount in the range of front 0 to 3%; optionally up to 2%, such as up to 0.5%, optionally around 0.2%, in the case of liquid compositions.

Sweeteners include artificial or natural sweetening agents, such as sodium saccharin, sucrose, glucose, saccharin, dextrose, levulose, lactose, mannitol, sorbitol, fructose, maltose, xylitol, thaumatin, aspartame, D-tryptophan, dihydrochalcones, acesulfame, and any combinations thereof, which may be present in an amount in the range of from 0 to 2%, optionally up to 1% w/w, such as 0.05 to 0.3% w/w of the oral composition.

Coloring agents are suitable natural or synthetic colors, such as titanium dioxide or CI 42090, or mixtures thereof. Coloring agents may be present in the compositions in an amount in the range of from 0 to 3%; optionally up to 0.1%, such as up to 0.05%, optionally around 0.005-0.0005%, in the ease of liquid compositions. Of the usual preservatives, sodium benzoate is typically used in concentrations insufficient substantially to alter the pH of the composition, otherwise the amount of buffering agent may need to be adjusted to arrive at the desired pH.

Other optional ingredients include humectants, surfactants (non-ionic, cationic or amphoteric), thickeners, gums and binding agents. A humectant adds body to the formulation and retains moisture in a dentifrice composition. In addition, a humectant helps to prevent microbial deterioration during storage of the formulation. It also assists in maintaining phase stability and provides a way to formulate a transparent or translucent dentifrice.

Suitable humectants include glycerin, xylitol, glycerol and glycols such as propylene glycol, which may be present in an amount of up to 50% w/w each, but total humectant may be no more than about 60-80% w/w of the composition. For example, liquid compositions may comprise up to about 30% glycerin plus up to about 5%, optionally about 2% w/w xylitol. Surfactants may be not anionic and may include polysorbate 20 or cocoamidobetaine or the like in an amount up to about 6%, optionally about 1.5 to 3%, w/w of the composition.

When the oral compositions as described herein are in a liquid form, said compositions typically may include a film-forming agent up to about 3% w/w of the oral composition, such as in the range of from 0 to 0.1%, optionally about 0.001 to 0.01%, such as about 0.005% w/w of the oral composition. Suitable film-formers include (in addition to sodium hyaluronate) those sold under the tradename, Gantrez™.

Liquid nutritional formulations for oral or enteral administration may comprise one or more nutrients such as fats, carbohydrates, proteins, vitamins, and minerals. Many different sources and types of carbohydrates, lipids, proteins, minerals and vitamins are known and can be used in the nutritional liquid embodiments described herein, provided that such nutrients are compatible with the added ingredients in the selected formulation, are safe and effective for their intended use, and do not otherwise unduly impair product performance.

These nutritional liquids are typically formulated with sufficient viscosity, flow, or other physical or chemical characteristics to provide a more effective and soothing coating of the mucosa while drinking or administering the nutritional liquid. These nutritional embodiments also may represent a balanced nutritional source suitable for meeting the sole, primary, or supplemental nutrition needs of the individual. Non-limiting examples of suitable nutritional liquids are described, e.g., in U.S. Pat. Nos. 5,700,782; 5,869,118; and 5,223,285.

Nutritional proteins suitable for use herein can be hydrolyzed, partially hydrolyzed or non-hydrolyzed, and can be derived from any known or otherwise suitable source such as milk (e.g., casein, whey), animal (e.g., meat, fish), cereal (e.g., rice, corn), vegetable (e.g., soy), or combinations thereof.

Eats or lipids suitable for use in the nutritional liquids include, but are not limited to, coconut oil, soy oil, corn oil, olive oil, safflower oil, high oleic safflower oil, MCT oil (medium chain triglycerides), sunflower oil, high oleic sunflower oil, structured triglycerides, palm and palm kernel oils, palm olein, canola oil, marine oils, cottonseed oils, and combinations thereof. Carbohydrates suitable for use in the nutritional liquids may be simple or complex, lactose-containing or lactose-free, or combinations thereof. Non-limiting examples of suitable carbohydrates include hydrolyzed corn starch, maltodextrin, glucose polymers, sucrose, corn syrup, corn syrup solids, rice-derived carbohydrate, glucose, fructose, lactose, high fructose corn syrup and indigestible oligosaccharides such as fructo-oligosaccharides (FOS), and combinations thereof.

The nutritional liquids as described herein may further comprise any of a variety of vitamins, non-limiting examples of which include vitamin A, vitamin D, vitamin E, vitamin K, thiamine, riboflavin, pyridoxine, vitamin B12, niacin, folic acid, pantothenic acid, biotin, vitamin C, choline, inositol, salts and derivatives thereof, and combinations thereof.

The nutritional liquids as described herein may further comprise any of a variety of minerals known or otherwise suitable for us in patients at risk of or suffering from T1D, non-limiting examples of which include calcium, phosphorus, magnesium iron, selenium, manganese, copper, iodine, sodium, potassium, chloride, and combinations thereof.

The LAB strains described herein can also be formulated as elixirs or solutions for convenient oral or rectal administration or as solutions appropriate for parenteral administration, for instance by intramuscular, subcutaneous or intravenous routes. Additionally, the nucleoside derivatives are also well suited for formulation as a sustained or prolonged release dosage forms, including dosage forms that release active ingredient only or optionally in a particular part of the intestinal tract, optionally over an extended or prolonged period of time to further enhance effectiveness. The coatings, envelopes, and protective matrices in such dosage forms may be made, for example, from polymeric substances or waxes well known in the pharmaceutical arts.

The compositions as described herein may include pharmaceutical dosage forms such as lozenges, troches or pastilles. These are typically discoid-shaped solids containing the active ingredient in a suitably flavored base. The base may be a hard sugar candy, glycerinated gelatin, or the combination of sugar with sufficient mucilage to give it form. Troches are placed in the mouth where they slowly dissolve, liberating the active ingredient for direct contact with the mucosa.

The troche embodiments can be prepared, for example, by adding water slowly to a mixture of the powdered active, powdered sugar, and a gum until a pliable mass is formed. A 7% acacia powder can be used to provide sufficient adhesiveness to the mass. The mass is rolled out and the troche pieces cut from the flattened mass, or the mass can be rolled into a cylinder and divided. Each cut or divided piece is shaped and allowed to dry, to thus form the troche dosage form.

If the active ingredient is heat labile, it may be made into a lozenge preparation by compression. For example, the granulation step in the preparation is performed in a manner similar to that used for any compressed tablet. The lozenge is made using heavy compression equipment to give a tablet that is harder than usual as it is desirable for the dosage form to dissolve or disintegrate slowly in the mouth. Ingredients are typically selected to promote slow-dissolving characteristics.

In an exemplary formulation, the LAB strains may be incorporated in a bioadhesive carrier containing pregelatinized starch and cross-linked poly (acrylic acid) to form a bioadhesive tablet and a bioadhesive gel suitable for buccal application (i.e., having prolonged bioadhesion and sustained drug delivery).

A powder mixture of the LAB strains, bioadhesive polymers (pregelatinized starch and cross-linked poly (acrylic acid) coprocessed via spray drying), sodium stearyl fumarate (lubricant) and silicon dioxide (glidant) may be processed into tablets (weight: 100 mg; diameter: 7 mm). The methods for the production of these tablets are well known to the person skilled in the art and has been described before for the successful development of bioadhesive tablets containing various drugs (miconazol, testosterone, fluoride, ciprofloxacin) (Bruschi M. L. and de Freitas O., *Drug Development and Industrial Pharmacy*, 2005 31: 293-310).

To optimize the formulation, the drug load in the tablets and the ratio between starch and poly (acrylic acid) can be varied. Based on previous research, the maximum drug load in the co-processed bioadhesive carrier is about 60% (w/w) and the starch/poly (acrylic acid) ratio can be varied between 75/25 and 95/5 (w/w). During the optimization study the bioadhesive properties of the tablets and the drug release from the tablets are the main evaluation parameters, with the standard tablet properties (hardness, friability) as secondary evaluation criteria.

The LAB strains may be incorporated into an aqueous dispersion of pregelatinized starch and cross-linked poly (acrylic acid). This polymer dispersion is prepared via a standard procedure using a high shear mixer.

Similar to the tablet, the drug load of the gel and the starchlpoly (acrylic acid) ratio may need to be optimized in order to obtain a gel having optimal adherence to the esophageal mucosa. For a gel, the concentration of the polymers in the dispersion is an additional variable as it determines the viscosity of the gel, hence its muco-adhesive properties.

The model to screen the bioadhesive properties of polymer dispersions to the mucosa of esophagus has been described in detail by Batchelor et al. (*Int. J. Pharm.*, 238: 123-32, 2002).

Other routes and forms of administration include food preparations containing the live LAB strains. In some examples, the bioactive polypeptide-expressing LAB strains may be included into a dairy product.

The pharmaceutical compositions described herein may be prepared by any known or otherwise effective method for formulating or manufacturing the selected dosage form. For example, the LAB strains can be formulated along with common, e.g., pharmaceutically acceptable carriers, such as excipients and diluents, formed into oral tablets, capsules, sprays, lozenges, treated substrates (e.g., oral or topical swabs, pads, or disposable, non-digestible substrate treated with the compositions described herein); oral liquids (e.g., suspensions, solutions, emulsions), powders, suppositories, or any other suitable dosage form. In some embodiments, the present disclosure provides a method for the manufacture of a pharmaceutical composition. Exemplary methods include: contacting the LAB strains (e.g., *L. lactis*) containing the IL-2 gene and the T1D-specific antigen gene (or which is capable of expressing the IL-2 and the T1D-specific antigen) with a pharmaceutically acceptable carrier, thereby forming the pharmaceutical composition. In some examples, the method may further include: growing the LAB strains in a medium. The method may further include freeze-drying a liquid containing the microorganism, wherein the liquid optionally includes the pharmaceutically acceptable carrier.

Unit Dosage Forms

The current disclosure further provides unit dosage forms comprising a certain amount of the LAB strain optionally in combination with a food-grade or pharmaceutically acceptable carrier, wherein the LAB strain comprises: an interleukin-2 (IL-2) gene; and a type-1 diabetes mellitus (T1D)-specific antigen gene. Exemplary unit dosage forms contain from about $1 \times 10^3$ to about $1 \times 10^{14}$ colony-forming units (cfu) of the LAB (e.g., *L. lactis*). Other exemplary unit dosage forms contain from about $1 \times 10^4$ to about $1 \times 10^{13}$ colony-forming units (cfu) of the LAB (e.g., *L. lactis*), or from about $1 \times 10^4$ to about $1 \times 10^{12}$ colony-forming units (cfu) of the LAB (e.g., *L. lactis*). In other embodiments, the unit dosage form comprises from about $1 \times 10^5$ to about $1 \times 10^{12}$ colony-forming units (cfu), or from about $1 \times 10^6$ to about $1 \times 10^{12}$ colony-forming units (cfu) of the LAB (e.g., *L. lactis*). In other embodiments, the unit dosage form comprises from about $1 \times 10^9$ to about $1 \times 10^{12}$ colony-forming units (cfu), or from about $1 \times 10^9$ to about $1 \times 10^{12}$ colony-forming units (cfu) of the LAB (e.g., *L. lactis*). In yet other embodiments, the unit dosage form comprises from about $1 \times 10^9$ to about $1 \times 10^{11}$ colony-forming units (cfu), or from about $1 \times 10^9$ to about $1 \times 10^{10}$ colony-forming units (cfu) of the LAB (e.g., *L. lactis*). In yet other embodiments, the unit dosage form comprises from about $1 \times 10^7$ to about $1 \times 10^{11}$ colony-forming units (cfu), or from about $1 \times 10^8$ to about $1 \times 10^{10}$ colony-forming units (cfu) of the LAB (e.g., *L. lactis*).

In yet other embodiments, the unit dosage form comprises from about $1 \times 10^9$ to about $1 \times 10^{10}$ colony-forming units (cfu), or from about $1 \times 10^9$ to about $100 \times 10^9$ colony-forming units (cfu) of the LAB (e.g., *L. lactis*).

The unit dosage form can have any physical form or shape. In some embodiments, the unit dosage form may be adapted for oral administration. In some examples according to these embodiments, the unit dosage form may be in the form of a capsule, a tablet, or a granule. Exemplary capsules include capsules filled with micro-granules. In some embodiments, the LAB (e.g., *L. lactis*) contained in the dosage form is in a dry-powder form. For example, the LAB is in a freeze-dried powder form, which is optionally compacted and coated.

EXAMPLES

The following examples are provided in order to demonstrate and further illustrate certain representative embodiments and aspect of the present disclosure and are not to be construed as limiting the scope of the specification or claims.

Example 1. Construction of *Lactococcus lactis* Secreting hIL-2 (LL-IL-2)

A *Lactococcus lactis* strain, which can secrete human IL-2 (LL-IL-2) was constructed relative to *Lactococcus lactis* MG1363 (parent strain). See, e.g., Casson M J, *J. Bacteriol.* 1983, 154(1):1-9. In LL-IL-2, the following modifications were introduced into the genome of the bacteria:

(a) The thymidylate synthase gene (thyA; Gene ID: 4798358; location: NC_009004.1 (930251 . . . 931090)) was removed to ascertain environmental containment.

(b) Trehalose-6-phosphate phosphorylase gene (trePP; Gene ID: 4797140; location: NC_909004.1 (449195 . . . 451504)) was removed to allow accumulation of exogenous trehalose.

(c) Trehalose-6-phosphate phosphatase (otsB; Gene ID: 1036914; Locus tag c2311) was positioned downstream of unidentified secreted 45-kDa protein gene (usp45; Gene ID: 4797218; location: NC_909004.1 (2462440 . . . 2463825, complement)) to facilitate conversion of trehalose-6-phosphate to trehalose.

(d) The constitutive promoter of the HU-like DNA-binding protein gene (PhllA; Gene ID: 4797353; location: NC_009004.1 (490275 . . . 490550)) was added to precede the putative phosphotransferase genes in the trehalose operon (trePTS; ptsI and ptsII; LLMG_RS02300 and LLMG_RS02305; Gene ID: 4797778; location: NC_009004.1 (446937 . . . 447422) and Gene ID: 4797093; location: NC_009004.1 (447563 . . . 449128), respectively) to potentiate trehalose uptake.

(e) The gene encoding cellobiose-specific PTS system IIC component (Gene ID: 4796893; location: NC_009004.1 (430271 . . . 431608)), ptcC, was deleted to increase trehalose retention.

(f) A gene encoding a fusion of usp45 secretion leader (Ssusp45) with the hIL-2 gene, encoding human interleukin-2 (hIL-2; UniProt: P60568, an 21-153) was positioned downstream of the phosphopyruvate hydratase gene (eno; Gene ID: 4797432; location: NC_009004.1 (606184 . . . 607485)), to allow expression and secretion of hIL-2. The hIl-2 expression unit was transcriptionally and translationally coupled to eno by use of the intergenic region preceding the highly expressed *L. lactis* MG1363 50S ribosomal protein L30 gene (rpmD; Gene ID: 4797873; location: NC_009004.1 (2316732 . . . 2316911, complement)). An exemplary nucleotide sequence encoding the above fusion of Ssusp45 and hIL-2 downstream of enoA, linked by rpmD is depicted in FIG. 1 (SEQ ID NO: 46).

FIG. 2 provides a schematic overview of the above described genetic loci.

The experiments also involve a control strain (LL-Control) having genetic traits comparable to LL-IL-2, except that the control strain does not contain the constructs for the expression of IL-2. The genetic traits for LL-IL-2 and the LL-Control strains are summarized in Table 1 below.

TABLE 1

Overview of Genetic Characteristics of Various LL Strains

| Strain | a) trehalose operon | | b) ptcC | c) otsB | d) thyA | e) eno locus | f) gapB locus |
| | trePTS | trePP | | | | | |
| --- | --- | --- | --- | --- | --- | --- | --- |
| MG1363 | wt | wt | wt | — | wt | wt | wt |
| LL-Control | PhllA>>PTS | Δ | Δ | usp45>>otsB | Δ | wt | wt |
| LL-IL-2 | PhllA>>PTS | Δ | Δ | usp45>>otsB | Δ | eno>>hIL-2 | wt |

Referring to Table 1, trePTS expression (at the trehalose operon) can be as in the wild type (wt) or driven by the HllA promoter (PhllA>>PTS); trePP can be wt or deleted (Δ); ptcC can be wt or Δ; otsB can be absent (−) or located downstream of and expressed from usp45 (usp45>>otsB); thyA can be wt or Δ; eno locus can be wt (−) or contain hIL-2. All gapB loci are wt, in contrast to LL-PINS/IL-2, which carries gapB>>pins as described herein below.

The genetic modifications were carried out using double homologous recombination at the 5' and 3' end of these genetic traits. A similar method has been described for the construction of L. lactis Thy12 (see, e.g., Steidler L., et al., Nat. Biotechnol. 2003, 21(7):785-789), with the difference that the helper plasmid pVE6007 was not used. The procedure involved erythromycin selection as an intermediate step, and the erythromycin selection marker was subsequently removed. As a result, LL-IL-2 has substantially no residual erythromycin resistance.

Carrier Plasmids

The modification method makes use of carrier plasmids derived from the conditionally non-replicative pORI19. See, e.g., Law J., et al., Bacteriol. 1995; 177(24):7011-7018. This replication protein A gene deficient (repA)− plasmid, as all of its repA− derivatives, cannot replicate in repA− L. lactis. The repA+ L. lactis strain LL108 (see Sanders et al., J. Bacteriol. 1995, 177(18):5254-5260) was used as a construction host. Carrier plasmids were designed so that up to 1 kb cross over (XO) areas, identical to the ones flanking the wild type sequence on the bacterial chromosome, are positioned 5' and 3' of the plasmid borne modification. Exemplary plasmids are used to insert hIL-2 downstream of eno in such way that both are coupled by the rpmD intergenic region. All plasmid construction was performed by use of standard molecular biological methods.

Chromosomal Modifications

Derivatives of plasmid pORI19 carry an erythromycin selection marker (enrmC, 23S RNA methylase gene; Gene ID: 1263245) and cannot replicate in MG1363 or any of its derivatives. Upon introduction of such plasmid into MG1363, erythromycin selection was applied to the culture. Resistant colonies were selected on solid agar plates containing erythromycin. Because of the replication incompetence of the carrier plasmids, erythromycin-resistant bacteria can only arise following a first homologous recombination either at the 5' or 3' target site. Homologous recombination can be verified further by PCR.

Release of erythromycin selection enabled the excision of the carrier plasmid from the bacterial chromosome by a second homologous recombination, at either the 5' or 3' target site. For some erythromycin sensitive progeny, the second homologous recombination can occur at the target site alternative to the one of the first homologous recombination. This event replaces the wild type with the mutant on the bacterial chromosome and can be identified by PCR. Adequate subculture will rapidly dilute out all remnants of the carrier plasmid.

The presence of the β-glucuronidase gene (uidA, Gene ID: 946149) in the carrier plasmids, where it propagates along with ermC enables the identification of erythromycin sensitive and erythromycin resistant colonies. For example, bacterial suspensions were plated on 5-bromo-4-chloro-3-indolyl-beta-D-glucuronic acid (X-Gluc) containing solid agar plates. Glueuronidase (GUS) expressing (and therefore erythromycin resistant) clones will appear blue by conversion of X-glue to its insoluble, blue reaction product dichlorodibromoindigo, while erythromycin sensitive clones have also lost the uidA gene and therefore remain white. The identification of blue and white clones at relevant stages in the above described process greatly facilitated this approach.

PCR Analysis

Figure 4:
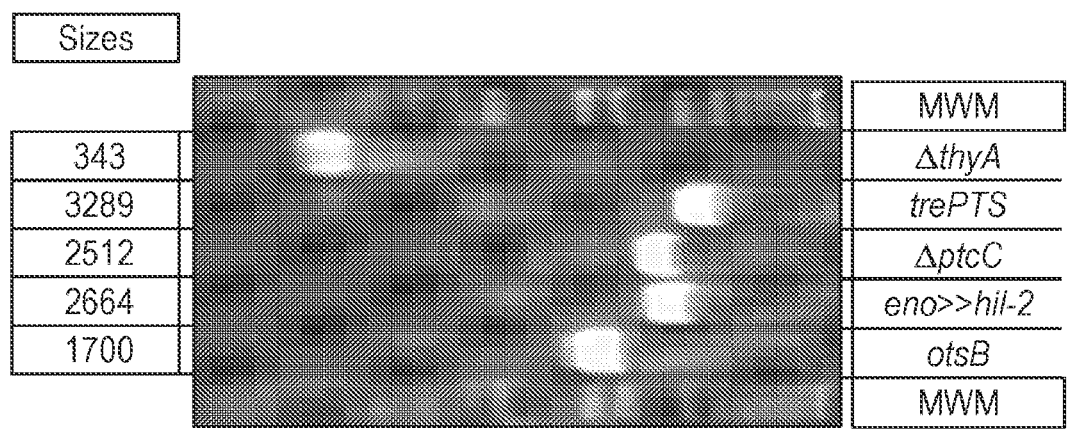
FIG. 4 depicts a 1.2% agarose gel analysis of PCR fragments generated from LL-IL-2.

Colonies showing the appropriate homologous recombination either at the 3' or 5' target site were analyzed by PCR. DNA fragments were purified using the Qiagen MinElute PCR Purification Kit. DNA sequences generated were identical to those predicted. FIG. 4 shows a 1.2% agarose gel of PCR fragments generated using the oligonucleotides listed in Table 2, Herculase II Fusion DNA polymerase (Agilent Teehnologies #600677), and appropriate temperature cycles 50/120/30. Results demonstrated the presence of the desired genetic traits in LL-IL-2.

TABLE 2

Oligonucleotides Used for the Construction of LL-IL-2

| | Sequence | Detection/ PCR of |
| --- | --- | --- |
| SEQ ID NO: 47 | AATCCAATGAC GGCACTTCTTC | thyA locus |
| SEQ ID NO: 48 | CTTGTCGTTAA AGCCTATTC | thyA locus |
| SEQ ID NO: 49 | CGTAACCATGT AAAAGCACTTC TG | otsB |

TABLE 2-continued

Oligonucleotides Used for
the Construction of LL-IL-2

| | Sequence | Detection/PCR of |
|---|---|---|
| SEQ ID NO: 50 | GTAATTCTAAT GCTGGTGGG | otsB |
| SEQ ID NO: 51 | ATTACGCCATC TAAATCAAAC | trePTS |
| SEQ ID NO: 52 | CATCGCTGAAG CTATCATCG | eno hil-2 locus |
| SEQ ID NO: 53 | GATGGCTGAAG CTCCAACTC | trePTS |
| SEQ ID NO: 54 | GCATGGAAGAG GACAAAGAG | eno hil-2 locus |
| SEQ ID NO: 55 | AACCTGTGGGA GGGCGAAAG | ptcC locus |
| SEQ ID NO: 56 | TGGGTCGTGAA TACTTCC | ptcC locus |

In FIG. 4, molecular weight markers (MWM; Invitrogen 10488-85 Trackit 1 kb plus DNA Ladder) indicate base pairs: 100, 200, 300, 400, 500, 650, 850, 1000, 1650, 2000, 3000, 4000, 5000, and higher. Expected sizes of DNA fragments are also indicated in base pairs.

The bacterial genome of LL-IL-2 was further sequenced. The experimentally determined DNA sequences of all genetic traits in LL-IL-2 that differ from those of the parent strain MG1363 were found to be identical as expected.

Expression hIL-2

Expression of hIL-2 by LL-IL-2 was measured using ELISA and western blot. In the ELISA experiment (utilizing R&D systems huIL-2 #DY202), 47.1 ng/mL of hIL-2 was measured in the culture supernatant, while a control strain did not produce hIL-2.

Figure 5:
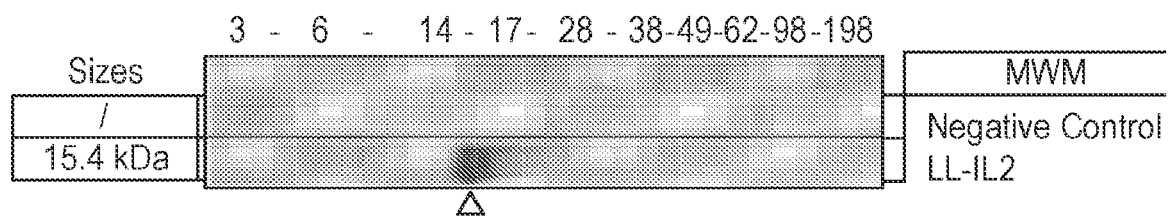
FIG. 5 depicts a Western blot showing the presence of hIL-2 in LL-IL-2 culture supernatants.

FIG. 5 is a Western blot showing the presence of hIL-2 in the culture supernatant of LL-IL-2. The Western blot was generated using goat anti-human IL-2 (1/1000 R&D systems AF-202-NA) as the first antibody, incubation with rabbit anti-goat—AP (1/1000 Southern Biotech #6160-04) as the detection antibody, and subsequent NBT/BCIP staining (Roche NBT/BCIP tablets, #11 697 471 001). Equivalents of 1 ml bacterial cultures of LL-IL-2 and control strains were loaded onto the protein gel. Invitrogen SeeBlue® Plus2 Pre-Stained standard was used as molecular weight marker (MWM). The data indicates that LL-IL-2 secretes full length hIL-2 (i.e., as encoded by SEQ ID NO: 46).

Bacteria were cultured in GM17 media, which is M17 broth (Oxoid; #CM0817) supplemented with 0.5% glucose or GM17T medium (GM17 supplemented with 200 µM thymidine).

Example 2. *Lactococcus lactis* Secreting PINS and hIL-2 (LL-PINS/IL-2)

The construction and selection of strain LL-PINS/IL-2, a derivative of *Lactococcus lactis* (*L. lactis*) MG1363, is described. LL-PINS/IL-2 includes the following genetic traits: (a) the thymidylate synthase gene (thyA; Gene ID: 4798358; location: NC_009004.1 (930251 . . . 931090)) was removed to warrant environmental containment; (b) the trehalose-6-phosphate phosphorylase gene (trePP; Gene ID: 4797140; location: NC_009004.1 (449195 . . . 451504)) was removed to allow accumulation of exogenously added trehalose; (c) the trehalose-6-phosphate phosphatase gene (otsB; Gene ID: 1036914; Locus tag c2311) was positioned downstream of unidentified secreted 45-kDa protein gene (usp45; Gene ID: 4797218; location: NC_909004.1 (2462440 . . . 2463825, complement)) to facilitate conversion of trehalose-6-phosphate to trehalose; (d) the otsB expression unit was transcriptionally and translationally coupled to gapB using the intergenic region preceding the highly expressed *L. lactis* MG1363 50S ribosomal protein L30 gene (rpmD; Gene ID: 4797873; location: NC_009004.1 (2316732 . . . 2316911, complement)); (e) the constitutive promoter of the HU-like DNA-binding protein gene (PhllA; Gene ID: 4797353; location: NC_009004.1 (490275 . . . 490550)) precedes the putative phosphotransferase genes in the trehalose operon (trePTS; ptsI and ptsII; LLMG_RS02300 and LLMG_RS02305; Gene ID: 4797778; location: NC_009004.1 (446937 . . . 447422) and Gene ID: 4797093; location: NC_009004.1 (447563 . . . 449128) respectively) to potentiate trehalose uptake; (f) the gene encoding cellobiose-specific PTS system IIC component (Gene ID: 4796893; location: NC_009004.1 (430271 . . . 431608)), ptcC, was disrupted (tga at codon position 30 of 446; tga30) to ascertain trehalose retention after accumulation; (g) a gene encoding a fusion of usp45 secretion leader (SSusp45) with the pins gene, encoding human proinsulin (PINS; UniProt: P01308, aa 25-110) is positioned downstream of the glyceraldehyde 3-phosphate dehydrogenase gene (gapB; Gene ID: 4797877; location: NC_009004.1 (2492509 . . . 2493519, complement)), to allow expression and secretion of proinsulin; (h) the pins expression unit was transcriptionally and translationally coupled to gapB by use of the intergenic region preceding the highly expressed *L. lactis* MG1363 50S ribosomal protein L30 gene (rpmD; Gene ID: 4797873; location: NC_009004.1 (2316732 . . . 2316911, complement)); and (i) a gene encoding a fusion of usp45 secretion leader (SSusp45) with the hIL-2 gene, encoding human interleukin-2 (hIL-2; UniProt: P60568, aa 21-153) was positioned downstream of the phosphopyruvate hydratase gene (eno; Gene ID: 4797432; location: NC_009004.1 (606184 . . . 607485)), to allow expression and secretion of hIL-2. The hIl-2 expression unit was transcriptionally and translationally coupled to eno by use of the intergenic region preceding the highly expressed *L. lactis* MG1363 50S ribosomal protein L30 gene (rpmD; Gene ID: 4797873; location: NC_009004.1 (2316732 . . . 2316911, complement)).

All genetic traits of LL-PINS/IL-2 reside on the bacterial chromosome. The genetic background of this strain warrants: constitutive secretion of PINS and hIL-2; strict dependence on exogenously added thymidine for growth and survival; and the capacity to accumulate and retain trehalose to resist, e.g., bile acid lysis.

Figure 7:
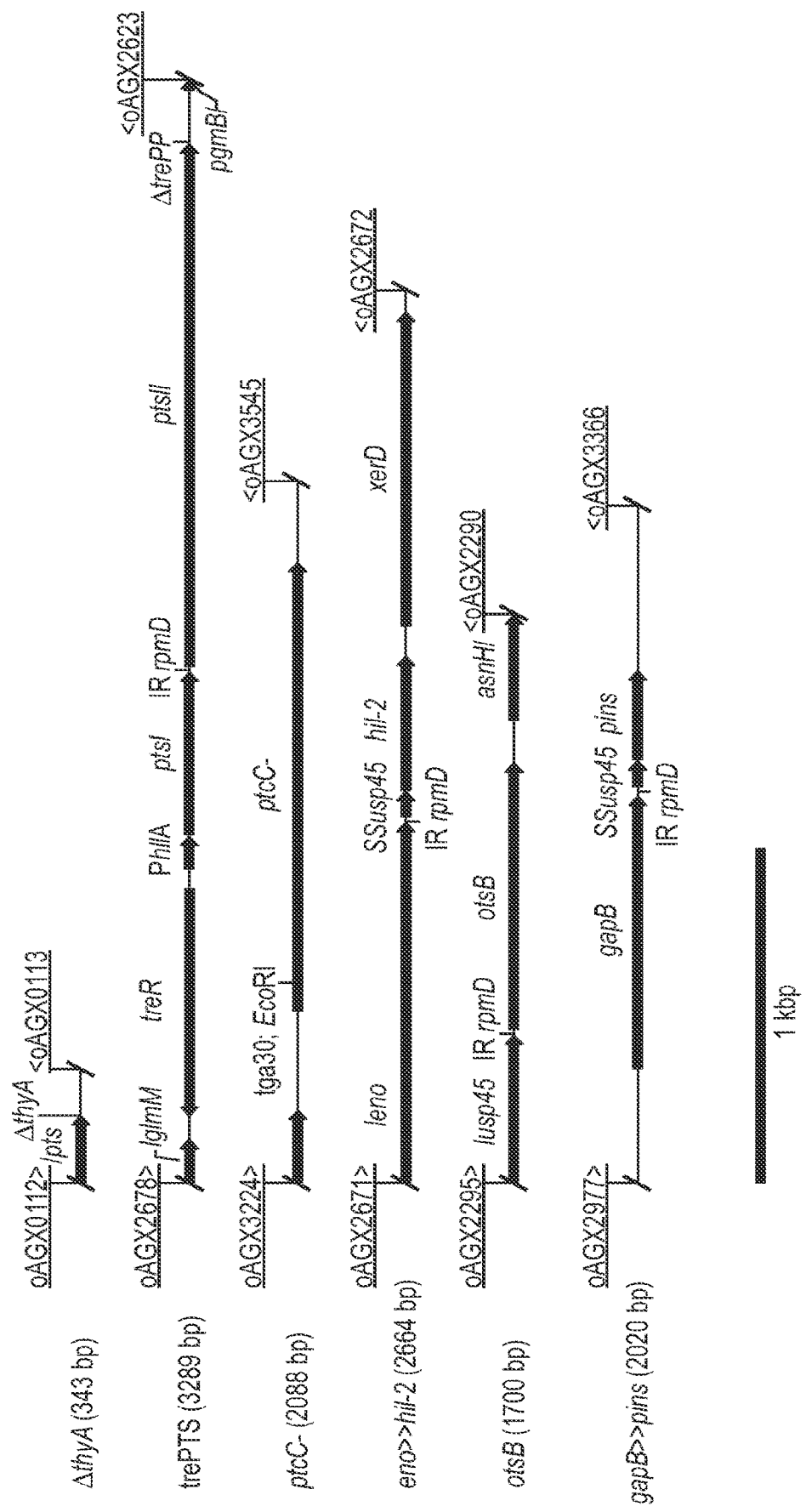
FIG. 7 depicts a schematic overview of relevant genetic loci of LL-PINS/IL-2: ΔthyA, trePTS (ΔtrePP), otsB, ptcC-, gapB>>pins and eno>>hIl-2 with indication of the relevant oligonucleotide binding sites, EcoRI restriction site, (/truncated/) genetic characters, intergenic regions (IR), PCR amplification product sizes (bp).

An exemplary nucleotide sequence encoding the above fusion of SSusp45 and PINS downstream of the gapB gene, linked by the intergenic region rpmD is depicted in FIG. 6 (SEQ ID NO: 57). FIG. 7 provides a schematic overview of the above described genetic loci. Genetic traits were introduced into the bacterial genome as outlined in Example 1. Bacterial strains were grown and analyzed as described in Example 1 above. Oligonucleotides used in the construction and analysis of LL-PINS/IL-2 are summarized in Table 3 below.

TABLE 3

Oligonucleotides Used for the Construction of LL-PINS/IL-2

| | Sequence | Detection/PCR of |
|---|---|---|
| SEQ ID NO: 47 | AATCCAATGAC GGCACTTCTTC | thyA locus |
| SEQ ID NO: 48 | CTTGTCGTTAA AGCCTATTC | thyA locus |
| SEQ ID NO: 49 | CGTAACCATGT AAAAGCACTTC TG | otsB |
| SEQ ID NO: 50 | GTAATTCTAA TGCTGGTGGG | otsB |
| SEQ ID NO: 51 | ATTACGCCATC TAAATCAAAC | trePTS |
| SEQ ID NO: 52 | CATCGCTGAAG CTATCATCG | eno hil-2 locus |
| SEQ ID NO: 58 | AACCGCTTTCA GAAGAAGGG | gapB pins locus |
| SEQ ID NO: 53 | GATGGCTGAAG CTCCAACTC | trePTS |
| SEQ ID NO: 54 | GCATGGAAGAG GACAAAGAG | eno hil-2 locus |
| SEQ ID NO: 59 | CACCGAATTAA CACGCATTATG ACTT | ptcC locus |
| SEQ ID NO: 60 | TTTCGCTGGG AAAGCACAC | gapB pins locus |
| SEQ ID NO: 61 | GCGTGTCCAAG CAATAGATG | ptcC locus |

Figure 9:
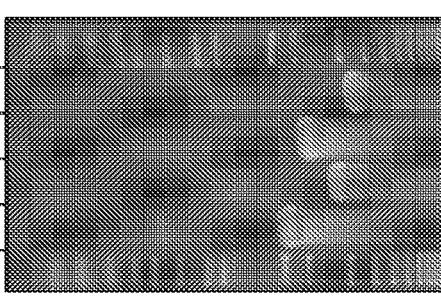
FIG. 9 depicts a 1.2% agarose gel analysis of PCR fragments generated from LL-PINS/IL-2.

FIG. 9 depicts a 1.2% agarose gel analysis of PCR fragments from LL-PINS/IL-2 indicating the presence of the desired genetic traits: trePTS, ptcC-, eno>>hIl-2, otsB, gapB>>pins. In FIG. 9, molecular weight markers (MWM; Invitrogen 10488-85 Trackit 1 kb plus DNA Ladder) indicate base pairs: 100, 200, 300, 400, 500, 650, 850, 1000, 1650, 2000, 3000, 4000, 5000, and higher. Expected sizes of DNA fragments are also indicated in base pairs.

The bacterial genome of LL-PINS/IL-2 was further sequenced. The experimentally determined DNA sequences of all genetic traits in LL-PINS/IL-2 that differ from those of the parent strain MG1363 were found to be identical to the predicted.

Figure 8:
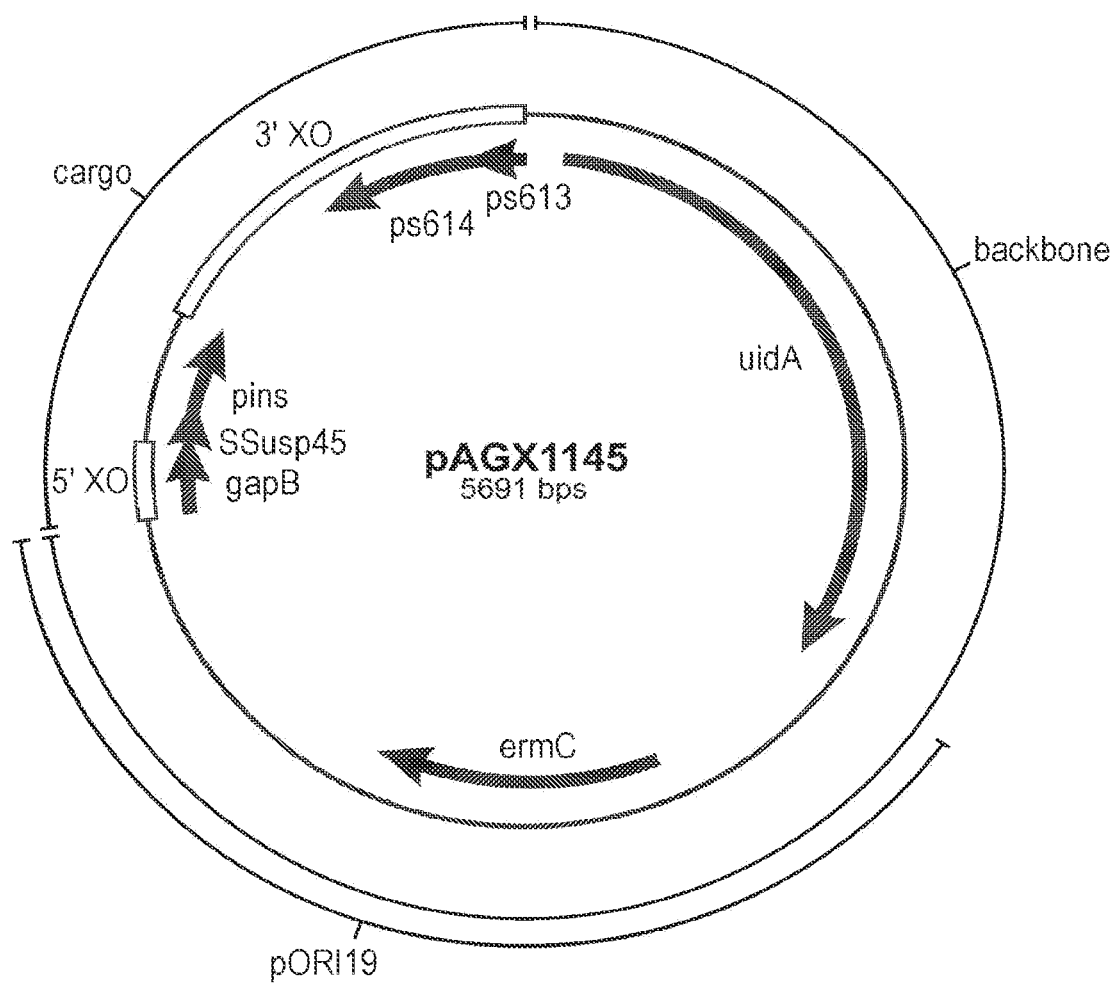
FIG. 8 depicts an exemplary carrier plasmid with a backbone that exists of a pORI19 fragment to which a PhllA>>β-glucuronidase (uidA; Gene ID: 946149) expression module was added; a cargo region containing pins downstream of gapB coupled by intergenic region rpmD, and flanked by cross over (XO) areas, positioned 5' and 3' of gapB>>pins; as well as an erythromycin selection marker: erythromycin resistant 23S RNA methylase gene (ermC).

Homologous recombination methods involved carrier plasmids derived from the conditionally non-replicative pORI19, described above. Carrier plasmids were designed in such way that up to 1 kb cross over (XO) areas, identical to the ones flanking the wild type sequence on the bacterial chromosome, are positioned 5' and 3' of the plasmid borne modification. An example of a carrier plasmid is pAGX1145, a diagram of which is shown in FIG. 8. The plasmid is used to insert pins downstream of gapB in such way that both are coupled by the rpmD intergenic region. A similar plasmid, pAGX1372 (see annex: pAGX1372.gbk) is used to insert hIl-2 downstream of eno. All plasmid construction was performed by use of standard molecular biological methods.

PINS and hIL-2 Expression

Expression of PINS and hIL-2 by LL-PINS/IL-2 was measured using ELISA and western blot. Culture supernatants from LL-PINS/IL-2 contained 0.6 ng/mL PINS and 28.2 ng/mL of hIL-2, while a control strain (LL-Control) did not produce either polypeptide. A MG 1363 bacterial strain expressing PINS from a plasmid vector (LL-PINS) was used as a positive control. PINS content in the supernatants was determined using Mercodia cat. No. 10-1118-01, and hIL-2 content was determined by use of R&D system's huIL-2 #DY202.

Figure 10A:
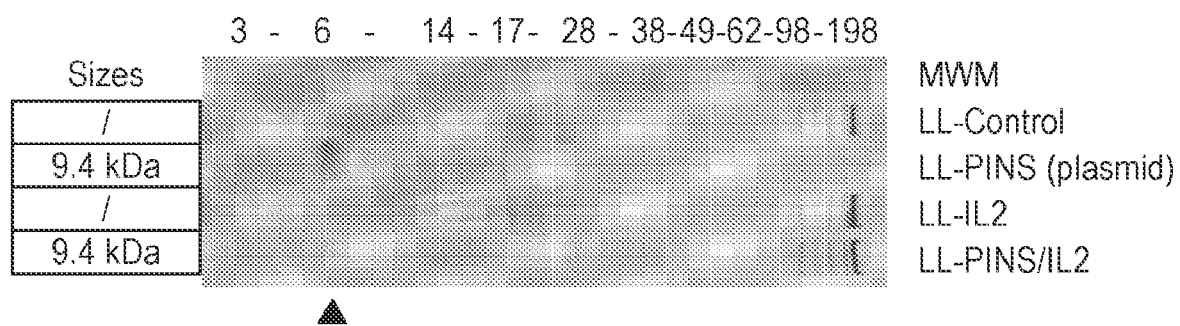
FIGS. 10A and 10B depict Western blots showing (1) the presence of PINS (black arrowhead) in LL-PINS/IL-2 culture supernatants (FIG. 10A), and (2) the presence of hIL-2 (open arrowhead) in LL-PINS/IL-2 culture supernatants (FIG. 10B).
Figure 10B:
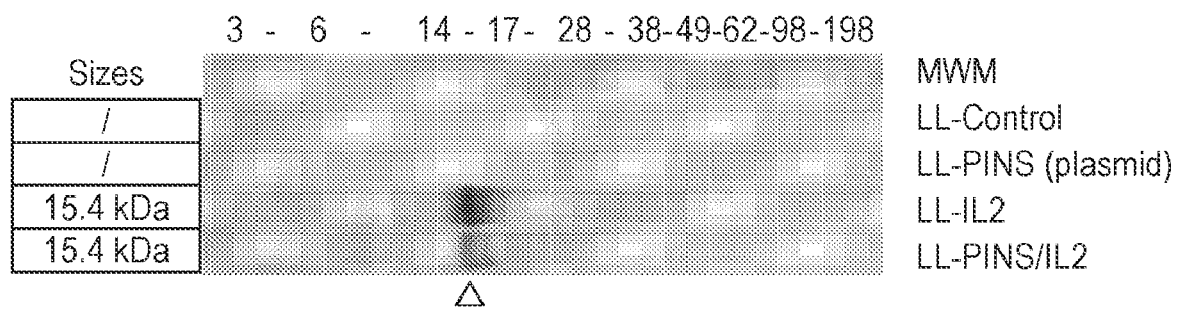

FIG. 10 is a Western blot showing the presence of PINS and hIL-2 in the culture supernatant of LL-PINS/IL-2. Equivalents of 1 ml bacterial cultures were loaded onto the protein gel. The Western blot was generated using goat polyclonal anal insulin B (Santa Cruz N-20; se-7838) and goat anti-human IL-2 (1/1000 R&D systems AF-202-NA) as first antibodies for PINS and hIL-2 respectively, incubation with rabbit anti-goat—AP (1/1000 Southern Biotech #6160-04) detection antibody, and subsequent NBT/BCIP staining (Roche NBT/BCIP tablets, #11 697 471 001. Invitrogen SeeBlue® Plus2 Pre-Stained standard was used as molecular weight marker (MWM). The data indicates that LL-PINS/IL-2 secretes full length PINS and hIL-2.

Bacteria were cultured in GM17 media, which is M17 broth (Oxoid; #CM0817) supplemented with 0.5% glucose or GM17T medium (GM17 supplemented with 200 µM thymidine).

Example 3. Pharmacodynamic Studies to Examine the Effect of Two Bacterial Strains on Diabetes Progression, *Lactococcus lactis* (LL) Secreting Proinsulin (LL-PINS) and hIL-2 (LL-IL-2)

Bacteria were cultured as described in Takiishi, T. et al., *J. Clin. Inv.* 2012, 122(5): 1717-1725.

For example, single colonies of the respective *L. lactis* were inoculated in GM17T (M17, Oxoid, Hampshire, UK, supplemented with 0.5% glucose, 200 µM thymidine) and grown overnight to saturation. A 1/25 dilution of this culture was pre-grown for 3 hours in GM17T. Bacteria were harvested by centrifugation and further incubated for 3 hours in buffered culture medium (1×BM9 salts, 0.5% casitone (Difco, BD Biosciences), 0.5% glucose, 25 mM NaHCO$_3$, 25 mM Na$_2$CO$_3$, 2 mM MgSO$_4$, 0.1 µM CaCl$_2$ ((BM9 Medium) (Schotte, et al. (2000) *Enzyme Microb. Technol.* 27(10):761-765) supplemented with 200 µM thymidine) (BM9T). Bacteria were removed by centrifugation and supernatant samples were taken for analysis by Western blot and ELISA. For the western blot, proteins were prepared from crude BM9T *L. lactis* supernatants by deoxycholate/TCA/acetone precipitation and were dissolved in SDS-PAGE sample buffer. Bacterial cell pellets were disrupted to obtain intracellular fractions. Culture supernatants (equivalent of 1 ml culture) and intracellular (equivalent of 50 µl culture) protein fractions were separated by SDS-12% PAGE, immunoblotted and revealed by goat anti-hIL-2 and detected using a rabbit anti-goat antibody and NBT/BCIP.

Stock solutions of all strains are stored in −20° C. in 50% glycerol iu GM17. Bacteria are cultured in GM17 medium, i.e. M17 (Difco Laboratories, Detroit, MI) supplemented with 0.5% glucose.

New-onset diabetic NOD mice, having positive glycosuria and two consecutive blood glucose measurements exceeding 200 mg/dl were used in the experimental set-up. Mice were allocated to three experimental treatment groups:

(1) untreated controls, (2) LL-PINS-treated, and (3) mice treated with a combination of LL-PINS and LL-IL-2, for a period of 6 weeks.

This experiment involved two different LL strains. One strain constitutively expresses PINS and the other strain constitutively expresses IL-2. Mice were treated at a dose of $2\times10^9$ CFU by oral gavage 5 times weekly for six (6) weeks.

Mice were followed for either 42 days (therapy stop) or 100 days (8 weeks after therapy stop). Besides the initial follow up for disease remission until 100 days, additional mice (untreated and LL-PINS+LL-IL-2 treated) were euthanized at 42 days after treatment initiation and peripheral blood and different organs were used for further analyses. Serum samples for measuring insulin autoantibodies (IAA), inflammatory cytokines, and glucose-stimulated C-peptide were collected prior to treatment and after stopping therapy (day 42). In all experimental groups (both disease remitters and non-remitters) the peripheral immune system (phenotype and function) was assessed. Pancreas samples were taken for histology (insulitis) and insulin content determination (IC) at therapy stop (day 42).

T1D and Insulitis Assessment

NOD mice were screened for the onset of diabetes by evaluating glucose concentrations in the urine (Clinistix; Bayer Diagnostics) and venous blood (Accu-Chek® Aviva; Roche Diagnostics). Random-fed blood glucose measurements were collected between 8 and 11 am. Mice were classified as diabetic when having positive glycosuria and two consecutive blood glucose measurements exceeding 200 mg/dl. Diabetes remission was defined as an absence of glycosuria and glycemia values <250 mg/dl on two consecutive days.

Pancreatic samples were fixed in formaldehyde solution and processed for paraffin embedding. 7-µm-thick sections were stained with hematoxylin/eosin and the degree of insulitis was evaluated microscopically. Damages to the islets were graded as follows: 0: no infiltration; 1: peri-insulitis; 2: islets with lymphocyte infiltration in less than 50% of the area; 3: islets with lymphocyte infiltration in more than 50% of the area; 4: islets completely destroyed.

Auto-Antibody Detection

Serum IAA were measured at disease onset and at therapy discontinuation (day 42) by RIA assay. It was tested whether LL-PINS+LL-IL-2 vaccination can correct hyperglycemia (disease remission) and maintain normoglyeernia in new-onset diabetic NOD mice. Blood glucose concentrations were followed for 14 weeks post-treatment initiation.

Results—Disease Remission

Figure 11:
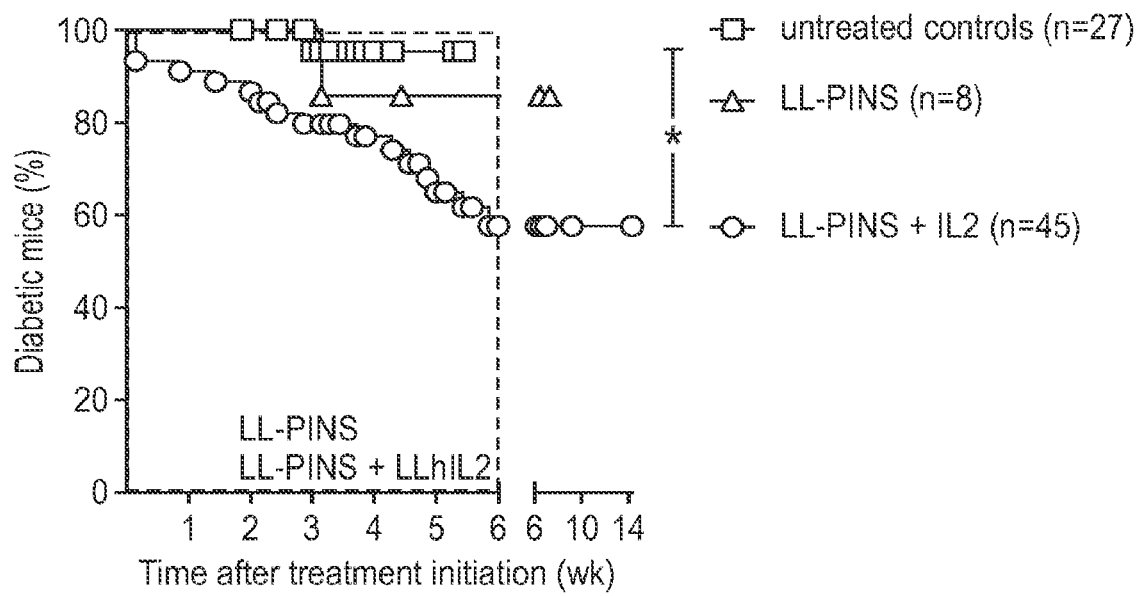
FIG. 11 depicts a stable reversal of hyperglycemia in new-onset diabetic NOD mice in an exemplary antigen-specific therapy according to the present disclosure. New-onset diabetic NOD mice were treated as described herein, e.g., in Example 3, and blood glucose concentrations were followed up for 14 weeks post-treatment initiation. Shown is the percentage of mice that remained diabetic upon treatment with mucosally delivered LL-PINS or mucosally delivered LL-PINS+LL-IL-2.

FIG. 11 shows the percentage of mice that remained diabetic after treatment. After NOD mice developed hyperglycemia (2 consecutive days of blood glucose concentrations >200 mg/dl), they generally progressed to severe hyperglycemia with minimal spontaneous remissions and most died within 3-6 weeks (n=27).

Mono-therapy with LL-PINS inoculation ($2\times10^9$ CFU/day, 5 days per week for 6 weeks; n=8) corrected hyperglycemia in 15% of mice. Remarkably, 43% of newly diabetic mice (n=45) treated with a combination of LL-PINS and LL-IL-2 rapidly re-established normoglyeemia. LL-PINS+LL-IL-2 therapy induced stable and permanent diabetes remission as cured mice maintained normoglycemia during an additional follow-up period of 8 weeks after stopping therapy.

Figure 12:
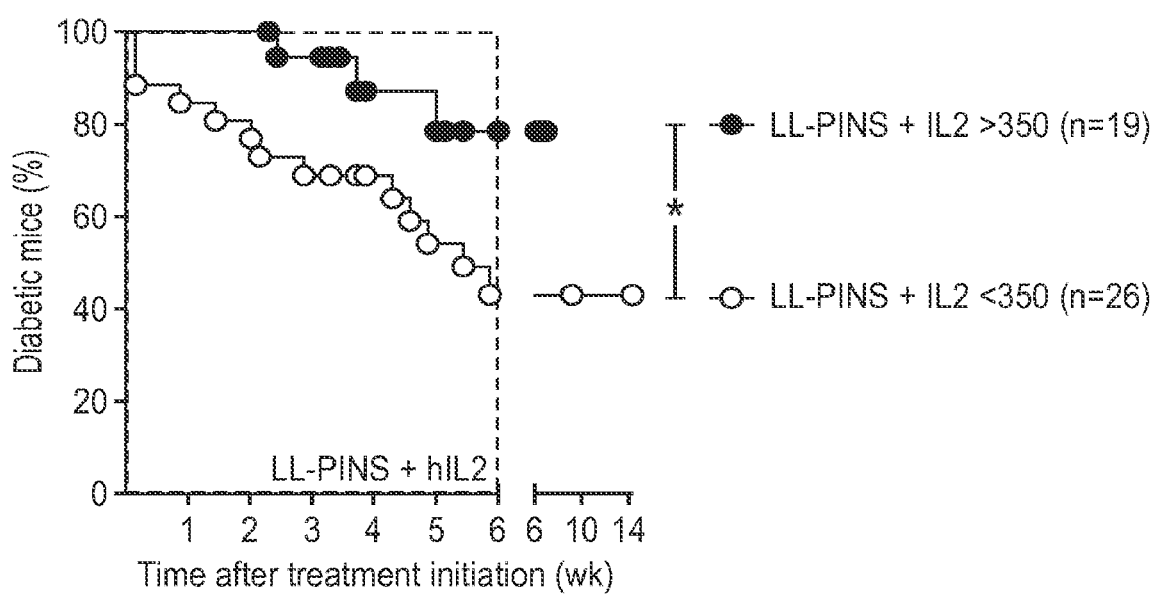
FIG. 12 depicts the effectiveness of an exemplary antigen-specific therapy according to the present disclosure in recent-onset diabetic mice with an initial blood glucose concentration of more than or less than 350 mg/dL. Shown is the percentage of mice that remained diabetic upon treatment with mucosally delivered LL-PINS+LL-IL-2 as described herein, e.g., in Example 3.

Clinical efficacy of LL-PINS and LL-IL-2 therapy is clearly affected by the blood glucose concentrations at treatment initiation. Recent-onset diabetic NOD mice were stratified based on initial blood glucose concentrations under or above 350 mg/dL. The LL-PINS plus LL-IL-2 therapy not only cured 57% of mice with starting glycemia below 350 mg/dL, but also 22% of mice with a starting glycemia above 350 mg/dL (FIG. 12). These data demonstrate for the first time that mucosal delivery of PINS with IL-2 by recombinant L. lactis bacteria effectively corrects hyperglycemia and restores immune tolerance to β-cells in NOD mice with overt recent-onset T1D.

In all Kaplan-Meier survival curves, statistical significance between groups was determined by Mantel-Cox logrank test (*: p<0.05).

Example 4. hIL-2 Secreted by L. lactis (LL-IL-2) Has Biological Activity Comparable to Recombinant hIL-2

This experiment involved the Lactococcus lactis strain expressing human IL-2 (LL-IL-2) as described herein (see, e.g, Example 1), and a control strain.

Figure 13:
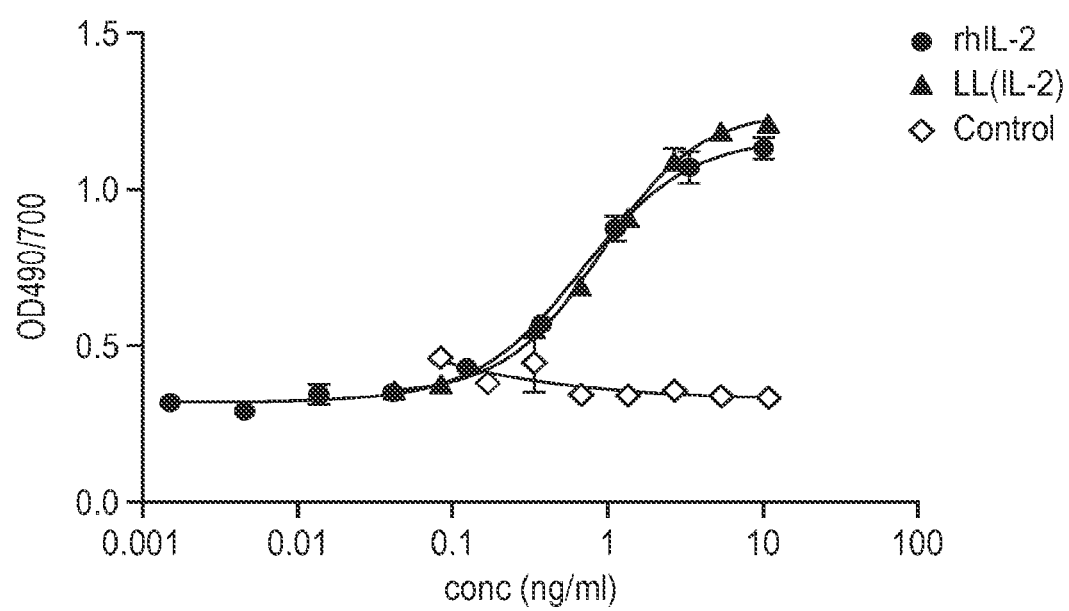
FIG. 13 depicts a comparison of the biological activities between LL-IL-2 and recombinant human IL-2 (rhIL-2).

Bioactivity of LL-IL-2 was measured based on IL-2 dependent survival/proliferation of a mouse T lymphocyte cell line HT2 clone A5E, HT2 cells were washed three times with medium without IL-2 and seeded at a density of $4\times10^3$ cells/96-well. A serial dilution series of recombinant hIL-2 (e.g. R&D systems #202-IL-010) or supernatant from LL-IL-2 and a control strain was added to the plated cells and incubated for 24 hrs at 37° C., 5% $CO_2$ and high humidity. Cell viability was measured using CellTiter96®AQueous One Solution (Promega #G3582). 20 µl MTT solution was added per well and after an incubation period of 4 hrs at 37° C., 5% $CO_2$ and high humidity, the plates were read at 490 nm using 700 nm as reference wavelength. Recombinant hIL-2 (R&D systems) and hIL-2 derived from LL-IL-2 show comparable dose-dependent responses, while the supernatant of the L. lactis control strain was inactive. The results are shown in FIG. 13.

Example 5. LL-IL-2 Delivers Low Doses of hIL-2 to the GI Tract of Non-Obese Diabetic Mice after Oral Administration This experiment involved the Lactococcus lactis strain expressing human IL-2 (LL-IL-2) as described herein, e.g., in Example 1.

Live Bacteria

Figure 14A:
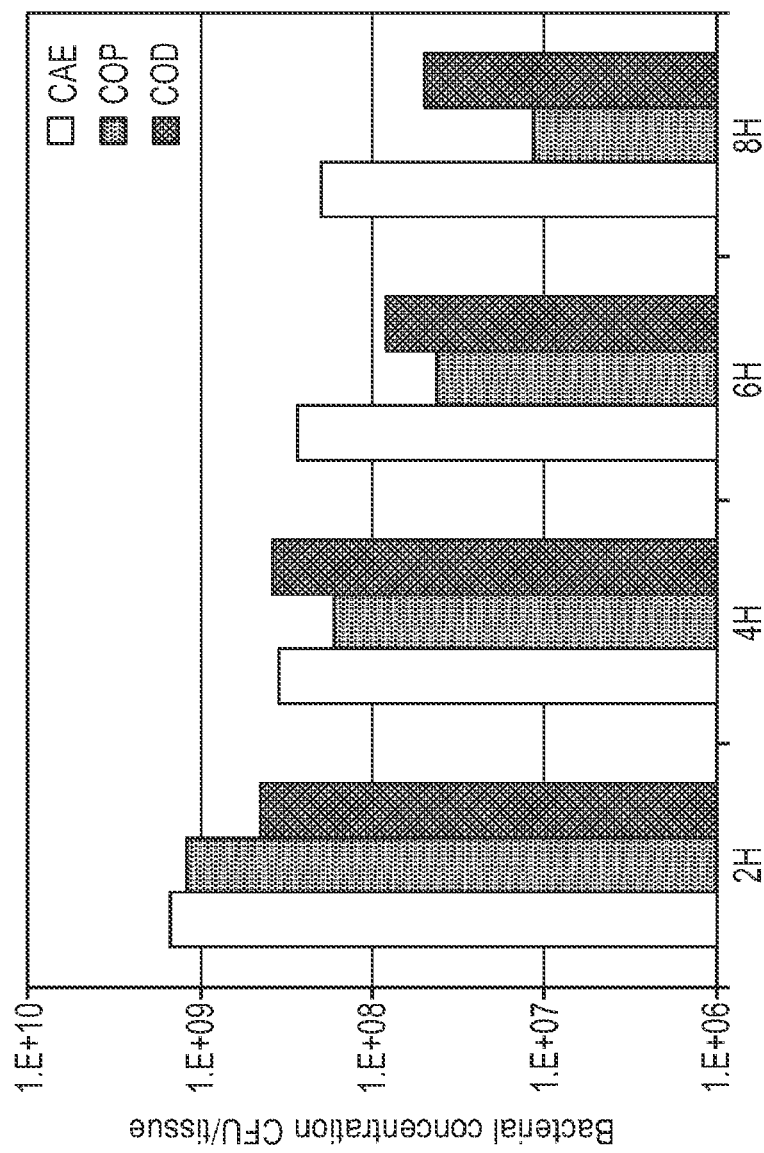
FIGS. 14A and 14B depict the concentrations of live bacteria (FIG. 14A: CFU/tissue.
Figure 14B:
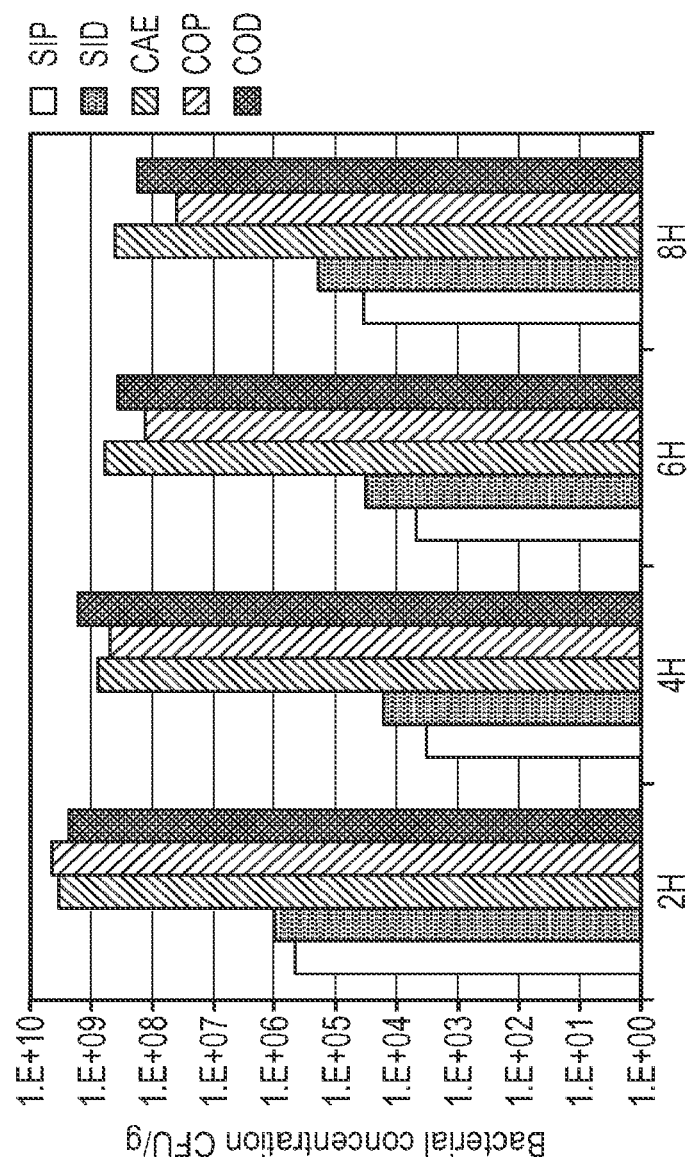

The concentrations of live bacteria (CFU/tissue and CFU/g) in different tissues of the GI tract were measured at different time-points after a single dose administration of $10^{10}$ CFU of LL-IL-2 by oral gavage. The results are depicted in FIGS. 14A and 14B, respectively, in which each bar represents an average of 3 mice (n=3). Referring to FIG. 14A (CFU/tissue), significant amounts of LL-IL-2 bacteria were found in the caecum (CAE), the proximal colon (COP), and the distal colon (COD) after 2, 4, 6, and 8 hours. The bacterial concentrations in the small intestine were found to be below $10^6$ CFU/tissue. Referring to FIG. 14B (CFU/g), concentrations of LL-IL-2 bacteria were found in the proximal small intestine (SIP), the distal small intestine (SID), the caecum (CAE), the proximal colon (COP), and the distal colon (COD) after 2, 4, 6, and 8 hours, respectively. No bacteria were detected in the blood.

hIL-2 Protein

The concentrations of hIL-2 protein (pg/tissue and pg/g) in different tissues of the GI tract were measured after administration of a single dose of LL-IL-2 bacteria ($10^{10}$ CFU). hIL-2 protein concentrations were found in the caecum (CAE), the proximal colon (COP), and the distal colon (COD) after 2 and 4 hours. The hIL-2 protein concentrations in the small intestine were found to be below the limit of quantification (LLOQ=10 pg/mL). hIL-2 protein was detected in the blood stream of the tested mice. The measured hIL-2 protein concentrations are summarized in Table 4 and Table 5 below.

At sacrifice, the complete tissue (SIP, SID, CAE, COP or COD) was weighed and homogenized. A sample of the homogenate was used for plating (to determine CFU) and for ELISA (to determine hIL-2). Total tissue in this context means that the concentration of bacteria or protein determined in the homogenate sample is recalculated to the weight of the total tissue.

TABLE 4

Concentration of hIL-2 protein (pg/tissue) in different tissues of the GI tract after single dose administration of $10^{10}$ CFU of LL-IL-2

| Time | CAE | COP | COD |
|---|---|---|---|
| 2 h | 32.6 (n = 1) | 91.5 (n = 3) | 36.1 (n = 3) |
| 4 h | <LLOQ | <LLOQ | 16.8 (n = 2) |
| 6 h | <LLOQ | <LLOQ | <LLOQ |
| 8 h | <LLOQ | <LLOQ | <LLOQ |

CAE = caecum;
COP = proximal colon;
COD = distal colon;
LLOQ = 10 pg/mL

TABLE 5

Concentration of hIL-2 protein (pg/g) in different tissues of the GI tract after administration of a single dose ($10^{10}$ CFU) of LL-IL-2

| Time | CAE | COP | COD |
|---|---|---|---|
| 2 h | 69.4 (n = 1) | 319.8 (n = 3) | 178.5 (n = 3) |
| 4 h | <LLOQ | <LLOQ | 65.3 (n = 2) |
| 6 h | <LLOQ | <LLOQ | <LLOQ |
| 8 h | <LLOQ | <LLOQ | <LLOQ |

CAE = caecum;
COP = proximal colon;
COD = distal colon;
LLOQ = 10 pg/mL

Viable *L. lactis* were found throughout the GI tract, with most bacteria located in the proximal and distal part of the large intestine and in the caecum. The bacterial concentration was a 1000-fold higher here than in the distal and proximal part of small intestine. This may be explained by the large amount of mucus and low motility in these parts of the intestine. About 50% of the administered *L. lactis* could be recovered from the distal parts of the colon 2 hours after administration. This finding is surprising because it had previously been reported that only about 10-30% of orally administered *L. lactis* survived the duodenal transit (Drouault S, et al., *Appl. Environ. Microbiol.* 1999; 65(11): 4881-6). It was speculated that inoculating the bacteria with BM9 inoculation buffer may protect the bacteria (at least partially) against GI conditions.

It was estimated that after dosing about $10^{10}$ CFU LL-IL-2, about 90 pg IL-2 was delivered to the tissue which corresponds to about 1.2 IU of IL-2 (based on 1 IU=73 pg).

Example 6. Pharmacodynamic and Mechanistic Studies to Examine the Effect of a Clinical Grade *Lactococcus lactis* (LL) Strain Secreting Both Proinsulin (PINS) and hIL-2

This experiment involves a *Lactococcus lactis* strain expressing both PINS and IL-2 (LL-PINS/IL-2) as described herein (see, e.g., Example 2). Bacteria can be cultured as previously described. See Takiishi, T. et al., *J. Clin. Inv.* 2012, 122(5): 1717-1725. NOD Mice can be screened, treated, and analyzed as described in Example 3 above. Mice can be treated with the bacteria, e.g., at a dose of $2 \times 10^9$ CFU by oral gavage 5 times weekly for six (6) weeks.

Phenotypic Analysis of the Local and Peripheral Immune System

Peripheral organs (i.e., blood, mesenteric and pancreatic lymph nodes and pancreas) can be isolated at therapy discontinuation (e.g., on day 42) and can be phenotypically examined, e.g., by flow cytometric analysis for canonical and non-canonical Treg makers (i.e., CD3, CD4, CD25, Foxp3, CD39, CD49b, LAG-3, and CD73). For example, co-expression of CD49b and LAG-3 enables the characterization of highly suppressive IL-10 producing Tr1 cells (see, e.g., Gagliani, N. et al., *Nat. Med.* 2013, 19(6): 739-746), while Tregs expressing both the ecto-enzymes CD39 and CD73 produce high concentrations of adenosine which is thought to be one of the Treg mechanisms of suppression. See, e.g., Antonioli, L., et al., *Trends Mol. Med.* 2013, 19(6): 355-367.

For intracellular cytokine staining, immune cells can be re-stimulated, with 1 μg/ml phorbol myristic acid (PMA, Sigma-Aldrich) and 0.5 μg/ml ionomycin (Sigma-Aldrich) for 4 hours in the presence of 1 μl/ml GoluiPlug™ (BD). After cell surface staining, intracellular staining can be performed, e.g., using the Cytofix/Cytoperm™ kit (BD) (i.e. CD3, CD4, CD8, IL-2, IL-4, Th-17, and IFN-γ).

For pSTAT-5 detection, cell suspensions can be rapidly fixed after sacrifice or after in vitro culture, e.g., in 10 volumes of a solution of PBS 1.5% formaldehyde for 10 minutes at room temperature. Cells can be washed, e.g., in a solution of PBS containing 0.2% of BSA, and permeabilized, e.g., with 100% methanol for 10 minutes on ice. The cells may be washed further, e.g., with PBS 0.2% BSA, and can be incubated with a phospho-specific antibody in combination with an antibodies of interest (e.g., anti CD3, CD4, CD8, CD25, CD69, CD44, CD122), e.g., for 30 minutes in the dark at room temperature. In some cases, anti-Ki67 antibody can be added together with an anti-Foxp3 antibody. The pSTAT5 negative threshold can be defined on unstimulated cells or on cells stained with all fluorescent antibodies minus psTAT5.

Multi-parameter analyses can be performed, e.g., using FACS Gallios (Beckman Coulter), FACS Canto II (Becton Dickinson (BD)), or FACS Fortessa (BD) and analyzed with FlowJo® software (Tree Star). Dead cells (live dead yellow 405 staining) and doublets can be excluded from all analyses.

In Vitro Polyclonal Suppression Assay and IFN-γ Detection

Suppressive function of peripheral Tregs isolated from spleen and lymph nodes (ideally isolated from hCD2, Foxp3 NOD mice) can be assessed, e.g., in an in vitro polyclonal suppression assay were conducted as described. See, e.g., Takiishi, T., et al., *J Clin.Invest.* 2012. 122(5):1717-1725. IFN-γ are measured in cell-free supernatants.

Results

LL-PINS/IL-2 treatment is expected to stimulate and recruit Tregs, and have biological activities comparable to LL-IL-2+LL-PINS treatments as described herein, e.g., in Examples 3 and 8.

Example 7. Construction of *Lactococcus lactis* Secreting Proinsulin (LL-PINS)

Figure 15:
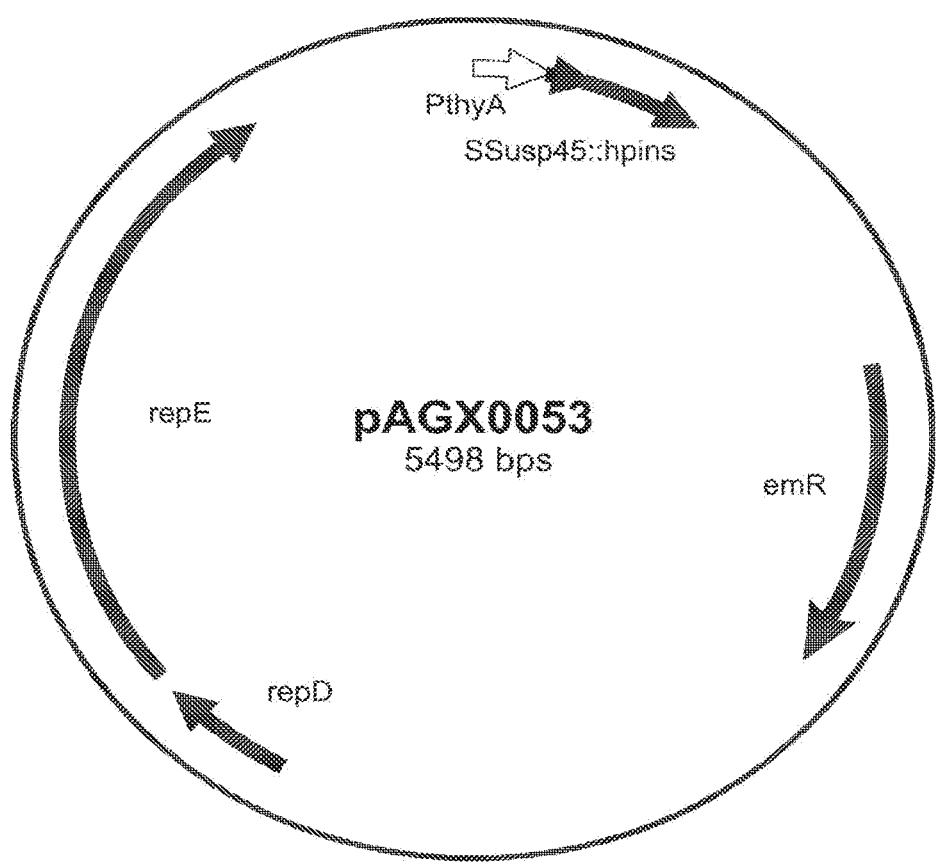
FIG. 15 depicts the structure of plasmid pAGX0053. The plasmid backbone exists of a pT1NX fragment to which a PthyA>>SSusp45: : hpins expression module was added. PthyA, promoter of the thymidylate synthase gene. EmR: erythromycin selection marker; repD, repE: Replication genes.

The DNA sequence encoding human proinsulin (hpins) was retrieved from GenBank (Accession number NM_00207.2). The hpins DNA sequence was extended at the 3' end with a TAA stop codon and SpeI restriction site. The DNA fragment was synthesized by PCR assembly of 40-mer oligonucleotides (oAGX0362 to oAGX0377) and Accu Prime DNA polymerase was used for amplification. The amplified fragment was fused to the usp45 secretion signal (SSusp45), downstream of the thyA lactococcal promoter (PthyA), which was extended at the 5' end with an EcoRI restriction site. The amplified product, which has a 5' EcoRI end and a 3' SpeI end, was inserted between the EcoRI and SpeI restriction sites of plasmid pT1NX (GenBank accession number HM585371.1) and ligated. The ligation was introduced in *L. lactis* MG1363 by electroporation and colonies were screened by PCR analysis. The resulting plasmid was designated pAGX0053 (FIG. 15).

From MG1363[pAGX0053], a PCR fragment that contains the PthyA>>SSusp45: : hpins expression module was generated using oAGX0169 and oAGX0170. The fragment was purified and it was confirmed that the DNA sequence of MG1363 [pAGX0053] is identical to the predicted sequence. Plasmid construction was performed by use of standard molecular biological methods.

Figure 16:
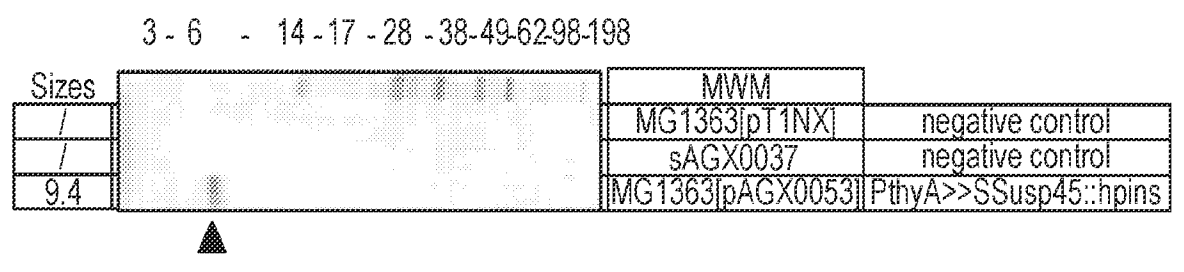

PINS expression was tested on culture supernatant (SN) from [MG1363]pAGX0053 by Elisa and western blot. MG1363 [pAGX0053] secretes 2.47 ng/m PINS, as determined by use of Pro-Insulin Elisa (Mercodia #10-1118-01). Crude SN samples were prepared for western blot Equivalents of 1 ml bacterial culture of [MG1363]pAGX0053 and reference strains MG1363[pT1NX] and sAGX0037 were loaded on the protein gel. Samples were incubated with goat polyclonal anti-insulin B (Santa Cruz N-20: se-7838, 1/500). Detection was done by incubation with rabbit anti-goat AP (Southern Biotech #6160-04, 1/1000) and subsequent:BT/BCIP staining (Roche NBT/BCIP tablets #11 697 471 001; used as indicated by the manufacturer). Invitrogen SeeBlue® Plus-2 pro-stained standard was used as molecular weight marker (MWM). Data is presented in FIG. 16 showing secretion of full-length PINS by LL-PINS.

*Lactococcus lactis* strains containing exogenous nucleic acids encoding T1D-specific antigens other than PINS, such as GAD65, IA-2, ICRP, ZnT8, ppIAPP, peripherin, chromogranin A, and GRP can be made in accordance with the above procedure using appropriate nucleic acids instead of hpins.

Example 8. Pharmacokinetic Profiling of Orally Administered LL-IL-2 Alone in Comparison to LL-PINS+LL-IL-2

Bacterial Culture

Bacteria were cultured as previously described in Takiishi, T. et al., *J. Clin. Inv.* 2012, 122(5): 1717-1725. For example, LL-pT1NX and LL-PINS were cultured in GM17TE medium (M17 broth supplemented with 0.5% glucose, 200 μM thymidine, and 5 μg/mL erythromycin). LL-IL-2 was cultured in GM17T medium (M17 broth supplemented with 0.5% glucose, and 200 μM thymidine). Stock suspensions of the LL strains were stored at −80° C. in glycerol. Stock suspensions were diluted 1/1000 in growth media (GM17TE or GM17T, respectively) and incubated for 16 hours at 30° C., reaching a saturation density of $2 \times 10^9$ CFU/mL. Bacteria were collected by centrifugation for 10 minutes at 4° C. and 2900 rpm arid concentrated 10-fold in BM9T medium (5×M9 salts, 10% casitone, 10% glucose, 0.5 M NatiCO$_3$, 0.5 M Na$_2$CO$_3$, 1 M MgCl$_2$, 100M CaCl$_2$, and 100 mM thymidine) for intragastric inoculations. Treatment consisted of 100 μL of this suspension for LL-pT1NX, LL-PINS and LL-IL-2. LL-PINS+LL-IL-2 were prepared by mixing equal parts of LL-PINS and LL-IL-2 suspensions. Treatment then consisted of 200 μL of this suspension.

Administration Schedule and Dosing

New-onset diabetic NOD mice (2 consecutive blood glucose measurements over 200 mg/dL and positive glucosuria) received $2 \times 10^9$ colony forming units (CFU) of live genetically modified *Lactococcus lactis* bacteria 5 times a week (weekdays) for 6 weeks. Mice treated with LL-PINS+LL-IL-2 received $2 \times 10^9$ CFU of LL-PINS and $2 \times 10^9$ CFU of LL-IL-2. Control 1 mice received no treatment, and control 2 mice received bacteria carrying an empty vector (LL-pT1NX). After a 6 week treatment period, some mice were reserved for further analysis after 14 weeks post treatment initiation.

Normoglycemic NOD mice (22 weeks of age) received one dose of $2 \times 10^9$ CFU of LL-IL-2. Two, four, six or eight hours after dose administration mice were euthanized and whole blood and serum were collected. Proximal small intestine (PSI), distal small intestine (DSI), caecum (CAE), proximal colon (PCO), and distal colon (DCO) were collected in homogenization buffer (10×M9 salts, 0.5 M NaHCO$_3$, 0.5 M Na$_2$CO$_3$, 10% bovine serum albumin, distilled water) at a concentration of 100 mg/mL and mechanically dissociated. Homogenates of gut tissues and whole blood were plated in serial dilutions on GM17 plates to quantify bacterial recovery. Concentration of IL-2 in serum and homogenates were measured by ELISA.

Organ Harvesting

Six weeks after treatment initiation, mice were euthanized with CO$_2$. Blood was collected by cardiac puncture with a heparinized needle. The blood was aliquoted (200 μL) for processing to single cells for flow cytometry and for plasma separation (centrifuged for 10 min at 2000 g at room temperature). Pancreata were harvested for histological analyses and stored in 5% paraformaldehyde (PFA). The following lymphoid organs were removed for analysis by flow cytometry; spleen (SPL), mesenteric lymph nodes (MLN) and pancreatic draining lymph nodes (PLN).

Histology of Pancreas and Insulitis Grading

PFA-fixed paraffin embedded pancreata were cut into sections of 6 μm and collected 100 μm apart, then stained with hematoxylin and eosin. Paraffin was removed using xylene followed by ethyl alcohol dehydration with 100%-90%-70%-50% ethanol solutions. Sections were rehydrated with tap water and distilled water. Sections were stained for 3 minutes in hematoxylin and rinsed with tap water. The sections were briefly rinsed in acid ethanol 3 times followed by an extensive wash with tap water. Samples were placed into saturated aqueous Li$_2$CO$_3$, and rinsed in tap water. Then samples were put in eosin Y-solution (0.5% aqueous) and rinsed in tap water. Slides were dehydrated with 50% ethanol, 70% ethanol, 90% ethanol, twice with 100% ethanol and twice with xyleen, for 10 seconds during each step. The cover glass was mounted and islets were observed under a light microscope at 20× or 40× and graded objectively. Islet infiltration was scored as follows; 0—no infiltration; 1—peri-insulitis; 2—islets with infiltration in less than 50% of the area; 3—islets with infiltration in more than 50% of the area; 4—completely destroyed islets/heavy insulitis.

C-Peptide ELISA

A commercially available ELISA kit for rat/mouse C-peptide (EZRMCP2-21K, EMD Millipore, St. Charles, MO) was used to determine C-peptide levels in plasma. Briefly, the 96-well plate was washed 3 times with 1×HRP wash buffer (50 mM Tris buffered saline containing TWEEN® 20 diluted 1:10 with distilled water). Matrix solution (serum matrix containing 0.008% sodium azide) was added to blank, standards and quality control wells. Assay buffer (0.05 M phosphosaline, 0.025 M ethylenediaminetetraacedic acid (EDTA), 0.08% sodium azide, 1% bovine serum albumin (BSA), pH 7.4) was then added to all wells. Standards and quality controls, containing known levels of rat C-peptide, were added to the respective wells and undiluted mouse plasma was added. Antibody solution mixture (1:1 mixture of pre-titered capture and biotinylated detection antibody to C-peptide) was added and the plate was incubated at room temperature for 2 hours on an orbital microtiter plate shaker at moderate speed. Wells were washed 3 times with 1×HRP wash buffer, and enzyme solution (pre-titered streptavidin-horseradish peroxidase) was added to each well to conjugate horseradish peroxidase to the immobilized biotinylated antibodies. The plate was incubated for 30 minutes at room temperature on a micro-titer plate shaker set to moderate speed. Wells were washed extensively with 1×HRP wash buffer. Substrate solution, containing 3,3'5,5'-tetra-methylbenzidine, was added to each well and the plate was shaken 15 minutes. The enzyme activity was stopped with stop solution (0.3 M HCl) and absorbance was measured at 450 nm within 5 minutes on a Victor spectrophotometer (Perkin Elmer).

Lymphocyte Isolation from Lymphoid Organs

Organs were harvested and placed in ice-cold wash medium (RPMI 1640 medium (Life Technologies/Invitrogen) supplemented with 4.5% antibiotics (G418 sulfate) and 2% fetal calf serum (FCS). Organs were mashed through a 70 μm strainer with wash medium. Cells were pelleted by centrifugation. For the spleen, $NH_4Cl$ was added for 3 minutes at 37° C. followed by washing with PBS. Cells were resuspended in 150 μL FACS buffer (1×PBS, 0.1% BSA, 2 mM EDTA). The following fluorochrome-conjugated antibodies were used for staining: CD3-PerCP-Cy5.5 (145-2C11), CD4-APC-H7 (GK1.5, BD), CD8α-eFluor450 (53-6.7), CD25-PE-Cy7 (PC61.5), CTLA4-PE (UC10-489), Foxp3-APC (FJK-165). All antibodies came from eBioscience unless mentioned otherwise. Anti-mouse CD16/CD32 (93, eBioscience) was used to block the Fc-γ II and III receptor to reduce non-specific binding of the fluorochrome-conjugated antibodies. Zombie Yellow Fixable Viability Dye (BioLegend) was used according to the manufacturer's specifications to stain dead cells.

Treg Cell Staining

Cells were washed with 1×PBS prior to staining. Approximately $1 \times 10^9$ cells were pelleted in a 96 well plate, and resuspended in 50 μl of Zombie Yellow Fixable Viability dye diluted 1/500 in 1×PBS. Cells were incubated at room temperature in the dark for 20 minutes. Cells were subsequently washed with 200 μL FACS buffer, and incubated with antibodies against extracellular epitopes diluted in FACS buffer in the dark for 30 minutes at 4° C. Cells were washed with 200 μL FACS buffer. Cells were fixed and permeabilized in Fixation/Permeabilization solution (Foxp3/Transcription Factor Staining Buffer Set, eBioscience) for 30 minutes at room temperature. Antibodies against intracellular epitopes were diluted in 1× permeabilization buffer and incubated with cells in the dark for 30 minutes at 4° C. The cells were washed and resuspended in FACS buffer and filtered for acquisition. The following antibodies were used in the following dilutions: CD3 (PerCP-Cy5.5; 1/100); CD25 (PE-Cy7; 1/625); CD4 (APC-H7; 1/160); CD8a (eFluor450; 1/300); CTLA4 (PE; 1/200); Foxp3 (APC 1/200).

Flow Cytometry

Flow cytometry data was acquired on a BD Canto II with FACSDiva and were analyzed with FlowJo® software (TreeStar). UltraComp eBeads™ (eBioscience) were used for compensation settings.

Statistical Analysis

Statistical analyses were performed using GraphPad Prism 6 software.

Results

Results generally indicate that (a) low dose IL2 (mucosally administered via LL-IL-2) with or without proinsulin as autoantigen (e.g., administered as LL-PINS) can safely revert new-onset diabetes in mice, (b) induction and activation of Tregs (CD4+CD25+Foxp3+CTLA4+) are possible mechanisms of action of LL-IL-2 and LL-IL-2+LL-PINS therapy, and (c) initial blood glucose concentrations are a predictive factor for therapeutic success in mice.

Mucosal Delivery of LL-IL-2 Induces Long-Lasting Diabetes Remission in NOD Mice

Diabetes onset was diagnosed when mice had blood glucose measurements over 200 mg/dL on two consecutive days, in combination with positive glucosuria. Treatment success ("remission") was defined as having two consecutive blood glucose measurements below 200 mg/dL and complete absence of positive glucosuria.

Figure 17:
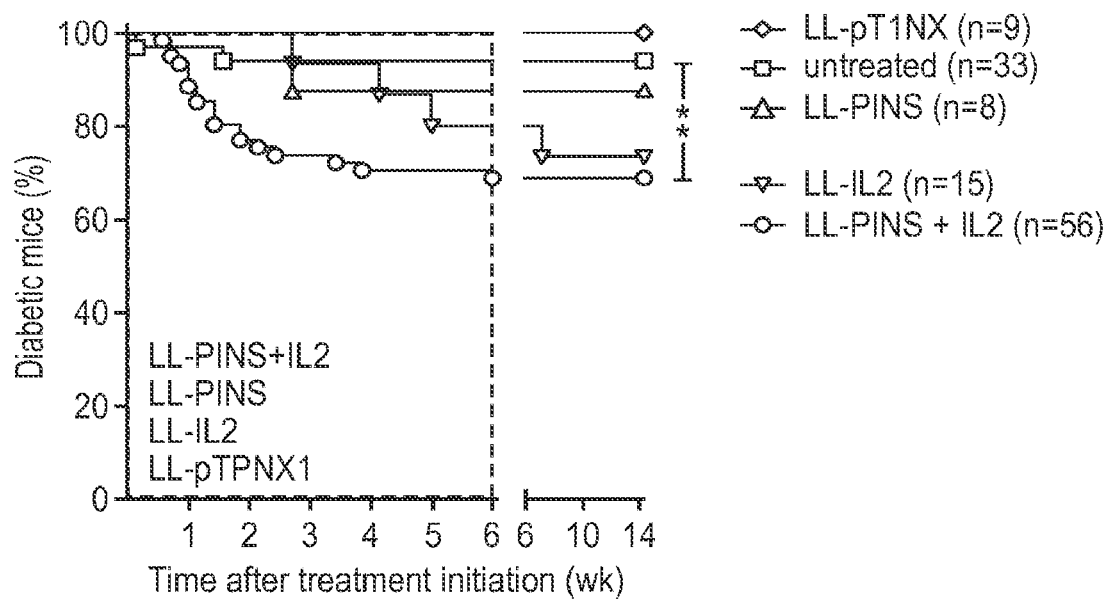
FIG. 17 depicts diabetes remission rates in new-onset diabetic NOD mice treated with various recombinant bacteria. Results demonstrate that mucosally delivered LL-IL-2 (e.g., providing low-dose IL-2), optionally in combination with an exemplary T1D-specific antigen (i.e., PINS) according to the present disclosure induces diabetes remission, and stably reverses hyperglycemia in new-onset diabetic NOD mice. Mice were treated for 6 weeks as described herein, and blood glucose concentrations were measured, including 14 weeks post-treatment initiation. Shown is the percentage of mice that remained diabetic after treatment (Mantel-Cox log-rank test; ** $p<0.01$).

Untreated diabetic NOD mice remained hyperglycemic and were euthanized when they had lost more than 20% of their initial body weight. Treatment with LL-pT1NX did not restore normoglycemia in diabetic mice. Mucosal delivery of LL-PINS caused diabetes reversal in about 12% of new-onset diabetic mice. Unexpectedly, after 6 weeks of treatment, LL-IL-2 alone caused diabetes reversal (i.e., resulted in re-established normoglycemia) in about 27% of new-onset diabetic mice. A combination therapy consisting of mucosal delivery of LL-IL-2 in combination with LL-PINS (LL-IL-2+LL-PINS) restored normoglycemia after diabetes in about 30% of mice. LL-IL-2 and LL-IL-2+LL-PINS induced long-lasting diabetes remission for at least an additional 8 weeks of follow-up after treatment termination. Compared to LL-IL-2 therapy alone, LL-IL-2+LL-PINS therapy may reverse diabetes faster. Results are illustrated in FIG. 17.

Figure 18:
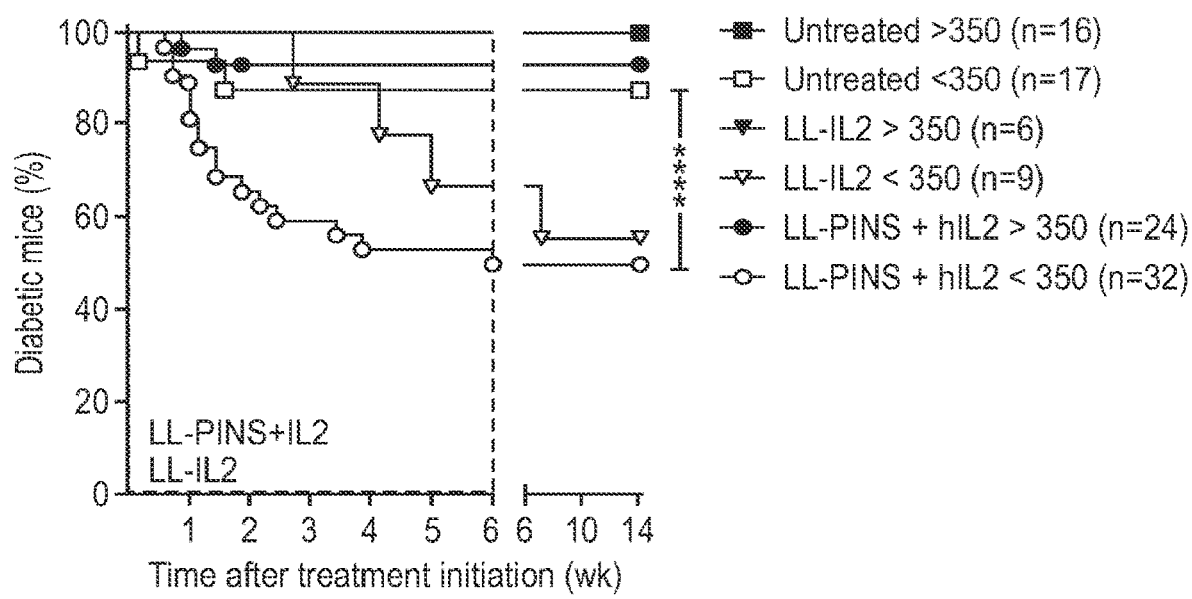
FIG. 18 depicts the diabetes remission rates according to starting blood glucose concentrations. Results indicate that starting blood glucose concentrations can predict therapeutic success in mice. Recent onset diabetic mice were stratified based on an initial (prior to treatment) blood glucose level of less than or greater than 350 mg/dL. Results demonstrate that mucosally delivered LL-IL-2, optionally in combination with an exemplary antigen-specific therapy (e.g., PINS) according to the present disclosure is particularly effective in recent-onset diabetic mice with an initial blood glucose concentration of less than 350 mg/dL. Shown is the percentage of mice that remained diabetic upon treatment with LL-IL-2 or LL-PINS+LL-IL-2 as described herein. It is noted that 6 mice treated with LL-IL-2 alone and having less than 350 mg/dl glucose, indicated as "LL-IL2<350 (n=9)" were sacrificed after 6 weeks of treatment and 3 mice were observed for the full 14 week period. A data timepoint for LL-IL-2>350 (n=6) (solid triangle) is hidden behind a data point for Untreated>350 (n=16) (solid square). All LL-IL-2 treated mice having >350 mg/dL of glucose were still diabetic after 6 weeks of treatment and after the 14 week follow-up period (Mantel-Cox log-rank test; **** $p<0.0001$).
Figure 22A:
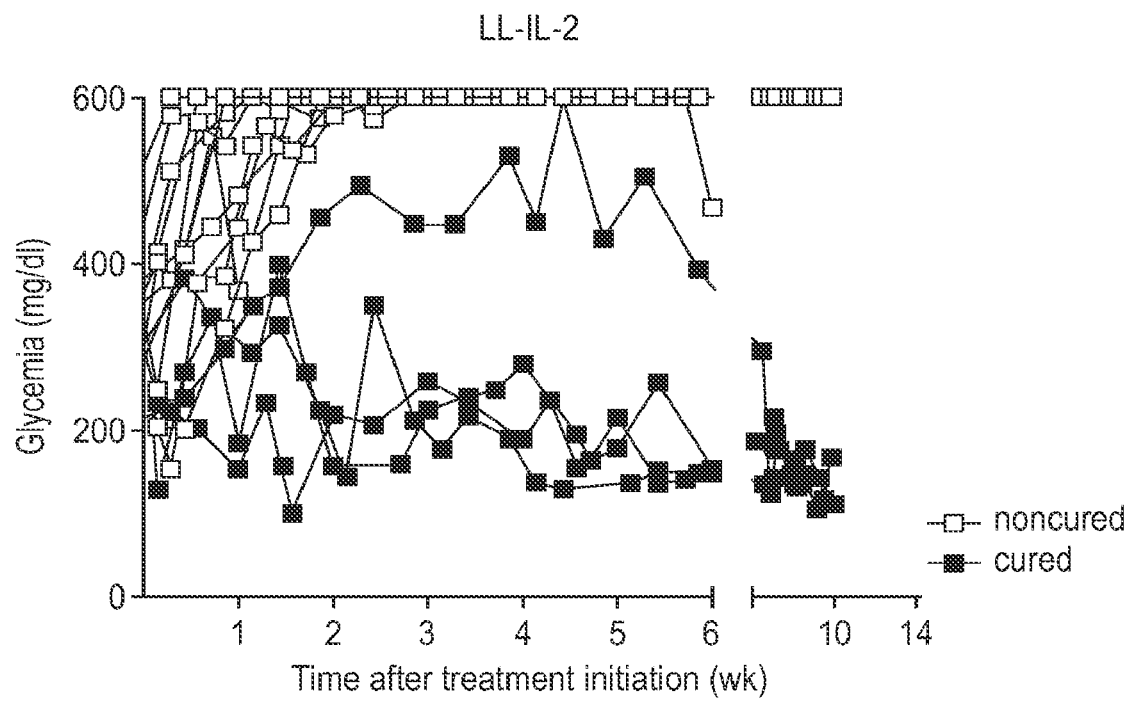
FIGS. 22A and 22B depict the blood glucose concentrations (mg/dL) in recent onset-diabetic mice treated with LL-IL-2 alone (FIG. 22A) and treated with LL-IL-2+LL-PINS (FIG. 22B).
Figure 22B:
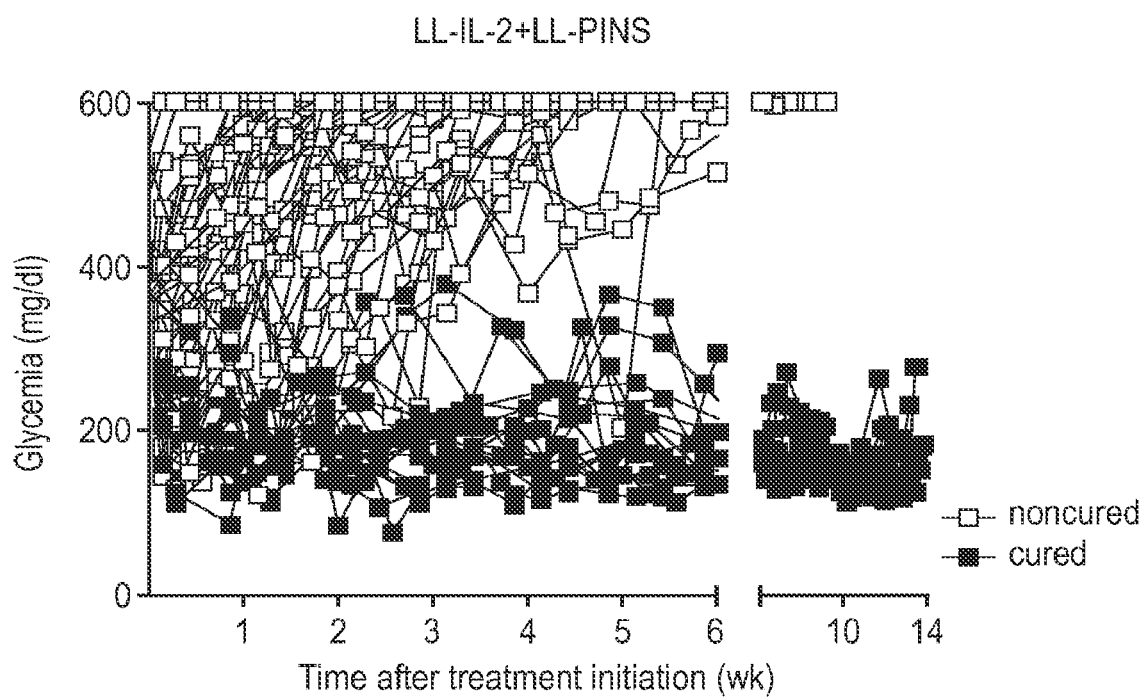

Blood Glucose Concentrations at the Beginning of Therapy Impact Therapeutic Success Therapy with LL-IL-2 and LL-IL-2+LL-PINS for 6 weeks reverted diabetes in about 45% and about 50%, respectively, of mice starting with blood glucose measurements below 350 mg/dL. For comparison, only about 8% of mice with a starting blood glucose measurement above 350 mg/dL were in remission. These results indicate that residual beta-cell mass at the initiation of treatment may predict therapeutic success. Results are illustrated in FIG. 18. FIGS. 22A and 22B illustrates blood glucose concentrations (mg/dL) in recent onset diabetic mice treated with LL-IL-2 alone (FIG. 22A) and LL-IL-2+LL-PINS (FIG. 22B) over the treatment and follow-up periods.

Mucosal Delivery of LL-IL-2 Preserves Functional Beta-Cell Mass

Figure 19:
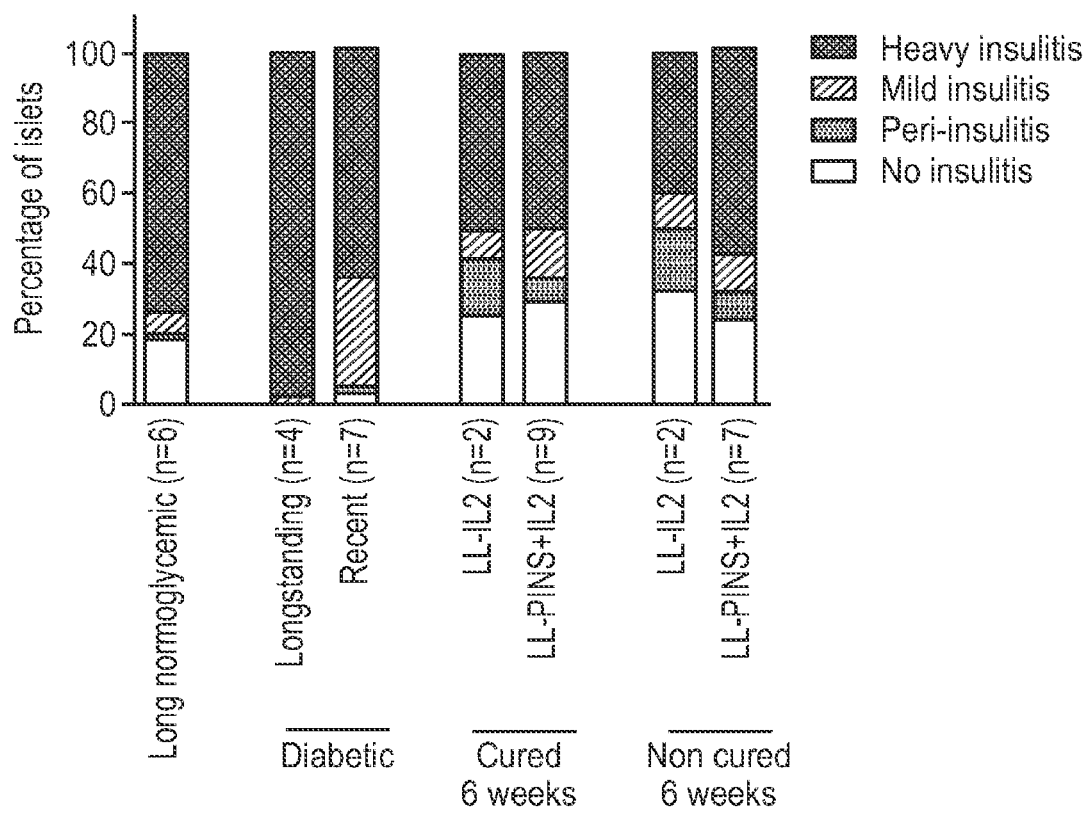
FIG. 19 depicts insulitis scoring of islet beta-cells in diabetic NOD mice. Results demonstrate that mucosally delivered LL-IL-2 (e.g., providing low-dose IL-2), optionally in combination with an exemplary antigen-specific therapy according to the present disclosure (e.g., LL-PINS+LL-IL-2) did not only prevent worsening of insulitis (normally seen during progression to long-standing diabetes when untreated), but reduces insulitis of islet beta-cells when compared to recent-onset and untreated longstanding diabetic mice (e.g., reduces insulitis to a degree comparable to insulitis found in longstanding "normoglycemic" NOD mice). The degree of heavy insulitis improved upon treatment when compared to untreated longstanding diabetic mice. The percentage of insulitis-free islet beta-cells dramatically increased when compared to recent-onset and untreated longstanding mice. A significant percentage of islets with mild-insulitis improved to "peri-insulitis" or "no insulitis." Unexpectedly, this significant reduction in insulitis was observed in all treated recent-onset mice (with and without remission—classified as "cured" and "uncured").

Plasma C-peptide can reflect pancreatic insulin content (see, e.g., Suarez-Pinzon W L et al., Combination therapy with glucagon-like peptide-1 and gastrin restores normoglycemia in diabetic NOD mice. Diabetes 2008; 57:3281-8.). C-peptide levels in mice treated and cured with LL-IL-2 (113.23±28.16 pM, n=3) and LL-IL-2+LL-PINS (167.63±64.38 pM, n=9) was 19% and 28%, respectively, of the C-peptide values measured in longstanding normoglycemic NOD mice (602.93±293.43 pM, n=6) and about twice as high as the values found in untreated long-standing diabetic NOD mice (n=4; 58.23±100.86 pM). C-peptide levels can be a measure for the amount of endogenous insulin produced by remaining islets. When NOD mice turn diabetic C-peptide levels drop, and in untreated longstanding diabetic mice, C-peptide levels were expected to be very low or non-detectable. This was in fact observed in 3 out of the 4 analyzed mice. Only one mouse had detectable levels of C-peptide. This observation suggests that functional beta-cells are still present at diabetes diagnosis and are preserved by the therapy. Mice treated with LL-IL-2+LL-PINS and exhibiting diabetic remission had statistically significantly higher C-peptide levels when compared to new-onset diabetic mice (p<0.05). Non-cured mice had undetectable C-peptide values, similar to what was found in most longstanding diabetic mice. Results indicate that recent onset animals have some beta cell function left. Cured mice had C-peptide levels comparable to the level found in recent onset diabetic mice. Non cured animals lost beta cell function represented by non-detectable C-peptide levels. Results are illustrated in FIG. 19.

Mucosal Delivery of LL-IL-2 Halts Insulitis Progression

Figure 20:
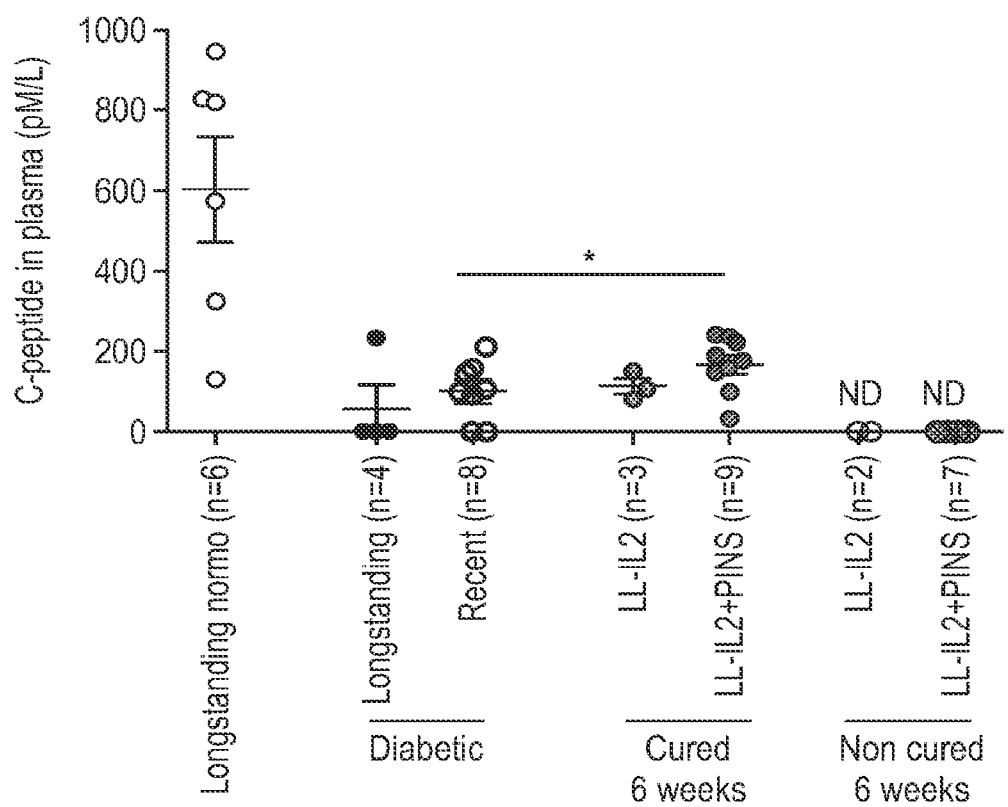
FIG. 20 depicts the random C-peptide concentrations in the plasma of diabetic NOD mice. Results demonstrate that low-dose IL-2 with or without proinsulin preserves beta-cell function in diabetic NOD mice. After 6 weeks of LL-IL-2 treatment, optionally in combination with an exemplary antigen-specific therapy according to the present disclosure (e.g., LL-PINS+LL-IL-2) plasma C-peptide concentrations in recent-onset diabetic mice showing remission (classified as "cured") increased when compared to recent-onset and untreated long-standing diabetic mice (Mann-Whitney T-test; *p<0.05). C-peptide concentrations in the plasma of treated, but "uncured" mice were not detected (ND) indicating that such mice may have little or no remaining active beta cells. The C-peptide levels measured for 3 out of the 4 analyzed untreated longstanding diabetic mice were also not detected.

Histological analysis of the pancreas after diabetes onset revealed pancreatic islets heavily infiltrated by leukocytes and only a few islets with remaining beta-cells. LL-IL-2 and LL-IL-2+LL-PINS halted (i.e., prevented worsening) of insulitis. Worsening of insulitis is typically observed during progression from new-onset to longstanding diabetes. Unexpectedly, both therapies improved the degree of insulitis when compared to insulitis found in longstanding normoglycemic NOD mice. While the percentage of islets with heavy insulitis was not significantly affected, both therapies dramatically increased the insulitis-free area. Even more unexpectedly, this improvement was also observed in animals not reaching normoglycemia ("non-cured" animals). Results are illustrated in FIG. 20.

The hemaloxylin and eosin staining did not allow for determining which immune cells infiltrated the pancreas, i.e. effector T cells (Teff) versus Treg cells.

Mucosal delivery of LL-IL-2 Induces Expansion of CD4+Foxp3+CTLA4+ Treg-Cells

Effects of LL-IL-2 on different immune cell subsets, both locally (i.e., MLN), systemically (i.e., spleen and blood) and at the target organ (i.e., PLN) were measured using flow cytometric analysis. Because low-dose IL-2 given systemically can induce expression of Treg cell-associated proteins including Foxp3, CD25, and CTLA4, the frequencies of CD4+, CD8+, and CD4+Foxp3+ cells or their activation status (CD44, CD62L) were determined.

CD4+ and CD8+ T-cell populations within live CD3+ T-cells were assessed. A small decrease of CD4+ T-cells in MLN was detected with LL-IL-2 and LL-IL-2+LL-PINS therapy in non-cured mice compared to cured animals (p=0.044 and p=0.068 respectively). In the examined peripheral organs (i.e. blood and spleen) and target organ (i.e. PLN), there were no statistically significant changes in the number of these leukocytes. Differences in CD4+ T-cell frequencies were limited to sites exposed to LL-IL-2 and LLIL-2+LL-PINS locally. Inversely, the CD8+ T-cell population was increased in the MLN of LL-IL-2+LL-PINS therapy non-cured mice compared to cured mice (p=0.012). This trend was also present in LL-IL-2 therapy. Furthermore, LL-IL-2 and LL-IL-2+LL-PINS treated non-cured mice had significantly higher CD8+ splenic T-cells (p=0.025 and p=0.011 respectively) compared to new-onset diabetic NOD mice. This systemic change may have been a consequence of disease progression rather than of *L. lactis*-based therapies.

The presence of Treg cells was also assessed using flow cytometry. At 6 weeks after therapy initiation, PLN of LL-IL-2 and LL-IL-2+LL-PINS cured mice showed a trend for higher frequencies of Foxp3+CTLA-4+ Treg cells, compared to new-onset diabetic mice (both about 17% compared to about 10% in recent-onset mice). This trend was also observed in LL-IL-2 and LL-IL-2+LL-PINS treated non-cured mice (about 14% and about 17%, respectively).

Figure 21:
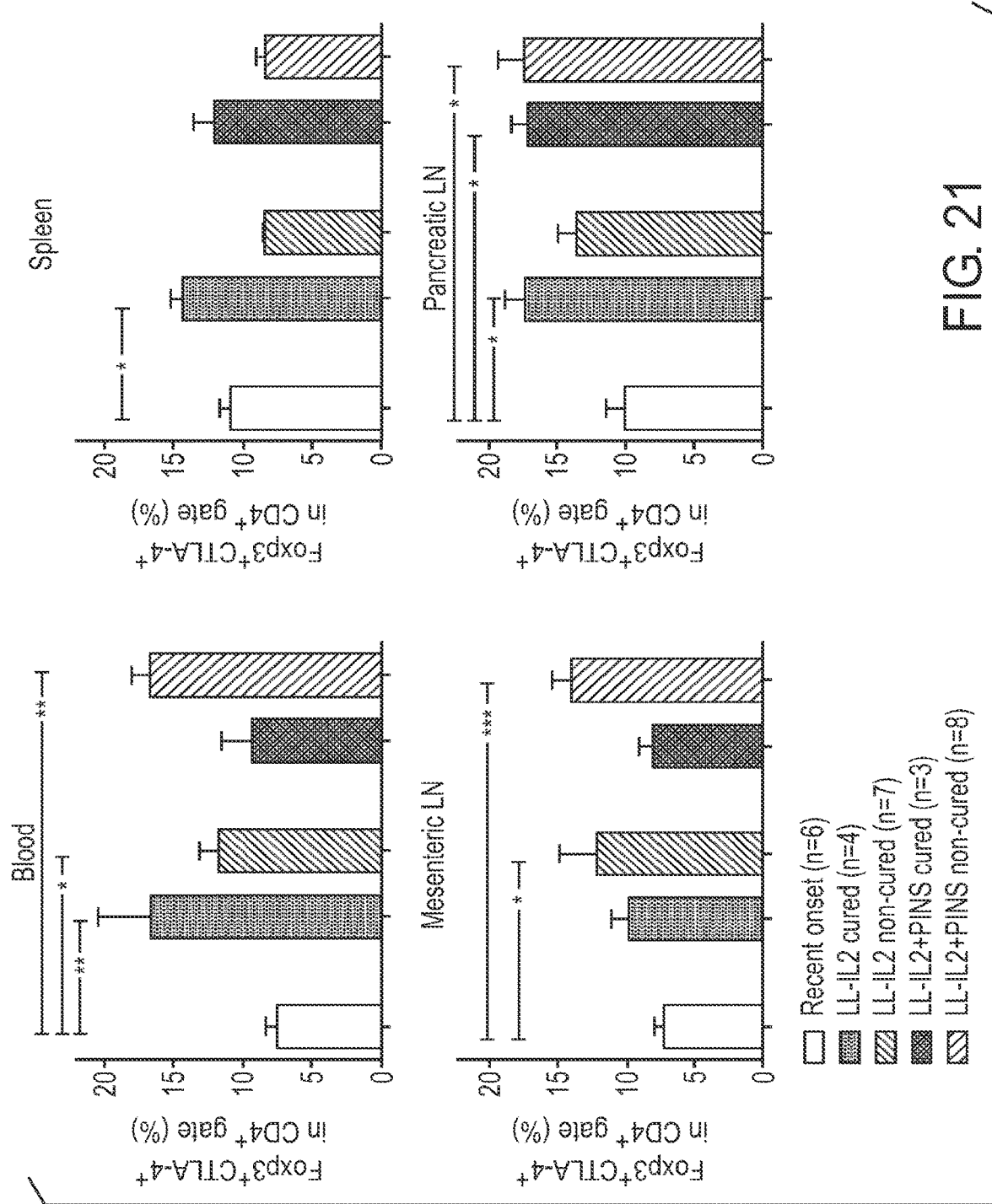
FIG. 21 depicts the expansion of foxp3+CTLA4+ regulatory T cells in different immune cell subsets, locally (i.e., mesenteric draining lymph nodes; MLN), systemically (i.e., spleen and blood), and at the target organ (i.e., pancreatic LN), of diabetic NOD mice measured by flow cytometry after 6 weeks of treatment. Results demonstrate that mucosally delivered LL-IL-2, optionally in combination with an exemplary antigen-specific therapy according to the present disclosure (e.g., LL-PINS+LL-IL-2) increases the number of foxp3+CTLA4+ regulatory T cells in the pancreatic LN when compared to recent-onset mice. Unexpectedly, increases in the pancreatic LN were observed in mice exhibiting remission ("cured") and those not exhibiting remission ("uncured") mice (Mann-Whitney T-test; *p<0.05,  p<0.01, * p<0.001).

In the spleen, non-cured mice exhibited a decrease of this Treg cell compartment when compared to cured mice, and compared to untreated recent-onset mice. In blood, both therapies induced a trend towards an increase in circulating Foxp3+CTLA-4+ Treg cells when compared to new-onset diabetic mice. Again, this increase was independent of therapy outcome and in non-cured LL-IL-2+LL-PINS treated mice this increase was significant (p=0.009). In the MLN, LL-IL-2+LL-PINS non-cured mice also have significantly higher frequencies of Foxp3+CTLA4+ Treg cells compared to new-onset diabetic mice (p=0.002). The above results are illustrated in FIG. 21.

Treg cell compartments were further defined measuring CD25 expression. A considerable number of Foxp3+CTLA4+ Treg cells did not express CD25 (CD25$^-$), but therapy with LL-IL-2 and LL-IL-2+LL-PINS still induced changes in this population. CD25−Foxp3+CTLA-4+ Treg cells were relatively abundant in the blood and were increased in LL-IL-2+LL-PINS non-cured mice (p=0.004), and in LL-IL-2 cured mice. In the spleen, a trend towards a decrease in this subset was observed in LL-IL-2 and LL-IL-2+LL-PINS treated non-cured mice compared to cured mice (p=0.06 and p=0.06 respectively). In mesenteric lymph nodes, there was little effect of LL-IL-2 or LL-IL-2+LL-PINS on CD25$^-$Foxp3+CTLA-4+ Tregs. In the target lymph nodes (i.e. PLN), this Treg cell subset was increased in LL-IL-2 and LL-IL-2+LL-PINS cured mice compared to new-onset diabetic mice.

The following trends were observed for CD25+ cells: In MLN, CD25+Foxp3+CTLA-4+ Treg cells were increased in non-cured mice treated with LL-IL-2 and LL-IL-2+LL-PINS when compared to new-onset diabetic mice (12% and 14% vs 7%, respectively). This was statistically significant in the latter group (p=0.001). In PLN, there was a visible trend towards an increase of this subset in LL-IL-2 and LL-IL-2+LL-PINS treated groups.

The distribution pattern of Foxp3+CTLA-4+ Treg cells seen in blood and spleen was similar upon further classification based on CD25 expression. In the local and target lymph nodes (i.e. the MLN and PLN), Foxp3+CTLA-4+ Treg cell increases were seen following both LL-IL-2 and LL-PINS+IL-2 therapies, which could be attributed largely to the CD25+Tree cell compartment.

The spleen size in new onset diabetic NOD mice treated with LL-PINS+IL-2 were assessed for the total period of 6 weeks (n=3). No splenomegaly was observed. Treatment with LL-IL-2 as well as LL-IL-2+LL-PINS was safe and well tolerated.

Conclusion

LL-IL-2 and LL-IL-2+LL-PINS therapies are safe and well-tolerated, and induced, diabetes remission in new-onset diabetic NOD mice. Both therapies have beneficial metabolic and immune effects. Unexpectedly, some effects are also present in non-cured mice, suggesting a potential benefit for subjects, which did not reach normoglycemia during the course of the experiments, or for which the treatment comes too late because the remaining beta cell mass was below a certain threshold when treatment began (in NOD mice the process of beta cell loss is faster when compared to the loss observed in humans). Thus, an immune effect may have been observed in all treated animals, but this effect may have translated into the defined therapeutic effect only in those animals that had sufficient beta cell mass left at the beginning of treatment.

LL-IL-2 and LL-IL-2+LL-PINS therapies halted insulitis progression, possibly through a mechanism involving expansion of Treg cells. Differences in the percentage of Foxp3+CTLA4+ Treg cells between treated and untreated new-onset diabetic mice were found in the PLN after LL-IL-2 and LL-IL-2+LL-PINS therapy. The increase in the number of Treg cells induced by the therapies may be a result of an improvement of Treg cell survival (see, e.g., Tang Q, Bluestone J A. *Nat. Immunol.* 2008; 9(3): 239-244). Alternatively, the increased number of Treg cells could be the result of the conversion of effector T cells (Teff) into induced Treg cells (Zheng Y, Rudensky A Y. *Nat. Immunol.* 2007; 8(5): 457-462), or the increased recruitment of Treg cells to the PLN (Grinberg-Bleyer Y. et al., *J. Exp. Med.* 2010; 207(9):1871-1878).

Example 9. Effect of Anti-CD3 Antibody Administration Upon Diabetes Remission Rate An anti-CD3 antibody dose finding study was performed in mice. Mice with a starting blood glucose level of greater than 200 mg/dl were dosed with 2.5 µg/day; 5 µg/day; 10 µg/day; 25 µg/day, or 50 µg/day of an anti-CD3 antibody (teptizumab) through IV injections. Dosages of 25 µg/day or 50 µg/day exhibited some toxicity. Treatments were given over a 5 day period, which means that a cumulative anti-CD3 antibody dosage was 12.5 µg; 25 µg; 50 µg; 125 µg; or 250 µg. The treatment group receiving 10 µg/day resulted in a maximal remission induction of approximately 50%. However, in order to reduce toxicity over a longer period of treatment, the dosage of 2.5 µg/day (12.5 µg cumulative) was selected, which is considered a sub-therapeutic dose (low-dose). Treatment with 2.5 µg/day of anti-CD3 antibody was less effective than at the higher 10 µg/day, and resulted in a remission induction of approximately 20%.

Similar to Example 8, LL-PINS, LL-IL2, LL-PINS+LL-IL2, were given by intragastric inoculation ($2 \times 10^9$ CFU/d), 5 times per week for 6 weeks to newly diabetic mice. Additionally, hamster anti-mouse CD3 monoclonal antibody (mAh) (145-2C11, BioXCell, New Hampshire, USA) was administered intravenously (2.5 µg/d) for 5 consecutive days to mice received LL-PINS+LL-IL2 inoculation. All tested newly diabetic mice had starting blood glucose concentrations below 350 mg/dl. Weight and glycemia were measured 3 times per week. Diabetes remission was defined as absence of glycosuria and glycemia values <200 mg/dl on two consecutive days.

Figure 23:
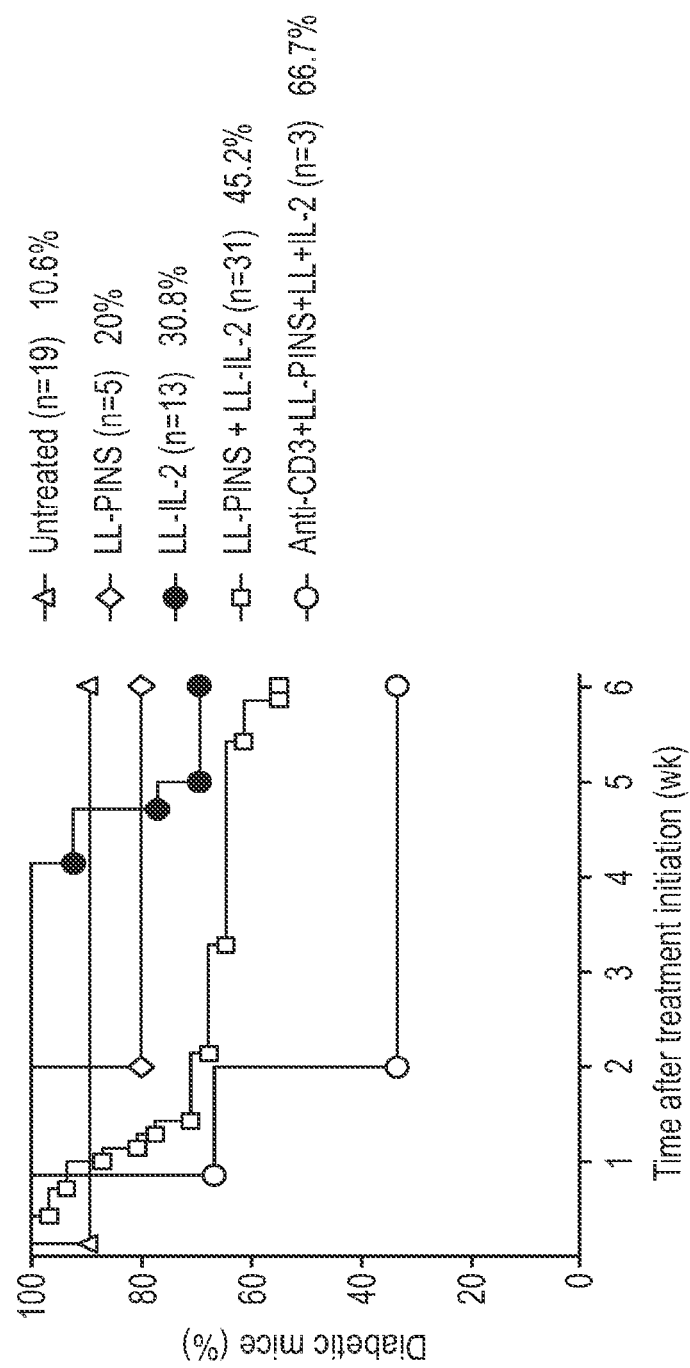
FIG. 23 depicts diabetes remission rate according to starting blood glucose concentrations under 350 mg/dl at study entry. Mice were allocated to 5 experimental treatment groups: untreated controls, LL-PINS, LL-IL2, a mixture of LL-PINS+LL-IL2 and a mixture of LL-PINS+LL-IL2 combined with a systemic immunomodulatory anti-CD3, as described in Example 9. Shown is the percentage of mice that remained diabetic at various time points after treatment.

As shown in FIG. 23, therapies with LL-PINS (n=5), LL-IL2 (n=13), and a mixture of LL-PINS+LL-IL2 (n=31) inoculation corrected hyperglycemia in 20%, 30.8%, and 45.2% of mice, respectively. Newly diabetic mice (n=3) treated with a combination of LL-PINS+LL-IL2 and anti-CD3 re-established normoglycemia in 65.7% of the mice. These data suggest that an additional immune-modulating substance, for example, an anti-CD3 antibody, improves the outcome of LL-IL-2+LL-PINS therapy in subjects having a lower starting blood glucose concentration.

What is claimed is:

1. A genetically modified *Lactococcus lactis* bacterium comprising an exogenous nucleic acid encoding human interleukin-2 (hIL-2) polypeptide and an exogenous nucleic acid encoding human proinsulin (hPINS) polypeptide, both of which are integrated into the chromosome of the genetically modified *L. lactis* bacterium, wherein said nucleic acid encoding said hPINS polypeptide comprises a polycistronic expression unit comprising, in 5' to 3' order, glyceraldehyde 3-phosphate dehydrogenase gene (gapB) with its promoter, and usp45 secretion leader (SSusp45) transcriptionally and translationally coupled to the sequence encoding said hPINS polypeptide;

wherein said nucleic acid encoding said hIL-2 polypeptide comprises a polycistronic expression unit comprising, in 5' to 3' order, phosphopyruvate hydratase gene (eno) with its promoter, and usp45 secretion leader (SSusp45) transcriptionally and translationally coupled to the sequence encoding said hIL-2 polypeptide; and wherein the genetically modified *L. lactis* bacterium further comprises the following genetic modifications:

(a) inactivation of thyA;
(b) inactivation of trePP;
(c) inactivation of ptcC;
(d) addition of an exogenous otsB; and
(e) expression of pts/and pts//under the control of a constitutive promoter.

2. The genetically modified *L. lactis* bacterium of claim 1, wherein said hPINS polypeptide comprises an amino acid sequence having at least 95% sequence identity to SEQ ID NO: 6, and wherein said hIL-2 polypeptide comprises an amino acid sequence having at least 95% sequence identity to SEQ ID NO: 3.

3. The genetically modified *L. lactis* bacterium of claim 1, wherein said nucleic acid encoding hPINS polypeptide comprises SEQ ID NO: 57.

4. The genetically modified *L. lactis* bacterium of claim 1, wherein said nucleic acid encoding said hIL-2 polypeptide comprises SEQ ID NO: 46.

5. A composition comprising the genetically modified *L. lactis* bacterium of claim 1, and a pharmaceutically acceptable carrier.

6. A method of treating type 1 diabetes mellitus (T1D) in a mammalian subject in need thereof comprising orally administering to the mammalian subject a therapeutically effective amount of the genetically modified *L. lactis* bacterium of claim 1.

7. The method of claim 6, wherein the genetically modified *L. lactis* bacterium delivers said hIL-2 polypeptide and said hPINS polypeptide to the mucosa of said mammalian subject.

8. The method of claim 6, wherein no anti-CD3 antibody is further administered to said mammalian subject.

9. The method of claim 6, further comprising administering an anti-CD3 antibody to said mammalian subject.

10. The method of claim 9, wherein said anti-CD3 antibody is administered simultaneously with said composition to said mammalian subject.

11. The method of claim 6, wherein said mammalian subject has been diagnosed with T1D within the previous 12 months prior to administering the genetically modified *L. lactis* bacterium.

12. The method of claim 6, wherein said mammalian subject is a human patient having a fasting blood C-peptide concentration between about 0.2 and about 1.0 nmol/L; or has a stimulated blood C-peptide concentration between about 0.5 and about 4.0 nmol/L.

13. The method of claim 6, wherein the genetically modified *L. lactis* bacterium is administered in a unit dosage form comprising from about $1\times10^4$ to about $1\times10^{12}$ colony-forming units (cfu); about $1\times10^6$ to about $1\times10^{12}$ cfu; or about $1\times10^9$ to about $1\times10^{12}$ cfu.

\* \* \* \* \*

SEQUENCE LISTING

```
Sequence total quantity: 61
SEQ ID NO: 1            moltype = AA  length = 153
FEATURE                 Location/Qualifiers
source                  1..153
                        mol_type = protein
                        organism = Homo sapiens
SEQUENCE: 1
MYRMQLLSCI ALSLALVTNS APTSSSTKKT QLQLEHLLLD LQMILNGINN YKNPKLTRML   60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153

SEQ ID NO: 2            moltype = DNA  length = 462
FEATURE                 Location/Qualifiers
misc_feature            1..459
                        note = CDS encodes SEQ ID NO: 1
source                  1..462
                        mol_type = genomic DNA
                        organism = Homo sapiens
SEQUENCE: 2
atgtacagga tgcaactcct gtcttgcatt gcactaagtc ttgcacttgt cacaaacagt   60
gctccaactt catcatcaac taaaaaaact caattgcaac ttgaacactt gcttttggat  120
cttcaaatga tcttgaacgg tatcaacaac tacaaaaacc caaaacttac tcgtatgttg  180
acttttaaat tttacatgcc aaaaaaagct actgaactta aacacttgca atgtcttgaa  240
gaagaattga aaccacttga agaagttttg aaccttgctc aatcaaaaaa ctttcacttg  300
cgtccacgtg atcttatctc aaacatcaac gttatcgttt tggaacttaa aggttcagaa  360
actactttta tgtgtgaata cgctgatgaa actgctacta tcgttgaatt tttgaaccgt  420
```

```
tggatcactt tttgtcaatc aatcatctca actttgactt aa                    462

SEQ ID NO: 3            moltype = AA  length = 133
FEATURE                 Location/Qualifiers
source                  1..133
                        mol_type = protein
                        organism = Homo sapiens
SEQUENCE: 3
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 4            moltype = AA  length = 20
FEATURE                 Location/Qualifiers
source                  1..20
                        mol_type = protein
                        organism = Homo sapiens
SEQUENCE: 4
MYRMQLLSCI ALSLALVTNS                                              20

SEQ ID NO: 5            moltype = DNA  length = 483
FEATURE                 Location/Qualifiers
misc_feature            1..483
                        note = /note="Description of Artificial Sequence: Synthetic
                        polynucleotide"
source                  1..483
                        mol_type = other DNA
                        organism = synthetic construct
SEQUENCE: 5
atgaaaaaaa agattatctc agctatttta atgtctacag tgatactttc tgctgcagcc   60
ccgttgtcag gtgtttacgc cgctccaact tcatcatcaa ctaaaaaaac tcaattgcaa  120
cttgaacact tgcttttgga tcttcaaatg atcttgaacg gtatcaacaa ctacaaaaac  180
ccaaaactta ctcgtatgtt gactttaaa ttttacatgc caaaaaaagc tactgaactt  240
aaacacttgc aatgtcttga agaagaattg aaaccacttg aagaagtttt gaaccttgct  300
caatcaaaaa actttcactt gcgtccacgt gatcttatct caaacatcaa cgttatcgtt  360
ttggaactta aaggttcaga aactactttt atgtgtgaat acgctgatga aactgctact  420
atcgttgaat ttttgaaccg ttggatcact tttgtcaat caatcatctc aactttgact  480
taa                                                                483

SEQ ID NO: 6            moltype = AA  length = 110
FEATURE                 Location/Qualifiers
source                  1..110
                        mol_type = protein
                        organism = Homo sapiens
SEQUENCE: 6
MALWMRLLPL LALLALWGPD PAAAFVNQHL CGSHLVEALY LVCGERGFFY TPKTRREAED   60
LQVGQVELGG GPGAGSLQPL ALEGSLQKRG IVEQCCTSIC SLYQLENYCN             110

SEQ ID NO: 7            moltype = DNA  length = 333
FEATURE                 Location/Qualifiers
misc_feature            1..330
                        note = CDS encodes SEQ ID NO: 6
source                  1..333
                        mol_type = genomic DNA
                        organism = Homo sapiens
SEQUENCE: 7
atggccctgt ggatgcgcct cctgcccctg ctggcgctgc tggccctctg gggacctgac   60
ccagccgcag cctttgtgaa ccaacacctg tgcggctcac acctggtgga agctctctac  120
ctagtgtgcg gggaacgagg cttcttctac acacccaaga cccgccggga ggcagaggac  180
ctgcaggtgg ggcaggtgga gctgggcggg ggccctggtg caggcagcct gcagcccttg  240
gccctggagg ggtccctgca gaagcgtggc attgtggaac aatgctgtac cagcatctgc  300
tccctctacc agctggagaa ctactgcaac tag                               333

SEQ ID NO: 8            moltype = DNA  length = 396
FEATURE                 Location/Qualifiers
source                  1..396
                        mol_type = genomic DNA
                        organism = Homo sapiens
SEQUENCE: 8
gccatcaagc aggtctgttc caagggcctt gcgtcagat cactgtcctt ctgccatggc    60
cctgtggatg cgcctcctgc ccctgctggc gctgctggcc ctctggggac tgacccagc   120
cgcagccttt gtgaaccaac acctgtgcgg ctcacacctg gtggaagctc tctacctagt  180
gtgcggggaa cgaggcttct tctacacacc caagacccgc cggaggcag aggacctgca  240
ggtgggcag gtggagctgg gcgggggccc tggtgcaggc agcctgcagc ccttggccct  300
ggagggggtcc ctgcagaagc gtggcattgt ggaacaatgc tgtaccagca tctgctccct  360
ctaccagctg gagaactact gcaactgac gcagcc                             396

SEQ ID NO: 9            moltype = DNA  length = 469
FEATURE                 Location/Qualifiers
```

```
source                   1..469
                         mol_type = genomic DNA
                         organism = Homo sapiens
SEQUENCE: 9
agccctccag gacaggctgc atcagaagag gccatcaagc agatcactgt ccttctgcca    60
tggccctgtg gatgcgcctc ctgcccctgc tggcgctgct ggccctctgg ggacctgacc   120
cagccgcagc ctttgtgaac caacacctgt gcggctcaca cctggtggaa gctctctacc   180
tagtgtgcgg ggaacgaggc ttcttctaca cacccaagac ccgccgggag cagaggacc    240
tgcaggtggg gcaggtggag ctgggcgggg gccctggtgc aggcagcctg cagcccttgg   300
ccctggaggg gtccctgcag aagcgtggca ttgtggaaca atgctgtacc agcatctgct   360
ccctctacca gctggagaac tactgcaact agacgcagcc cgcaggcagc cccacacccg   420
ccgcctcctg caccgagaga gatggaataa agcccttgaa ccagcaaaa              469

SEQ ID NO: 10            moltype = DNA  length = 495
FEATURE                  Location/Qualifiers
source                   1..495
                         mol_type = genomic DNA
                         organism = Homo sapiens
SEQUENCE: 10
agccctccag gacaggctgc atcagaagag gccatcaagc aggtctgttc caagggcctt    60
tgcgtcagat cactgtcctt ctgccatggc cctgtggatg cgcctcctgc ccctgctggc   120
gctgctggcc ctctgggac ctgacccagc cgcagccttt gtgaaccaac acctgtgcca   180
ctcacacctg gtggaagctc tctacctagt gtgcggggaa cgaggcttct tctacacacc   240
caagacccgc cgggaggcag aggacctgca ggtggggcag gtggagctgg gcggggccc   300
tggtgcaggc agcctgcagc ccttggccct ggaggggtcc ctgcagaagc gtggcattgt   360
ggaacaatgc tgtaccagca tctgctccct ctaccagctg gagaactact gcaactagac   420
gcagcccgca ggcagcccca cacccgccgc ctcctgcacc gagagagatg gaataaagcc   480
cttgaaccag caaaa                                                   495

SEQ ID NO: 11            moltype = DNA  length = 648
FEATURE                  Location/Qualifiers
source                   1..648
                         mol_type = genomic DNA
                         organism = Homo sapiens
SEQUENCE: 11
agccctccag gacaggctgc atcagaagag gccatcaagc aggtctgttc caagggcctt    60
tgcgtcaggt gggctcagga ttccagggtg gctggacccc aggccccagc tctgcagcag   120
ggaggacgtg gctgggctcg tgaagcatgt ggggtgagc caggggccc aaggcaggg    180
cacctggcct tcagcctgcc tcagccctgc ctgtctccca gatcactgtc cttctgccat   240
ggccctgtgg atgcgcctcc tgcccctgct ggcgctgctg gccctctggg gacctgacc   300
agccgcagcc tttgtgaacc aacacctgtg cggctcacac ctggtggaag ctctctacct   360
agtgtgcggg gaacgaggct tcttctacac acccaagacc cgccgggagg cagaggacct   420
gcaggtggga caggtggagc tgggcggggg ccctggtgca ggcagcctgc agcccttgg   480
cctggagggg tccctgcaga agcgtggcat tgtggaacaa tgctgtacca gcatctgctc   540
cctctaccag ctggagaact actgcaacta gacgcagccc gcaggcagcc ccacacccgc   600
cgcctcctgc accgagagag atggaataaa gcccttgaac cagcaaaa               648

SEQ ID NO: 12            moltype = DNA  length = 529
FEATURE                  Location/Qualifiers
source                   1..529
                         mol_type = genomic DNA
                         organism = Homo sapiens
SEQUENCE: 12
agccctccag gacaggctgc atcagaagag gccatcaagc aggtctgttc caagggcctt    60
tgcgtcaggt gggctcagga ttccagggtg gctggacccc agatcactgt ccttctgcca   120
tggccctgtg gatgcgcctc ctgcccctgc tggcgctgct ggccctctgg ggacctgacc   180
cagccgcagc ctttgtgaac caacacctgt gcggctcaca cctggtggaa gctctctacc   240
tagtgtgcgg ggaacgaggc ttcttctaca cacccaagac ccgccgggag cagaggacc   300
tgcaggtggg gcaggtggag ctgggcgggg gccctggtgc aggcagcctg cagcccttgg   360
ccctggaggg gtccctgcag aagcgtggca ttgtggaaca atgctgtacc agcatctgct   420
ccctctacca gctggagaac tactgcaact agacgcagcc cgcaggcagc cccacacccg   480
ccgcctcctg caccgagaga gatggaataa agcccttgaa ccagcaaaa              529

SEQ ID NO: 13            moltype = AA   length = 585
FEATURE                  Location/Qualifiers
source                   1..585
                         mol_type = protein
                         organism = Homo sapiens
SEQUENCE: 13
MASPGSGFWS FGSEDSGDS ENPGTARAWC QVAQKFTGGI GNKLCALLYG DAEKPAESGG     60
SQPPRAAARK AACACDQKPC SCSKVDVNYA FLHATDLLPA CDGERPTLAF LQDVMNILLQ   120
YVVKSFDRST KVIDFHYPNE LLQEYNWELA DQPQNLEEIL MHCQTTLKYA IKTGHPRYFN   180
QLSTGLDMVG LAADWLTSTA NTNMFTYEIA PVFVLLEYVT LKKMREIIGW PGGSGDGIFS   240
PGGAISNMYA MMIARFKMFP EVKEKGMAAL PRLIAFTSEH SHFSLKKGAA ALGIGTDSVI   300
LIKCDERGKM IPSDLERRIL EAKQGFVPF LVSATAGTTV YGAFDPLLAV ADICKKYKIW   360
MHVDAAWGGG LLMSRKHKWK LSGVERANSV TWNPHKMMGV PLQCSALLVR EEGLMQNCNQ   420
MHASYLFQQD KHYDLSYDTG DKALQCGRHV DVFKLWLMWR AKGTTGFEAH VDKCLELAEY   480
LYNIIKNREG YEMVFDGKPQ HTNVCFWYIP PSLRTLEDNE ERMSRLSKVA PVIKARMMEY   540
GTTMVSYQPL GDKVNFFRMV ISNPAATHQD IDFLIEEIER LGQDL                   585
```

```
SEQ ID NO: 14            moltype = DNA  length = 1758
FEATURE                  Location/Qualifiers
misc_feature             1..1755
                         note = CDS encodes SEQ ID NO: 13
source                   1..1758
                         mol_type = genomic DNA
                         organism = Homo sapiens
SEQUENCE: 14
atggcatctc cgggctctgg cttttggtct ttcgggtcgg aagatggctc tggggattcc    60
gagaatcccg gcacagcgcg agcctggtgc caagtggctc agaagttcac gggcggcatc   120
ggaaacaaac tgtgcgccct gctctacgga gacgccgaga gccggcgga gagcggcggg    180
agccaacccc cgcgggccgc cgcccggaag gccgcctgcg cctgcgacca gaagccctgc   240
agctgctcca aagtggatgt caactacgcg tttctccatg caacagcct gctgccggcg    300
tgtgatggag aaaggcccac tttggcgttt ctgcaagatg ttatgaacat tttacttcag   360
tatgtggtga aagtttcga tagatcaacc aaagtgattg atttccatta tcctaatgag    420
cttctccaag aatataattg ggaattgca gaccaaccac aaaatttgga ggaaattttg    480
atgcattgcc aaacaactct aaaatatgca attaaaacag ggcatcctag atacttcaat   540
caactttcta ctggtttgga tatggttgga ttagcagcag actggctgac atcaacagca   600
aatactaaca tgttcaccta tgaaattgct ccagtatttg tgcttttgga atatgtcaca   660
ctaaagaaaa tgagagaaat cattggctgg ccagggggct ctggcgatgg gatattttct   720
cccggtggcg ccatatctaa catgtatgcc atgatgatcg cacgctttaa gatgttccca   780
gaagtcaagg agaaaggaat ggctgctctt cccaggctca ttgccttcac gtctgaacat   840
agtcattttt ctctcaagaa gggagctgca gccttaggga ttggaacaga cagcgtgatt   900
ctgattaaat gtgatgagag agggaaaatg attccatctg atcttgaaag aaggattctt   960
gaagccaaac agaaagggtt tgttccttct ctcgtgagg ccacagctgg aaccaccgtg   1020
tacggagcat tgaccccct cttagctgtc gctgacattt gcaaaaagta taagatctgg   1080
atgcatgtgg atgcagcttg gggtggggga ttactgatgt cccgaaaaca caagtggaaa   1140
ctgagtggcg tggagagggc caactctgtg acgtggaatc cacacaagat gatgggagtc   1200
cctttgcagt gctctgctct cctggttaga gaagagggat ttgcagaa ttgcaaccaa    1260
atgcatgcct cctacctctt tcagcaagat aaacattatg acctgtccta tgacactgga   1320
gacaaggcct acagtgcgg acgccacgtt gatgttttta aactatggct gatgtggagg    1380
gcaaagggga ctaccgggtt tgaagcgcat gttgataaat gtttggagtt ggcagagtat   1440
ttatacaaca tcataaaaaa ccgagaagga tatgagatgg tgtttgatgg aagcctcag   1500
cacacaaatg tctgcttctg gtacattcct ccaagcttgc gtactctgga agacaatgaa   1560
gagaatgaa gtcgcctctc gaaggtggcc ccagtgatta aagccagaat gatggagtat    1620
ggaaccacaa tggtcagcta ccaaccttg ggagacaagg tcaatttctt ccgcatggtc    1680
atctcaaacc cagcggcaac tcaccaagac attgacttcc tgattgaaga aatagaacgc   1740
cttggacaag atttataa                                                 1758

SEQ ID NO: 15            moltype = DNA  length = 2400
FEATURE                  Location/Qualifiers
source                   1..2400
                         mol_type = genomic DNA
                         organism = Homo sapiens
SEQUENCE: 15
agctcgcccg cagctcgcac tcgcaggcga cctgctccag tctccaaagc cgatggcatc    60
tccgggctct ggcttttggt ctttcgggtc ggaagatggc tctggggatt ccgagaatcc   120
cggcacagcg cgagcctggt gccaagtggc tcagaagttc acgggcggca tcggaaacaa   180
actgtgcgcc ctgctctacg gagacgccga gaagccggcg gagagcggcg ggagccaacc   240
ccgcgggccg gccgcccgga aggccgcctg cgcctgcgac cagaagccct gcagctgctc   300
caaagtggat gtcaactacg cgtttctcca tgcaacagca ctgctgccgg cgtgtgatgg   360
agaaaggccc actttggcgt ttctgcaaga tgttatgaac attttacttc agtatgtggt   420
gaaagtttc gatagatcaa ccaaagtgat tgatttccat tatcctaatg agcttctcca    480
agaatataat tgggaattgg cagaccaacc acaaaatttg gaggaaattt tgatgcattg   540
ccaaacaact ctaaaatatg caattaaaac agggcatcct agatacttca atcaactttc   600
tactggtttg gatatggttg gattagcagc agactggctg acatcaacag caaatactaa   660
catgttcacc tatgaaattg ctccagtatt tgtgcttttg gaatatgtca cactaaagaa   720
aatgagagaa atcattggct ggccaggggg ctctggcgat gggatattt ctcccggtgg    780
cgccatatct aacatgtatg ccatgatgat cgcacgcttt aagatgttcc cagaagtcaa   840
ggagaaagga atggctgctc ttcccaggct cattgccttc acgtctgaac atagtcattt   900
ttctctcaag aagggagctg cagccttagg gattggaaca gacagcgtga ttctgattaa   960
atgtgatgag agagggaaaa tgattccatc tgatcttgaa agaaggattc ttgaagccaa   1020
acagaaaggg tttgttcctt cctcgtgag tgccacagct ggaaccaccg tgtacggagc    1080
atttgacccc ctcttagctg tcgctgacat ttgcaaaaag tataagatct ggatgcatgt   1140
ggatgcagct tggggtgggg gattactgat gtcccgaaaa cacaagtgga aactgagtgg   1200
cgtggagagg gccaactctg tgacgtgaa tccacacaag atgatgggag tccctttgca    1260
gtgctctgct ctcctggtta gagaaggga ttgcagaa attgcaacc aaatgcatgc      1320
ctcctacctc tttcagcaag ataaacatta tgacctgtcc tatgacactg gagacaaggc   1380
cttacagtgc ggacgccacg ttgatgtttt taaactatgg ctgatgtgga gggcaaaggg   1440
gactaccggg tttgaagcgc atgttgataa atgtttggag ttggcagagt atttatacaa   1500
catcataaaa aaccgagaag gatatgagat ggtgtttgat gggaagcctc agcacacaaa   1560
tgtctgcttc tggtacattc tccaagcttg cgtactctg aagacaatga agagagaat     1620
gagtcgcctc tcgaaggtgg ctccagtgat taaagccaga atgatggagt atggaaccac   1680
aatggtcagc taccaaccct ggggagacaa ggtcaatttc ttccgcatgg tcatctcaaa   1740
cccagcggca actcaccaag acattgactt cctgattgaa gaaatagaac gccttggaca   1800
agatttataa taaccttgct caccaagctg ttccacttct ctaggtagac aattaagttg   1860
tcacaaactg tgtgaatgta tttgtagttt gttccaaagt aaatctattt ctatattgtg   1920
gtgtcaaagt agagtttaaa aattaaacaa aaaagacatt gctcctttta aaagtccttt   1980
```

-continued

```
cttaagttta gaataccact ctaagaattc gtgacaaaag gctatgttct aatcaataag    2040
gaaaagctta aaattgttat aaatacttcc cttactttta atatagtgtg caaagcaaac    2100
tttattttca cttcagacta gtaggactga atagtgccaa attgcccctg aatcataaaa    2160
ggttctttgg ggtgcagtaa aaaggacaaa gtaaatataa aatatatgtt gacaataaaa    2220
actcttgcct ttttcatagt attagaaaaa aatttctaat ttacctatag caacatttca    2280
aatgtattta aatacatata attttacaaa aggaaaatat atatattaaa aaagatatcc    2340
tattttgtaa catatagatt tttattttat ataggttata caaactgcgg gggcggaatt    2400

SEQ ID NO: 16            moltype = DNA   length = 3610
FEATURE                  Location/Qualifiers
source                   1..3610
                         mol_type = genomic DNA
                         organism = Homo sapiens
SEQUENCE: 16
gaattcttcg taggaattat cttttccctc ctctcacccg acagcctgcc tatttccaaa      60
ggaaaaaaaa aaagcgtgtt gagtacgttc tggattactc ataagacctt ttttttttcc     120
ttccgggcgc aaaaccgtga gctggattta taatcgccct ataaagctcc agaggcggtc     180
aggcacctgc agaggagccc cgccgctccg ccgactagct ccgactagct ccccccgcga     240
cgtgatttcc ccgccgatcc ggtccccgcc tccccactgt gcccccgcct acccccggagc    300
cgtgcagccg cctctccgaa tctctctctt ctcctggcgc tcgcgtgcga gagggaacta     360
gcgagaacga ggaagcagct ggaggtgacg ccgggcagat tacgcctgtc agggccgagc    420
cgagcggatc gctgggcgct gtgcagagga aaggccggag gccggctc gctgtcgcag      480
agccgagcct gtttctgcgc cggaccagtc gaggactctg gacagtagag gccccggag     540
gaccgagctg atgcgtcttt cgaccccatc ttcgtccgca acctcctcga acgcgggagc    600
ggaccccaat accactaacc tgcgcccac aacgtacgat acctggtgcg cgtggcccac     660
tggatgcacc agaaaactgg ggctcaagat ctgcggcttc ttgcaaagga ccaacagcct    720
ggaagagaag agtcgccttg tgagtgcctt cagggagagg caatcctcca agaacctgct    780
ttcctgtgaa aacagcgacc gggatgcccg cttccggcgc acagagactg acttctctaa    840
tctgtttgct agagatctgc ttccggctaa gaacggtgag gagcaaaccg tgcaattcct    900
cctggaagtg gtggacatac tcctcaacta tgtccgcaaa acatttgatc gctccaccaa    960
ggtgctggac tttcatcacc cacaccagtt gctggaaggc atggagggct tcaacttgga   1020
gctctctgac caccccgagt ccctggagca gatcctggtt gactgcagag acaccttgaa   1080
gtatgggggtt cgcacaggtc atcctcgatt tttcaaccag ctctccactg gattggatat   1140
tattggccta gctggagaat ggctgacatc aacggccaat accaacatgt ttacatatga   1200
aattgcacca gtgtttgtcc tcatggaaca aataacactt aagaagatga gagagatagt   1260
tggatggtca agtaaagatg gtgatgggat atttttctcct ggggggcgcca tatccaacat  1320
gtacagcatc atggctgctc gctacaagta cttcccggaa gttaagacaa agggcatggc   1380
ggctgtgcct aaactggtcc tcttccactc agaacagagt cactattcca taaagaaagc   1440
tggggctgca cttggctttg gaactgacaa tgtgattttg ataaagtgca atgaaagggg   1500
gaaaataatt ccagctgatt ttgaggcaaa aattcttgaa gccaaacaga agggatatgt   1560
tccctttttat gtcaatgcaa ctgctggcac gactgtttat ggagcttttg atccgataca   1620
agagattgca gatatatgtg agaaaataaa cctttggttg catgtcgatg ctgcctgggg   1680
aggtggcctg atcatgtcca ggaagcaccg ccataaactc aacggcatag aaaagggcaa   1740
ctcagtcacc tggaaccctc acaagatgat gggcgtgctg ttgcagtgct ctgccattct   1800
cgtcaaggaa aagggtatac tccaaggatg caaccagatg tgtgcaggat atctcttcca   1860
gccagacaag cagtatgatg tctcctacga caccggggac aaggcaattc agtgtggccg   1920
ccacgtggat atcttcaagt tctggcgtga tggaaagca aagggcacag tgggatttga   1980
aaaccagatc aacaaatgcc tggaactggc tgaatacctc tatgccaaga ttaaaaacag   2040
agaagaattt gagatggttt tcaatggcga gcctgagcac acaaacgtct gttttttggta   2100
tattccacaa agcctcaggg gtgtgccaga cagccctcaa cgacgggaaa agctacacaa   2160
ggtggctcca aaaatcaaag ccctgatgat ggagtcagat acgaccatgg ttggctacca   2220
gccccaaggg gacaaggcca acttcttccg gatggtcatc tccaacccag ccgctaccca   2280
gtctgacatt gacttcctca ttgaggagat agaagactg ggccaggatc tgtaatcatc   2340
cttcgcagaa catgagttta tgggaatgcc ttttccctct ggcactccag aacaaacctc   2400
tatatgttgc tgaaacacac aggccatttc attgagggaa aacataatat cttgaagaat   2460
attgttaaaa ccttacttaa agcttgtttg ttctagttag caggaaatag tgttctttttt   2520
aaaaagttgc acattaggaa cagagtatat atgtacagtt atacatacct ctctctatat   2580
atacatgtat agtgagtgtg gcttagtaat agatcacggc atgtttcccg ctccaagaga   2640
attcacttta ccttcagcag ttaccgagga gctaaacatg ctgccaacca gcttgtccaa   2700
caactccagg aaaactgttt tccaaaacgc catgtcctag gggccaaggg aaatgctgtt   2760
ggtgagaatc gacctcactg tcagcgtttc tccacctgaa gtgatgatgg atgagaaaaa   2820
acaccaccaa atgacaagtc acaccctccc cattagtatc ctgttagggg aaaatagtag   2880
cagagtcatt gttacaggtg tactatggct gtattttaga gattaatttg tgtagattgt   2940
gtaaattcct gttgtctgac cttggtggtg ggaggggaaa ctatgtgtca tgattcaat   3000
gattgtttaa ttgtaggtca atgaaatatt tgcttattta tattcagaga tgtaccatgt   3060
taaagaggcg tcttgtattt tcttcccatt tgtaatgtat cttatttata tatgaagtaa   3120
gttctgaaaa ctgtttatgg tattttcgtg catttgtgag ccaaagagaa aagattaaaa   3180
ttagtgagat ttgtatttat attagagtgc ccttaaaata atgatttaag cattttactg   3240
tctgtaagag aattctaaga ttgtacatga cataagttat agtaatcatg gcaaatcctg   3300
ttacttaaat agcatctgct cttctcttac gctctctgtc tggctgtacg tctggtgttc   3360
tcaatgcttt tctagcaact gttggataat aactagatct cctgtaattt tgtagtagtt   3420
gatgaccaat ctctgtgact cgcttagctg aaacctaagg caacatttcc gaagaccttc   3480
tgaagatctc agataaagtg accaggctca caactgtttt tgaagaaggg aaattcacac   3540
tgtgcgtttt gagtatgcaa gaagaatata aataaataaa atatctcatg gagattgaca   3600
aaaaaaaaa                                                             3610

SEQ ID NO: 17            moltype = DNA   length = 2824
FEATURE                  Location/Qualifiers
source                   1..2824
```

```
                        mol_type = genomic DNA
                        organism = Homo sapiens
SEQUENCE: 17
gcggccgccc gcacttcccg cctctggctc gcccgaggac gcgctggcac gcctcccacc    60
ccctcactct gactccagct ggcgtgcatg gtctgcctcg catcctcacg actcagctcc   120
ctccctctct cgtgtttttt tcctccgccg cccctcatt catcccact gggctccctc    180
tccctcaaat gctctgggc tctccgcgct ttcctgagtc cgggctccga ggacccttag    240
gtagtcccgg tctcttttaa agctcccgg cttccaaagg gttgccacgt ccctaaaccc    300
tgtctccag tcgcatacac acacgcacag acacgcacgt tttctgttcc tgcgtgacac    360
ccgccctcgc cgctcggccc cgccggtccc cgcgcggtgc cctcctcccg ccacacgggc    420
acgcacgcgc gcgcagggcc aagcccgagg cagctcgccc gcagctcgca ctcgcaggcg    480
acctgctcca gtctccaaag ccgatggcat ctccgggctc tggcttttgg tctttcgggt    540
cggaagatgg ctctggggat tccgagaatc cggcacacag gcgagcctgg tgccaagtgg    600
ctcagaagtt cacgggcggc atcggaaaca aactgtcgcc cctgctctac gagacgccg    660
agaagccggc ggagagcggc gggagccaac ccccgcgggc cgccgcccgg aaggccgcct    720
gcgcctgcga ccagaagccc tgcagctgct ccaaagtgga tgtcaactac gcgtttctcc    780
atgcaacaga cctgctgccg gcgtgtgatg gagaaaggcc cactttggcg tttctgcaag    840
atgttatgaa cattttactt cagtatgtgg tgaaaagttt cgatagatca accaaagtga    900
ttgatttcca ttatcctaat gagcttctcc aagaatataa ttgggaattg gcagaccaac    960
cacaaaattt ggaggaaatt ttgatgcatt gccaaacaac tctaaaatat gcaattaaaa   1020
cagggcatcc tagatacttc aatcaacttt ctactggttt ggatatggtt ggattagcag   1080
cagactggct gacatcaaca gcaaatacta acatgttcac ctatgaaatt gctccagtat   1140
ttgtgctttt ggaatatgtc acactaaaga aaatgagaga aatcattggc tggccagggg   1200
gctctggcga tgggatattt tctcccggtg gcgccatatc taacatgtat gccatgatga   1260
tcgcacgctt taagatgttc ccagaagtca aggagaaagg aatggctgct cttcccaggc   1320
tcattgcctt cacgtctgaa catagtcatt ttctctcaa gaagggagct gcagccttag   1380
ggattggaac agacagcgtg attctgatta aatgtgatga gagagggaaa atgattccat   1440
ctgatcttga aagaaggatt cttgaagcca aacagaaagg gtttgttcct ttcctcgtga   1500
gtgccacagc tggaaccacc gtgtacgag catttgaccc cctcttagct gtcgctgaca   1560
tttgcaaaaa gtataagatc tggatgcatg tggatgcagc ttggggtggg ggattactga   1620
tgtcccgaaa acacaagtgg aaactgagtg gcgtgagag ggccaactct gtgacgtgag   1680
atccacacaa gatgatggga gtcccttgc agtgctctgc tctcctggtt agagaagagg   1740
gattgatgca gaattgcaac caaatgcatg cctcctacct ctttcagcaa gataaacatt   1800
atgacctgtc ctatgacact ggagacaagg ccttacagtg cggacgccac gttgatgttt   1860
ttaaactatg gctgatgtgg agggcaaagg ggactaccgg gtttgaagcg catgttgata   1920
aatgtttgga gttggcagag tatttataca acatcataa aaaccgagaa ggatatgaga   1980
tggtgtttga tgggaagcct cagcacacaa atgtctgctt ctggtacatt cctccaagct   2040
tgcgtactct ggaagacaat gaagagagaa tgagtcgcct ctccaaggtg gctccagtga   2100
ttaaagccag aatgatggag tatgaagcca caatggtcag ctaccaaccc ttgggagaca   2160
aggtcaattt cttccgcatg gtcatctcaa acccagcggc aactcaccaa gacattgact   2220
tcctgattga agaaatagaa cgccttggac aagatttata taaccttgc tcaccaagct   2280
gttccacttc tctagagaac atgccctcag ctaagccccc tactgagaaa cttccttga   2340
gaattgtgcg acttcacaaa atgcaaggtg aacaccattg tctctgag aacagacgtt   2400
accaattatg gagtgtcacc agctgccaaa atcgtaggtg ttggctctgc tggtcactgg   2460
agtagttgct actcttcaga atatggacaa agaaggcaca ggtgtaaata tagtagcagg   2520
atgaggaacc tcaaactggg tatcattttg cacgtgctct tctgttctca aatgctaaat   2580
gcaaacactg tgtatttatt agttaggtgt gccaaactac cgttcccaaa ttggtgtttc   2640
tgaatgacat caacattccc ccaacattac tccattacta aagacagaaa aaaataaaaa   2700
cataaaatat acaaacatgt ggcaacctgt tcttcctacc aaatataac ttgtgtatga   2760
tccaagtatt ttatctgtgt tgtctctcta aacccaaata aatgtgtaaa tgtggacaca   2820
tctc                                                                 2824

SEQ ID NO: 18             moltype = DNA   length = 2419
FEATURE                   Location/Qualifiers
source                    1..2419
                        mol_type = genomic DNA
                        organism = Homo sapiens
SEQUENCE: 18
gcggccgccc gcacttcccg cctctggctc gcccgaggac gcgctggcac gcctcccacc    60
ccctcactct gactccagct ggcgtgcatg gtctgcctcg catcctcacg actcagctcc   120
ctccctctct cgtgtttttt tcctccgccg cccctcatt catcccact gggctccctt    180
tccctcaaat gctctgggc tctccgcgct ttcctgagtc cgggctccga ggacccttag    240
gtagtcccgg tctcttttaa agctcccgg cttccaaagg gttgccacgt ccctaaaccc    300
tgtctccag tcgcatacac acacgcacag acacgcacgt tttctgttcc tgcgtgacac    360
ccgccctcgc cgctcggccc cgccggtccc cgcgcggtgc cctcctcccg ccacacgggc    420
acgcacgcgc gcgcagggcc aagcccgagg cagctcgccc gcagctcgca ctcgcaggcg    480
acctgctcca gtctccaaag ccgatggcat ctccgggctc tggcttttgg tctttcgggt    540
cggaagatgg ctctggggat tccgagaatc cggcacacag gcgagcctgg tgccaagtgg    600
ctcagaagtt cacgggcggc atcggaaaca aactgtcgcc cctgctctac gagacgccg    660
agaagccggc ggagagcggc gggagccaac ccccgcgggc cgccgcccgg aaggccgcct    720
gcgcctgcga ccagaagccc tgcagctgct ccaaagtgga tgtcaactac gcgtttctcc    780
atgcaacaga cctgctgccg gcgtgtgatg gagaaaggcc cactttggcg tttctgcaag    840
atgttatgaa cattttactt cagtatgtgg tgaaaagttt cgatagatca accaaagtga    900
ttgatttcca ttatcctaat gagcttctcc aagaatataa ttgggaattg gcagaccaac    960
cacaaaattt ggaggaaatt ttgatgcatt gccaaacaac tctaaaatat gcaattaaaa   1020
cagggcatcc tagatacttc aatcaacttt ctactggttt ggatatggtt ggattagcag   1080
cagactggct gacatcaaca gcaaatacta acatgttcac ctatgaaatt gctccagtat   1140
ttgtgctttt ggaatatgtc acactaaaga aaatgagaga aatcattggc tggccagggg   1200
gctctggcga tgggatattt tctcccggtg gcgccatatc taacatgtat gccatgatga   1260
```

```
tcgcacgctt taagatgttc ccagaagtca aggagaaagg aatggctgct cttcccaggc  1320
tcattgcctt cacgtctgaa catagtcatt tttctctcaa gaaggagct gcagccttag   1380
ggattggaac agacagcgtg attctgatta aatgtgatga gagagggaaa atgattccat   1440
ctgatcttga aagaaggatt cttgaagcca acagaaagg gtttgttcct ttcctcgtga    1500
gtgccacagc tggaaccacc gtgtacgacg catttgccc cctcttagct gtcgctgaca    1560
tttgcaaaaa gtataagatc tggatgcatg tggatgcagc ttggggtggg ggattactga   1620
tgtcccgaaa acacaagtgg aaactgagtg gcgtggagag ggccaactct gtgacgtgga   1680
atccacacaa gatgatggga gtcccttgc agtgctctgc tctcctggtt agagaagagg    1740
gattgatgca gaattgcaac caaatgcatg cctcctacct ctttcagcaa gataaacatt   1800
atgacctgtc ctatgacact ggagacaagg ccttacagtg cggacgccac gttgatgttt   1860
ttaaactatg gctgatgtgg agggcaaagg ggactaccgg gtttgaagcg catgttgata   1920
aatgtttgga gttggcagag tatttataca acatcataaa aaaccgagaa ggatatgaga   1980
tggtgtttga tgggaagcct cagcacacaa atgtctgctt ctggtacatt cctccaagct   2040
tgcgtactct ggaagacaat gaagagaa tgagtcgcct ctcgaaggtg gctccagtga    2100
ttaaagccag aatgatggag tatggaacca caatggtcag ctaccaaccc ttgggagaca   2160
aggtcaattt cttccgcatg gtcatctcaa acccagcggc aactcaccaa gacattgact   2220
tcctgattga agaaatagaa cgccttggac aagatttata ataaccttgc tcaccaagct   2280
gttccacttc tctaggtaga caattaagtt gtcacaaact gtgtgaatgt atttgtagtt   2340
tgttccaaag taaatctatt tctatattgt ggtgtcaaag tagagtttaa aaattaaaca   2400
aaaaagacat tgctccttt                                                2419

SEQ ID NO: 19         moltype = AA  length = 979
FEATURE               Location/Qualifiers
source                1..979
                      mol_type = protein
                      organism = Homo sapiens
SEQUENCE: 19
MRRPRRPGGL GGSGGLRLLL CLLLLSSRPG GCSAVSAHGC LFDRRLCSHL EVCIQDGLFG    60
QCQVGVGQAR PLLQVTSPVL QRLQGVLRQL MSQGLSWHDD LTQYVISQEM ERIPRLRPPE   120
PRPRDRSGLA PKRPGPAGEL LLQDIPTGSA PAAQHRLPQP PVGKGGAGAS SSLSPLQAEL   180
LPPLLEHLLL PPQPPHPSLS YEPALLQPYL FHQFGSRDGS RVSEGSPGMV SVGPLPKAEA   240
PALFSRTASK GIFGDHPGHS YGDLPGPSPA QLFQDSGLLY LAQELPAPSR ARVPRLPEQG   300
SSSRAEDSPE GYEKEGLGDR GEKPASPAVQ PDAALQRLAA VLAGYGVELR QLTPEQLSTL   360
LTLLQLLPKG AGRNPGGVVN VGADIKKTME GPVEGRDTLA LPARTSPMPG HPTASPTSSE   420
VQQVPSPVSS EPPKAARPPV TPVLLEKKSP LGQSQPTVAG QPSARPAAEE YGYIVTDQKP   480
LSLAAGVKLL EILAEHVHMS SGSFINISVV GPALTFRIRH NEQNLSLADV TQQAGLVKSE   540
LEAQTGLQIL QTGVGQREEA AAVLPQTAHS TSPMRSVLLT LVALAGVAGL LVALAVALCV   600
RQHARQQDKE RLAALGPEGA HGDTTFEYQD LCRQHMATKS LFNRAEGPPE PSRVSSVSSQ   660
FSDAAQASPS SHSSTPSWCE EPAQANMDIS TGHHMILAYME DHLRNRDRLA KEWQALCAYQ   720
AEPNTCATAQ GEGNIKKNRH PDFLPYDHAR IKLKVESSPS RSDYINASPI IEHDPRMPAY   780
IATQGPLSHT IADFWQMVWE SGCTVIVMLT PLVEDGVKQC DRYWPDEGAS LYHVYEVNLV   840
SEHIWCEDFL VRSFYLKNVQ TQETRTLTQF HFLSWPAEGT PASTRPLLDF RRKVNKCYRG   900
RSCPIIVHCS DGAGRTGTYI LIDMVLNRMA KGVKEIDIAA TLEHVRDQRP GLVRSKDQFE   960
FALTAVAEEV NAILKALPQ                                                979

SEQ ID NO: 20         moltype = DNA  length = 2940
FEATURE               Location/Qualifiers
misc_feature          1..2937
                      note = CDS encodes SEQ ID NO: 19
source                1..2940
                      mol_type = genomic DNA
                      organism = Homo sapiens
SEQUENCE: 20
atgcggcgcc cgcggcggcc tgggggtctc gggggatccg ggggtctccg gctgctcctc    60
tgcctcctgc tgctgagcag ccgccccggg ggctgcagcg ccgttagtgc ccacggctgt   120
ctatttgacc gcaggctctg ctctcacctg gaagtctgta ttcaggatgg cttgtttggg   180
cagtgccagg tgggagtggg gcaggccggg ccccttttgc aagtcaccct cccagttctc   240
caacgcttac aaggtgtgct ccgacaactc atgtcccaag gattgcctg gcacgatgac    300
ctcacccagt atgtgatctc tcaggagatg gagcgcatcc ccaggcttcg gccccccagg   360
ccccgtccaa gggacaggtc tggcttggca cccaagagac ctggtcctgc tggagagctg   420
cttttacagg acatccccac tggctccgcc cctgctgccc agcatcggct tccacaacca   480
ccagtgggca aggtggagc tggggccagc tcctctctgt cccctctgca ggctgagctg    540
ctcccgcctc tcttggagca cctgctgctg ccccacagc ctcccaccc ttcactgagt     600
tacgaacctg ccttgctgca gccctacctg ttccaccagt ttggctcccg tgatggctcc   660
agggtctcag agggctcccc agggatggtc agtgtcggcc cctgcccaa ggctgaagcc    720
cctgccctct tcagcagaac tgcctccaag ggcatatttg ggaccaccc tggccactcc    780
tacgggga cc ttcagggcc ttcacctgcc agcttttc aagactctgg gctgctctat     840
ctggcccagg agttgccagc acccagcagg gccagggtgc caagctgcc agacaaggg     900
agcagcagc gggcagagga ctccccagag aggaagact agcagcgag   agggatcgt     960
ggagagaagc ctgcttcccc agctgtgcag ccagatgcgg ctctgcagag gctggccgct  1020
gtgctggcgg gctatgggt agagctgcg cagctgaccc ctgagcagct ctccacactc    1080
ctgacccctg tgcagctact gcccaagggt gcaggaagaa atccgggagg ggttgtaaat  1140
gttggagctg atatcaagaa aacaatggag gggccggtga aggcagag acacagcgag   1200
cttccagacc gcacatcccc catgcctgga cacccccatgc ctccagtga                1260
gtccagcagg tgccaagccc tgtctcctct gagcctccca agctgccag accccctgtg  1320
acacctgtcc tgctagagaa gaaaagccca ctgggccaga gccagccac ggtgcagga    1380
cagccctcag ccgcccagc agcagaggaa tatggctaca tcgtcactga tcagaagccc  1440
ctgagcctgg ctgcaggagt gaagctgctg gagatcctgg ctgagcatgt gcacatgtcc  1500
tcaggcagct tcatcaacat cagtgtgtg ggaccagccc tcaccttccg catccggcac   1560
```

```
aatgagcaga acctgtctttt ggctgatgtg acccaacaag cagggctggt gaagtctgaa    1620
ctggaagcac agacagggct ccaaatcttg cagacaggag tgggacagag ggaggaggca    1680
gctgcagtcc ttccccaaac tgcgcacagc acctcaccca tgcgctcagt gctgctcact    1740
ctggtggccc tggcaggtgt ggctgggctg ctggtggctc tggctgtggc tctgtgtgtg    1800
cggcagcatg cgcggcagca agacaaggag cgcctggcag ccctggggcc tgaggggggc    1860
catggtgaca ctacctttga gtaccaggac ctgtgccgcc agcacatggc cacgaagtcc    1920
ttgttcaacc gggcagaggg tccaccggag ccttcacggg tgagcagtgt gtcctcccag    1980
ttcagcgacg cagcccaggc cagccccagc tcccacagca gcacccgtc ctggtgcgag    2040
gagccggccc aagccaacat ggacatctcc acgggacaca tgattctgac atacatggag    2100
gatcacctgc ggaaccggga ccgccttgcc aaggagtggc aggccctctg tgcctaccaa    2160
gcagagccaa acacctgtgc caccgcgcag ggggagggca acatcaaaaa gaaccggcat    2220
cctgacttcc tgccctatga ccatgcccgc ataaaactga aggtggagag cagcccttct    2280
cggagcgatt acatcaacgc cagccccatt attgagcatg accctcggat gccagcctac    2340
atagccacgc agggcccgct gtcccatacc atcgcagact tctggcagat ggtgtgggaa    2400
agcggctgca ccgtcatcgt catgctgacc ccgctggtgg aggatggtgt caagcagtgt    2460
gaccgctact ggccagatga gggtgcctcc ctctaccacg tatatgaggt gaacctggtg    2520
tcggagcaca tctggtgcga ggactttctg gtgcggagct tctacctgaa gaacgtgcag    2580
acccaggaga cgcgcacgct cacgcagttc cacttcctca gctggccggc agagggcaca    2640
ccggcctcca cgcggcccct gctggacttc cgcaggaagg tgaacaagtg ctaccggggc    2700
cgctcctgcc ccatcatcgt gcactgcagt gatggtgcgg gaggaccgg cacctacatc    2760
ctcatcgaca tggtcctgaa ccgcatggca aaggagtgaa aggagattga catcgctgcc    2820
accctggagc atgtccgtga ccagcggcct ggccttgtcc gctctaagga ccagtttgaa    2880
tttgccctga cagccgtggc ggaggaagtg aatgccatcc tcaaggccct gccccagtga    2940
```

SEQ ID NO: 21        moltype = DNA  length = 3801
FEATURE               Location/Qualifiers
source                1..3801
                        mol_type = genomic DNA
                        organism = Homo sapiens
SEQUENCE: 21

```
aggtaggtcc cccgctccga cagggctctt acgccatatg tgacgcaaat tagcttacga     60
gccgggggtg gaggtgtcgt cagcaccgc ctgcggttgg ccgcgttgca gcagaggggg    120
catgtagacc ccgcctcgta gggaggtggg gagcggcaag ccccgcctca gcccctctgg    180
caggctcccg ccagcgtcgc tgcggctccg gcccgggagc gagcgcccgg agctcggaaa    240
gatgcagcag ccgcggcggc ctgggggtct cggggggatcc ggggtctcc gctgctcct    300
ctgcctcctg ctgctgagca gccgcccggg gggctgcagc gccgttagtg cccacgctg    360
tctatttgac cgcaggctct gctctcacct ggaagtctgt attcaggatg gcttgtttgg    420
gcagtgccag gtgggagtgg ggcaggcccg gccccttttg caagtcacct cccagttct    480
ccaacgctta caaggtgtgc tccgacaact catgtccaca ggattgtcct ggcacgatga    540
cctcacccag tatgtgatct ctcaggagat ggagcgcatc cccaggcttc gccccccaga    600
gccccgtcca agggacaggt ctggcttggc acccaagaga cctggtcctg ctggagagct    660
gcttttacag gacatcccca ctggctccgg ccctgctgcc cagcatcggc ttccacaacc    720
accagtgggc aaaggtggag ctggggccag ctcctctctg tcccctctgc aggctgagct    780
gctcccgcct ctcttggagc acctgctgct gccccacag cctccccacc cttcactgag    840
ttacgaacct gccttgctgc agccctacct gttccaccag tttggctccc gtgatggctc    900
cagggtctca gagggctccc cagggatggt cagtgtcggc cccctgccca aggctgaagc    960
ccctgccctc ttcagcagaa ctgcctccaa gggcatattt gggaccaccc tggccactc    1020
ctacggggac cttccaggc cttcacctgc ccagcttttt caagactctg gctgctctta    1080
tctgccccag gagttgccag cacccagcag ggccagggtg ccaaggctgc cagagcaagg    1140
gagcagcagc cgggcagagg actcccagga gggctatgag aaggaaggac tagggatcg    1200
tggagagaag cctgcttccc cagctgtgca gccagatgcg gctctgcaga ggctggccgc    1260
tgtgctggcg ggctatgggg tagagctgcg tcagctgacc cctgagcagc tctccacact    1320
cctgaccctg ctgcagctac tgcccaaggg tgcaggaaga aatccgggag gggttgtaaa    1380
tgttggagct gatatcaaga aaacaatgga ggggccggtg gagggcagag acacagcaga    1440
gcttccagcc cgcacatccc ccatgcctgg acacccact gccagcccta cctccagtga    1500
agtccagcag gtgccaagcc ctgtctcctc tgagcctccc aaagctgcca gacccctgt    1560
gacacctgtc ctgctagaga agaaaagcc actgggccag agccagccca ggtggcagg    1620
acagccctca gcccgcccag cagcagagga atatggctac atcgtcactg atcagaagcc    1680
cctgagcctg gctgcaggag tgaagctgct ggatgatctg gctgagcatg tgcacatgtc    1740
ctcaggcagc ttcatcaaca tcagtgtggt gggaccagc ctcaccttcc gcatccggca    1800
caatgagcag aacctgtctt ggctgatgt gacccaacaa gcagggctgg tgaagtctga    1860
actggaagca cagacagggc tccaaatctt gcagacagga gtgggacaga ggaggaggc    1920
agctgcagtc cttccccaaa ctgcgcacag cacctcaccc atgcgctcag tgctgctcac    1980
tctggtggcc ctggcaggtg tggctggct gctggtggct ctggctgtgt    2040
gcggcagcat gcgcggcagc aagacaagga gcgcctggca gccctggggc ctgaggggc    2100
ccatggtgac actacctttg agtaccagga cctgtgccgc cagcacatgg ccacgaagtc    2160
cttgttcaac cgggcagagg gtccaccgga ccttcacgg gtgagcagtg tgtcctccca    2220
gttcagcgac gcagcccagg ccagcccag ctcccacagc agcacccgt cctggtgcga    2280
ggagccggcc caagccaaca tggacatctc cacgggacac atgattctga catacatgga    2340
ggatcacctg cggaaccggg accgccttgc caaggagtgg caggccctct gtgcctacca    2400
agcagagcca aacacctgtg ccaccgcgca ggggagggc aacatcaaaa agaaccggca    2460
tcctgacttc ctgccctatg accatgcccg cataaaactg aaggtggaga gcagcccttc    2520
tcggagcgat tacatcaacg ccagccccat tattgagcat gaccctcgga tgccagccta    2580
catagccacg cagggccgct gtcccatac catcgcagac ttctggcaga tggtgtgggt    2640
gagcggctgc accgtcatcg tcatgctgac cccgctggtg gaggatggtg tcaagcagtg    2700
tgaccgctac tggccagatg agggtgcctc cctctaccac gtatatgagg tgaacctggt    2760
gtcggagcac atctggtgcg aggactttct ggtgcggagc ttctacctga gaacgtgca    2820
gacccaggag acgcgcacgc tcacgcagtt ccacttcctc agctgccgg cagagggcac    2880
accggcctcc acgcggcccc tgctggactt ccgcaggaag gtgaacaagt gctaccgggg    2940
```

-continued

```
ccgctcctgc cccatcatcg tgcactgcag tgatggtgcg gggaggaccg gcacctacat 3000
cctcatcgac atggtcctga accgcatggc aaaaggagtg aaggagattg acatcgctgc 3060
caccctggag catgtccgtg accagcggcc tggccttgtc cgctctaagg accagtttga 3120
atttgccctg acagccgtgg cggaggaagt gaatgccatc ctcaaggccc tgccccagtg 3180
agaccctggg gcccttggc gggcagccca gcctctgtcc ctcttgcct gtgtgagcat 3240
ctctgtgtac ccactcctca ctgcccacc agccacctct tgggcatgct cagcccttcc 3300
tagaagagtc aggaagggaa agccagaagg ggcacgcctg cccagcctcg catgccagag 3360
cctgggcat cccagagccc agggcatccc atggggtgc tgcagccagg aggagaggaa 3420
aggacatggg tagcaattct acccagagcc ttctcctgcc tacattccct ggcctggctc 3480
tcctgtagct ctcctggggt tctgggagtt ccctgaacat ctgtgtgtgt ccccctatgc 3540
tccagtatgg aagaatgggg tggagggtcg ccacacccgg ctcccctgc ttctcagccc 3600
cgggcctgcc tctgactcac acttgggcgc tctgccctcc ctggcctcac gcccagcctc 3660
ctcccaccac cctcccacca tgcgctgctc aacctctctc cttctggcgc aagagaaat 3720
ttctagaaaa aactacttt gtaccagtgt gaataaagtt agtgtgttgt ctgtgcagct 3780
gcaaaaaaaa aaaaaaaaaa a                                            3801

SEQ ID NO: 22            moltype = DNA   length = 3712
FEATURE                  Location/Qualifiers
source                   1..3712
                         mol_type = genomic DNA
                         organism = Homo sapiens
SEQUENCE: 22
aggtaggtcc cccgctccga cagggctctt acgccatatg tgacgcaaat tagcttacga   60
gccgggggtg gaggtgtcgt cagcacccgc ctgcggttgg ccgcgttgca gcagagggg   120
catgtagacc ccgcctcgta gggaggtggg gagcggcaag ccccgcctca gccctctgg   180
caggctcccg ccagcgtcgc tgcggctccg gcccgggagc gagcgccgg agctccgaaa   240
gatgcggcgc ccgcggcggc ctgggggtct cggggggatcc gggggtctcc ggctgctcct   300
ctgcctcctg ctgctgagca gccgcccggg gggctgcagc gccgttagtg cccacggctg   360
tctatttgac cgcaggctct gctctcacct ggaagtctgt attcaggatg gcttgtttgg   420
gcagtgccag gtgggagtgg ggcaggcccg gcccctttg caagtcacct ccccagttct   480
ccaacgctta caaggtgtgc tccgacaact catgtcccaa ggattgtcct ggcacgatga   540
cctcacccag tatgtgatct ctcaggagat ggagcgcatc cccaggcttc gccccccaga   600
gccccgtcca agggacaggt ctggcttggc acccaagaga cctggtcctg ctggagagct   660
gcttttacag gacatcccca ctggccgc ccctgctcc cagcatcggc ttccacaacc   720
accagtgggc aaaggtggag ctggggccag ctcctctctg tccccctgc aggctgagct   780
gctcccgcct ctcttggagc acctgctgct gccccacag cctccccacc cttcactgag   840
ttacgaacct gccttgctgc agccctacct gttccaccag tttggctccc gtgatggctc   900
cagggtctca gagggctccc cagggatggt cagtgtcggc ccctgccca aggctgaagc   960
ccctgccctc ttcagcagaa ctgcctccaa gggcatattt gggaccacc ctggccactc  1020
ctacggggac cttccagggc cttcacctgc ccagcttttt caagactctg gctgctcta  1080
tctgccccag gagttgccag cacccagcag ggccagggtg ccaaggctgc cagagcaagg  1140
gagcagcagc cgggcagagg actccccaga gggctatgag aaggaaggac taggggatcg  1200
tggagagaag cctgcttccc cagctgtgca gccagatgcg gctctgcaga ggctggccgc  1260
tgtgctggcg ggctatgggg tagagctgcg tcagctgacc cctgagcagc tctccacact  1320
cctgaccctg ctgcagctac tgcccaaggg tgcaggaaga aatccgggag gggttgtaaa  1380
tgttggagct gatatcaaga aaacaatgga ggggccggtg gagggcagag acacagcaga  1440
gcttccagcc cgcacatccc ccatgcctgg acacccccact gccagcccta cctccagtga  1500
agtccagcag gtgccaagcc ctgtctcctc tgagcctccc aaagctgcca gaccccctgt  1560
gacacctgtc ctgctagaga agaaaagccc actgggccag agccagccca cggtggcagg  1620
acagccctca gcccgcccag cagcagagga atatggctac atcgtcactg atcagaatgt  1680
ggtgggacca gccctcacct tccgcatccg gcacaatgag cagaacctgt ctttggctga  1740
tgtgacccaa caagcagggc tggtgaagtc tgaactggaa gcacagacag ggctccaaat  1800
cttgcagaca ggagtgggac agagggagga ggcagctgca gtccttcccc aaactgcgca  1860
cagcacctca cccatgcgct cagtgctgct cactctggtg gccctggcag gtgtggctgg  1920
gctgctggtg gctctggctg tggctctgtg tgtgcggcag catgcgcggc agcaagacaa  1980
ggagcgcctg gcagccctgg ggcctgaggg gcccatggt gacactacct ttgagtacca  2040
ggacctgtgc cgccagcaca tggccacgaa gtccttgttc aaccgggcag agggtccacc  2100
ggagccttca cgggtgagca gtgtgtcctc ccagttcagc gacgcagccc aggccagccc  2160
cagctcccac agcagcaccc cgtcctggtg cgaggagccc gccaagcca acatggacat  2220
ctccacggga cacatgattc tggcatacat ggaggatcac cgcggaacc gggaccgcct  2280
tgccaaggag tggcaggccc tctgtgccta ccaagcagag ccaaacacct gtgccaccgc  2340
gcagggggag ggcaacatca aaaagaaccg gcatcctgac ttcctgccct atgaccatgc  2400
ccgcataaaa ctgaaggtgg agagcagccc ttctcggagc gattacatca acgccagccc  2460
cattattgag catgaccctc ggatgccagc ctacatagcc acgcagggcc cgctgtccca  2520
taccatcgca gacttctggc agatggtgtg ggagagcgc tgcaccgtca tcgtcatgct  2580
gaccccgctg gtgaaggatg tgtcaagca gtgtgaccgc tactgccagg atgagggtgc  2640
ctccctctac cacgtatatg aggtgaacct ggtgtcggag cacatctggt gcgaggactt  2700
tctggtgcgg agcttctacc tgaagaacgt gcagacccga gagcgcgca cgctcacgca  2760
gttccacttc ctcagctggc cggcagaggg cacaccggtc tcctgctgga  2820
cttccgcagg aaggtgaaca agtgctaccg gggccgctcc tgccccatca tcgtgcactg  2880
cagtgatggt gcgggggagga ccggcaccta tcctcatc gacatggtcc tgaaccgcat  2940
ggcaaaagga gtgaaggaga ttgacatcgc tgccaccctg agcatgtcc gtgaccagcg  3000
gcctggcctt gtccgctcta aggaccagtt tgaatttgcc ctgacagccg tggcggagga  3060
agtgaatgcc atcctcaagg cctgccca gtgagaccct gggggcagc gcctctgtcc  3120
ccagcctctg tccctctttg cctgtgtgag catctctgtg tacccactcc tcactgccc  3180
accagccacc tctttgggcat gctcagccct tcctagaaga gtcaggaagg gaaagccaga  3240
aggggcacgc ctgcccagcc tcgcatgcca gagcctgggg catcccagag cccagggcat  3300
cccatggggg tgctgcagcc aggaggagag gaaaggacat gggtagcaat tctacccaga  3360
gccttctcct gcctacattc cctggcctgg ctctcctgta gctctcctgg ggttctggga  3420
```

```
gttccctgaa catctgtgtg tgtccccta tgctccagta tggaagaatg gggtggaggg   3480
tcgccacacc cggctccccc tgcttctcag ccccgggcct gcctctgact cacacttggg   3540
cgctctgccc tccctggcct cacgcccagc ctcctcccac caccctccca ccatgcgctg   3600
ctcaacctct ctccttctgg cgcaagagaa catttctaga aaaaactact tttgtaccag   3660
tgtgaataaa gttagtgtgt tgtctgtgca gctgcaaaaa aaaaaaaaaa aa           3712

SEQ ID NO: 23           moltype = DNA   length = 3570
FEATURE                 Location/Qualifiers
source                  1..3570
                        mol_type = genomic DNA
                        organism = Homo sapiens
SEQUENCE: 23
aagagaattg ggctctgggg aaaattgcag gttcgggaga aggacacggg gtgcatgtgg   60
gcagagggac ttagagaccg gctgcgagac cacaggagga gccacttgct ccgaggcgcc   120
tgggaggctg tctatttgac cgcaggctct gctctcacct ggaagtctgt attcaggatg   180
gcttgtttgg gcagtgccag gtgggagtgg ggcaggcccg gccccttttg caagtcacct   240
ccccagttct ccaacgctta caaggtgtgc tccgacaact catgtcccaa ggattgtcct   300
ggcacgatga cctcacccag tatgtgatct ctcaggagat gggagcgcat cccaggcttc   360
gcccccaga gccccgtcca agggacaggt ctggcttggc acccaagaga cctggtcctg   420
ctggagagct gcttttacag gacatcccca ctggctccgc ccctgctgcc cagcatcggc   480
ttccacaacc accagtgggc aaaggtggag ctggggccag ctcctctctg tccctctgc   540
aggctgagct gctcccgcct ctcttggagc acctgctgct gccccacag cctccccacc   600
cttcactgag ttacgaacct gccttgctgc agccctacct gttccaccag tttggctccc   660
gtgatggctc cagggtctca gagggctccc cagggatggt cagtgtcggc ccctgccca   720
aggctgaagc ccctgccctc ttcagcagaa ctgcctccaa gggcatattt ggggaccacc   780
ctggccactc ctacggggac cttccagggc cttcacctgc ccagctttt caagactctg   840
ggctgctcta tctggcccag gagttgccag cacccagcag gccagggtg ccaaggctgc   900
cagagcaagg gagcagcagc cgggcagagg actcccagga gggctatgag aaggaaggac   960
taggggatcg tggagagaag cctgcttccc cagctgtgca gccagatgcg gctctgcaga   1020
ggctggccgc tgtgctggcg ggctatgggg tagagctgac tcagctgacc cctgagcagc   1080
tctccacact cctgaccctg ctgcagctac tgcccaaggg tgcaggaaga atccgggag   1140
gggttgtaaa tgttggagct gatatcaaga aaacaatgga ggggccggtg gagggcagag   1200
acacagcaga gcttccagcc cgcacatccc ccatgcctgg acaccccact gccagcccta   1260
cctccagtga agtccagcag gtgccaagcc ctgtctcctc tgagcctccc aaagctgcca   1320
gaccccctgt gacacctgtc ctgctagaga agaaaagccc actgggccag agccagccca   1380
cggtggcagg acagccctca gcccgcccag cagcagagga atatggctac atcgtcactg   1440
atcagaagcc cctgagcctg gctgcaggag tgaagctgct ggagatcctg ctgagcatg   1500
tgcacatgtc ctcaggcagc ttcatcaaca tcagtgtggt gggaccagcc ctcaccttcc   1560
gcatccgtgca caatgagcag aacctgtctt tggctgatgt gacccaacaa gcagggctgg   1620
tgaagtctga actggaagca cagacagggc tccaaatctt gcagacagga gtgggacaga   1680
gggaggaggc agctgcagtc cttccccaaa ctgcgcacag cacctcaccc atgcgctcag   1740
tgctgctcac tctggtggcc ctggcaggtg tggctgggct gctggtggct ctggctgtgg   1800
ctctgtgtgt gcggcagcat gcgcggcagc aagacaagga gcgcgctggca gccctgggc   1860
ctgaggggc ccatggtgac actacctttg agtaccagga cctgtgccgc cagcacatgg   1920
ccacgaagtc cttgttcaac cgggcagagg gtccaccgga gccttcacgg gtgagcagtg   1980
tgtcctccca gttcagcgac gcagcccagg ccagccccag ctcccacagc agcacccgt   2040
cctggtgcga ggagccggcc caagccaaca tggacatctc cacgggacac atgattctgg   2100
catacatgga ggatcacctg cggaaccggg accgccttgc caaggagtgg caggccctct   2160
gtgcctacca gcagagcca aacacctgtg ccaccgcgca gggggaggc aacatcaaaa   2220
agaaccggca tcctgacttc ctgccctatg accatgcccg cataaaactg aaggtgggaga   2280
gcagcccttc tcggagcgat tacatcaacg ccagccccat tattgagcat gaccctcgga   2340
tgccagccta catgccacg cagggcccgc tgtcccatac catcgcagac ttctggagagca   2400
tggtgtggga gagcggctgc accgtcatcg tcatgctgac cccgctgtg gaggatggtg   2460
tcaagcagtg tgaccgctac tggccagatg agggtgcctc cctctaccac gtatatgagg   2520
tgaacctggt gtcggagcac atctggcgcg aggactttc ggtgcggaac ttctacctga   2580
agaacgtgca gacccaggag acgcgcacgc tcacgcagt ccacttcctc agctggccgg   2640
cagagggcac accggcctcc acgcggcccc tgctggactt ccgcaggaag gtgaacaagt   2700
gctaccgggg ccgctcctgc cccatcatcg tgcactgcag tgatggtgcg gggaggaccg   2760
gcacctacat cctcatcgac atggtcctga accgcatggc aaaaggagtg aaggagattg   2820
acatcgctgc caccctggag catgtccgtg accagcggtc tggccttgtc cgctctaagg   2880
accagtttga atttgccctg acagccgtgg cggaggaagt gaatgccatc ctcaaggccc   2940
tgcccagtg agaccctggg gcccttggc gggcagccca gcctctgtcc ctcttgcct   3000
gtgtgagcat ctctgtgtac ccactcctca ctgcccacc agccacctct tgggcatgct   3060
cagcccttcc tagaagagtc aggaaggaa agccagaagg gcacgcctg cccagcctcg   3120
catgccagag cctggggcat cccagagccc aggcatcc atggggtgc tgcagccagg   3180
aggagagaa aggacatggg tagcaattct acccagagcc ttctcctgcc tacattccct   3240
ggcctggctc tcctgtagct ctcctgggt tctgggagtt ccctgaacat ctgtgtgtgt   3300
ccccctatgc tccagtatgg aagaatgggg tggagggtcg ccacacccgg ctccccctgc   3360
ttctcagcc cggcctgcc tctgactcac acttgggcac ctgcctcac                3420
gcccagcctc ctcccaccac cctcccacca tgcgctgctc aacctctctc cttctggcgc   3480
aagagaacat ttctagaaaa aactactttt gtaccagtgt gaataaagtt agtgtgttgt   3540
ctgtgcagct gcaaaaaaaa aaaaaaaaa                                    3570

SEQ ID NO: 24           moltype = AA   length = 355
FEATURE                 Location/Qualifiers
source                  1..355
                        mol_type = protein
                        organism = Homo sapiens
SEQUENCE: 24
```

```
MDFLHRNGVL IIQHLQKDYR AYYTFLNFMS NVGDPRNIFF IYFPLCFQFN QTVGTKMIWV    60
AVIGDWLNLI FKWILFGHRP YWWVQETQIY PNHSSPCLEQ FPTTCETGPG SPSGHAMGAS   120
CVWYVMVTAA LSHTVCGMDK FSITLHRLTW SFLWSVFWLI QISVCISRVF IATHFPHQVI   180
LGVIGGMLVA EAFEHTPGIQ TASLGTYLKT NLFLFLFAVG FYLLLRVLNI DLLWSVPIAK   240
KWCANPDWIH IDTTPFAGLV RNLGVLFGLG FAINSEMPLL SCRGGNNYTL SFRLLCALTS   300
LTILQLYHFL QIPTHEEHLF YVLSFCKSAS IPLTVVAFIP YSVHMLMKQS GKKSQ        355

SEQ ID NO: 25           moltype = DNA   length = 1068
FEATURE                 Location/Qualifiers
misc_feature            1..1065
                        note = CDS encodes SEQ ID NO: 24
source                  1..1068
                        mol_type = genomic DNA
                        organism = Homo sapiens
SEQUENCE: 25
atggatttcc ttcacaggaa tggagtgctc ataattcagc atttgcagaa ggactaccga     60
gcttactaca ctttttctaaa ttttatgtcc aatgttggag accccaggaa tatctttttc   120
atttattttc cactttgttt tcaatttaat cagacagttg gaaccaagat gatatgggta   180
gcagtcattg gggattggtt aaatcttata tttaaatgga tattatttgg tcatcgacct   240
tactggtggg tccaagaaac tcagatttac ccaaatcact caagtccatg ccttgaacag   300
ttccctacta catgtgaaac aggtccagga agtccatctg gccatgcaat gggcgcatcc   360
tgtgtctggt atgtcatggt aaccgctgcc ctgagccaca ctgtctgtgg gatggataag   420
ttctctatca ctctgcacag actgacctgg tcatttcttt ggagtgtttt ttggttgatt   480
caaatcagtg tctgcatctc cagagtattc atagcaacac attttcctca tcaagttatt   540
cttggagtaa ttggtggcat gctggtggca gaggcctttg aacacactcc aggcatccaa   600
acggccgtc tgggcacata cctgaagacc aacctctttc tcttcctgtt tgcagttggc   660
ttttacctgc ttcttagggt gctcaacatt gacctgctgt ggtccgtgcc catagccaaa   720
aagtggtgtg ctaaccccga ctggatccac attgacacca cgccttttgc tggactcgtg   780
agaaaccttg gggtcctctt tggcttgggc tttgcaatca actcagagat gttcctcctg   840
agctgccgag ggggaaataa ctacacactg agcttccggt tgctctgtgc cttgacctca   900
ttgacaatac tgcagctcta ccatttcctc cagatcccga ctcacgaaga gcatttattt   960
tatgtgctgt cttttgtaa aagtgcatcc attcccctaa ctgtggttgc tttcattccc  1020
tactctgttc atatgttaat gaaacaaagc ggaaagaaga gtcagtaa              1068

SEQ ID NO: 26           moltype = DNA   length = 3096
FEATURE                 Location/Qualifiers
source                  1..3096
                        mol_type = genomic DNA
                        organism = Homo sapiens
SEQUENCE: 26
tcgacatgcc acaaaggcac agtataaaaa cggtgggaat cagagcactt cagctccaat     60
tgctctatgt ttagaattgc ctcttttcca agatggattt ccttcacagg aatggagtgc   120
tcataattca gcatttgcag aaggactacc gagcttacta cactttttcta aattttatgt   180
ccaatgttgg agaccccagg aatatctttt tcatttattt tccactttgt tttcaattta   240
atcagacagt tggaaccaag atgatatggg tagcagtcat tggggattgg ttaaatctta   300
tatttaaatg gatattattt ggtcatcgac cttactggtg ggtccaagaa actcagattt   360
acccaaatca ctcaagtcca tgccttgaac agttccctac tacatgtgaa acaggtccag   420
gaagtccatc tggccatgca atgggcgcat cctgtgtctg gtatgtcatg gtaaccgctg   480
ccctgagcca cactgtctgt gggatggata agttctctat cactctgcac agactgacct   540
ggtcatttct tggagtgtt ttttggttga ttcaaatcag tgtctgcatc tccagagtat   600
tcatagcaac acattttcct catcaagtta ttcttggagt aattggtggc atgctggtgg   660
cagaggcctt tgaacacact ccaggcatcc aaacggccag tctgggcaca tacctgaaga   720
ccaacctctt tctcttcctg tttgcagttg gcttttacct gcttcttagg gtgctcaaca   780
ttgacctgct gtggtccgtg cccatagcca aaaagtggtg tgctaacccc gactggatcc   840
acattgacac cacgcctttt gctggactcg tgagaaacct tgggtcctc tttggcttgg   900
gctttgcaat caactcagag atgttcctcc tgagctgccg agggggaaat aactacacac   960
tgagcttccg gttgctctgt gccttgacct cattgacaat actgcagctc taccatttcc  1020
tccagatccc gactcacgaa gagcatttat ttatgtgct gtcttttgtg aaaagtgcat  1080
ccattcccct aactgtggtt gctttcattc cctactctgt tcatatgtta atgaaacaaa  1140
gcggaaagaa gagtcagtag agtggtgcct agagttagtg ctctgtgtca cagatcaccc  1200
ttctccatcc accagtagag ccacagagta ggcacagacc agaggcttct aatccgactt  1260
cacagaatag cggcacaggc cccattcccc atagagatgt ttagtttggc cttcgcactg  1320
gtcttttttt taatccttc agttaccaat atttagatac aagaatattt gacataaaaa  1380
tcggaagttc tgtatttctt gaaaaatctg atagtatgac aacacagagc tgcatcccc  1440
agctggagac aactgaccag agctgcatac taacagtccc cagtaggagg caaggactcc  1500
atttttctcac agtcttcagc atcccagcag gagccccact atgattcctt tatcttctta  1560
aggccaggct gcatctgatt cctgttgaca tttttagtggg gaccacagcc atatccagtt  1620
tcagttttca gatgaggaaa tggaagccta tttaggtaaa agaacttgcc tggagtcacg  1680
ccaccttcag agcaggaatt agaacccaag gcttctgaca catatcccca ttacactgtg  1740
tgtttgagtg tgcacacatg cacatgcttt ttgtttgtat gtttccttttt tagaaccagg  1800
gacttgctct gttgcccagg ctggagtgca gtggtggata cggctcact gcagcctcaa  1860
actcctggct caaatgatcc tccctcctca gcctcccatt agctaagact acaggtgtgc  1920
accaccatgc ctggctaatt tttgaatatt ttttagagcc agctcttac tatatttgcc  1980
caggctggtc ttgaactcct ggcctcaagg agttccctgg aggatgttcc acccatgtca  2040
gcctcccaca gtgctgggat tgcaggcttg agcattgta ttaatagttg gcctacactg  2100
tcttttgttt cttcatttac aagaggtaaa atcagtaag aatgaatgct ttcatttaga  2160
ttctatgatg actgccatat aaatcagcta ccttttcaga aatgacattg aaatactgca  2220
tcctctttga cttataccccc acacatacat gcagggtcta ggtgggacca acagtggctc  2280
cagatgtata tacacacggg tccagggaca acagaacagg ccaggctaca gtatggactt  2340
```

```
gaacctctgc ttcacttctg gtctctgttt tacagtagtg ctcaccaata tttcaataaa    2400
ttctactgaa cttactctaa tagaacatta ttcaacccc aaaagactat ctcttcacta     2460
tgacatctcc atactttatt tttaggagac agactttcaa aaccagagaa atcaggtgcc    2520
ttcctcaagg tcatgctcca acccaggcca actattaaat gcttgcatct gttagctgga   2580
ttagtctcta tgtatactga actgtgatga aaatctatag cttttgtttta gaaaattatt  2640
gttgatggac tattaatatt atattaacaa tttctcagta agtgtgtttt ttcctcattg   2700
aatctaggaa tgctgggctt taagttgata actgtgtcat ttcaatcaag tacaaggatt   2760
ttgaggcaga ttttgctaga tatcttagta atccccaca atgtttatg taactcttct     2820
cagaatatca atacattaat tattttagat gacatatata ataatctatg aatattaatg   2880
aaaacaatac agttgaagtg agtgttgttt aacatgatag tagctgagga taacaaacct   2940
caaaaaatca aagtattaat tactccttc caagtatatg tatagagcat gtgtcattgc    3000
ttttataaaa cgcacttaat agctttcttt ctaaaaggca actgaacttt ctaaaaggta   3060
aataaactga acttgatatt aaaaaaaaaa aaaaaa                             3096

SEQ ID NO: 27           moltype = DNA  length = 2980
FEATURE                 Location/Qualifiers
source                  1..2980
                        mol_type = genomic DNA
                        organism = Homo sapiens
SEQUENCE: 27
tcgacatgcc acaaaggcac agtataaaaa cggtgggaat cagagcactt cagctccaat    60
tgctctatgt ttagaattgc ctctttttca agatgatttt ccttcacagg aatggagtgc   120
tcataattca gcatttgcag aaggactacc gagcttacta cacttttcta aatttttatgt  180
ccaatgttgg agaccccagg aatatctttt tcatttattt tccactttgt tttcaattta   240
atcagacagt tggaaccaag atgatatggg tagcagtcat tggggattgg ttaaatctta   300
tatttaaatg gatattattt ggtcatcgac cttactgtg ggtccaagaa actcagattt     360
acccaaatca ctcaagtcca tgccttgaac agttccctac tacatgtgaa acaggtccag   420
gaagtccatc tggccatgca atgggcgcat cctgtgtctg gtatgtcatg gtaaccgctg   480
ccctgagcca cactgtctgt gggatggata agttctctat cactctgcac aggcatgctg   540
gtgtgcagagg cctttgaaca cactccaggc atccaaacgg ccagtctggg cacatacctg   600
aagaccaacc tctttctctt cctgtttgca gttggctttt acctgcttct tagggtgctc   660
aacattgacc tgctgtggtc cgtgcccata gccaaaaagt ggtgtgctaa ccccgactgg   720
atccacattg acaccacgcc ttttgctgga ctcgtgagaa accttggggt cctctttggc   780
ttgggctttg caatcaactc agagatgttc ctcctgagct gccgagggg aaataactac    840
acactgagct tccggttgct ctgtgccttg acctcattga caatactgca gctctaccat   900
ttcctccaga tcccgactca cgaagagcat ttattttatg tgctgtcttt ttgtaaaagt   960
gcatccattc ccctaactgt ggttgctttc attcctact ctgttcatat gttaatgaaa    1020
caaagcggaa agaagagtca gtagagtggt gcctagagtt agtgctctgt gtcacagatc   1080
accctctcc atccaccagt agagccacag agtaggcaca gaccagaggc ttctaatccg   1140
acttcacaga atagcggcac aggcccatt cccataagaa atgtttagtt tggccttcgc    1200
actggtcttt ttttttaatc cttcagttac caatatttag atacaagaat atttgacata   1260
aaaatcggaa gttctgtatt tcttgaaaaa tctgatagta tgacaacaca gagcctgcat   1320
ccccagctgg agacaactga ccagactgc atactaacag tccccagtag gaggcaagga   1380
ctccattttc tcacagtctt cagcatccca gcaggagccc cactatgatt cctttatctt   1440
cttaaggcca ggctgcatct gattcctgtt gacattgag tggggaccac agccatatcc     1500
agtttcagtt ttcagatgag gaaatggaag cctatttagg taaaagaact tgcctggagt   1560
cacgccacct tcagagcagg aattagaacc caaggcttct gacacatatc cccattacac   1620
tgtgtgtttg agtgtgcaca catgcacatg cttttgttt gtatgtttcc ttttagaac     1680
cagggacttg ctctgttgcc caggctggag tgcagtggtg gatagcggct cactgcagcc   1740
tcaaactcct ggctcaaatg atcctccctc ctcagcctcc cattagctaa gactacaggt   1800
gtgcaccacc atgcctggct aattttttga tatttttag agccagcttc ttactatatt   1860
tgcccaggct ggtcttgaac tcctggcctc aaggagttcc cttgaggatg ttccacccat   1920
gtcagcctcc cacagtgctg ggattgcagg cttgagccat tgtattaata gttggcctac   1980
actgtctttt gtttcttcat ttacaagagg taaaaatcag taagaatgaa tgctttcatt   2040
tagattctat gatgactgcc atataaatca gctaccttt cagaaatgac attgaaatac    2100
tgcatcctct ttgacttata ccccacacat acatgcaggg tctaggtggg accaacagtg   2160
gctccagatg tatatacaca cgggtccagg gacaacagaa caggccaggc tacagtatgg   2220
acttgaacct ctgcttcact tctggtctct gttttacagt agtgctcacc aatatttcaa   2280
taaattctac tgaacttact ctaatagaac attattcaac ccccaaagac ttatctcttc   2340
actatgacat ctccatactt tattttagg agacagact tcaaaaccag agaaatcagg     2400
tgccttcctc aaggtcatgc tccaacccag gccaactatt aaatgcttgc atctgttagc   2460
tggattagtc tctatgtata ctgaactgtg atgaaaatct atagctttgt tttagaaaat   2520
tattgttgat ggactattaa tattatatta acaatttctc agtaagtgtg ttttttcctc   2580
attgaatcta ggaatgctgg gctttaagtt gataactgtg tcattttcaat caagtacaag   2640
gattttgagg cagattttgc tagatatctt agtaatcccc acaatgtttt tatgtaactc   2700
ttctcagaat atcaatacat taattatttt agatgacata ttaataatc tatgaatatt   2760
aatgaaaaca atacagttga agtgagtgtt gtttaacatg atagtagctg aggataacaa   2820
acctcaaaaa atcaaagtat taattactcc tttccaagta tatgtataga gcatgtgtca   2880
ttgcttttat aaaacgcact taatagcttt cttttctaaaa ggcaactgaa ctttctaaaa   2940
ggtaaataaa ctgaacttga tattaaaaaa aaaaaaaaa                           2980

SEQ ID NO: 28           moltype = DNA  length = 4092
FEATURE                 Location/Qualifiers
source                  1..4092
                        mol_type = genomic DNA
                        organism = Homo sapiens
SEQUENCE: 28
atagcagagc aatcaccacc aagcctggaa taactgcaag ggctctgctg acatcttcct    60
gaggtgccaa ggaaatgagg atggaggaag gaatgaatgt tctccatgac tttgggatcc   120
```

```
agtcaacaca ttacctccag gtgaattacc aagactccca ggactggttc atcttggtgt    180
ccgtgatcgc agacctcagg aatgccttct acgtcctctt ccccatctgg ttccatcttc    240
aggaagctgt gggcattaaa ctcctttggg tagctgtgat ggagactggc tcaacctcg     300
tctttaagtg gattctcttt ggacagcgtc atactggtg ggttttggat actgactact     360
acagcaacac ttccgtgccc ctgataaagc agttccctgt aacctgtgag actgaccag    420
ggaaagataa agccgaccta cagatttcgg tgcttgaatg tcattttgtg gttgggattc    480
tgggctgtgc agctgaatgt ctgtctgtca cgaatctacc ttgctgctca ttttcctcat    540
caagttgttg ctggagtcct gtcaggcatt gctgttgcag aaactttcag ccacatccac    600
agcatctata atgccagcct caagaaatat tttctcatta ccttcttcct gttcagcttc    660
gccatcggat tttatctgct gctcaaggga ctgggtgtag acctcctgtg gactcctggag   720
aaagcccaga ggtggtgcga gcagccagaa tgggtccaca ttgacaccac acccttgcc    780
agcctcctca agaacctggg cacgctcttt ggcctgggc tggctctcaa ctccagcatg    840
tacagggaga gctgcaaggg gaaactcagc aagtggctcc cattccgcct cagctctatt    900
gtagcctccc tcgtcctcct gcacgtcttt gactccttga aaccccatc ccaagtcgag    960
ctggtcttct acgtcttgtc cttctgcaag agtgcggtag tgccctggc atccgtcagt   1020
gtcatccctt actgcctcgc ccaggtcctg ggccagccgc acaagaagtc gttgtaagag   1080
atgtggagtc ttccggtgttt aaagtcaaca accatgccag ggattgagga ggactactat  1140
ttgaagcaat gggcactggt atttggaagca agtgacatgc catccattct gccgtcgtgg  1200
aattaaatca cggatggcag attggagggt cgcctggctt attcccatgt gtgactccag   1260
cctgccctca gcacagactc tttcagatgg aggtgccata tcgctacac catatgcaag    1320
tttcccgcca ggaggtcctc ctctctctac ttgaatactc tcacaagtag ggagctcact   1380
cccactggaa cagcccattt tatctttgaa tggtcttctg ccagcccatt ttgaggccag    1440
aggtgctgtc agctcaggtg gtcctctttt acaatcctaa tcatattggg taatgttttt   1500
gaaaagctaa tgaagctatt gagaaagacc tgttgctaga agttgggttg ttctggatt    1560
tccctgaag acttacttat tcttccgtca catatacaaa agcaagactt ccaggtaggg    1620
ccagctcaca agcccaggct ggagatccta actgagaatt ttctacctgt gttcattctt    1680
accgagaaaa ggagaaagga gctctgaatc tgataggaaa agaaggctgc ctaaggagga    1740
gttttagta tgtggcgtat catgcaagtc ctatgccaag ccatgctaa atggcttaa     1800
ttatatagta atgcactctc agtaatgggg accagcttca agtataatta atagatggtt    1860
agtgggtaa ttctgcttct agtatttttt ttactgtgca tacatgttca tcgtatttcc    1920
ttggatttct gaatggctgc agtgaccag atattgcact aggtcaaaac attcaggtat   1980
agctgacatc tcctctatca cattacatca tcctccttat aagcccagct ctgcttttc    2040
cagattcttc cactggctcc acatccaccc cactggatct tcagaaggct agagggcgac    2100
tctggtggtg cttttgtatg tttcaattag gctctgaaat cttgggcaaa atgacaaggg    2160
gagggccagg attcctctct caggtcactc cagtgttact tttaattcct agagggtaaa    2220
tatgactcct ttctctatcc caagccaacc aagagcacat tcttaaagga aaagtcaaca    2280
tcttctctct tttttttttt ttttgagaca gggtctcact atgttgccca ggctgctctt    2340
gaattcctgg gctcaagcag tcctcccacc ctaccacagc gtcccgcgta gctgggacta    2400
caggtgcaag ccactatgtc cagctagcca actcctcctt gcctgctttt ctttttttt    2460
cttttttga gacggcgcac ctatcaccca ggctggagtg gagtggcacg atcttggctc    2520
actgcaacct cttcctcctg gttcaagcga ttctcatgtc tcagcctcct cagtagctag    2580
gactaccggc gtgcaccacc atgccaggct aattttata ttttttagaat tttagaagag    2640
atggggtttc atcatgttgg ccaggctggt ctcgaactcc tgacctcaag tgatccacct   2700
gccttggcct cccaaggtgc taggattaca ggcatgagcc accgcaccgg gcctccttg    2760
cctgtttttc aatctcatct gatatgcaga gtatttctgc cccaccacc taccccccaa    2820
aaaaagctga agcctattta tttgaaagtc cttgttttg ctactaatta tatagtatac    2880
catacattat cattcaaaac aaccatcctg ctcataacat ctttgaaaag aaaaatatat    2940
atgtgcagta ttttattaaa gcaacatttt atttaagaat aaagtcttgt taattactat    3000
attttagatg caatgtgatc tgaagttct aattctggcc caactaaatt tctagctctg    3060
tttccctaaa caaataattt ggtttctctg tgcctgcatt ttccctttgg agaagaaaag    3120
tgctctctct tgagttgacc gagagtccca ttagggatag ggagacttaa atgcatccat    3180
aggggcacag gcagagttga gcacataaac ggaggcccaa aatcagcata gaaccagaaa    3240
gattcagagt tggccaagaa tgaacattgg ctaccagacc acaagtcagc atgagttgct    3300
ctatggcatc aaattgcaac ttgagagtag atgggcaggg tcactatcaa attaagcaat    3360
cagggcacac aagttgcagt aacacaacaa gactaggcca gctctggaat ccagtaactc    3420
agtgtcagca aggttttggg ttatagttca agaaagtcta aacagagcca gtcacgcac    3480
caaggaatgc tcaagggagc tattgcaggt ttctctgcta agagatttat ttcatcctgg    3540
gtgcagggtt cgacctccaa aggcctcaaa tcatcaccgt atcaatggat ttcctgaggg    3600
taaggtccgc tatttcacac ctgaactccg gagtctgtat attcagggaa gattgcattc    3660
tcctactgga tttgggctct cagagggcgt tgtgggaacc aggcccctca cagaatcaaa    3720
tggtcccaac cagggagaaa gaaaatagtc ttttttttt ttttaataga atggggggtc    3780
tcactatgct gcccaggctg gtcttgaact cctgggttca agtgatcctc ctgcctcagc    3840
ctcccaaagt gctgggatta cagtgtgagc cactgcgctt ggccagaaat ggttttgatc    3900
tgtctgaact gaaccctact gcttaggcat agccccatcc ttgataatct atttgctccc    3960
aaggaccaag tccaagatcc ttacaagaaa ggtctgccag aaagtaaata ctgccccac     4020
tccctgaagt ttatgaggtt gataagaaaa cataacagat aaagtttatt gagtgctaac    4080
tttaaaaaaa aa                                                       4092

SEQ ID NO: 29          moltype = AA  length = 369
FEATURE                Location/Qualifiers
source                 1..369
                       mol_type = protein
                       organism = Homo sapiens
SEQUENCE: 29
MEFLERTYLV NDKAAKMYAF TLESVELQQK PVNKDQCPRE RPEELESGGM YHCHSGSKPT     60
EKGANEYAYA KWKLCSASAI CFIFMIAEVV GGHIAGSLAV VTDAAHLLID LTSFLLSLFS    120
LWLSSKPPSK RLTFGWHRAE ILGALLSILC IWVVTGVLVY LACERLLYPD YQIQATVMII   180
VSSCAVAANI VLTVVLHQRC LGHNHKEVQA NASVRAAFVH ALGDLFQSIS VLISALIIYF   240
KPEYKIADPI CTFIFSILVL ASTITILKDF SILLMEGVPK SLNYSGVKEL ILAVDGVLSV   300
```

```
HSLHIWSLTM NQVILSAHVA TAASRDSQVV RREIAKALSK SFTMHSLTIQ MESPVDQDPD    360
CLFCEDPCD                                                           369

SEQ ID NO: 30           moltype = DNA  length = 1110
FEATURE                 Location/Qualifiers
misc_feature            1..1107
                        note = CDS encodes SEQ ID NO: 29
source                  1..1110
                        mol_type = genomic DNA
                        organism = Homo sapiens
SEQUENCE: 30
atggagtttc ttgaaagaac gtatcttgtg aatgataaag ctgccaagat gtatgctttc     60
acactagaaa gtgtggaact ccaacagaaa ccggtgaata aagtcagtg tcccagagag     120
agaccagagg agctggagtc aggaggcatg taccactgcc acagtggctc caagcccaca    180
gaaaaggggg cgaatgagta cgcctatgcc aagtggaaac tctgttctgc ttcagcaata    240
tgcttcattt tcatgattgc agaggtcgtg ggtgggcaca ttgctgggag tcttgctgtt    300
gtcacagatg ctgcccacct cttaattgac ctgaccagtt cctgctcag tctcttctcc     360
ctgtggttgt catcgaagcc tccctctaag cggctgacat ttggatggca ccgagcagag    420
atccttggtg ccctgctctc catcctgtgc atctgggtgg tgactggcgt gctagtgtac    480
ctggcatgtg agcgcctgct gtatcctgat taccagatcc aggcgactgt gatgatcatc    540
gtttccagct gcgcagtggc ggccaacatt gtactaactg tggttttgca ccagagatgc    600
cttggccaca atcacaagga agtacaagcc aatgccagcg tcagagctgc ttttgtgcat    660
gcccttggag atctatttca gagtatcagt gtgctaatta gtgcacttat tatctacttt    720
aagccagagt ataaaatagc cgacccaatc tgcacattca tctttccat cctggtcttg    780
gccagcacca tcactatctt aaaggacttc tccatcttac tcatgaagg tgtgccaaag    840
agcctgaatt acagtggtgt gaaagagctt attttagcag tgcacggggt gctgtcctg    900
cacagcctgc acatctggtc tctaacaatg aatcaagtaa ttctctcagc tcatgttgct    960
acagcagcca gccgggacag ccaagtggtt cggagagaaa ttgctaaagc ccttagcaaa   1020
agctttacga tgcactcact caccattcag atggaatctc cagttgacca ggaccccgac   1080
tgccttttct gtgaagaccc ctgtgactaa                                    1110

SEQ ID NO: 31           moltype = DNA  length = 1955
FEATURE                 Location/Qualifiers
source                  1..1955
                        mol_type = genomic DNA
                        organism = Homo sapiens
SEQUENCE: 31
ctcggcctcg cgttataaaa agcggtgggg cagggccggc gagacaatct gggaggcggg     60
taccggcct cacggatccg cgccgcgccc ccacctgtg gctgcgcgcg gggtgggctg     120
cgctcccctg ggcggcgccg ggcgcccggg gctggtggcg agatgggccg ctactctggc    180
aagacgtgcc ggctgctctt catgctggtg ctcaccgtcg ccttcttcgt ggcggagctg    240
gtctccggct acctgggcaa ctccatcgcg ctgctctccg actccttcaa catgttctcc    300
gacctgatct cgctgtgcgt gggcctgagc gccgctaca tcgccggcg ccccacccgg    360
ggcttcagcg ccacctacgg ctacgcccgc gccgaggtgg tgggcgcgct gagcaacgcg    420
gtcttcctca ccgcgctctg cttcaccatc ttcgtggagg ccgtgctgcg cctgcccgg    480
cccgagcgca tcgatgaccc cgagctggtg ctcatcgtcg gcgtcctggg gctgttggtc    540
aacgtgtggg ggctgctcat cttccaggac tgcgccggg ggttcgcgtg ctgcctccgg    600
ggacgcagtc gccgcctgca gcagcggcag cagctcggcg gagggctgtgt ccccggcgct    660
ttcgggggg ctcagggcgc ggaggaccg cggcgcgcgg cggacccgac agccccaggc    720
tcggactcgc ccgtaaccct ccgggggacc tcggtgaaa ggaagcggga aaggggggcg    780
accgtgttcg caaacgtagc aggtgattcc ttcaacaccc agaatgagcc agaagacatg    840
atgaaaaaag agaaaaagtc tgaagctctg aatatcagag gtgtacttt gcatgtgatg    900
ggagatgccc tggggtccgt ggttgtggtc atcacggcca tcatattcta tgtgcttccc    960
ctgaagagtg aggacccgtg taactggcag tgttacattg accccagcct gactgtcctc   1020
atggtcatca tcatttttgtc atctgccttc ccgcttatca aggagaccgc tgccattctg   1080
ctacagatgg tcccaaaagg agtcaacatg gaagagctga tgagtaaact ctctgctgtg   1140
cctggaatta gcagtgtaca tgaagtgcaa atctgggaac ttgtaagtgg aaagattat    1200
gccaccctgc acatcaagta tcctaaggac aggggatatc aagatgccag cacaaaaatt   1260
cgagaaatct tccaccatgc gggaatccaa aatgtgacca tccagtttga aaatgtggac   1320
ttgaaggaac ccctggagca gaaggactta ctgttgctct gcaactcacc ctgcatctcc   1380
aagggctgtg ctaagcagct gtgttgttccc cccgggggcac tgcctctggc tcacgtcaat   1440
ggctgtgctg agcacttcct ctgtcacgtc aatggctgtg ctgagcacaa tggtgggccc    1500
tctctagaca catacggaag tgatggcctc agtagaagag acgcaagaga gtggctatt    1560
gaagtgtctt tggatagctg tctgagtgac cacggaccaa gtcttaacaa aactcaggag    1620
gaccaatgtt atgtcaacag aacgcatttt taatctggta ctcacataat cagaccatat    1680
agacgaggca ctttggaacc acaagcttgg ctcacaaaaa gagcttttcct gggttgtagg    1740
cccagactag acttgcagca tgcatgtctc tgtgttcacta gggttggct gtttgggatt    1800
ttagttaaac gtgtctgtga atttttatgt aactaactcc tttccattcc cctgggtgtc    1860
tcatgctgct cttttgactgt ttcagcttga acatgcattt tctaaagcaa actgcactag    1920
tgtatatatc agggtttgaa gctcatgggc tctct                              1955

SEQ ID NO: 32           moltype = DNA  length = 5373
FEATURE                 Location/Qualifiers
source                  1..5373
                        mol_type = genomic DNA
                        organism = Homo sapiens
SEQUENCE: 32
agcagttttt gtaggtgaaa acaatgaagc caggtaatat tgcaaggagg ctgtaatttt     60
agcagaccta ccaacaacac tgatgtagga agctcattat tttaatttct ggagcctttt    120
```

```
aattttttct ttagaaagtg tataaataat tgcagtgctg cttttgcttcc aaaactgggc    180
agtgagttca acaacaacga caacaacagc cgcagctcat cctggccgtc atggagtttc    240
ttgaaagaac gtatcttgtg aatgataaag ctgccaagat gtatgctttc acactagaaa    300
gtgtggaact ccaacagaaa ccggtgaata agatcagtg tcccagagag agaccagagg     360
agctggagtc aggaggcatg taccactgcc acagtgctc caagcccaca gaaaagggg     420
cgaatgagta cgccatgcc aagtggaaac tctgttctgc ttcagcaata tgcttcattt    480
tcatgattgc agaggtcgtg ggtgggcaca ttgctgggag tcttgctgtt gtcacagatg    540
ctgcccacct cttaattgac ctgaccagtt tcctgctcag tctcttctcc ctgtggttgt    600
catcgaagcc tccctctaag cggctgacat ttggatggca ccgagcagag atccttggtg    660
ccctgctctc catcctgtgc atctgggtgg tgactggcgt gctagtgtac ctggcatgtg    720
agcgcctgct gtatcctgat taccagatcc aggcgactgt gatgatcatc gtttccagct    780
gcgcagtggc ggccaacatt gtactaactg tggttttgca ccagagatgc cttggccaca    840
atcacaagga agtacaagcc aatgccagcg tcagagctgc ttttgtgcat gcccttggag    900
atctatttca gagtatcagt gtgctaatta gtgcacttat tatctacttt aagccagagt    960
ataaaatagc cgacccaatc tgcacattca tcttttccat cctggtcttg gccagcacca   1020
tcactatctt aaaggacttc tccatcttac tcatggaagg tgtgccaaag agcctgaatt   1080
acagtggtgt gaaagagctt attttagcag tcgacgggc gctgtctgtg cacagcctgc   1140
acatctggtc tctaacaatg aatcaagtaa ttctctcagc tcatgttgct acagcagcca   1200
gccgggacag ccaagtggtt cggagagaaa ttgctaaagc ccttagcaaa agctttacga   1260
tgcactcact caccattcag atggaatctc cagttgacca ggaccccgac tgccttttct   1320
gtgaagaccc ctgtgactag ctcagtcaca ccgtcagttt cccaaatttg acaggccacc   1380
ttcaaacatg ctgctatgca gttcttgcat catagaaaat aaggaaccaa aggaagaaat   1440
tcatgtcatg gtgcaatgca cattttatct atttattttag ttccattcac catgaaggaa   1500
gaggcactga gatccatcaa tcaattggat tatatactga tcagtagctg tgttcaattg   1560
caggaatgtg tatatagatt attcctgagt ggagccgaag taacagctgt ttgtaactat   1620
cggcaatacc aaattcatct ccccttccaat aatgcatctt gagaacacat aggtaaattt   1680
gaactcagga aagtcttact agaaatcagt ggaagggaca aatagtcaca aaattttacc   1740
aaaacattag aaacaaaaaa taaggagagc caagtcagga ataaaagtga ctctgtatgc   1800
taacgccaca ttagaacttg gttctctcac caagctgtaa tgtgatttttt ttttctactc   1860
tgaattggaa atatgtatga atatacagag aagtgcttac aactaattt tattttacttg   1920
tcacattttg gcaataaatc cctcttattt ctaaattcta acttgtttat ttcaaaactt   1980
tatataatca ctgttcaaaa ggaaatattt tcacctacca gagtgcttaa acactggcac   2040
cagccaaaga atgtggttgt agagacccag aagtcttcaa gaacagccga caaaaacatt   2100
cgagttgacc ccaccaagtt gttgccacag ataatttaga tatttacctg caagaaggaa   2160
taaagcagat gcaaccaatt cattcagtcc acgagcatga tgtgagcact gctttgtgct   2220
agacattggg cttagcattg aaactataaa gaggaatcag acgcagcaag tgcttctgtg   2280
ttctggtagc aactcaacac tatctgtgga gagtaaactg aagatgtgca ggccaacatt   2340
ctggaaatcc tatgtcaatg ggtttggttt ggaacctgga cttctgcatt tttaaaagtt   2400
acccagagat gcttctaaag atgagccata gtctagaaag ttgtcaacca caggagttca   2460
ttgagtggga cagctagaca catacattgg cagctacaat agtatcatga attgcaatga   2520
tgtagtgggg tataaaagga aagcgatgga tattgccgga tgggcatggc cagtgatgtt   2580
tcacgtcatt gaggtgacag ctctgctgga ctttgaatta catatggagg ctctccagga   2640
agacgaagaa gagaaggaca ttctaggcaa aaagaagact aggcacaagg cacacttatg   2700
tttgtctgtt agcttttagt tgaaaaagca aaatacatga tgcaagaaa cctctccacg   2760
ctgtgatttt taaaactaca tactttttgc aactttatgg ttatgagtat tgtagagaac   2820
aggagatagg tcttagatga ttttttatgt tgttgtcagac tctagcaagg tactagaaac   2880
ctagcaggca ttaataattg ttgaggcaat gactctgagg ctatatctgg gccttgtcat   2940
tatttatcat ttatatttgt attttttttct gaaatttgag ggccaagaaa acattgactt   3000
tgactgagga ggtcacatct gtgccatctc tgcaaatcaa tcagcaccac tgaaataact   3060
acttagcatt ctgctgagct ttccctgctc agtagagaca aatatactca tccccacct    3120
cagtagcttt gtttaggcaa ccaggattag agctgctcag gttcccaacg tctccctgca   3180
catcgggttc tcaaaatgga agaatggtt tatgccaaat cacttttcct gtctgaagga    3240
ccactgaatg gttttgtttt tccatatttt gcataggacg ccctaaagac taggtgactt   3300
ggcaaacaca caagtgttag tataattctt tgcttctgct tcttttttgaa aatcatgttt   3360
agatttgatt ttaagtcaga aattcactga atgtcaggta atcattatgg agggagattt   3420
gtgtgtcaac caaagtaatt gtcccatggc cccagggtat ttctgttgtt tccctgaaat   3480
tctgcttttt tagtcagcta gattgaaaac tctgaacagt agatgtttat atggcaaaat   3540
gcaagacaat ctacaaggga gattttaagg attttgagat gaaaaacag atgctactca    3600
ggggcttat gaaccatcca tcaattctga agttctgact ctcccattac cctttccctg    3660
gtgtggtcag aactccaggt cactggaagt tagtggaatc atgtagttga attctttact    3720
tcaagacatt gtattctctc cagctatcaa aacattaatg atcttttatg tctttttttt   3780
gttattgtta tactttaagt tctggggtac atgtgcggaa catgtaggtt tgttacatag    3840
gtatacatgt gccatggtgg tttgctgcac tcatcaacct gtcatcataca ttcttttatg    3900
tctgtctttc aaagcaacac tctgttcttc tgagtagtga aatcaggtca acttaccac     3960
cagcctccat ttttaatatg cttcaccatc atccagcacc tacttaagat ttatctaggg   4020
ctctgtggtg atgttaggac ccataaaaga aatttatgcc ttccatatgt ttggttacag   4080
atgggaaatg ggaatgttga aggacatgaa agaaaggatg tttacacatt aagcatcagt   4140
tctgaagcta gattgtctga gtttgaatct tagctcttcc ctttattagc tctgctgacct   4200
cgagctagtt acttaaatgc tctgatcctc tatttcctga tcagtgaaac ctccctattc    4260
aaatgtgtga gagtttaata aattaggaca cttaaaaatg ttggagcagt gcatagcatg    4320
tagtgttcag tacatgttaa atgttgtttt ttattatgta caaacatgag tgggcacaga    4380
attttaaatc atctcaactt tgagaaatt tgagttatc aacaccgttc ccacaagaca     4440
gtggcaaaat tattggtgag aattaaacag ctgtttctca gaggaagcaa tggaggcttg    4500
ctgggataaa ggcatttact gagaggctgt tacctagtga gagtgatgaa ttaattaaaa   4560
tagtcgaatc ccttttctgac tgtctctgaa agcttccgct tttatctttg aagagcagaa    4620
ttgtcactcc aaggacattt attaataaaa agaacaactg tccagtgcaa tgaaggcaaa    4680
gtcataggtc tcccaagtct tacccccattc ctgtgaaata tcaagttctt ggcttttctc   4740
tgtcatgtag cctcaacttt ctctgaccgg gtgcatttct ttctctggtt tctaaattgc   4800
cagtggcaaa tttggatcac ttacttaata tctgttaaat tttgtgaccc aacaaagtct   4860
```

```
tttagcactg tggtgtcaaa agaaaaaaca cctcccaggc atatacattt tatagattcc  4920
tggagaatgt tgctctccag ctccatcccc acccaatgaa atatgatcca gagagtcttg  4980
caaagagaca agcctcattt tccacaatta gctctaaagt gcctccagga aatgattttc  5040
tcagctcatc tctctgtatt ccctgttttg gatcacaggg caatctgttt aaatgactaa  5100
ttacagaaat cattaaaggc accaagcaaa tgtcatctct gaatacacac atcccaagct  5160
ttacaaatcc tgcctggctt gacagtgatg aggccactta acagtccagc gcaggcggat  5220
gttaaaaaaa ataaaaaggt gaccatctgc ggtttagttt tttaactttc tgatttcaca  5280
cttaacgtct gtcattctgt tactgggcac ctgtttaaat tctattttaa aatgttaatg  5340
tgtgttgttt aaaataaaat caagaaagag aga                                5373

SEQ ID NO: 33         moltype = DNA  length = 5403
FEATURE               Location/Qualifiers
source                1..5403
                      mol_type = genomic DNA
                      organism = Homo sapiens
SEQUENCE: 33
agcagttttt gtaggtgaaa acaatgaagc caggtaatat tgcaaggagg ctgtaatttt   60
agcagaccta ccaacaacac tgatgtagga agctcattat tttaatttct ggagcctttt  120
aattttttct ttagaaagtg tataaataat tgcagtgctg ctttgcttcc aaaactgggc  180
agtgagttca acaacaacga caacaacagc cgcagctcat cctggccgtc atggagtttc  240
ttgaaagaac gtatcttgtg aatgataaag ctgccaagat gtatgctttc acactagaaa  300
gaaggagctg caaatgaaca cttcatagca atgtggaact ccaacagaaa ccggtgaata  360
aagatcagtg tcccagagag agaccagagg agctggagtc aggaggcatg taccactgcc  420
acagtggctc caagcccaca gaaaagggga cgaatgagta cgcctatgcc aagtggaaac  480
tctgttctgc ttcagcaata tgcttcattt tcatgattgc agaggtcgtg ggtgggcaca  540
tgctgggag tcttgctgtt gtcacagatg ctgcccacct cttaattgac ctgaccagtt  600
tcctgctcag tctcttctcc ctgtggttgt catcgaagcc tccctctaag cggctgacat  660
ttggatggca ccgagcagag atccttgtg ccctgctctc catcctgtgc atctgggtgg  720
tgactggcgt gctagtgtac ctggcatgtg agcgcctgct gtatcctgat taccagatcc  780
aggcgactgt gatgatcatc gtttccagct gcgcagtggc ggccaacatt gtactaactg  840
tggttttgca ccagagatgc cttggccaca atcacaagga agtacaagcc aatgccagcg  900
tcagagctgc ttttgtgcat gcccttggag atctatttca gagtatcagt gtgctaatta  960
gtgcacttat tatctacttt aagccagagt ataaaatagc cgacccaatc tgcacattca  1020
tcttttccat cctggtcttg gccagcacca tcactatctt aaaggacttc tccatcttac  1080
tcatgtgaagg tgtgccaaag agctgaatt acagtggtgt gaaagagctt attttagcag  1140
tcgacggggt gctgtctgtg cacagcctgc acatctggtc tctaacaatg aatcaagtaa  1200
ttctctcagc tcatgttgct acagcagcca gccgggacag ccaagtggtt cggagagaaa  1260
ttgctaaagc ccttagcaaa agctttacga tgcactcact caccattcag atggaatctc  1320
cagttgacca ggaccccgac tgcctttct gtgaagaccc ctgtgactag ctcagtcaca  1380
ccgtcagttt cccaaatttg acaggccacc ttcaaacatg ctgctatgca gtttctgcat  1440
catagaaaat aaggaaccaa aggaagaaat tcatgtcatg gtgcaatgca catttatatct  1500
atttatttag ttccattcac catgaaggaa gaggcactga gatccatcaa tcaattggat  1560
tatatactga tcagtagctg tgttcaattg caggaatgta tatatagatt attcctgagt  1620
ggagccgaag taacagctgt ttgtaactat cggcaatacc aaattcatct cccttccaat  1680
aatgcatctt gagaacacat aggtaaattt gaactcagga aagtcttact agaaatcagt  1740
ggaagggaca aatagtcaca aaattttacc aaaacattag aaacaaaaaa taggagagc   1800
caagtcagga ataaaagtga ctctgctatgc taacgccaca ttagaacttg gttctctcac  1860
caagctgtaa tgtgattttt ttttctactc tgaattggaa atatgtatga atatacagag  1920
aagtgcttac aactaatttt tatttacttg tcacatttg gcaataaatc cctcttattt   1980
ctaaattcta acttgtttat ttcaaaactt tatataatca ctgttcaaaa ggaaatattt   2040
tcacctacca gagtgcttaa acactggcac cagccaaaga atgtggttgt agagacccag   2100
aagtcttcaa gaacagccga caaaacatt cgagttgacc ccaccaagtt gttgccacag    2160
ataatttaga tatttacctg caagaaggaa taaagcagat gcaaccaatt cattcagtcc   2220
acgagcatga tgtgagcact gctttgtgct agacattggg cttagcattg aaactataaa    2280
gaggaatcag acgcagcaag tgcttctgtg ttctggtagc aactcaacac tatctgtgga    2340
gagtaaactg aagatgtgca ggccaacatt ctgaaaatcc tatgtcaatg ggtttggttt    2400
ggaacctgga cttctgcatt tttaaaagtt acccagagat gcttctaaag atgagccata    2460
gtctagaaga ttgtcaacca caggagttca ttgagtggga cagctagaca catacattgg    2520
cagctacaat agtatcatga attgcaatga tgtagtgggg tataaaagga aagcgatgga    2580
tattgccgga tgggcatggc cagtgatgtt tcacgtcatt gaggtgacag ctctgctgga    2640
ctttgaatta catatggagg ctctccagga gacgaagaa gagaaggaca ttctaggcaa    2700
aaagaagact aggcacaagg cacacttatg tttgtctgtt agcttttagt tgaaaaagca    2760
aaatacatga tgcaaagaaa cctctccacg ctgtgatttt taaaactaca tacttttttgc    2820
aactttatgg ttatgagtat tgtagagaac aggagatag tcttagataa ttttatgtt     2880
gttgtcagac tctagcaagg tactagaaac ctagcaggca ttaataattg ttgaggcaat    2940
gactctgagg ctatatctgg gccttgtcat tatttatcat ttatatttgt atttttttct    3000
gaaatttgag ggcaagaaa acattgactt tgactgagga ggtcacatct gtgccatctc    3060
tgcaaatcaa tcagcaccac tgaaataact acttagtact ctgctgagct ttccctgctc    3120
agtagagaca aatatactca tccccacct cagtgagctt gttaggcaa ccaggattag    3180
agctgctcag gttccaacg tctcctgcca catcgggttc tcaaaatgga agaatggtt    3240
tatgccaaat cacttttcct gtctgaagga ccactgaatg gttttgtttt tccatatttt    3300
gcataggacg ccctaaagac taggtgactt ggcaaacaca caagtgttag tataattctt    3360
tgcttctgct tctttttgaa aatcatgttt agatttgatt taagtcaga aattcactga    3420
atgtcaggta atcattatgg agggagattt gtgtgtcaac caaagtaatt gtccatggc    3480
cccagggtat ttctgttgtt tccctgaaat tctgcttttt tagtcagcta gattgaaaac   3540
tctgaacagt agatgtttat atggcaaaat gcaagacaat ctacaaggga gatttaaagg    3600
attttgagat gaaaaacag atgctactca ggggctttat gaaccatcca tcaattctga    3660
agttctgact ctcccattac ccttttcctg gtgtggtcag aactccaggt cactggaagt    3720
tagtggaatc atgtagttga attctttact tcaagacatt gtattctctc cagctatcaa    3780
```

```
aacattaatg atcttttatg tcttttttt gttattgtta tactttaagt tctgggtac  3840
atgtgcggaa catgtaggtt tgttacatag gtatacatgt gccatggtgg tttgctgcac  3900
tcatcaacct gtcatctaca ttcttttatg tctgtctttc aaagcaacac tctgttcttc  3960
tgagtagtga aatcaggtca actttaccac cagcctccat ttttaatatg cttccacatc  4020
atccagcacc tacttaagat ttatctaggg tctctgtgtg atgttaggac ccataaaaga  4080
aatttatgcc ttccatatgt ttggttacag atgggaaatg ggaatgttga aggacatgaa  4140
agaaaggatg tttacacatt aagcatcagt tctgaagcta gattgtctga gtttgaatct  4200
tagctcttcc ctttattagc tctgtgacct cgagctagtt acttaaatgc tctgatcctc  4260
tatttcctga tcagtgaaac ctccctattc aaatgtgtga gagtttaata aattaggaca  4320
cttaaaaatg ttggagcagt gcatagcatg tagtgttcag tacatgttaa atgttgtttt  4380
ttattatgta caaacatgag tgggcacaga atttaaatc atctcaactt ttgagaaatt  4440
ttgagttatc aacaccgttc ccacaagaca gtggcaaaat tattggtgag aattaaacag  4500
ctgtttctca gaggaagcaa tggaggcttg ctgggataaa ggcatttact gagaggctgt  4560
tacctagtga gagtgatgaa ttaattaaaa tagtcgaatc cctttctgac tgtctctgaa  4620
agcttccgct tttatctttg aagagcagaa ttgtcactcc aaggacattt attaataaaa  4680
agaacaactg tccagtgcaa tgaaggcaaa gtcataggtc tcccaagtct taccccattc  4740
ctgtgaaata tcaagttctt ggcttttctc tgtcatgtag cctcaacttt ctctgaccgg  4800
gtgcatttct ttctctggtt tctaaattgc cagtggcaaa tttggatcac ttacttaata  4860
tctgttaaat tttgtgaccc aacaaagtct tttagcactg tggtgtcaaa aagaaaaaca  4920
cctcccaggc atatacattt tatagattcc tggagaatgt tgctctccag ctccatcccc  4980
acccaatgaa atatgatcca gagagtcttg caaagagaca agcctcattt tccacaatta  5040
gctctaaagt gcctccagga aatgatttc tcagctcatc tctctgtatt ccctgtttg  5100
gatcacaggg caatctgttt aaatgactaa ttacagaaat cattaaaggc accaagcaaa  5160
tgtcatctct gaatacacac atcccaagct ttacaaatcc tgcctggctt gacagtgatg  5220
aggccactta acagtccagc gcaggcggat gttaaaaaa ataaaaggt gaccatctgc  5280
ggtttagttt tttaactttc tgatttcaca cttaacgtct gtcattctgt tactgggcac  5340
ctgtttaaat tctattttaa aatgttaatg tgtgttgttt aaaataaaat caagaaagag  5400
aga                                                               5403

SEQ ID NO: 34        moltype = DNA  length = 5316
FEATURE              Location/Qualifiers
source               1..5316
                     mol_type = genomic DNA
                     organism = Homo sapiens
SEQUENCE: 34
gggctgccag catgctgtca cctctcaata ggagatcagt taatgcatac tgaaggaagg   60
cttgttggaa aagaatcctc tcctgaaccc tgtggagact ctagaatcct gcggatgtct  120
ctctccctaa gtaagagatg ttacttcctg gagggaatgc agtgttggga atctgaagac  180
ccagctttga gctgaatttg ctttgtgata cctgaaggag ctgcaaatga acacttcata  240
gcaatgtgga actccaacag aaaccggtga ataaagatca gtgtcccaga gagagaccag  300
aggagctgga gtcaggaggc atgtaccact gccacagtgg ctccaagccc acagaaaagg  360
gggcgaatga gtacgcctat gccaagtgga aactctgttc tgcttcagca atatgcttca  420
ttttcatgat tgcagaggtc gtgggtgggc acattgctgg ggagtcttgct gttgtcacag  480
atgctgccca cctcttaatt gacctgacca gtttcctgct cagtctcttc tccctgtggt  540
tgtcatcgaa gcctccctct aagcggctga catttggatg gcaccgagca gagatccttg  600
gtgccctgct ctccatcctg tgcatctggg tggtgactgg cgtgctagtg tacctggcat  660
gtgagcgcct gctgtatcct gattaccaga tccaggcgac tgtgatgatc atcgtttcca  720
gctgcgcagt ggcggccaac attgtactaa ctgtggtttt gcaccagaga tgccttggcc  780
acaatcacaa ggaagtacaa gccaatgcca gcgtcagagc tgcttttgtg catgcccttg  840
gagatctatt tcagagtatc agtgtgctaa ttagtgcact tattatctac tttaagccag  900
agtataaaat agccgaccca atctgcacat tcatctttc catcctggtc ttggccaaca  960
ccatcactat cttaaaggac ttctccatct tactcatgga aggtgtgcca aagagcctga 1020
attacagtgg tgtgaaagag cttattttag cagtcgacgg ggtgctgtct gtgcacagcc 1080
tgcacatctg gtctctaaca atgaatcaag taattctctc agctcatgtt gctacagcag 1140
ccagccggga cagccaagtg gttcggagag aaattgctaa agcccttagc aaaagcttta 1200
cgatgcactc actcaccatt cagatggaat ctccagttga ccaggacccc gactgccttt 1260
tctgtgaaga cccctgtgac tagctcagtc acaccgtcag tttcccaaat ttgacaggcc 1320
accttcaaac atgctgctat gcagtttctg catcatagaa ataaggaac caaaggaaga 1380
aattcatgtc atggtgcaat gcacatttta tctatttatt tagttccatt caccatgaag 1440
gaagaggcac tgagatccat caatcaattg gattatatac tgatcagtag ctgtgttcaa 1500
ttgcaggaat gtgtatatag attattcctg agtggagccg aagtaacagc tgtttgtaac 1560
tatcggcaat accaaattca tctcccttcc aataatgcat cttgagaaca cataggtaaa 1620
tttgaactca ggaaagtctt actagaaatc agtgaaggg acaaatagtc acaaaatttt 1680
accaaaacat tagaaacaaa aaataaggag agccaagtca ggaaaaatga tgactctgta 1740
tgctaacgcc acattagaac ttggttctct caccaagctg taatgtgatt tttttttcta 1800
ctctgaattg gaaatatgta tgaatataca gagaagtgct tacaactaat ttttatttac 1860
ttgtcacatt ttggcaataa atccctctta tttctaaatt ctaacttgtt tatttcaaaa 1920
ctttatataa tcactgttca aaaggaaata ttttcaccta ccagagtgct taaacactgg 1980
caccagccaa agaatgtggt tgtagagacc tagaggtctt caagaacagc cgacaaaaac 2040
attcgagttg accccaccaa gttgttgcca cagataattt agatatttac ctgcaagaag 2100
gaataaagca gatgcaacca attcattcag tccacgagca tgatgtgagc actgctttgt 2160
gctagacatt gggcttagca ttgaaactat aaagaggaat cagacgcagc aagtgcttct 2220
gtgttctggt agcaactcaa cactatctgt ggagagtaaa ctgaagatgt gcaggccaac 2280
attctggaaa tcctatgtca atgggtttgg tttggaacct ggacttctgc atttttaaaa 2340
gttacccaga gatgcttcta aagatgagcc atagtctaga agattgtcaa ccacaggagt 2400
tcattgagtg ggacagctag acacatacat tggcagctac aatagtatca tgaattgcaa 2460
tgatgtagtg gggtataaaa ggaaagcgat ggatattgcc ggatgggcat ggccagtgat 2520
gtttcacgtc attgaggtga cagctctgct ggactttgaa ttacatatgg aggctctcca 2580
ggaagacgaa aagagaagg acattctagg caaaaagaag actaggcaca aggcacactt 2640
```

```
atgtttgtct gttagctttt agttgaaaaa gcaaaataca tgatgcaaag aaacctctcc   2700
acgctgtgat tttaaaact acatacttt tgcaactta tggttatgag tattgtagag   2760
aacaggagat aggtcttaga tgatttttat gttgttgtca gactctagca aggtactaga   2820
aacctagcag gcattaataa ttgttgaggc aatgactctg aggctatatc tgggccttgt   2880
cattattat catttatatt tgtatttttt tctgaaattt gagggccaag aaaacattga   2940
cttttgactga ggaggtcaca tctgtgccat ctctgcaaat caatcagcac cactgaaata   3000
actacttagc attctgctga gctttccctg ctcagtagag acaaatatac tcatcccca   3060
cctcagtgag cttgtttagg caaccaggat tagagctgct caggttccca acgtctcctg   3120
ccacatcggg ttctcaaaat ggaaagaatg gtttatgcca aatcacttt cctgtctgaa   3180
ggaccactga atggttttgt ttttccatat tttgcatagg acgccctaaa gactaggtga   3240
cttggcaaac acacaagtgt tagtataatt cttttgcttct gcttctttt gaaaatcatg   3300
tttagatttg atttttaagtc agaaattcac tgaatgtcag gtaatcatta tggagggaga   3360
tttgtgtgtc aaccaaagta attgtcccat ggccccaggg tatttctgtt gtttccctga   3420
aattctgctt ttttagtcag ctagattgaa aactctgaac agtagatgtt tatatggcaa   3480
aatgcaagac aatctacaag ggagatttta aggattttga gatgaaaaaa cagatgctac   3540
tcaggggctt tatgaaccat ccatcaattc tgaagttctg actctcccat tacccttcc   3600
ctggtgtggt cagaactcca ggtcactgga agttagtgga atcatgtagt tgaattcttt   3660
acttcaagac attgtattct ctccagctat caaaacatta atgatctttt atgtcttttt   3720
tttgttattg ttatactta agttctgggg tacatgtgcg aacatgtag gtttgttaca   3780
taggtataca tgtgccatgg tggtttgctg cactcatcaa cctgtcatct acattctttt   3840
atgtctgtct ttcaaagcaa cactctgttc ttctgagtag tgaaatcagg tcaactttac   3900
caccagcctc cattttaat atgcttcacc atcatccagc acctacttaa gatttatcta   3960
gggctctgtg gtgatgttag gacccataaa agaaatttat gccttccata tgtttggtta   4020
cagatgggaa atgggaatgt tgaaggacat gaaagaaagg atgtttacac attaagcatc   4080
agttctgaag ctagattgtc tgagtttgaa tcttagctct tcccttatt agctctgtga   4140
cctcgagcta gttacttaaa tgctctgatc ctctatttco tgatcagtga aacctccta   4200
ttcaaatgtg tgagagttta ataaattagg acacttaaaa atgttggagc agtgcatagc   4260
atgtagtgtt cagtacatgt taaatgttgt ttttattat gtacaaacat gagtgggcac   4320
agaattttaa atcatctcaa ctttgagaa attttgagtt atcaacaccg ttcccacaag   4380
acagtggcaa aattattggt gagaattaaa cagctgttttc tcagaggaag caatggaggc   4440
ttgctgggat aaaggcattt actgagaggc tgttacctag tgagagtgat gaattaatta   4500
aaatagtcga atccctttct gactgtctct gaaagcttcc gctttatct ttgaagagca   4560
gaattgtcac tccaaggaca tttattaata aaaagaacaa ctgtccagtg caatgaaggc   4620
aaagtcatag gtctcccaag tcttacccca ttcctgtgaa atatcaagtt cttggctttt   4680
ctctgtcatg tagcctcaac tttctctgac cgggtgcatt tctttctctg gtttctaaat   4740
tgccagtggc aaatttggat cacttactta atatctgtta aattttgtga cccaacaaag   4800
tcttttagca ctgtggtgtc aaaaagaaa cacctccca ggcatataca ttttatagat   4860
tcctggagaa tgttgctctc cagctccatc cccacccaat gaaatatgat ccagagagtc   4920
ttgcaaagag acaagcctca ttttccacaa ttagctccaa agtgcctcca gcgaaatgatt   4980
ttctcagctc atctctctgt attccctgtt ttggatcaca gggcaatgtc tttaaatgac   5040
taattacaga aatcattaaa ggcaccaagc aaatgtcatc tctgaataca cacatcccaa   5100
gctttacaaa tcctgcctgg cttgacagtg atgaggccac ttaacagtcc agcgcaggcg   5160
gatgttaaaa aaaataaaa ggtgaccatc tgcggttag atttttaact ttctgatttc   5220
acacttaacg tctgtcattc tgttactggg cacctgttta aattctattt taaaatgtta   5280
atgtgtgttg tttaaaataa aatcaagaaa gagaga                             5316

SEQ ID NO: 35          moltype = DNA   length = 5561
FEATURE                Location/Qualifiers
source                 1..5561
                       mol_type = genomic DNA
                       organism = Homo sapiens
SEQUENCE: 35
ttttaagaag catcaagaaa gcctgcctgt ctaactttgg aaatatcacc ctcatgctgt     60
cttcccagga tgtctctctc cctaagtaag agatgttact tcctggaggg aatgcagtgt    120
tgggaatctg aagacccagc tttgagctga atttgctttg tgatacctga gacagcattt    180
ccccatgttg gccaggctgg tcttgaactc ctgacctcaa gtgatccgcc cgcctcggcc    240
tcccaaagtg ctgggtttac aagcgtgagc caccgcgccc cggggagtc agaaagtgta    300
taaataattg cagtgctgct ttgcttccaa aactgggcag tgagttcaac aacaacgaca    360
acaacagccg cagctcatcc tggccgtcat ggagtttcct gaaagaacgt atcttgtgaa    420
tgataaagct gccaagatgt atgctttcac actagaaaga aggagctgca aatgaacact    480
tcatagcaat gtggaactcc aacagaaacc ggtgaataaa gatcagtgtc ccagagagag    540
accagaggag ctggagtcag gaggcatgta ccactgccac agtggctcca gcccacagaa   600
aaaggggcg aatgagtacg cctatgccaa gtggaaactc tgttctgctt cagcaatatg    660
cttcatttc atgattgcag aggtcgtggg tgggcacatt gtcatctgtg ttgcttgtgt    720
cacagatgct gcccacctct taattgacct gaccagtttc ctgctcagtc tcttctccct    780
gtgggttgtca tcgaagcctc cctctaagcg gctgacattt ggatggcacc gagcagagat    840
ccttggtgcc ctgctctcca tcctgtgcat ctgggtggtg actggcgtgc tagtgtacct    900
ggcatgtgag cgcctgctgt atcctgatta ccagatccag gcgctgtgga tgatcatcgt    960
ttccagctgc gcagtggcgg ccaacattgt actaactgtg gttttgcacc agagatgcct   1020
tggccacaat cacaaggaag tacaagccaa tgccagcgtc agagctgctt ttgtgcatgc   1080
ccttggagat ctatttcaga gtatcagtgt gctaattagt gcacttattta ctcatttaa   1140
gccagagtat aaaatagccg acccaatctg cacattcatc ttttccatcc tggtcttggc   1200
cagcaccatc actatcttaa aggacttctc catcttactc atggaaggtg tgccaaagag   1260
cctgaattac agttggtgta aagagcttaa ttagcagtgc gacgggtgc tgtctgttga   1320
cagcctgcac atctggtctc taacaatgaa tcagtaatt ctctcagctc atgttgctac   1380
agcagccagc cgggacagcc aagtggttcg gagagaaatt gctaaagccc ttagcaaaag   1440
ctttacgatg cactcactca ccattcagat ggaatctcca gttgaccagg acccgactg   1500
cctttctgt gaagacccct gtgactagct cagtcacacc gtcagtttcc caaatttgac   1560
aggccacctt caaacatgct gctatgcagt ttctgcatca tagaaaataa ggaaccaaag   1620
```

```
gaagaaattc atgtcatggt gcaatgcaca ttttatctat ttatttagtt ccattcacca 1680
tgaaggaaga ggcactgaga tccatcaatc aattggatta tatactgatc agtagctgtg 1740
ttcaattgca ggaatgtgta tatagattat tcctgagtgg agccgaagta acagctgttt 1800
gtaactatcg gcaataccaa attcatctcc cttccaataa tgcatcttga aacacatag  1860
gtaaatttga actcaggaaa gtcttactag aaatcagtgg aagggacaaa tagtcacaaa 1920
attttaccaa aacattagaa acaaaaaata aggagagcca agtcaggaat aaaagtgact 1980
ctgtatgcta acgccacatt agaacttggt tctctcacca agctgtaatg tgatttttt  2040
ttctactctg aattggaaat atgtatgaat atacagagaa gtgcttacaa ctaattttta 2100
tttacttgtc acatttttggc aataaatccc tcttatttct aaattctaac ttgtttattt 2160
caaaacttta tataatcact gttcaaaagg aaatattttc acctaccaga gtgcttaaac 2220
actggcacca gccaaagaat gtggttgtag agacccagaa gtcttcaaga acagccgaca 2280
aaaacattcg agttgacccc accaagttgt tgccacagat aatttagata tttacctgca 2340
agaaggaata aagcagatgc aaccaattca ttcagtccac gagcatgatg tgagcactgt 2400
tttgtgctag acattgggct tagcattgaa actataaaga ggaatcagac gcagcaagtg 2460
cttctgtgtt ctggtagcaa ctcaacacta tctgtggaga gtaaactgaa gatgtgcagg 2520
ccaacattct ggaaatccta tgtcaatggg tttggtttgg aacctggact tctgcatttt 2580
taaaagttac ccagagatgc ttctaaagat gagccatagt ctagaagatt gtcaaccaca 2640
ggagttcatt gagtgggaca gctagacaca tacattggca gctacaatag tatcatgaat 2700
tgcaatgatg tagtggggta taaaaggaaa gcgatggata ttgccggatg ggcatggcca 2760
gtgatgtttc acgtcattga ggtgacagct ctgctggact ttgaattaca tatggaggct 2820
ctccaggaag acgaagaaga aaggacatt ctaggcaaaa agaagactag gcacaaggca 2880
cacttatgtt tgtctgttag cttttagttg aaaaagcaaa atacatgatg caaagaaacc 2940
tctccacgct gtgattttta aaactacata cttttttgcaa ctttatggtt atgagtattg 3000
tagagaacag gagataggtc ttagatgatt tttatgttgt tgtcagactc tagcaaggta 3060
ctagaaacct agcaggcatt aataattgtt gaggcaatga ctctgaggct atatctgggc 3120
cttgtcatta tttatcattt atatttgtat ttttttctga ttttgaggg ccaagaaaac 3180
attgactttg actgaggagg tcacatctgt gccatctctg caaatcaatc agcaccactg 3240
aaataactac ttagcattct gctgagcttt ccctgctcag tagagacaaa tatactcatc 3300
ccccacctca gtgagcttgt ttaggcaacc aggattagag ctgctcaggt tcccaacgtc 3360
tcctgccaca tcgggttctc aaaatggaaa gaatggttta tgccaaatca ctttttcctgt 3420
ctgaaggacc actgaatggt ttttgttttttc catattttgc ataggacgcc ctaaagacta 3480
ggtgacttgg caaacacaca agtgttagta taattctttg cttctgcttc tttttgaaaa 3540
tcatgtttag atttgatttt aagtcagaaa ttcactgaat gtcaggtaat cattatggag 3600
ggagatttgt gtgtcaacca aagtaattgt cccatggccc cagggtattt ctgttgtttc 3660
cctgaaattc tgctttttta gtcagctaga ttgaaaactc tgaacagtag atgtttatat 3720
ggcaaaatgc aagacaatct acaagggaga ttttaaggat tttgagatga aaaaacagat 3780
gctactcagg ggctttatga accatccatc aattctgaag ttctgactct cccattaccc 3840
tttccctggt gtggtcagaa ctccaggtca ctggaagtta gtggaatcat gtagttgaat 3900
tctttacttc aagacattgt attctctcca gctatcaaaa cattaatgat ctttatgtc  3960
tttttttgt tattgttata ctttaagttc tggggtacat gtgcggaaca tgtaggtttg 4020
ttacataggt atacatgtgc catggtggtt tgctgcactc atcaacctgt catctacatt 4080
cttttatgtc tgtcttcaa agcaacactc tgttcttctg agtagtgaaa tcaggtcaac 4140
tttaccacca gcctccattt ttaatatgct tcaccatcat ccagcaccta cttaagattt 4200
atctagggct ctgtggtgat gttaggaccc ataaagaaa tttatgcctt ccatatgttt 4260
ggttacagat gggaaatggg aatgttgaag gacatgaaag aaaggatgtt tacacattaa 4320
gcatcagttc tgaagctaga ttgtctgagt ttgaatctta gctcttccct ttattagctc 4380
tgtgacctcg agctagttac ttaaatgctc tgatcctctc tttcctgatc agtgaaacct 4440
ccctattcaa atgtgtgaga gtttaataaa ttaggacact taaaaatgtt ggagcagtgc 4500
atagcatgta gtgttcagta catgttaaat gttgtttttt attatgtaca aacatgagtg 4560
ggcacagaat tttaaatcat ctcaacttttt gagaaatttt gagttatcaa caccgttccc 4620
acaagacagt ggcaaaatta ttggtgagaa ttaaacagct gtttctcaga ggaagcaatg 4680
gaggcttgct gggataaagg catttactga gaggctgtta cctagtgaga gtgatgaatt 4740
aattaaaata gtcgaatccc tttctgactg tctctgaaag cttccgcttt tatctttgaa 4800
gagcagaatt gtcactccaa ggacatttat taataaaaag aacaactgtc cagtgcaatg 4860
aaggcaaagt cataggtctc ccaagtctta ccccattcct gtgaaatatc aagttcttgg 4920
cttttctctg tcatgtagcc tcaacttttct ctgaccgggt gcatttcttt ctctggtttc 4980
taaattgcca gtgcaaatt tggatcactt acttaatatc tgttaaattt tgtgacccaa 5040
caaagtcttt tagcactgtg gtgtcaaaaa gaaaaacacc tcccaggcat atacattta  5100
tagattcctg gagaatgttg ctctccagct ccatccccac ccaatgaaat atgatccgaa 5160
gagtcttgca aagagacaag cctcatttct cacaattagc tctaaagtgc ctccaggaaa 5220
tgattttctc agctcatctc tctgtattcc ctgttttgga tcacagggca atctgtttaa 5280
atgactaatt acagaaatca ttaaaggcac caagcaaatg tcatctctga atacacacat 5340
cccaagcttt acaaatcctg cctggcttga cagtgatgag gccacttaac agtccagcgc 5400
aggcggatgt taaaaaaaat aaaaaggtga ccatctgcag tttagttttt taactttctg 5460
atttcacact taacgtctgt cattctgtta ctgggcacct gtttaaattc tattttaaaa 5520
tgttaatgtg tgttgtttaa aataaaatca agaaagagag a                     5561
```

```
SEQ ID NO: 36      moltype = DNA  length = 5430
FEATURE            Location/Qualifiers
source             1..5430
                   mol_type = genomic DNA
                   organism = Homo sapiens
SEQUENCE: 36
ttttaagaag catcaagaaa gcctgcctgt ctaactttgg aaatatcacc ctcatgctgt  60
cttcccagga tgtctctctc cctaagtaag agatgttact tcctggaggg aatgcagtgt 120
tgggaatctg aagacccagc tttgagctga atttgctttg tgatacctgg agagaagacg 180
tgttttcttg acaacagcac agtacctagt gagttcaaca acaacgacaa caacagccgc 240
agctcatcct ggccgtcatg gagtttcttg aaagaacgta tcttgtgaat gataaagctg 300
ccaagatgta tgctttcaca ctagaaagaa ggagctgcaa atgaacactt catagcaatg 360
```

```
tggaactcca acagaaaccg gtgaataaag atcagtgtcc cagagagaga ccagaggagc    420
tggagtcagg aggcatgtac cactgccaca gtggctccaa gcccacagaa aaggggggcga   480
atgagtacgc ctatgccaag tggaaactct gttctgcttc agcaatatgc ttcattttca    540
tgattgcaga ggtcgtgggt gggcacattg ctgggagtct tgctgttgtc acagatgctg    600
cccacctctt aattgacctg accagtttcc tgctcagtct cttctccctg tggtttgtcat   660
cgaagcctcc ctctaagcgg ctgacatttg gatggcaccg agcagagatc cttggtgccc    720
tgctctccat cctgtgcatc tgggtggtga ctggcgtgct agtgtacctg gcatgtgagc    780
gcctgctgta tcctgattac cagatccagg cgactgtgat gatcatcgtt tccagctgcg    840
cagtggcggc caacattgta ctaactgtgg ttttgcacca gagatgcctt ggccacaatc    900
acaaggaagt acaagccaat gccagcgtca gagctgcttt tgtgcatgcc cttggagatc    960
tatttcagag tatcagtgtg ctaattagtg cacttattat ctactttaag ccagagtata   1020
aaatagccga cccaatctgc acattcatct tttccatcct ggtcttggcc agcaccatca   1080
ctatcttaaa ggacttctcc atcttactca tggaaggtgt gccaaagagc ctgaattaca   1140
gtggtgtgaa agagcttatt ttagcagtcg acggggtgtc gtctgtgcac agctgcaca    1200
tctggtctct aacaatgaat caagtaattc tctcagctca tgttgctaca gcagccagcc   1260
gggacagcca agtggttcgg agagaaattg ctaaagccct tagcaaaagc tttacgatgc   1320
actcactcac cattcagatg gaatctccag ttgaccagga ccccgactgc cttttctgtg   1380
aagaccctg tgactagctc agtcacaccg tcagtttccc aaatttgaca ggccaccttc    1440
aaacatgctg ctatgcagtt tctgcatcat agaaaataag gaaccaaagg aagaaattca   1500
tgtcatggtg caatgcacat tttatctatt tatttagttc cattcaccat gaaggaagag   1560
gcactgagat ccatcaatca attggattat atactgatca gtagctgtgt tcaattgcag   1620
gaatgtgtat atagattatt cctgagtgga gccgaagtaa cagctgtttg taactatcgg   1680
caataccaaa ttcatctccc ttccaataat gcatcttgag aacacatagg taaatttgaa   1740
ctcaggaaag tcttactaga aatcagtgga agggacaaat agtcacaaaa ttttaccaaa   1800
acattagaaa caaaaataa ggagagccaa gtcaggaata aaagtgactc tgtatgctaa    1860
cgccacatta gaacttggtt ctctccaccaa gctgtaatgt gattttttt tctactctga    1920
attggaaata tgtatgaata tacagagaag tgcttacaac taatttttat ttacttgtca   1980
cattttggca ataaatccct cttatttcta aattctaact tgtttatttc aaaactttat   2040
ataatcactg ttcaaaagga aatattttca cctaccagag tgcttaaaca ctggcaccag   2100
ccaaagaatg tggttgtaga gacccagaag tcttcaagaa cagccgacaa aaacattcga   2160
gttgacccca ccaagttgtt gccacagata atttagatat ttacctgcaa gaaggaataa   2220
agcagatgca accaattcat tcagtccacg agcatgatgt gagcactgct ttgtgctaga   2280
cattgggctt agcattgaaa ctataaagag gaatcagacg cagcaagtgc ttctgtgttc   2340
tggtagcaac tcaacactat ctgtggagag taaactgaag atgtgcaggc caacattctg   2400
gaaatcctat gtcaatgggt ttggtttgga acctggactt ctgcatttt aaaagttacc     2460
cagagatgct tctaaagatg agccatagtc tagaagattg tcaaccacag gagttcattg   2520
agtgggacac ctagacacat acattggcag ctacaatagt atcatgaatt gcaatgatgt   2580
agtgggtat aaaaggaaag cgatggatat tgccggatgg gcatggccag tgatgtttca     2640
cgtcattgag gtgacagctc tgctggactt tgaattacat atggaggctc tccaggaaga   2700
cgaagaagag aaggacattc taggcaaaaa gaagactagg cacaaggcac acttatgttt   2760
gtctgttagc ttttagttga aaaagcaaaa tacatgatgc aaagaaacct ctccacgctg   2820
tgatttttaa aactacatac ttttttgcaac tttatggtta tgagtattgt agagaacagg   2880
agataggtct tagatgattt ttatgttgtt gtcagactct gcaaggtac tagaaaccta    2940
gcaggcatta ataattgttg aggcaatgac tctgaggcta tatctgggcc ttgtcattat   3000
ttatcattta tatttgtatt tttttctgaa atttgagggc caagaaaaca ttgactttga   3060
ctgaggaggt cacatctgtg ccatctctgc aaatcaatca gcaccactga aataactact   3120
tagcattctg ctgagctttc cctgctcagt agagacaaat atactcatcc cccacctcag   3180
tgagcttgtt taggcaacca ggattagagc tgctcaggtt cccaacgtct cctgccacat   3240
cgggttctca aaatggaaag aatggtttat gccaaatcac ttttcctgtc tgaaggacca   3300
ctgaatggtt ttgtttttcc atattttgca taggacgccc taaagactag gtgacttggc   3360
aaacacacaa gtgttagtat aattcttgc ttctgctttt ttttgaaaat catgttttga    3420
tttgatttta agtcagaaat tcactgaatg tcaggtaatc attatggagg gagatttgtg   3480
tgtcaaccaa agtaattgtc ccatggcccc agggtatttc tgttgtttcc ctgaaattct   3540
gcttttttag tcagctagat tgaaaactct gaacagtaga tgtttatatg gcaaaatgca   3600
agacaatcta caagggagat tttaaggatt ttgagatgaa aaaacagatg ctactcaggg   3660
gctttatgaa ccatccatca attctgaagt tctgactctc ccattaccct ttccctggtg   3720
tggtcagaac tccaggtcac tggaagttag tggaatcatg tagttgaatt ctttacttca   3780
agacattgta ttctctccag ctatcaaaac attaatgatc ttttatgtct ttttttttgtt  3840
attgttatac tttaagttct ggggtacatg tgcggaacat gtaggtttgt tacataggta   3900
tacatgtgcc atgtggtttt gctgcactca tcaacctgtc atctacattc ttttatgtct   3960
gtctttcaaa gcaacactct gttcttctga gtagtgaaat caggtcaact ttaccaccag   4020
cctccatttt taatatgctt caccatcatc cagcacctac ttaagattta tctagggctc   4080
tgtggtgatg ttaggaccca taaagaaat ttatgccttc catatgtttg gttacagatg     4140
ggaaatggga atgttgaagg acatgaaaga aaggatgttt acacattaag catcagttct   4200
gaagctagat tgtctgagtt tgaatcttag ctcttccctt tattagctct gtgacctcga   4260
gctagttact taaatgctct gatcctctat ttcctgatca gtgaaacctc cctattcaaa   4320
tgtgtgagag tttaataaat taggacactt aaaaatgttg gagcagtgca tagcatgtag   4380
tgttcagtac atgttaaatg ttgtttttta ttatgtacaa acatgagtgg gcacagaatt   4440
ttaaatcatc tcaactttg agaaattttg agttatcaac accgttccca caagacagtg    4500
gcaaaattat tggtgagaat taaacagctg tttctcagag gaagcaatgg aggcttgctg   4560
ggataaaggc atttactgag aggctgttac ctagtgagag tgatgaatta attaaaatag   4620
tcgaatccct ttctgactgt ctctgaaagc ttccgctttt atctttgaag agcagaattg   4680
tcactccaag gacatttatt aataaaaaga caactgtcc agtgcaatga aggcaaagtc    4740
ataggtctcc caagtcttac cccattcctg tgaaatatca agttcttggc ttttctctgt   4800
catgtagcct caactttctc tgaccggggtg catttcttc tctggtttct aaattgccag    4860
tggcaaattt ggatcactta cttaatatct gttaaatttt gtgacccaac aaagtctttt   4920
agcactgtgg tgtcaaaaag aaaaacacct cccaggcata tacattttat agattcctgg   4980
agaatgttgc tctccagctc catccccacc caatgaaata tgatccagag agtccttgaa   5040
agagacaagc ctcattttcc acaattagct ctaaagtgcc tccaggaaat gattttctca   5100
```

```
gctcatctct ctgtattccc tgttttggat cacagggcaa tctgtttaaa tgactaatta    5160
cagaaatcat taaaggcacc aagcaaatgt catctctgaa tacacacatc ccaagcttta    5220
caaatcctgc ctggcttgac agtgatgagg ccacttaaca gtccagcgca ggcggatgtt    5280
aaaaaaaata aaaaggtgac catctgcggt ttagtttttt aactttctga tttcacactt    5340
aacgtctgtc attctgttac tgggcacctg tttaaattct attttaaaat gttaatgtgt    5400
gttgtttaaa ataaaatcaa gaaagagaga                                     5430

SEQ ID NO: 37           moltype = AA  length = 89
FEATURE                 Location/Qualifiers
source                  1..89
                        mol_type = protein
                        organism = Homo sapiens
SEQUENCE: 37
MGILKLQVFL IVLSVALNHL KATPIESHQV EKRKCNTATC ATQRLANFLV HSSNNFGAIL    60
SSTNVGSNTY GKRNAVEVLK REPLNYLPL                                      89

SEQ ID NO: 38           moltype = DNA  length = 267
FEATURE                 Location/Qualifiers
misc_feature            1..267
                        note = CDS encodes SEQ ID NO: 37
source                  1..267
                        mol_type = genomic DNA
                        organism = Homo sapiens
SEQUENCE: 38
atgggcatcc tgaagctgca agtatttctc attgtgctct ctgttgcatt gaaccatctg    60
aaagctacac ccattgaaag tcatcaggtg gaaaagcgaa aatgcaacac tgccacatgt    120
gcaacgcagc gcctggcaaa ttttttagtt cattccagca acaactttgg tgccattctc    180
tcatctacca acgtgggatc caatacatat ggcaagagga atgcagtaga ggttttaaag    240
agagagccac tgaattactt gcccctt                                        267

SEQ ID NO: 39           moltype = AA  length = 470
FEATURE                 Location/Qualifiers
source                  1..470
                        mol_type = protein
                        organism = Homo sapiens
SEQUENCE: 39
MSHHPSGLRA GFSSTSYRRT FGPPPSLSPG AFSYSSSSRF SSSRLLGSAS PSSSVRLGSF    60
RSPRAGAGAL LRLPSERLDF SMAEALNQEF LATRSNEKQE LQELNDRFAN FIEKVRFLEQ    120
QNAALRGELS QARGQEPARA DQLCQQELRE LRRELELLGR ERDRVQVERD GLAEDLAALK    180
QRLEEETRKR EDAEHNLVLF RKDVDDATLS RLELERKIES LMDEIEFLKK LHEEELRDLQ    240
VSVESQQVQQ VEVEATVKPE LTAALRDIRA QYESIAAKNL QEAEEWYKSK YADLSDAANR    300
NHEALRQAKQ EMNESRRQIQ SLTCEVDGLR GTNEALLRQL RELEEQFALE AGGYQAGAAR    360
LEEELRQLKE EMARHLREYQ ELLNVKMALD IEIATYRKLL EGEESRISVP VHSFASLNIK    420
TTVPEVEPPQ DSHSRKTVLI KTIETRNGEV VTESQKEQRS ELDKSSAHSY                470

SEQ ID NO: 40           moltype = DNA  length = 1413
FEATURE                 Location/Qualifiers
misc_feature            1..1410
                        note = CDS encodes SEQ ID NO: 39
source                  1..1413
                        mol_type = genomic DNA
                        organism = Homo sapiens
SEQUENCE: 40
atgagccacc acccgtcggg cctccgggcc ggcttcagct ccacctcata ccgccgtacc    60
ttcggtccac cgccctcact atcccccggg gccttctctc actcgtccag ctcccgcttc    120
tccagcagcc gcctgctggg ctccgcgtcc ccgagctcct cggtgcgcct gggcagcttc    180
cgtagccccc gagcgggagc gggcgccctc ctgcgcctgc cctcggagcg cctcgacttc    240
tccatggccg aggccctcaa ccaggagttc ctggccacgc gcagcaacga gaagcaggag    300
ctgcaggagc tcaacgaccg cttcgccaac ttcatcgaga aggtacgctt tctggagcag    360
cagaacgcag ccctgcgcgg ggagctgagc caagcccggg gccaggagcc ggcgcgcgcc    420
gaccagctgt gccagcagga gctgcgcgag ctgcggcgag agctggagct gttgggccgc    480
gagcgtgacc gggtgcaggt ggagcgcgac gggctggcgg aggacctggc ggcgctcaag    540
cagaggttgg aggaggagac gcgcaagcgg gaggacgcgg agcacaacct cgtgctcttc    600
cgcaaggacg tggacgatgc cactctgtcc cgcctgagac tagagcgcaa gattgagtct    660
ctgatggatg agattgagtt cctcaagaag ctgcacgagg aggagctgcg agacctgcag    720
gtgagtgtgg agagccagca ggtgcagcag gtggaggtgg aagccacggt gaagcccgag    780
ctgacggcag cgctgaggga catccgcgcg cagtacgaga gcatcgccgc gaagaacctg    840
caggaggcgg aggagtggta caagtccaag tacgcggacc tgtccgacgc tgccaaccgg    900
aaccacgagg ccctgcgcca ggccaagcag gagatgaacg agtcccgacg ccagatccgg    960
agtctaacgt gcgaggtgga cgggctgcgc ggcacgaacg aggcgctgct caggcagttg    1020
agagagctgg aggagcagtt cgccctggag gcggggggct accagcgggg cgctgcgcgg    1080
ctcgaggagg agctgcgaca gctaaaagag gagatggcgc ggcacctgag ggagtaccag    1140
gagctcctca acgtcaagat ggccctggac atcgagatcg ccacctaccg caagctgctg    1200
gagggcgagg agagccggat ctccgtgccc gtccattctt ttgcctcctt aaatataaag    1260
acgactgtgc ctgaggtgga gcctcccag gacagccaca gccggaagac ggttctgatc    1320
aagaccattg agacccggaa tggggaggtg gtgacagagt cccagaagga gcagcgcagt    1380
gagctggaca gtcttctgc ccacagttac taa                                  1413

SEQ ID NO: 41           moltype = DNA  length = 1833
```

| FEATURE | Location/Qualifiers |
|---|---|
| source | 1..1833<br>mol_type = genomic DNA<br>organism = Homo sapiens |

SEQUENCE: 41

```
cctcgcagcg gtctgcggct ccttcccagc ccccggccta gctctgcgaa cggtgactgc   60
ccatccttgg ccgcaatgag ccaccacccg tcgggcctcc gggccggctt cagctccacc  120
tcataccgcc gtaccttcgg tccaccgccc tcactatccc ccggggcctt ctcctactcg  180
tccagctccc gcttctccag cagccgcctg ctgggctccg cgtccccgag ctcctcggtg  240
cgcctgggca gcttccgtag ccccccgagcg ggagcgggcg ccctcctgcg cctgccctcg  300
gagcgcctcg acttctccat ggccgaggcc ctcaaccagg agttcctggc cacgcgcagc  360
aacgagaagc aggagctgca ggagctcaac gaccgcttcg ccaacttcat cgagaaggta  420
cgctttctgg agcagcagaa cgcggccctg cgcggggagc tgagccaagc ccggggccag  480
gagccggcgc gcgccgacca gctgtgccag caggagctgc gcgagctgca cgagagctg  540
gagctgttgg gccgcgagcg tgaccgggtg caggtggagc gcgacgggct ggcggaggac  600
ctggcggcgc tcaagcagag gttggaggag gagacgcgca gcggggagga cgcggagcac  660
aacctcgtgc tcttccgcaa ggacgtggac gatgccactc tgtcccgcct ggaactagag  720
cgcaagattg agtctctgat ggatgaagatt gagttcctca agcaggactgca cgaggaggag 780
ctgcgagacc tgcaggtgag tgtgagagc cagcaggtgc agcaggtgga ggtggaagcc  840
acggtgaagc ccgagctgac ggcagcgctg agggacatcc gcgcgcagta cgagagcatc  900
gccgcgaaga acctgcagga ggcggaggag tggtacaagt ccaagtacgc ggacctgtcc  960
gacgctgcca accggaacca cgaggccctg cgccaggcca agcaggagt gaacgagtcc 1020
cgacgccaga tccagagtct aacgtgcgag gtgacgggc tgcgcggcac gaacgaggcg 1080
ctgctcaggc agttgagaga gctgaggag cagttcgccc tggagcgggg gggctaccag 1140
gcgggcgctg cgcggctcga ggaggagctg cgacagctaa aagagggagat ggcgcggcac 1200
ctgagggagt accaggagct cctcaacgtc aagatgcgct tggacatcga gatcgccac 1260
taccgcaagc tgctggaggg cgaggagagc cggatctccg tgcccgtcca ttcttttgcc 1320
tccttaaata taaagacgac tgtgcctgag gtgagcctc cccaggacag ccacagccgg 1380
aagacggttc tgatcaagac cattgagacc cggaatgggg aggtggtgac agagtcccag 1440
aaggagcagc gcagtgagct ggacaagtct tctgcccaca gttactgaac cccttggtcc 1500
ggagccttga ctctgcccta ggcctgctca aagcccaaac cctaagacca ctcctgaatt 1560
gtctcctctc cctctgcatg tgtctaaaag gtggtaccag gcatcccttt cctggcttat 1620
ggccaagccc tacccggcca gcagtcgctg ggcctctccc tgccctgaca cttgatgtga 1680
cctatgtgct tcccttttca tgtcccgata agaagccaat gatccccct caggacaaat 1740
ctactccagc cacgatgaga agtgggtgag ccagggtctg agtttcacat ttgaaccaaa 1800
taaaatgctg tcaagagaaa actctccagt gca                              1833
```

| SEQ ID NO: 42 | moltype = DNA length = 1949 |
|---|---|
| FEATURE | Location/Qualifiers |
| source | 1..1949<br>mol_type = genomic DNA<br>organism = Homo sapiens |

SEQUENCE: 42

```
tgttccgcag gggtgggca tccccctccc catacaaccc ccctccagcg ggccatcagg    60
ccagtgggag gagctgcccg tgcccccct gagaccgcag ggctataaag ccgcctcgca   120
gcggtctgcg gctccttccc agcccccggc ctagctctgc gaacggtgac tgcccatcct   180
tggccgcaat gagccaccac ccgtcgggcc tccgggctcc cttcagctcc acctcatacc   240
gccgtacctt cggtccaccg ccctcactat ccccggggc cttctcctac tcgtccagct   300
cccgcttctc cagcagccgc ctgctgggct ccgcgtcccc gagctcctcg gtgcgcctgg   360
gcagcttccg tagccccga gcgggagcgg gcgccctcct gcgcctgccc tcggagcgcc   420
tcgacttctc catggccgag gccctcaacc aggagttcct ggccacgcgc agcaacgag   480
agcaggagct gcaggagctc aacgaccgct tcgccaactt catcgagaag gtacgctttc   540
tggagcagca gaacgcggcc ctgcgcgggg agctgagcca agcccgggc caggagccgg   600
cgcgcgccga ccagctgtgc cagcaggagc tgcgcgagct gcggcgagag ctggagctgt   660
tgggccgcga gcgtgaccgg gtgcaggtgg agcgcgacgg gctggcggag gacctggcgg   720
cgctcaagca gaggttggag gaggagacgc gcaagcggga ggacgcggag cacaacctcg   780
tgctcttccg caaggacgtg gacgatgcca ctctgtcccg cctggaacta gagcgcaaga   840
ttgagtctct gatggatgag attgagttcc tcaagaagct gcacgaggag agctgcgag   900
acctgcaggt gagtgtggag agccagcagg tgcagcaggt ggagtggaa gccacggtga   960
agcccgagct gacggcagcg ctgagggaca tccgcgcgca gtacgagagc atcgccgcga  1020
agaacctgca ggaggcggag gagtggtaca agtccaagta cgcggacctg tccgacgctg  1080
ccaaccggaa ccacgaggcc ctgcgccagg ccaagcagga gatgaacgag tcccgacgcc  1140
agatccagag tctaacgtgc gaggtggacg gctgcgcgg cacgaacgag gcgctgctca  1200
ggcagttgag agactgaggag cagttcgccc tggagcgggg ggctac caggcggggcg  1260
ctgcgcggct cgaggaggag ctgcgacagc taaaagagga gatggcgcgg cacctgaggg  1320
agtaccagga gctcctcaac gtcaagatgg ccctggacat cgagatcgcc acctaccgca  1380
agctgctgga gggcgaggag agccggatct ccgtgcccgt ccattctttt gcctcctta  1440
atataaagac gactgtgcct gaggtggagc ctccccagga cagccacagc cggaagacgg  1500
ttctgatcaa gaccattgag acccggaatg gggaggtgac agagtcccag agg         1560
agcagcgcag tgagctggac aagtcttctg cccacagtta ctgaacccct tggtccggag  1620
ccttgactct gccctaggcc tgctcaaagc ccaaaccta gaccactcc tgaattgtct  1680
cctctccctc tgcatgtgtc taaaggtgg taccaggcat cccttcctg cttatggcc  1740
aagccctacc cggccagcag tcgctgggcc tctccctgcc ctgacacttg atgtgaccta  1800
tgtgcttccc ttttcatgtc ccgataagaa gccaatgatc cccctcagg acaaatctac  1860
tccagccacg atgagaagtg ggtgagccag ggtctgagtt tcacatttga accaaataaa  1920
atgctgtcaa gagaaaactc tccagtgca                                    1949
```

| SEQ ID NO: 43 | moltype = DNA length = 1628 |
|---|---|
| FEATURE | Location/Qualifiers |

```
source                    1..1628
                          mol_type = genomic DNA
                          organism = Homo sapiens
SEQUENCE: 43
tgttccgcag gggtggggca tcccctccc catacaaccc ccctccagcg ggccatcagg    60
ccagtgggag gagctgcccg tgccccccct gagaccgcag ggctataaag ccgcctcgca   120
gcggtctgcg gctccttccc agccccggc ctagctctgc gaacggtgac tgcccatcct   180
tggccgcaat gagccaccac ccgtcgggcc tccgggccgg cttcagctcc acctcatacc   240
gccgtacctt cggtccaccg ccctcactat ccccggggc cttctcctac tcgtccagct   300
cccgcttctc cagcagccgc ctgctgggct ccgcgtcctc gagctcctcg gtgcgcctgg   360
gcagcttccg tagcccccga gcgggagcgg gcgcccctcct gcgcctgccc tcggagcgcc   420
tcgacttctc catggccgag gccctcaacc aggagttcct ggccacgcgc agcaacgaga   480
agcaggagct gcaggagctc aacgaccgct cgccaacttt catcgagaag gtacgctttc   540
tggagcagca gaacgcggcc ctgcgcgggg agctgagcca agcccggggc caggagcgg    600
cgcgcgccga ccagctgtgc cagcaggagc tgcgcgagct gcggcgagag ctggagctgt   660
tgggccgcga gcgtgaccgg gtgcaggtgg agcgcgacgg gctggcggag gacctggcgg   720
cgctcaagca gaggtcaggg ggcagggctg ggccgctgcc gtcgaggcga ggtcgaagcg   780
gccgtcgagg cggctgctct tgcctcccct cgcttcccct ctccatcagc agcccaaggg   840
tgtggctccc cttaccaacc caggttggag gaggagagc gcaagcggga ggacgcggaa   900
cacaacctcg tgctcttccg caaggacgtg gacgatgcca ctctgtcccg cctggaacta   960
gagcgcaaga ttgagtctct gatggatgag attgagttcc tcaagaagct gcacgaggag  1020
gagctgcgag acctgcaggt gagtgtggaa agccagcagg tgaggtggaa                1080
gccacggtga agcccgagct gacggcagcg ctgaggcaca tccgcgcgca gtacgagagc   1140
atcgccgcga gaacctgca ggaggcgag gagtggtaca agtccaagta cgcggacctg    1200
tccgacgctg ccaaccggaa ccacgaggcc ctgcccagg caagcagga gatgaacgag    1260
tcccgacgcc agatccagag tctaacgtgc gaggtgacg ggctgcgcgg cacgaacgag    1320
gcgctgctca ggcagttgag agagctggag gagcagttcg ccctggaggc gggggggctac   1380
caggcgggcg ctgcgcggct cgaggaggag ctgcacagc taaaagagga gatggcgcgg   1440
cacctgaggg agtaccagga gctcctcaac gtcaagatgg ccctgacat cgagatcgcc    1500
acctaccgca agctgctgga gggcgaggag agccggatct ccgtgccgt ccattctttt    1560
gcctccttaa atataaagac gactgtgcct gaggtggagc ctcccagga cagccacagc    1620
cggaagac                                                              1628

SEQ ID NO: 44            moltype = AA  length = 653
FEATURE                  Location/Qualifiers
source                   1..653
                          mol_type = protein
                          organism = Homo sapiens
SEQUENCE: 44
MKLSLVAAML LLLSAARAEE EDKKEDVGTV VGIDLGTTYS CVGVFKNGRV EIIANDQGNR     60
ITPSYVAFTP EGERLIGDAA KNQLTSNPEN TVFDAKRLIG RTWNDPSVQQ DIKFLPFKVV    120
EKKTKPYIQV DIGGGQTKTF APEEISAMVL TKMKETAEAY LGKKVTHAVV TVPAYFNDAQ    180
RQATKDAGTI AGLNVMRIIN EPTAAAIAYG LDKREGEKNI LVFDLGGGTF DVSLLTIDNG    240
VFEVVATNGD THLGGEDFDQ RVMEHFIKLY KKKTGKDVRK DNRAVQKLRR EVEKAKALSS    300
QHQARIEIES FYEGEDFSET LTRAKFEELN MDLFRSTMKP VQKVLEDSDL KKSDIDEIVL    360
VGGSTRIPKI QQLVKEFFNG KEPSRGINPD EAVAYGAAVQ AGVLSGDQDT GDLVLLHVCP    420
LTLGIETVGG VMTKLIPSNT VVPTKNSQIF STASDNQPTV TIKVYEGERP LTKDNHLLGT    480
FDLTGIPPAP RGVPQIEVTF EIDVNGILRV TAEDKGTGNK NKITITNDQN RLTPEEIERM    540
VNDAEKFAEE DKKLKERIDT RNELESYAYS LKNQIGDKEK LGGKLSSEDK ETMEKAVEEK    600
IEWLESHQDA DIEDFKAKKK ELEEIVQPII SKLYGSAGPP PTGEEDTAEK DEL           653

SEQ ID NO: 45            moltype = DNA  length = 1962
FEATURE                  Location/Qualifiers
misc_feature             1..1959
                          note = CDS encodes SEQ ID NO: 44
source                   1..1962
                          mol_type = genomic DNA
                          organism = Homo sapiens
SEQUENCE: 45
atgaagctct ccctggtggc cgcgatgctg ctgctgctca gcgcggcgcg ggccgaggag     60
gaggacaaga aggaggacgt gggcacggtg gtcggcatcg acttggggac cacctactcc    120
tgcgtcggcg tgttcaagaa cggccgcgtg gagatcatcg ccaacgatca gggcaaccgc    180
atcacgccgt cctatgtcgc cttcactcct gaaggggaac gtctgattgg cgatgccgcc    240
aagaaccagc tcacctccaa ccccgagaac acggtctttg accgcaagcg gctcatcgga    300
cgcacgtgga atgacccgtc tgtgcagcag gacatcaagt tcttgccgtt caaggtggtt    360
gaaaagaaaa ctaaaccata cattcaagtt gatattggag gtgggcaaac aaagacattt    420
gctcctgaag aaatttctgc catggttctc actaaaatga agaaaccgc tgaggcttat    480
ttgggaaaga aggttaccca tgcagttgtt actgtaccag cctattttaa tgatgcccaa    540
cgccaagcaa ccaaagacgc tggaactatt gctggctcaa atgttatgag gatcatcaac    600
gagcctacgg cagctgctat tgcttatggc ctggataaga gggagggggaa gaaaacatc    660
ctggtgtttg acctggtgg cggaaccttc gatgtgtctc ttctcaccat tgacaatggt    720
gtcttcgaag ttgtggccac taatggagat actcatctgg gtgagaagaa ctttgaccag    780
cgtgtcatgg aacacttcat caaactgtac aaaaagaaga cggcaaaga tgtcaggaag    840
gacaatagag ctgtgcagaa actccggcgc gaggtagaaa aggccaagg cctgtcttct    900
cagcatcaag caagaattga aattgagtcc ttctatgaag agaagacttt tctgagacc    960
ctgactcggg ccaaatttga agagctcaac atggatctgt tccggtctac tatgaagccc   1020
gtccagaaag tgttggaaga ttctgattg aagaagtctg atattgatga aattgttctt    1080
gttggtggcc gactcgaat tccaaagatt cagcaactgg ttaaagagtt cttcaatggc   1140
aaggaaccat cccgtggcat aaacccagat gaagctgtag cgtatggtgc tgctgtccag   1200
```

```
gctggtgtgc tctctggtga tcaagataca ggtgacctgg tactgcttca tgtatgtccc   1260
cttacacttg gtattgaaac tgtaggaggt gtcatgacca aactgattcc aagtaataca   1320
gtggtgccta ccaagaactc tcagatcttt tctacagctt ctgataatca accaactgtt   1380
acaatcaagg tctatgaagg tgaaagaccc ctgacaaaag acaatcatct tctgggtaca   1440
tttgatctga ctggaattcc tcctgctcct cgtggggtcc cacagattga agtcacctt    1500
gagatagatg tgaatggtat tcttcgagtg acagctgaag acaagggtac agggaacaaa   1560
aataagatca caatcaccaa tgaccagaat cgcctgacac ctgaagaaat cgaaaggatg   1620
gttaatgatg ctgagaagtt tgctgaggaa gacaaaaagc tcaaggagcg cattgatact   1680
agaaatgagt tggaaagcta tgcctattct ctaaagaatc agattggaga taaagaaaag   1740
ctgggaggta aactttcctc tgaagataag gagaccatgg aaaaagctgt agaagaaaag   1800
attgaatggc tggaaagcca ccaagatgct gacattgaag acttcaaagc taagaagaag   1860
gaactggaag aaattgttca accaattatc agcaaactct atggaagtgc aggccctccc   1920
ccaactggtg aagaggatac agcagaaaaa gatgagttgt ag                      1962

SEQ ID NO: 46           moltype = DNA  length = 700
FEATURE                 Location/Qualifiers
misc_feature            1..700
                        note = /note="Description of Artificial Sequence: Synthetic
                         polynucleotide"
source                  1..700
                        mol_type = other DNA
                        organism = synthetic construct
SEQUENCE: 46
aactgaagat tcaacaatct cagacatcgc tgttgcaact aacgctggtc aaatcaaaac   60
tggttcactt tcacgtacag accgtatggc taaatacaac caattgcttc gtattgaaga   120
ccaattggct gaagttgctc aatacaaagg tcttaaagca ttctacaacc ttaaaaaata   180
aggaggaaaa aatgaaaaaa aagattatct cagctatttt aatgtctaca gtgatactt    240
ctgctgcagc cccgttgtca ggtgtttacg ccgctccaac ttcatcatca actaaaaaaa   300
ctcaattgca acttgaacac ttgctttgg atcttcaat gatcttgaac ggtatcaaca     360
actacaaaaa cccaaaactt actcgtatgt tgacttttaa attttacatg ccaaaaaaag   420
ctactgaact taaacacttg caatgtcttg aagaagaatt gaaccacttg gaagaagttt   480
tgaaccttgc tcaatcaaaa aactttcact tgcgtccacg tgatcttatc tcaaacatca   540
acgttatcgt tttggaactt aaaggttcag aaactacttt tatgtgtgaa tacgctgatg   600
aaaactgctac tatcgttgaa ttttgaacc gttggatcac tttttgtcaa tcaatcatct   660
caactttgac ttaaggttta gatggttta attagcaata                         700

SEQ ID NO: 47           moltype = DNA  length = 22
FEATURE                 Location/Qualifiers
misc_feature            1..22
                        note = /note="Description of Artificial Sequence: Synthetic
                         oligonucleotide"
source                  1..22
                        mol_type = other DNA
                        organism = synthetic construct
SEQUENCE: 47
aatccaatga cggcacttct tc                                            22

SEQ ID NO: 48           moltype = DNA  length = 20
FEATURE                 Location/Qualifiers
misc_feature            1..20
                        note = /note="Description of Artificial Sequence: Synthetic
                         oligonucleotide"
source                  1..20
                        mol_type = other DNA
                        organism = synthetic construct
SEQUENCE: 48
cttgtcgtta aagcctattc                                               20

SEQ ID NO: 49           moltype = DNA  length = 24
FEATURE                 Location/Qualifiers
misc_feature            1..24
                        note = /note="Description of Artificial Sequence: Synthetic
                         oligonucleotide"
source                  1..24
                        mol_type = other DNA
                        organism = synthetic construct
SEQUENCE: 49
cgtaaccatg taaaagcact tctg                                          24

SEQ ID NO: 50           moltype = DNA  length = 20
FEATURE                 Location/Qualifiers
misc_feature            1..20
                        note = /note="Description of Artificial Sequence: Synthetic
                         oligonucleotide"
source                  1..20
                        mol_type = other DNA
                        organism = synthetic construct
SEQUENCE: 50
gtaattctaa tgctggtggg                                               20
```

| | | |
|---|---|---|
| SEQ ID NO: 51 | moltype = DNA  length = 21 | |
| FEATURE | Location/Qualifiers | |
| misc_feature | 1..21 | |
| | note = /note="Description of Artificial Sequence: Synthetic oligonucleotide" | |
| source | 1..21 | |
| | mol_type = other DNA | |
| | organism = synthetic construct | |
| SEQUENCE: 51 | | |
| attacgccat ctaaatcaaa c | | 21 |
| | | |
| SEQ ID NO: 52 | moltype = DNA  length = 20 | |
| FEATURE | Location/Qualifiers | |
| misc_feature | 1..20 | |
| | note = /note="Description of Artificial Sequence: Synthetic oligonucleotide" | |
| source | 1..20 | |
| | mol_type = other DNA | |
| | organism = synthetic construct | |
| SEQUENCE: 52 | | |
| catcgctgaa gctatcatcg | | 20 |
| | | |
| SEQ ID NO: 53 | moltype = DNA  length = 20 | |
| FEATURE | Location/Qualifiers | |
| misc_feature | 1..20 | |
| | note = /note="Description of Artificial Sequence: Synthetic oligonucleotide" | |
| source | 1..20 | |
| | mol_type = other DNA | |
| | organism = synthetic construct | |
| SEQUENCE: 53 | | |
| gatggctgaa gctccaactc | | 20 |
| | | |
| SEQ ID NO: 54 | moltype = DNA  length = 20 | |
| FEATURE | Location/Qualifiers | |
| misc_feature | 1..20 | |
| | note = /note="Description of Artificial Sequence: Synthetic oligonucleotide" | |
| source | 1..20 | |
| | mol_type = other DNA | |
| | organism = synthetic construct | |
| SEQUENCE: 54 | | |
| gcatggaaga ggacaaagag | | 20 |
| | | |
| SEQ ID NO: 55 | moltype = DNA  length = 20 | |
| FEATURE | Location/Qualifiers | |
| misc_feature | 1..20 | |
| | note = /note="Description of Artificial Sequence: Synthetic oligonucleotide" | |
| source | 1..20 | |
| | mol_type = other DNA | |
| | organism = synthetic construct | |
| SEQUENCE: 55 | | |
| aacctgtggg agggcgaaag | | 20 |
| | | |
| SEQ ID NO: 56 | moltype = DNA  length = 18 | |
| FEATURE | Location/Qualifiers | |
| misc_feature | 1..18 | |
| | note = /note="Description of Artificial Sequence: Synthetic oligonucleotide" | |
| source | 1..18 | |
| | mol_type = other DNA | |
| | organism = synthetic construct | |
| SEQUENCE: 56 | | |
| tgggtcgtga atacttcc | | 18 |
| | | |
| SEQ ID NO: 57 | moltype = DNA  length = 500 | |
| FEATURE | Location/Qualifiers | |
| misc_feature | 1..500 | |
| | note = /note="Description of Artificial Sequence: Synthetic polynucleotide" | |
| source | 1..500 | |
| | mol_type = other DNA | |
| | organism = synthetic construct | |
| SEQUENCE: 57 | | |
| tcagctaacg gagctcaact tgttaaaact gtatcttggt acgataacga aatgtcatac | | 60 |
| acttcaaacc ttgttcgtac acttgcatac ttcgctaaaa tcgctaaata aggaggaaaa | | 120 |
| aatgaagaag aaaatcatta gtgccatctt aatgtcataca gtgattcttt cagctgcagc | | 180 |

```
tcctttatca ggcgtttatg catttgtgaa ccaacacctg tgcggctcac acctggtgga    240
agctctctac ctagtgtgcg gggaacgagg cttcttctac acacccaaga cccgccggga    300
ggcagaggac ctgcaggtgg ggcaggtgga gctgggcggg ggccctggtg caggcagcct    360
gcagcccttg gccctggagg ggtccctgca gaagcgtggc attgtggaac aatgctgtac    420
cagcatctgc tccctctacc agctggagaa ctactgcaac taattttccg attttaacgg    480
tataaaaacc agtcttcggg                                                500

SEQ ID NO: 58          moltype = DNA  length = 20
FEATURE                Location/Qualifiers
misc_feature           1..20
                       note = /note="Description of Artificial Sequence: Synthetic
                        oligonucleotide"
source                 1..20
                       mol_type = other DNA
                       organism = synthetic construct
SEQUENCE: 58
aaccgctttc agaagaaggg                                                20

SEQ ID NO: 59          moltype = DNA  length = 26
FEATURE                Location/Qualifiers
misc_feature           1..26
                       note = /note="Description of Artificial Sequence: Synthetic
                        oligonucleotide"
source                 1..26
                       mol_type = other DNA
                       organism = synthetic construct
SEQUENCE: 59
caccgaatta acacgcatta tgactt                                         26

SEQ ID NO: 60          moltype = DNA  length = 19
FEATURE                Location/Qualifiers
misc_feature           1..19
                       note = /note="Description of Artificial Sequence: Synthetic
                        oligonucleotide"
source                 1..19
                       mol_type = other DNA
                       organism = synthetic construct
SEQUENCE: 60
tttcgctggg aaagcacac                                                 19

SEQ ID NO: 61          moltype = DNA  length = 20
FEATURE                Location/Qualifiers
misc_feature           1..20
                       note = /note="Description of Artificial Sequence: Synthetic
                        oligonucleotide"
source                 1..20
                       mol_type = other DNA
                       organism = synthetic construct
SEQUENCE: 61
gcgtgtccaa gcaatagatg                                                20
```